(12) United States Patent
Griffin et al.

(10) Patent No.: US 7,183,285 B2
(45) Date of Patent: Feb. 27, 2007

(54) COMPOSITIONS AND TREATMENTS FOR INHIBITING KINASE AND/OR HMG-COA REDUCTASE

(75) Inventors: John Griffin, Atherton, CA (US); Guido Lanza, San Francisco, CA (US); Jessen Yu, San Francisco, CA (US)

(73) Assignee: Pharmix Corp., Brisbane, CA (US)

( * ) Notice: Subject to any disclaimer, the term of this patent is extended or adjusted under 35 U.S.C. 154(b) by 10 days.

(21) Appl. No.: 11/118,066

(22) Filed: Apr. 29, 2005

(65) Prior Publication Data

US 2005/0261354 A1  Nov. 24, 2005

Related U.S. Application Data

(60) Provisional application No. 60/630,684, filed on Nov. 23, 2004, provisional application No. 60/630,683, filed on Nov. 23, 2004, provisional application No. 60/567,118, filed on Apr. 29, 2004.

(51) Int. Cl.
  *A01N 43/58*  (2006.01)
(52) U.S. Cl. ............... 514/256; 514/247; 514/183
(58) Field of Classification Search ............... None
  See application file for complete search history.

(56) References Cited

U.S. PATENT DOCUMENTS

| | | | |
|---|---|---|---|
| 4,735,958 A | 4/1988 | Roth et al. | |
| 4,808,621 A | 2/1989 | Roth et al. | |
| 4,957,971 A | 9/1990 | Picard et al. | |
| 5,013,749 A | 5/1991 | Watson et al. | |
| 5,102,893 A | 4/1992 | Picard et al. | |
| 5,190,029 A | 3/1993 | Byron et al. | |
| 5,376,359 A | 12/1994 | Johnson | |
| 5,776,434 A | 7/1998 | Purewal et al. | |
| 6,177,121 B1 | 1/2001 | Elkin et al. | |
| 6,414,011 B1 | 7/2002 | Hogenkamp et al. | |
| 6,506,779 B1 | 1/2003 | Cheng et al. | |
| 6,548,529 B1 | 4/2003 | Robl et al. | |
| 2001/0034364 A1 | 10/2001 | Gasper et al. | |
| 2002/0048746 A1 | 4/2002 | Lynch et al. | |
| 2002/0147197 A1 | 10/2002 | Newman et al. | |
| 2002/0156122 A1 | 10/2002 | Mach | |
| 2003/0064967 A1 | 4/2003 | Luchoomum et al. | |
| 2003/0087430 A1 | 5/2003 | Catron et al. | |
| 2003/0114495 A1 | 6/2003 | Finke et al. | |
| 2004/0122077 A1 | 6/2004 | Walsh | |
| 2004/0127692 A1 | 7/2004 | David et al. | |
| 2004/0192667 A1 | 9/2004 | Makriyannis et al. | |
| 2005/0043364 A1 | 2/2005 | Kennedy et al. | |
| 2005/0129729 A1 | 6/2005 | Schreiner | |
| 2005/0272770 A1 | 12/2005 | Griffin et al. | |
| 2005/0277653 A1 | 12/2005 | Griffin et al. | |
| 2005/0282883 A1 | 12/2005 | Griffin et al. | |
| 2005/0288306 A1 | 12/2005 | Griffin et al. | |
| 2006/0084695 A1 | 4/2006 | Griffin et al. | |
| 2006/0111436 A1 | 5/2006 | Griffin | |

FOREIGN PATENT DOCUMENTS

| | | |
|---|---|---|
| EP | 0436851 | 7/1991 |
| JP | 07267931 | 10/1995 |
| JP | 08217754 | 8/1996 |
| JP | 10162430 | 6/1998 |
| JP | 2002122952 | 4/2002 |
| WO | WO 93/09100 | 5/1993 |
| WO | WO 95/06032 | 3/1995 |
| WO | WO 98/06702 | 2/1998 |
| WO | WO 01/37876 | 5/2001 |
| WO | WO 01/93806 | 12/2001 |
| WO | WO 03/068738 | 8/2003 |
| WO | WO 03/086379 | 10/2003 |
| WO | WO 03/086418 | 10/2003 |
| WO | WO 04/069824 | 8/2004 |
| WO | WO 04/105752 | 12/2004 |

OTHER PUBLICATIONS

Johnson et al. Relationships between drug activity in NCI preclinical n vitro and in vivo modles and early clinical trials. British Journal of Cancer (2001) 84(10), 1424-1431.*
HGNC Gene Family Nomenclature. http://www.gene.ucl.ac.uk/nomenclature/genefamily/prkm.html Retrieved Apr. 4, 2006.*
Arthritis:Inflammation and Arthritis http://www.webmd.com/content/article/78/95595.htm Retrieved Apr. 4, 2006.*
Awasthi, et al. CD40 Signaling Is Impaired In L. Major-Infected Macrophages And Is Rescued By A P38MAPK Activator Establishing A Host-Protective Memory T Cell Response. *J. Exp. Med.,* 2003; 197(8): 1037-1043.
Bangham, et al. Diffusion Of Univalent Ions Across The Lamellae Of Swollen Phospholipids. *J. Mol. Biol.,* 1965; 13:238-252.
Barros, et al. Evidence Of Two Mechanisms For The Activation Of The Glucose Transporter GLUT1 by Anisomycin: p38 (MAP Kinase) Activation And Protein Synthesis Inhibition In Mammalian Cells. *J. Physiol.* 1997; 504: 517-525.
Barry, Brian W. Dermatological Formulations: Percutaneous absorption. *Marcel Dekker Inc.* New York, NY; 1983.
Blumberg, et al. Animal Models Of Mucosal Inflammation And Their Relation To Human Inflammatory Bowel Disease. *Current Opinion in Immunology.* 1999; 11: 648-656.
Bocan, et al. Antiatherosclerotic activity of inhibitors of 3-hydroxy-3-methylglutaryl coenzyme A reductase in cholesterol-fed rabbits: a biochemical and morphological evaluation. *Artherosclerosis.* 1994; 111:127-142.

(Continued)

*Primary Examiner*—Ardin H. Marschel
*Assistant Examiner*—Michel Graffeo
(74) *Attorney, Agent, or Firm*—Wilson Sonsini Goodrich and Rosati

(57) ABSTRACT

The present invention provides compositions of matter, kits and methods for their use in the treatment of MAP kinase-related conditions and/or HMG-CoA reductase-related conditions. In particular, the invention provides compositions for treating inflammatory and/or cardiovascular conditions in an animal subject by inhibiting p38α MAP kinase and/or HMG-CoA reductase, as well as providing formulations and modes of administering such compositions. The invention further provides methods for the rational design of inhibitors of MAP kinase, HMG-CoA reductase, or both for use in the practice of the present invention.

15 Claims, 23 Drawing Sheets

OTHER PUBLICATIONS

Bocan, et al. Hepatic and nonhepatic sterol synthesis and tissue distribution following administration of a liver selective HMG-CoA reductase inhibitor, CI-981: comparison with selected HMG-CoA reductase inhibitors. *Biochimica et Biophysica Acta.* 1992; 1123(2):133-144.

Boisemenu, et al. Insights From Mouse Models Of Colitis. *Journal of Leukocyte Biology.* 2000; 67(3): 267-278.

Cantatore, et al. Evaluation of Bone Turnover and Osteoclastic Cytokines in Early Rheumatoid Arthritis Treated with Alendronate. *J. Rheumatolgy.* 1996; 26(11):2318-2323.

Chakravarty, et al. Chapter 18: Inhibitors of p38αMAP Kinase. *Annual Reports in Medicinal Chemistry.* 2002; 37:177-186.

Chan, et al. Inhibitors of cholesterol biosynthesis, I. 3,5-dihydroxy-7-(N-imidazolyl)-6-heptenoates and -heptanoates, a novel series of HMG-CoA reductase inhibitors. *J. Med. Chem.* 1993; 36(23): 3646-3657.

Clerk, et al. The p38-MAPK inhibitor, SB203580, inhibits cardiac stress-activated protein kinases/c-Jun N-terminal kinases (SAPKs/JNKs). *FEBS Letters* 1998; 426: 93-96.

Curtin, et al. Anisomycin activates JNK and sensitises DU 145 prostate carcinoma cells to Fas mediated apoptosis. *Br. J. Cancer.* 2002; 87(10): 1188-1194.

Dhawan, et al. Critical role of p42/44MAPK activation in anisomycin and hepatocyte growth factor-induced LDL receptor expression: activation of Raf-1/MEK-1/p42/44MAPK cascade alone is sufficient to induce LDL receptor expression. *J. Lipid Res.* 1999; 40: 1911-1919.

Evans, et al. Nitric Oxide And Bone. *J Bone Miner Res.* 1996; 11(3): 300-305.

Forrester, et al. Increasing High-Density Lipoprotein Cholesterol in Dyslipidemia by Cholesteryl Ester Transfer Protein Inhibition—An Update for Clinicians. *Circulation.* 2005; 111(14): 1847-1854.

Gennaro, A. *Remington: The Science and Practice of Pharmacy.* 20th edition; Lippincott Williams & Wilkins; 2000.

Golenbock, et al. Lipid A-Like Molecules That Antagonize The Effects Of Endotoxins On Human Monocytes. *Journal of Biological Chemistry.* 1991; 266(29): 19490-19489.

Graul, et al. ZD-4522: Hypolipidermic HMG-CoA reductase inhibitor. *Drugs of the Future,* 1999; 24(5): 511-513.

Joyce, et al. Pravastatin, A 3-hydroxy-3-methylglutaryl Coenzyme A Reductase Inhibitor, Attenuates Renal Injury in an Experimental Model of Ischemia-Reperfusion. *J. of Surgical Research.* 2001; 101(1): 79-84.

Karanewsky, et al. Phosphorus-containing inhibitors of HMG-CoA reductase 1. 4-[(2-Arylethyl) hydroxyphosphinyl]-3-hydroxybutanoic Acids: a new class of cell-selective inhibitors of cholesterol biosynthesis. *Journal of Medicinal Chemistry.* 1990; 33(11): 2952-2956.

Katznelson, et al. Dual Roles Of HMG-Coa Reductase Inhibitors In Solid Organ Transplantation: Lipid Lowering And Immunosuppression., Kidney Int. Suppl., 1995; 48(52): S112-115.

Katznelson, et al. Effect Of HMG-Coa Reductase Inhibitors On Chronic Allograft Rejection. *Kidney Int Suppl.* 1999; 56(71): S117-121.

Katznelson, et al. The Effect Of Pravastatin On Acute Rejection After Kidney Transplantation—A Pilot Study. *Transplantation.* 1996; 61(10):1469-1474.

Kiener, et al. Stimulation of inflammatory responses in vitro and in vivo by lipophilic HMG-CoA reductase inhibitors. *Intl. Immunopharmacol.* 2001; 1: 105-118.

Krause, et al. Inhibition of cholesterol synthesis in target tissues and extrahepatic organs after administration of HMG-CoA reductase inhibitors in normolipidaemic rats: organ selectivity and time course of the inhibition. *Journal of Drug Development.* 1990; 3(Supplement 1): 255-257.

Kureishi, et al. The HMG-CoA reductase inhibitor simvastatin activates the protein kinase Akt and promotes angiogenesis in normocholesterolemic animals. *Nature Medicine.* 2000; 6(8): 1004-1010.

Nagai, et al. Effect of overproduction of interleukin 5 on dinitrofluorobenzenc-induced allergic cutaneous response in mice. *The Journal of Pharmacology and Experimental Therapeutics.* 1999; 288(1): 43-50.

Namazi, M.R. Statins: Novel Additions To The Dermatologic Arsenal? *Experimental Dermatology.* 2004; 13: 337-339.

Nofer, et al. Involvement of CDC42 signaling in ApoA-I-induced cholesterol efflux. *J. Biol. Chem.* 2003; 278(52): 53055-53062.

Ono, et al. The P38 Signal Transduction Pathway Activation And Function. *Cell. Signal.* 2000; 12(1): 1-13.

Palinski, et al. Immunomodulatory effects of statins: mechanisms and potential impact on arteriosclerosis. *Journal of the American Society of Nephrology.* 2002; 13(6): 1673-1681.

Pearlman, B.L. The new cholesterol guidelines: Applying them in clinical practice. *Post Graduate Medicine.* 2002; 112(2): 13-26.

Reiss, et al. Cholesterol In Neurologic Disorders Of The Elderly: Stroke And Alzheimer's Disease. *Neurobiology of Aging.* 2004; 25: 977-989.

Roth, et al. Inhibitors of cholesterol biosynthesis. 3. tetrahydro-4-hydroxy-6-[2-(1H-pyrrol-1-yl)ethyl]-2H-pyran-2-one inhibitors of HMG-CoA reductase. 2. effects of introducing substituents at positions three and four of the pyrrole nucleus. *J. Med. Chem.* 1991; 34(1): 357-366.

Roth, et al. Relationship between tissue selectivity and lipophilicity for inhibitors of HMG-CoA reductase. *J. Med. Chem.* 1991; 34(1): 463-466.

Roux, et al. Bone Loss—Factors That Regulate Osteoclast Differentiation: An Update. *Arthritis Res.* 2000; 2(6):451-456.

Schauer, et al. Induction Of Cellular Resistance Against Kupffer Cell-Derived Oxidant Stress: A Novel Concept Of Hepatoprotection By Ischemic Preconditioning. *Hepatology.* 2003; 37(2): 286-295.

Schindler, et al. Correlations And Interactions In The Production Of Interleukin-6 (IL-6), IL-1, and Tumor Necrosis Factor (TNF) In Human Blood Mononuclear Cells: IL-6 Suppresses IL-1 and TNF. *Blood.* 1990; 75(1): 40-47.

Shum, et al. Development, validation, and interlaboratory comparison of an HMG-CoA reductase inhibition assay for quantitation of atorvastatin in plasma matrices. *Therapeutic Drug Monitoring.* 1998; 20(1): 41-49.

Sliskovic, et al. Inhibitors of cholesterol biosynthesis. 6. trans-6-[2-(2-N-Heteroaryl-3, 5-disubstituted-pyrazole-4-yl)ethyl/ethenyl]tetrahydro-4-hydroxy-2H-pyran-2-ones. *J. Med. Chem.,* 1992; 35(11): 2095-2103.

Sliskovic, et al. Tissue selectivity of HMG-CoA reductase inihibitors. *Drug New and Perspectives.* 1992; 5(9): 517-533.

Stokker, G.E. et al., Synthesis and characterization of a novel 6-heteroaryl-3,6-dihydro-2H-pyran-2-acetic acid. *Heterocycles.* 1987; 26(1): 157-162.

Stuve, et al. The Potential Therapeutic Role Of Statins In Central Nervous System Autoimmune Disorders. *Cell Mol Life Sci.* 2003; 60(11): 2483-2491.

Szoka, et al. Procedure for preparation of liposomes with large internal aqueous space and high capture by reverse-phase evaporation. *Proc. Natl. Acad. Sci. USA.* 1978; 75(9): 4194-4198.

Welker, et al. Glucocorticoid-induced modulation of cytokine secretion from normal and leukemic human myelomonocytic cells. *International Archives of Allergy and Immunology.* 1996; 109(1): 110-115.

Wenke, et al. Simvastatin Reduces Graft Vessel Disease And Mortality After Heart Transplantation: A Four-Year Randomized Trial. *Circulation.* 1997; 96(5): 1398-1402.

Wolozin, W. Cholesterol, Statins And Dementia. *Curr. Op. Lipidol.* 2004; 15(6):667-672.

Griffin, et al., U.S. Appl. No. 11/118,090, entitled "Compositions and Treatments for Inhibiting Kinase and/or HMG-CoA Reductase,", filed Apr. 29, 2005.

Griffin, U.S. Appl. No. 11/118,098, entitled "Compositions and Treatments for Modulating Kinase and/or HMG-CoA Reductase,", filed Apr. 29, 2005.

Griffin, et al., U.S. Appl. No. 11/118,065, entitled "Compositions and Treatments for Inhibiting Kinase and/or HMG-CoA Reductase,", filed Apr. 29, 2005.

Griffin, et al., U.S. Appl. No. 11/118,064, entitled "Compositions and Treatments for Inhibiting Kinase and/or HMG-CoA Reductase,", filed Apr. 29, 2005.

Griffin, et al., U.S. Appl. No. 11/118,113, entitled "Compositions and Treatments for Inhibiting Kinase and/or HMG-CoA Reductase,", filed Apr. 29, 2005.

Griffin, et al., U.S. Appl. No. 11/262,521, entitled "Compositions and Treatments for Inhibiting Kinase and/or HMG-CoA Reductase,", filed Oct. 28, 2005.

Boehm, Jeffrey C. et al. 1-Substituted 4-aryl-5-pyridinylimidazoles: A new class of cytokine suppressive drugs with low 5-lipoxygenase and cyclooxygenase inhibitory potency. *J. Med. Chem.* 1996;39(20): 3929-3937.

Liverton, Nigel J. et al. Design and synthesis of potent, selective, and orally bioavailable tetrasubstituted imidazole inhibitors of p38 mitogen-activated protein kinase. *J. Med. Chem.* 1999;42(12): 2180-2190.

Tong, Liang et al. A highly specific inhibitor of human p38 MAP kinase binds in the ATP pocket. *Nature Structural Biology.* 1997;4(4): 311-316.

Wilson, Keith P. et al. The structural basis for the specificity of pyridinylimidazole inhibitors of p38 MAP kinase. *Chemistry & Biology.* 1997;4(6): 423-431.

Aktas, O. et al. 2003, Treatment of relapsing paralysis in experimental encephalomyelitis by targeting Th 1 cells through atorvastatin. *Journal of Experimental Medicine*, 197(6): 725-733.

Bustos, C. et al. 1998, HMG-CoA reductase inhibition by atorvastatin reduces neointimal inflammation in a rabbit model of atherosclerosis *JACC* 32(7): 2057-2064.

Prueksaritanont, T. et al. 2002, Glucuronidation of statins in animals and humans: a novel mechanism of statin lactonization *Drug Metabolism and Disposition.* 30(5): 505-512.

Wagner, A.H. et al. 2002, Atorvastatin inhibition of cytokine-inducible nitric oxide synthase expression in native endothelial cells in situ. *British Journal of Pharmacology.* 136: 143-149.

* cited by examiner

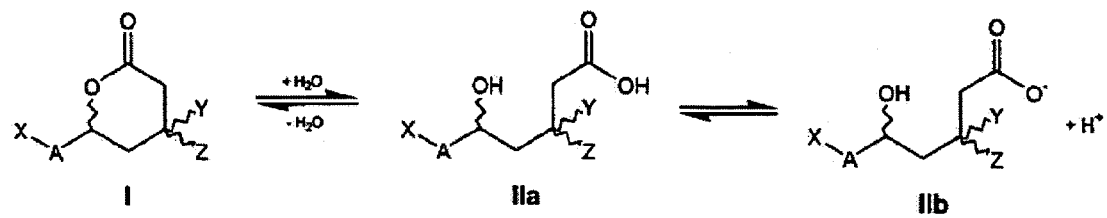
Figure 3a
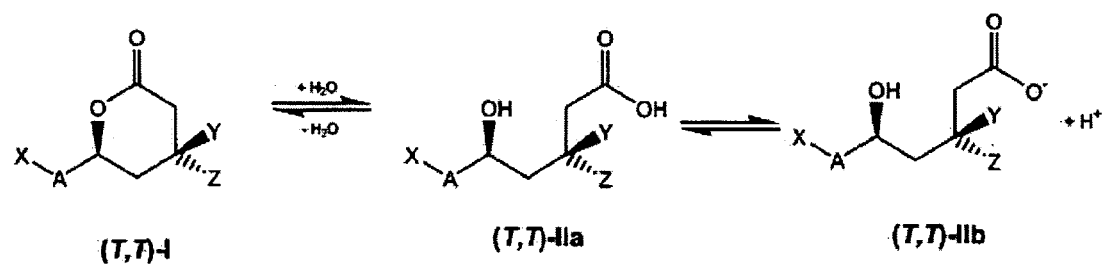
Figure 3b
Figure 3

Figure 4a (pyrazoles)

Figure 4b (oxazole)

Figure 4c (imidazoles)

1018

1019

Figure 4d (pyrrolo[2,3-*b*]pyrimidines)

1020

Figure 4e (diazaisoquinolinone)

1021

Figure 4f (1,2-pyrazine)

1022

Figure 4g (pyrrole)

1023

Figure 4h (4-aminobenzophenone)

1024

Figure 4i (3-amidobenzamide)

1025

Figure 4j (pyridine)

1026

Figure 4k (pyrimidino [4,5-*d*] pyrimidinone)

1027

Figure 4l (indole)

Figure 5a (pyrazoles)

Figure 5b (oxazoles)

Figure 5c (imidazoles)

Figure 5d (pyrrolo[2,3-b]pyrimidines)

Figure 5e (diazaisoquinolinones)

Figure 5f (1,2-pyrazines)

Figure 5g (pyrroles)

Figure 5h (4-aminobenzophenones)

Figure 5i (3-amidobenzamides)

Figure 5j (pyridines)

Figure 5k (pyrimidino[4,5-d]pyrimidinones)

Figure 5l (indoles)

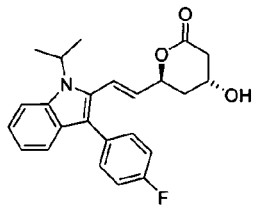
Fluvastatin Lactone
Figure 6a
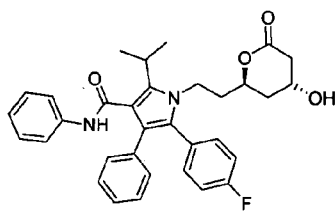
Atorvastatin Lactone
Figure 6b
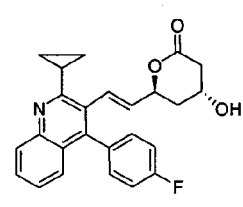
Pitavastatin Lactone
Figure 6c
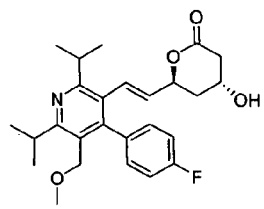
Cerivastatin Lactone
Figure 6d
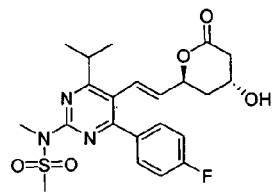
Rosuvastatin Lactone
Figure 6e
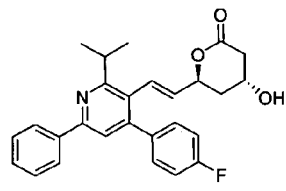
Glenvastatin Lactone
Figure 6f
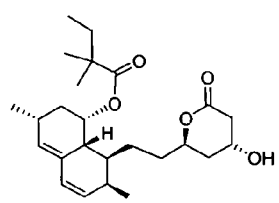
Simvastatin Lactone
Figure 6g
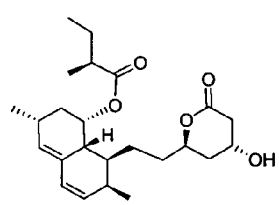
Lovastatin Lactone
Figure 6h
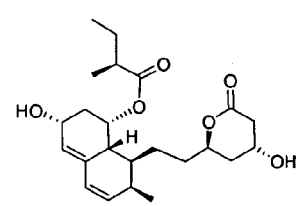
Pravastatin Lactone
Figure 6i
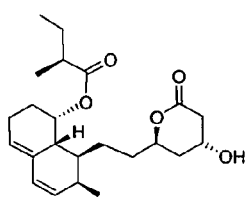
Mevastatin Lactone
Figure 6j
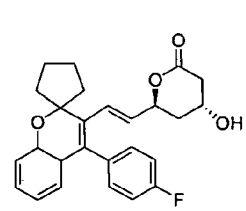
Bervastatin Lactone
Figure 6k
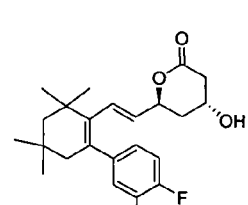
Dalvastatin Lactone
Figure 6l
Figure 6

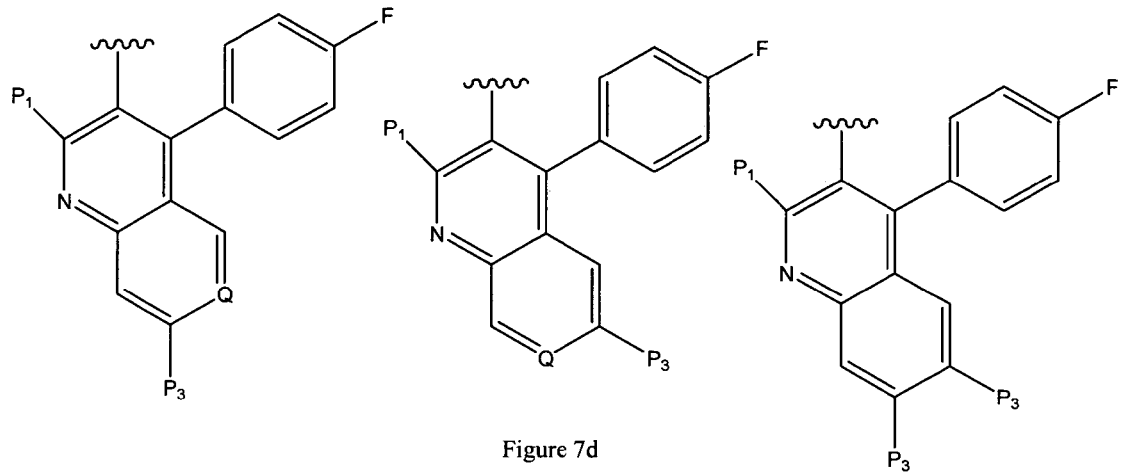
Figure 7d
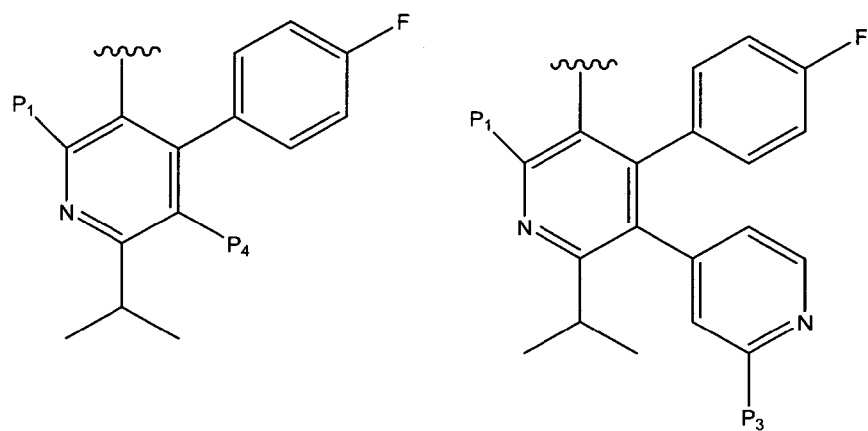
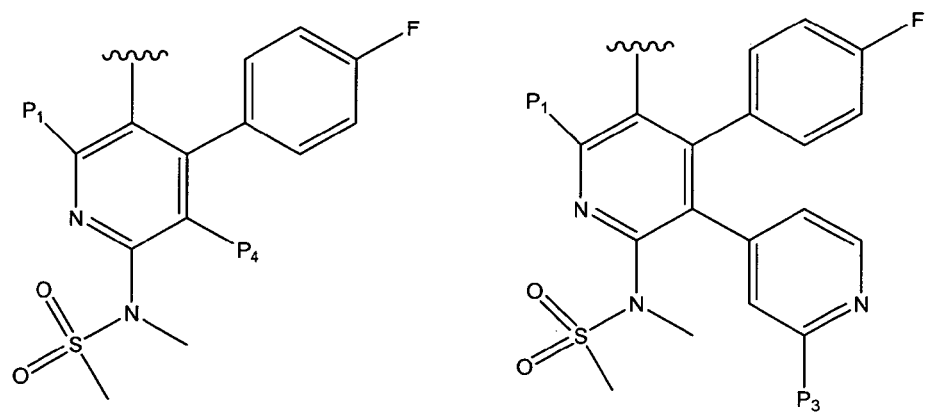
Figure 7e
Figure 7 (continued)

Fluvastatin

Family I

Atorvastatin

Family II

Family III

Cerivastatin

Rosuvastatin

Family VI

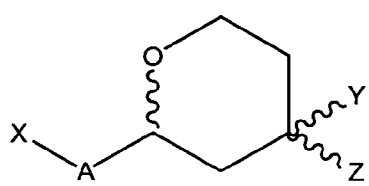
III
Figure 9a
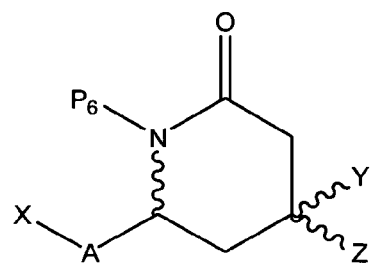
IV
Figure 9b
Figure 9

COMPOSITIONS AND TREATMENTS FOR INHIBITING KINASE AND/OR HMG-COA REDUCTASE

RELATED APPLICATIONS

This application claims priority to U.S. Provisional Patent Applications Ser. Nos. 60/567,118, filed Apr. 29, 2004 and 60/630,684, filed Nov. 23, 2004. Such applications are incorporated by reference herein, for all purposes. U.S. Provisional Patent Applications Ser. No. 60/630,683, filed Nov. 23, 2004, is also incorporated by reference herein, for all purposes.

BACKGROUND

The pro-inflammatory cytokines, such as tumor necrosis factor-α (TNF-α) and interleukin-1β (IL-1β), contribute to the pathogenesis of various allergic, inflammatory and autoimmune diseases. Consequently, multiple therapeutic approaches have been aimed at reducing the expression and/or activity of such pro-inflammatory cytokines. Examples of these include the use of IL-1 receptor antagonists, TNF-α converting enzyme inhibitors, and inhibitors of certain enzymes that play a role in signal transduction pathways associated with inflammation, including responses to and expression of TNF-α and IL-1β.

Immunomodulatory and inflammatory effects also play a role in cardiovascular conditions, such as atherogenesis and its associated cardiovascular risks, such as atherosclerosis, thrombosis, myocardial infarction, ischemic stroke, ischemic-reperfusion injury and peripheral vascular diseases. For example, inflammatory responses, including those involving TNF-α and IL-1β, play a role in the initiation, growth and disruption of atheroslerotic plaques. Treatments of such cardiovascular conditions typically address hypercholesterolemia, for example, by inhibiting the enzymes involved in cholesterol biosynthesis. Statins, for example, inhibit 3-hydroxy-3-methylglutaryl CoA (HMG-CoA) reductase, the rate-limiting enzyme in the cholesterol biosynthesis pathway.

With heart disease being the most prevalent illness of industrialized counties, and inflammatory conditions affecting millions of individuals worldwide, there remains a need for compounds that can treat one or both of these types of conditions. These compounds can form the basis for pharmaceutical compositions useful in the prevention and treatment of atherogenesis and/or inflammatory conditions in humans and other mammals. Moreover, the interplay between inflammatory and cardiovascular conditions means that compounds or combinations of compounds addressing both may be particularly beneficial.

BRIEF SUMMARY OF THE INVENTION

In one aspect, the present invention provides compounds and compositions that show MAP kinase inhibitory activity and/or HMG-CoA reductase inhibitory activity. Some embodiments are compounds comprising novel analogs of MAP kinase inhibitors. Some embodiments are compounds comprising novel analogs of HMG-CoA reductase inhibitors. Some embodiments are compounds comprising novel series of substituted imidazoles, substituted pyrazoles, or substituted pyrroles. Some embodiments are compounds comprising novel series of substituted indoles, substituted pyridines, substituted pyrimidines, or substituted quinolines. Some embodiments are compounds comprising structures modified to favor and/or enforce a closed ring structure, e.g., a δ-lactam or a des-oxo-structure. Some embodiments are combinations comprising two more compounds described herein and/or two or more forms of a compound described herein.

In another aspect, the present invention provides methods of treating a MAP kinase- and/or an HMG-CoA reductase-related condition by administering an effective amount of a compound or combination of compounds to a subject. In some embodiments, known inhibitors of HMG-CoA reductase are used to inhibit a MAP kinase, e.g., p38α MAP kinase, in the treatment of a MAP kinase-related condition or in the treatment of both a MAP kinase- and an HMG-CoA reductase-related condition. In other embodiments, novel compounds that inhibit both a MAP kinase and HMG-CoA reductase are superior to compounds that target a MAP kinase but not HMG-CoA reductase or to compounds that target HMG-CoA reductase and not MAP kinase, for example, in treating a MAP kinase- and/or an HMG-CoA reductase-related condition. In some embodiments, novel combinations of compounds or forms of compounds are used to treat MAP kinase- and/or HMG-CoA reductase-related conditions that are inflammatory conditions. For example, in some embodiments, combinations comprising a statin lactone and a salt form of a hydroxy acid statin are used to treat skin and/or vascular inflammatory conditions. In preferred embodiments, such combinations provide synergistic effects in treating inflammation.

In another aspect, the present invention provides pharmaceutical compositions, formulations and modes of administering one or more compounds, e.g., compounds of the present invention, for use in methods of treating a MAP kinase-related and/or an HMG-CoA reductase-related condition, including inflammatory conditions. For example, in some embodiments, a statin lactone can be formulated with a hydroxy acid form of the same or different statin, a pharmaceutically acceptable salt thereof, or with another active agent. For example, in some embodiments, a statin lactone can be formulated with a non-statin anti-inflammatory agent. Such combination formulations are administered orally or topically in preferred embodiments, e.g., in the treatment of inflammatory conditions.

In yet another aspect, the present invention provides methods for the rational design of inhibitors of MAP kinase, HMG-CoA reductase, or both for use in the practice of the present invention. In certain embodiments, such methods involve designing a compound comprising a lipophilic moiety, e.g., a lipophilic MAP kinase inhibitor, or a moiety or analog thereof, or comprising a lipophilic moiety or analog of an HMG-CoA reductase inhibitor; testing the designed compound for MAP kinase and/or HMG-CoA reductase inhibitory activity; and using the compound to make a composition for inhibiting MAP kinase and/or HMG-CoA reductase, e.g., for use in the practice of the present invention. In some embodiments, two or more designed compounds or forms thereof are used in preparing combination formulations, e.g., as described herein.

In one aspect, the present invention provides compositions that show MAP kinase inhibitory and/or 3-hydroxy-3-methyl glutaryl-coenzyme A reductase (HMG-CoA reductase) inhibitory activity. Some embodiments are compositions comprising novel analogs of MAP kinase inhibitors. Some embodiments are compositions comprising novel analogs of HMG-CoA reductase inhibitors. Some embodiments are compositions comprising structures modified to favor and/or enforce a closed ring structure, e.g., a δ-lactam or a des-oxo-structure.

In another aspect, the present invention provides pharmaceutical compositions comprising combinations of a lactone form of a "statin" inhibitor of HMG-CoA reductase with one or more additional pharmacologically active agents. Some embodiments are compositions comprising a statin lactone and the hydroxy acid form of a statin, or a pharmaceutically acceptable salt thereof. An embodiment of the invention includes compositions where the ratio of lactone statin to hydroxy acid statin is between about 99:1 and about 1:99. Preferred embodiments include a composition comprising an atorvastatin lactone and a composition comprising an atorvastatin hydroxy acid or a pitavastatin hydroxy acid. Some embodiments are compositions comprising a statin lactone and a non-statin anti-inflammatory agent. An embodiment of the invention includes compositions where the ratio of lactone statin to non-statin anti-inflammatory agent is between about 99:1 and about 1:99. Preferred embodiments include compositions comprising an atorvastatin lactone and/or indomethacin. In a most preferred embodiment, a composition comprising an atorvastatin lactone and indomethacin has a synergistic effect.

In another aspect, the present invention provides methods of treating an inflammatory condition by administering an effective amount of a pharmaceutical composition, e.g., a composition of the present invention, to a subject. In other embodiments, the invention provides methods which target both a MAP kinase, e.g., p38α MAP kinase and HMG-CoA reductase for inhibition that are superior to methods that that target a MAP kinase but not HMG-CoA reductase or to methods that target HMG-CoA reductase and not MAP kinase, for example, in the treatment of a MAP kinase- and/or an HMG-CoA reductase-related condition.

In another aspect, the present invention relates to the use, in the treatment of a MAP kinase-related conditions that are inflammatory diseases and disorders associated with inflammation, of pharmaceutical compositions comprising combinations of a lactone form of a "statin" inhibitor of the enzyme 3-hydroxy-3-methyl glutaryl-coenzyme A reductase (HMG-CoA reductase) with one or more additional pharmacologically active agents. Some embodiments are the use of a pharmaceutical composition comprising a combination of a statin lactone and a hydroxy acid statin salt, e.g., as a therapy to treat inflammatory diseases and disorders associated with inflammation, preferably vascular diseases and disorders. Some embodiments are the use of a pharmaceutical composition comprising a combination of a statin lactone and a hydroxy acid statin salt, e.g., as a topical therapy to treat inflammatory diseases and disorders of the skin. Some embodiments are the use of a pharmaceutical composition comprising a combination of a statin lactone and a non-statin anti-inflammatory agent, e.g., as a therapy to treat inflammatory diseases and disorders. In some embodiments, a combination of a statin lactone and another active agent provides a synergistic effect in treating a MAP kinase-related condition, e.g., an inflammatory condition.

One aspect of the present invention provides methods of inhibiting a MAP kinase comprising administering an effective amount of at least one compound comprising formula V:

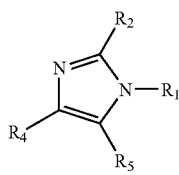

Formula V wherein $R_1$ is

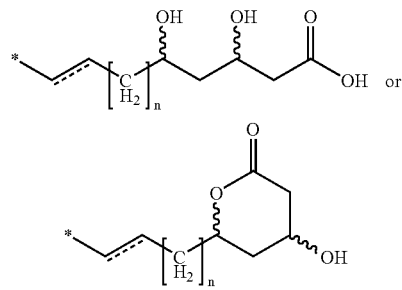

n being 0 or any integer;
$R_2$ is optionally substituted alkyl, aryl, or heteroaryl;
$R_4$ is optionally substituted

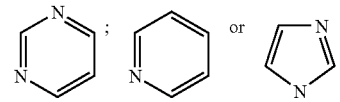

and $R_5$ is optionally substituted aryl or heteroaryl, or a salt thereof.

Another aspect of the present invention provides a compound comprising formula V:

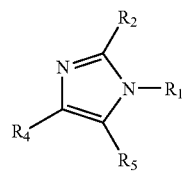

Formula V wherein $R_1$ is

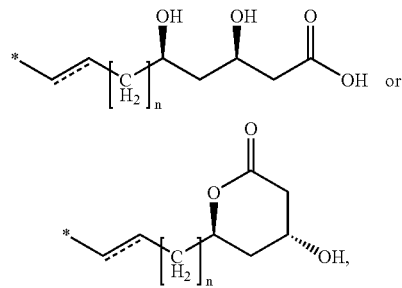

being 0 or any integer;
$R_2$ is optionally substituted alkyl, aryl, or heteroaryl;
$R_4$ is optionally substituted

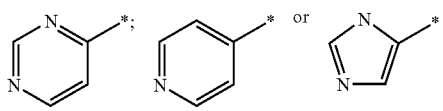

and $R_5$ is optionally substituted aryl or heteroaryl, or a salt thereof, with the proviso that when $R_4$ is the pyridinyl ring optionally substituted with one or more substituents selected from halogen atoms and hydroxyl, $C_{1-3}$ alkyl, $C_{1-3}$ alkoxy and trifluoromethyl groups, then the bridging group of $R_1$ is —$CH_2$—$CH_2$—.

Some embodiments provide a compound comprising formula V:

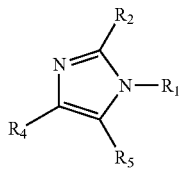

Formula V wherein $R_1$ is

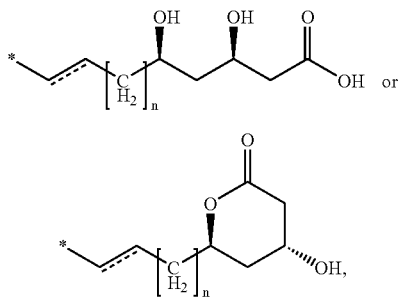

being 0 or any integer;
$R_2$ is optionally substituted alkyl, aryl, or heteroaryl;
$R_4$ is optionally substituted

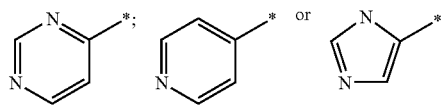

and $R_5$ is optionally substituted aryl or heteroaryl, or a salt thereof, with the proviso that when $R_4$ is the pyridinyl ring, said pyridinyl ring is substituted with one or more optionally substituted amino groups.

In some embodiments, a compound comprising formula Va is provided:

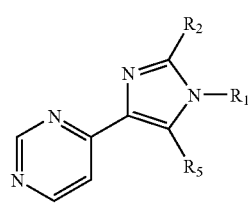

Formula Va wherein $R_1$ is

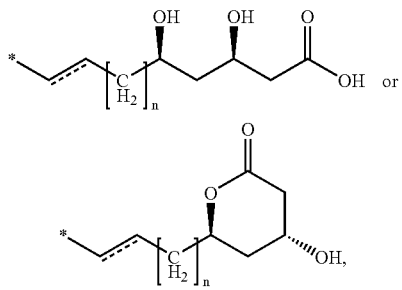

being 0 or any integer;
$R_2$ is optionally substituted alkyl, aryl, or heteroaryl;
the pyrimidinyl ring is optionally substituted;
and $R_5$ is optionally substituted aryl or heteroaryl, or a salt thereof.

In some embodiments, a compound comprising formula Vb is provided:

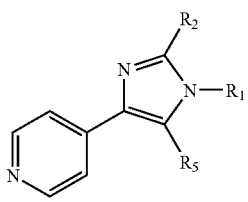

Formula Vb wherein $R_1$ is

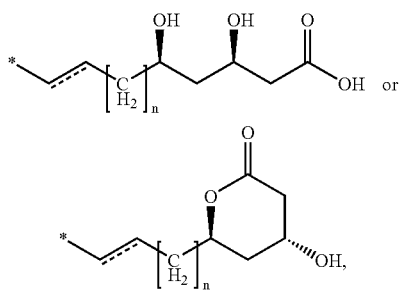

being 0 or any integer;
$R_2$ is optionally substituted alkyl, aryl, or heteroaryl;
the pyridinyl ring is optionally substituted, with the proviso that when the pyridinyl ring is unsubstituted or substituted with one or more substituents selected from halogen atoms and hydroxyl, $C_{1-3}$ alkyl, $C_{1-3}$ alkoxy and trifluoromethyl groups, then the bridging group of $R_1$ is —$CH_2$—$CH_2$—;
and $R_5$ is optionally substituted aryl or heteroaryl, or a salt thereof.

Another aspect of the present invention provides methods of inhibiting a MAP kinase comprising administering an effective amount of at least one compound comprising formula VI:

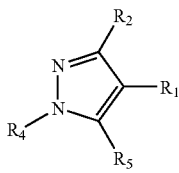

Formula VI wherein $R_1$ is

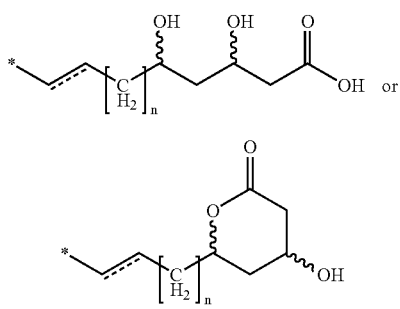

or n being 0 or any integer;
$R_2$ is optionally substituted alkyl, aryl, or heteroaryl;
$R_4$ is optionally substituted

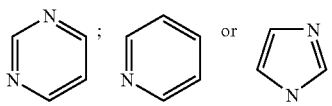

and $R_5$ is optionally substituted aryl or heteroaryl, or a salt therof.

Another aspect of the present invention provides a compound comprising formula VI:

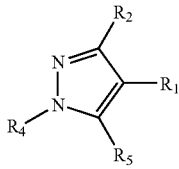

Formula VI wherein $R_1$ is

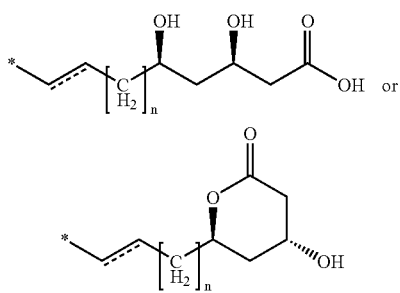

or n being 0 or any integer;
$R_2$ is optionally substituted alkyl, aryl, or heteroaryl;
$R_4$ is optionally substituted

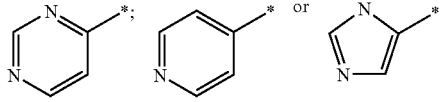

and $R_5$ is optionally substituted aryl or heteroaryl, or a salt thereof, with the proviso that when $R_2$ is an alkyl from 1-3 carbon atoms, trifluoromethyl, diakylamino where alkyl is 1-4 carbon atoms, pyrrolidino, piperidino, morpholino or piperazino, then $R_4$ is substituted.

Some embodiments provide a compound comprising formula VI:

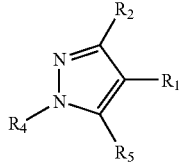

Formula VI wherein $R_1$ is

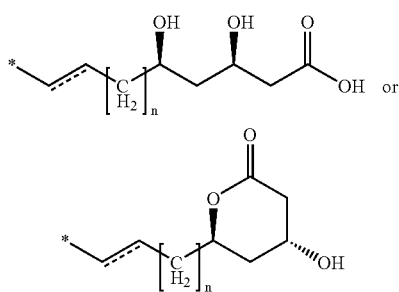

or n being 0 or any integer;
$R_2$ is optionally substituted alkyl, aryl, or heteroaryl;
$R_4$ is substituted

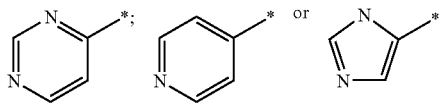

and $R_5$ is optionally substituted aryl or heteroaryl, or a salt thereof.

In some embodiments, a compound comprising formula VIa is provided:

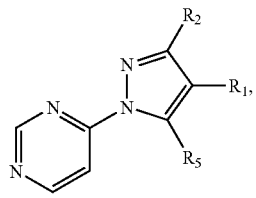

Formula VIa wherein $R_1$ is

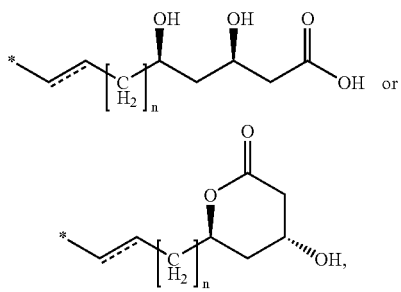 or

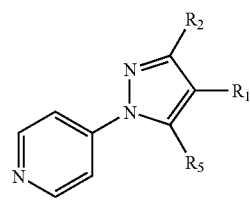, being 0 or any integer;
$R_2$ is optionally substituted alkyl, aryl, or heteroaryl;
the pyrimidinyl ring is optionally substituted;
and $R_5$ is optionally substituted aryl or heteroaryl, or a salt thereof, with the proviso that when $R_2$ is an alkyl from 1-3 carbon atoms, trifluoromethyl, diakylamino in which alkyl is 1-4 carbon atoms, pyrrolidino, piperidino, morpholino or piperazino, then $R_4$ is substituted.

In some embodiment, a compound comprising formula VIb is provided:

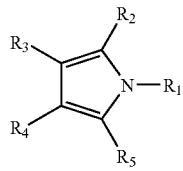

Formula VIb wherein $R_1$ is

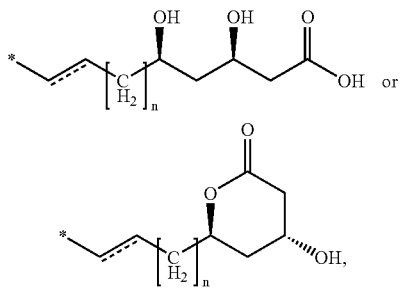 or being 0 or any integer;
$R_2$ is optionally substituted alkyl, aryl, or heteroaryl;
the pyridinyl ring is optionally substituted;
and $R_5$ is optionally substituted aryl or heteroaryl, or a salt thereof, with the proviso that when $R_2$ is an alkyl from 1-3 carbon atoms, trifluoromethyl, diakylamino in which alkyl is 1-4 carbon atoms, pyrrolidino, piperidino, morpholino or piperazino, then $R_4$ is substituted.

Another aspect of the present invention provides methods of inhibiting a MAP kinase comprising administering an effective amount of at least one compound comprising formula VII

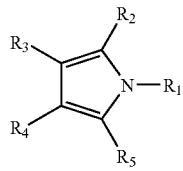

Formula VII wherein $R_1$ is

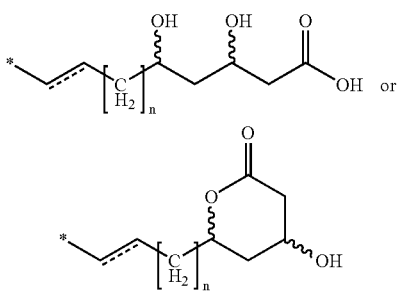 or n being 0 or any integer;
$R_2$ is optionally substituted alkyl, aryl, or heteroaryl;
$R_3$ is any substituent;
$R_4$ is optionally substituted

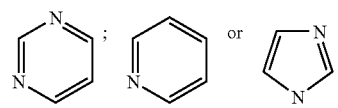

and $R_5$ is optionally substituted aryl or heteroaryl, or a salt thereof.

Another aspect of the present invention provides a compound comprising formula VII:

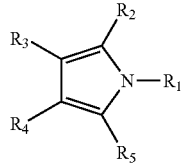

Formula VII wherein $R_1$ is

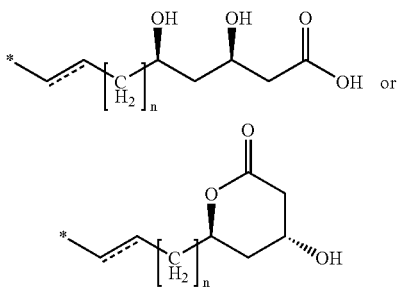

being 0 or any integer;
$R_2$ is optionally substituted alkyl, aryl, or heteroaryl;
$R_3$ is any substituent;
$R_4$ is optionally substituted

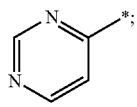

optionally substituted

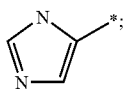

or substituted

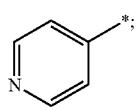

and $R_5$ is optionally substituted aryl or heteroaryl, or a salt thereof.

Some embodiments provide a compound comprising formula VII:

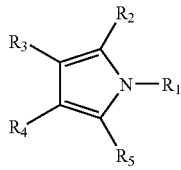

Formula VII wherein $R_1$ is

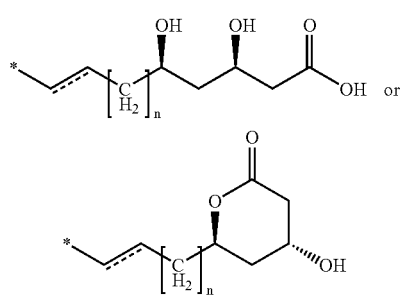

being 0 or any integer;
$R_2$ is optionally substituted alkyl, aryl, or heteroaryl;
$R_3$ is any substituent;
$R_4$ is substituted

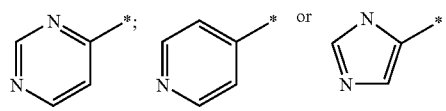

wherein said $R_4$ is substituted with one or more optionally substituted amino groups or optionally substituted alkoxy groups;
and $R_5$ is optionally substituted aryl or heteroaryl, or a salt thereof.

In some embodiments, a compound comprising formula VIIa is provided:

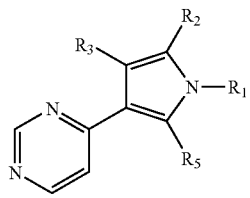

Formula VIIa wherein $R_1$ is

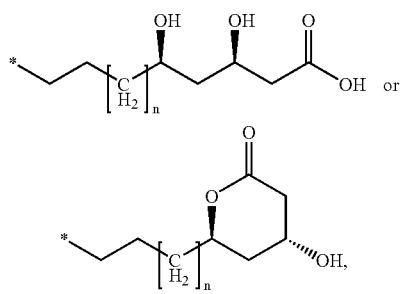

being 0 or any integer;
$R_2$ is optionally substituted alkyl, aryl, or heteroaryl;
the pyridinyl ring is substituted;
and $R_5$ is optionally substituted aryl or heteroaryl, or a salt thereof.

In some embodiments, a compound comprising formula VIIb is provided:

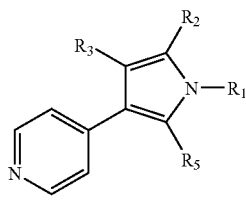

Formula VIIb wherein $R_1$ is

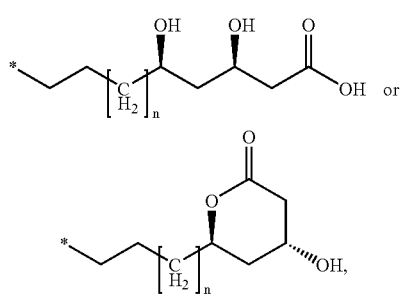

being 0 or any integer;

R$_2$ is optionally substituted alkyl, aryl, or heteroaryl;

the pyrimidinyl ring is optionally substituted;

and R$_5$ is optionally substituted aryl or heteroaryl, or a salt thereof.

In some embodiments, the inhibited MAP kinase is p38 MAP kinase. In some embodiments, the method further comprises inhibiting an HMG CoA reductase. In some embodiments, the administering treats a MAP kinase-related condition. In some embodiments, the administering treats a MAP kinase-related condition and an HMG CoA reductase-related condition. In some embodiments, the administering treats an inflammatory condition.

Still another aspect of the instant invention provides a pharmaceutical composition comprising an effective amount of at least one compound as recited above with a pharmaceutically acceptable carrier.

Still other aspects of the instant invention provide methods of treating a condition in a subject in need thereof comprising administering to the subject an effective amount of at least one compound comprising formula V, VI and/or VII.

BRIEF DESCRIPTION OF THE FIGURES

FIG. 3 illustrates the inter-conversion of a lactone (formula I) and acid forms (formulas IIa and IIb) of a compound of the present invention; FIG. 3a illustrates non-specific configurations at each of the two stereogenic centers of formulas I, IIa, and IIb; FIG. 3b illustrates a preferred absolute configuration, designated (T,T).

FIG. 6 illustrates an example of each of twelve classes (a–l) of statin inhibitors of HMG-CoA reductase in lactone form.

FIG. 9 illustrates two examples of modified closed ring structures of a δ-lactone; FIG. 9a represents a des-oxo-form (formula III); FIG. 9b represents a δ-lactam form (formula IV).

FIG. 11 illustrates a design approach for developing compounds that inhibit MAP kinase and/or HMG-CoA reductase.

DETAILED DESCRIPTION OF THE INVENTION

I. Kinase and/or HMG-CoA Reductase Inhibitors

One aspect of the present invention relates to compounds that inhibit protein kinases, e.g., protein kinases involved in inflammatory signaling cascades. In some embodiments, these compounds can inhibit mitogen-activated protein kinases (MAP kinases). For example, these compounds can inhibit p38 MAP kinases and/or stress-activated protein kinases/Jun N-terminal kinases (SAPKs/JNKs). In some embodiments, these compounds can inhibit p38α MAP kinase. In preferred embodiments, such compounds exert anti-inflammatory effects in vitro and in vivo, e.g., as described in more detail below.

Figure 1:
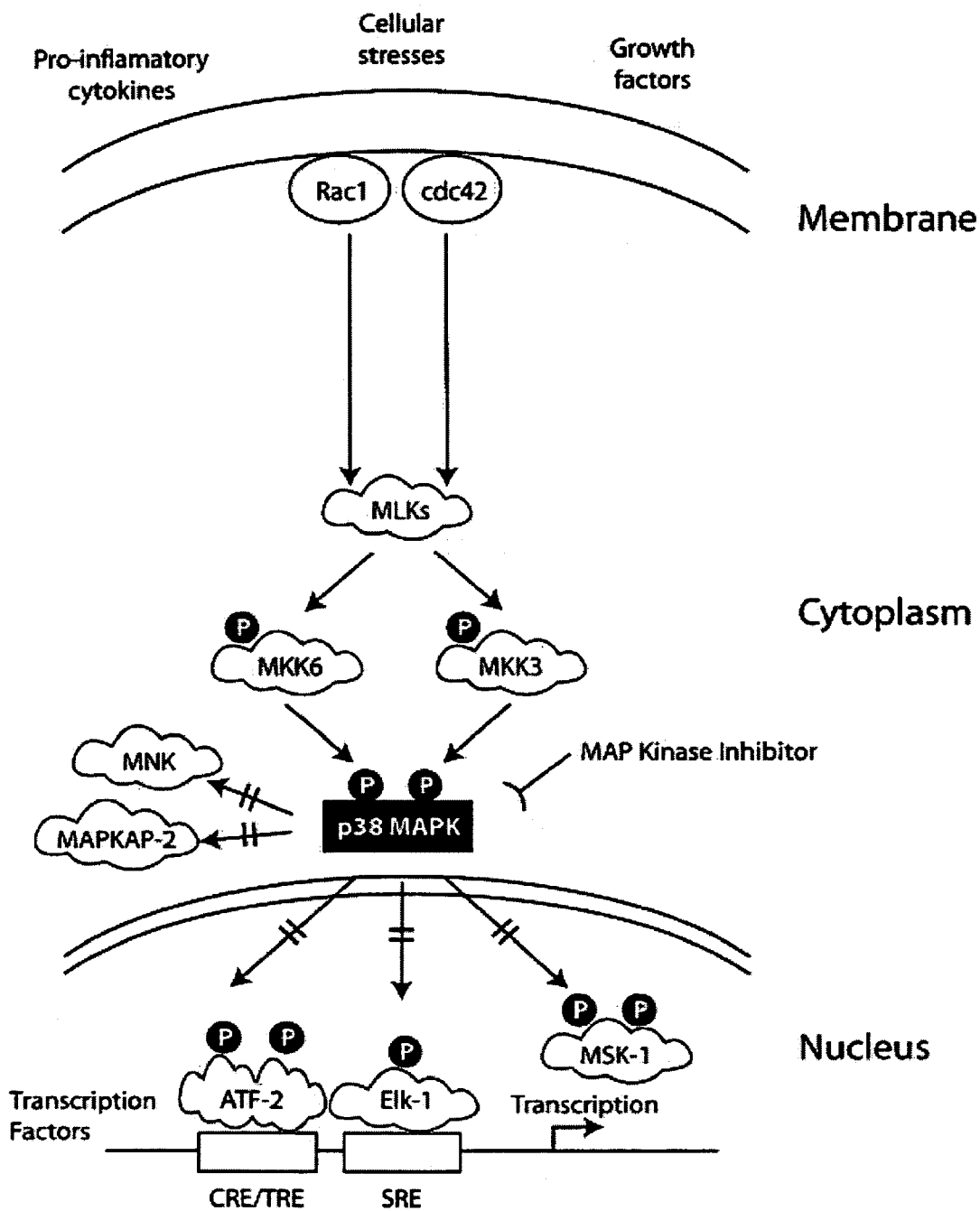
FIG. 1 illustrates some of the pathways involved in inflammatory signaling cascades and the interruption of certain of these pathways by a MAP kinase inhibitor.

FIG. 1 illustrates some of the pathways involved in inflammatory signaling cascades and the interruption of certain of these pathways by a MAP kinase inhibitor. This figure provides an overview only, and is in no way intended to be limiting with respect to the present invention. For example, those skilled in the art will readily appreciate variations and modifications of the scheme illustrated.

As FIG. 1 illustrates, inflammatory signaling cascades transmit signals from outside a cell membrane 101 to the cytoplasm 102 and ultimately the nucleus 103. Pro-inflammatory cytokines 104 (e.g., TNF-α and IL-1), as well as cellular stresses 105 and growth factors 106, initiate a signal transduction cascade leading to the activation of several serine/threonine kinases, including MKK3, MKK6 and p38 MAP kinase. Chakravarty et al, Annual Reports in Medicinal Chemistry, Chapter 18, Elsevier Science (2002). As is known in the art, p38 MAP kinases exist in at least four isoforms, p38α (expressed in all tissues), p38β (expressed in all tissues), p38γ (primarily expressed in skeletal tissue), and p38δ (primarily expressed in the lungs, kidneys, testes, pancreas and small intestine). One or more of these MAP kinases can be inhibited by a compound of the instant invention, or a combination comprising one or more such compounds, e.g., by interaction with their shared Thr-Gly-Tyr dual phosphorylation activation motif and/or with their highly conserved amino acid sequences, e.g., the conserved binding pocket for ATP. In preferred embodiments, p38α MAP kinase is inhibited, p38α MAP kinase serving as the primary MAP kinase associated with the pro-inflammatory cytokines. As such, p38α MAP kinase presents a target for small molecule therapeutics aimed at reducing cytokine production and treating associated inflammatory and/or autoimmune conditions.

As FIG. 1 illustrates, activation of p38 MAP kinase by upstream kinases leads to phosphorylation of downstream substrates, including MNK and MAPKAP-2, as well as transcription factors ATF-2, Elk-1, and MSK-1, which control transcription and production of pro-inflammatory cytokines. FIG. 1 also illustrates points of action of an inhibitor that can reduce downstream effects of p38 MAP kinase, illustrated by double bars. For example, inhibition of p38α

MAP kinase using a compound of the present invention, or a composition comprising one or more such compounds, can reduce phosphorylation of MNK, MAPKAP-2, ATF-2, Elk-1 and/or MSK-1, reducing production of pro-inflammatory cytokines, in certain embodiments, as discussed in detail below.

Figure 2A:
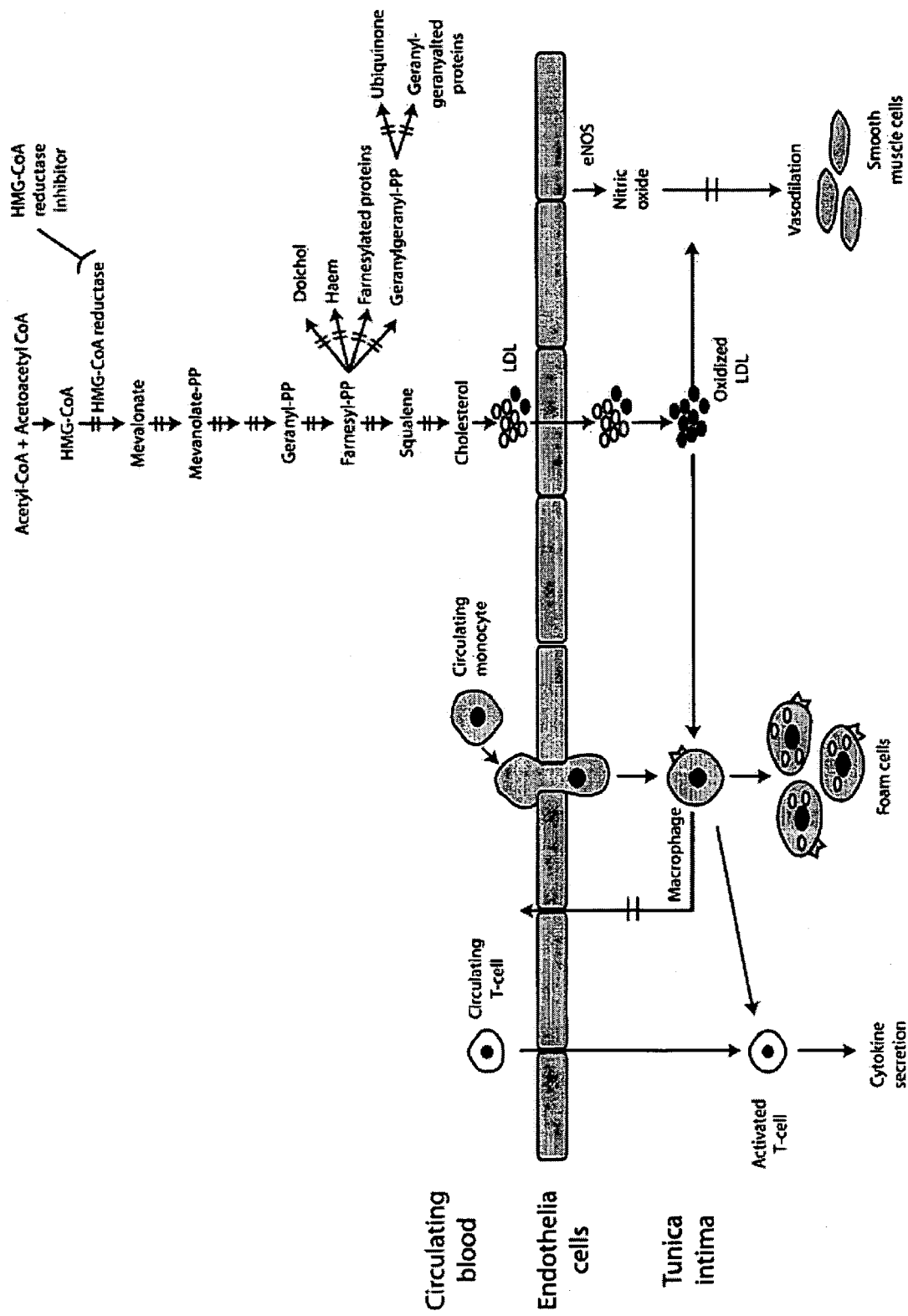
FIG. 2a illustrates some of the pathways involved in cholesterol biosynthesis and some of the atherogenic mechanisms of hypercholesterolemia, as well as the interruption of certain of these pathways by an HMG-CoA reductase inhibitor.

A second aspect of the present invention relates to compounds that can inhibit the enzyme 3-hydroxy-3-methyl glutaryl-coenzyme A reductase (HMG-CoA reductase). These compounds can lower cholesterol levels in vitro and in vivo. FIG. 2a illustrates some of the pathways involved in cholesterol biosynthesis and some of the atherogenic mechanisms of hypercholesteremia, as well as the interruption of certain of these pathways by an HMG-CoA reductase inhibitor. This figure provides an overview only, and is in no way intended to be limiting. For example, those skilled in the art will readily appreciate variations and modifications of the scheme illustrated, and more detailed descriptions can be found in standard texts on biochemistry, metabolism, pathophysiology, and the like.

As is known in the art, HMG-CoA reductase catalyzes the committed, rate-limiting step of terpene and cholesterol synthesis in mammalian cells. It thus represents a target for small molecule therapeutics (e.g., the "statins") aimed at reducing atherogenesis and its associated cardiovascular risks. HMG-CoA reductase acts on 3-hydroxy-3-methylglutaryl CoA (HMG-CoA) to produce mevalonate. Mevalonate is converted into cholesterol, which is carried in the blood mainly in two specialized particles known as low-density lipoprotein (LDL) and high-density lipoprotein (HDL). The pathway also produces other non-sterol isoprenoid products, such as farnesol, dolichol, and ubiquinone.

As illustrated in FIG. 2a, LDL adheres to the arterial wall and is progressively oxidized. Palinski et al., *J. Am. Soc. Nephrol.*, 13: 1673–1681 (2002). Extensively oxidized LDL is taken up by macrophages to form foam cells, a key feature of atherosclerosis. This leads to recruitment of monocytes and T-cells and secretion of cytokines in immune response cascades. The double bars indicate currently known effects of HMG-CoA reductase inhibitors (e.g., statins) on these processes, not only in reducing the production of cholesterol, but also in modulating immune responses through the actions of other metabolites such as farnesyl pyrophosphate and geranylgeranyl pyrophosphate. For example, geranylgeranyl-PP decreases endothelial cell nitric oxide synthase (eNOS) expression, inhibiting nitric oxide-induced vasodilation. Inhibition of HMG CoA reductase using a compound of the present invention, or a composition comprising one or more such compounds, can also produce these effects, in certain embodiments, as discussed in detail below.

A compound of the present invention, or a composition comprising one or more such compounds, can increase HDL levels ("good cholesterol") in some embodiments. HDL plays a role in carrying excess cellular cholesterol in what is known as the reverse cholesterol transport pathway. Generally, HDL is a complex of protein, lipids and cholesterol, which "scours" the walls of blood vessels to remove excess cholesterol. In reverse cholesterol transport, peripheral tissues (e.g., vessel-wall macrophages) remove excess cholesterol through ABCA1 to apolipoprotein A–I, forming pre-β-HDL. Lecithin-cholesterol acyltransferase then esterifies free cholesterol to cholesteryl esters, converting pre-β-HDL to mature spherical α-HDL. Forrester, J. S., Makkar, R., Shah, P. K. *Circulation* 111: 1847–1854 (2005), incorporated herein by reference. A compound of the present invention, or a combination comprising one or more such compounds, can decrease serum LDL/HDL ratios, in some embodiments.

Several steps in the cholesterol biosynthesis pathway have been implicated in Alzheimer's disease-related processes. Alzheimer's has been linked to several proteins of the cholesterol biosynthesis pathway. As is known in the art, neuronal cells obtain cholesterol in two ways: through de novo synthesis or by internalizatioin through endosomal mechanisms. Cells which utilize the former synthesize cholesterol de novo in the endoplasmic reticulum and thereafter transport it to the cell membrane. Cells that utilize the latter internalize cholesterol synthesized by other neuronal cells such as astrocytes. For example, cholesterol secreted via the ATP-binding cassette transporter 1 (ABCA1) transporter protein is taken up by brain HDL, containing apoliproteins E and J. Cholesterol-containing brain HDL can be internalized by neuronal cells through an extracellular membrane receptor, called low-density lipoprotein-related receptor (LRP). Uptake is further assisted by LRP8 and very-low-density lipoprotein receptor (VLDLR). Polymorphisms in genes encoding cholesterol pathway proteins are putative risk factors for Alzheimer's. Such cholesterol pathway proteins include, e.g., the transport molecule apolipoprotein E, the uptake molecules LRP, LRP8, and VLDLR, as well as ABCA1 (a catabolism-related molecule), and Cyp46 (an oxysterol producer). Wolozin, W., Cholesterol, statins and dementia (review), Curr. Op. Lipidol. 15:667–672 (2004).

The pathology of Alzheimer's disease is characterized by the presence of neuritic plaques composed largely of β-amyloid (Aβ) protein fragments. Aβ is produced when membrane bound amyloid precursor protein (APP) is cleaved by proteolytic enzymes, β-secretase and γ-secretase. Soluble Aβ fragments cluster with one another to form oligomers, then fibrillar Aβ aggregates, and eventually neuritic Aβ plaques.

Figure 2B:
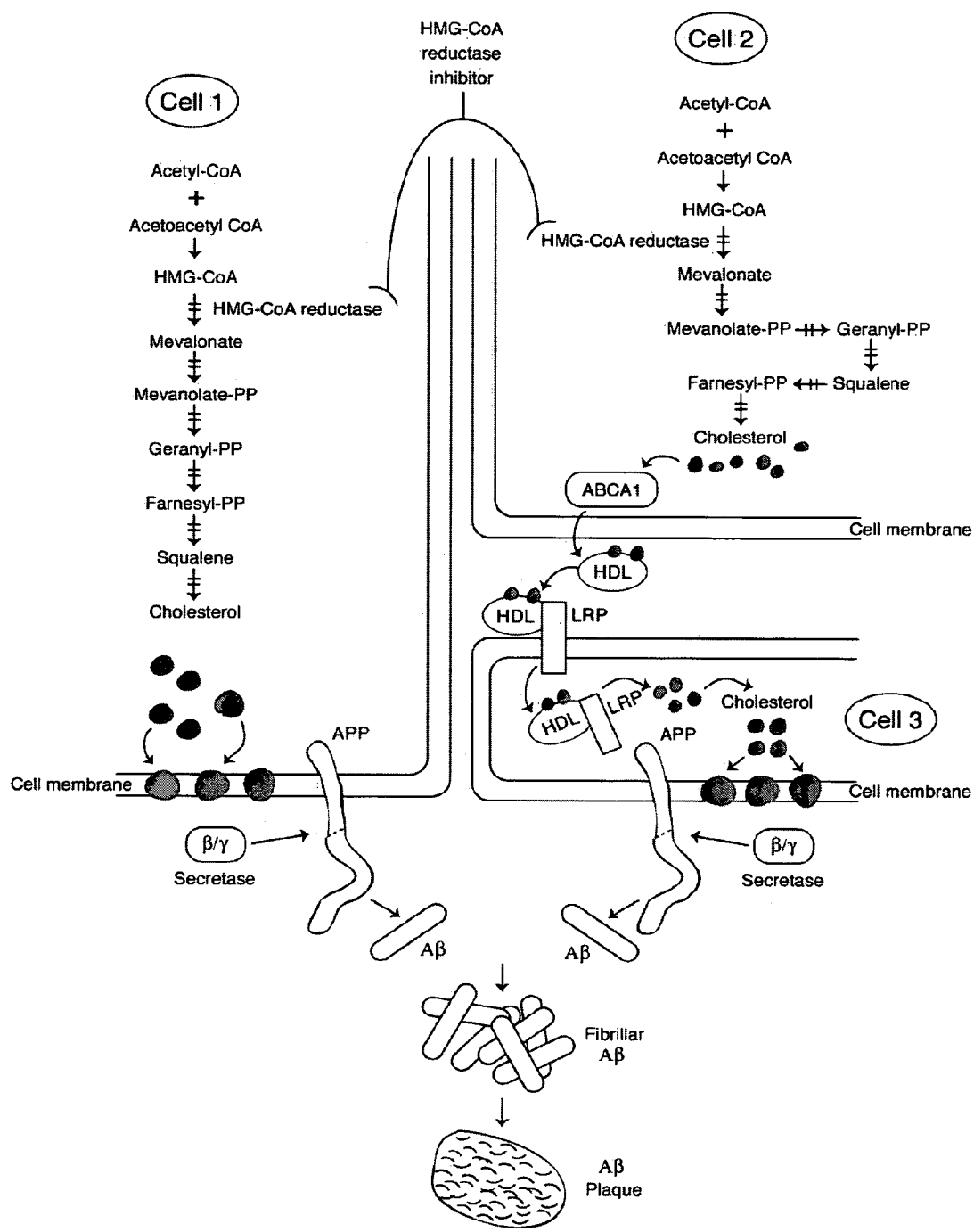
FIG. 2b illustrates some of the pathways involved in processing amyloid precursor protein, the role played by cholesterol in such pathways, as well as the interruption of certain of these pathways by an HMG-CoA reductase inhibitor.

FIG. 2b illustrates some of the pathways involved in processing amyloid precursor protein, the role played by cholesterol in such pathways, as well as the interruption of certain of these pathways by an HMG-CoA reductase inhibitor. This figure provides an overview only, and is in no way intended to be limiting. For example, those skilled in the art will readily appreciate variations and modifications of the scheme illustrated, and more detailed descriptions can be found in standard texts on biochemistry, metabolism, pathophysiology, and the like.

As shown in FIG. 2b, a cholesterol-rich membrane is required for proteolysis of APP, which subsequently leads to the production of Aβ and eventual Aβ plaque formation. Wolozin, W., Cholesterol, statins and dementia (review), Curr. Op. Lipidol. 15:667–672 (2004). Cell 1 of FIG. 2b shows a neuronal cell in the process of synthesizing its own cholesterol de novo and then transporting it to the cell membrane to allow APP processing. Cell 2 shows a neuronal cell in the process of synthesizing and secreting it through the ABCA1 transporter protein where brain HDL protein binds cholesterol. Cell 3 shows a neuronal cell in the process of internalizing the HDL-cholesterol complex by way of LRP. The subsequent transport of cholesterol to Cell 3's membrane allows APP processing to occur. FIG. 2b also illustrates how inhibition of HMG CoA reductase in Cell 1 and Cell 2 using an HMG CoA reductase inhibitor can produce an inhibitory effect on cholesterol synthesis and thereby affect APP processing. The double bars indicate currently known effects of HMG-CoA reductase inhibitors (e.g., statins) on these processes. For example, HMG-CoA reductase inhibitors have been found to reduce β-secretase proteolysis of APP in cultured human cells overexpressing APP, while applying solubilized cholesterol to such cells resulted in a significant increase in Aβ products. In addition, reducing cellular cholesterol levels in hippocampal neurons has been shown to inhibit Aβ formation. Reiss, A. B. et al., Cholesterol in neurologic disorders of the elderly: stroke and Alzheimer's disease (review), Neurobiology of Aging 25:977–89 (2004). Inhibition of HMG CoA reductase using a compound of the present invention, or a composition comprising one or more such compounds, can also produce these effects, in certain embodiments, as discussed in detail below.

A third aspect of this invention relates to compounds that inhibit both MAP kinase and HMG-CoA reductase activities. Such compounds can inhibit both inflammatory responses and cholesterol biosynthetic pathways in vitro and in vivo, and can exert, for example, anti-inflammatory, lipid-modulating, and anti-atherogenic properties in vivo. Further, such compounds can provide superior benefits in treating HMG-CoA reductase-related conditions, such as cardiovascular disease, compared with treatments that inhibit HMG-CoA reductase but not MAP kinase, due to the interplay between inflammatory and cardiovascular disorders. In other embodiments, such compounds can provide superior benefits in treating MAP kinase-related conditions, such as inflammation, compared with treatments that inhibit MAP kinase but not HMG-CoA reductase, again due to the interplay between inflammatory and cardiovascular conditions.

A fourth aspect of this invention relates to combinations of two or more compounds or forms of compounds that inhibit MAP kinase and/or HMG-CoA reductase activities, e.g., to produce one or more of the effects described above. Such combinations find particular use in treating inflammatory conditions. Without being limited to a particular hypothesis, theory or mechanism, HMG-CoA reductase and MAP kinase may both play a role in certain inflammatory conditions, making the use of combination therapies particularly effective. For example, HMG-CoA reductase and MAP kinase both have been implicated in inflammatory conditions of the skin.

Acne is an example of a skin inflammatory conditon involving activities of both MAP kinase and HMG-CoA reductase. Acne results from the formation of a comedone followed by pericomedonian inflammation (or folliculitis). A comedone (or blackhead) forms when a pilo-sebaceous duct is obstructed and/or when there is increased production of sebum by a sebaceous gland. Formation of the comedone is followed by inflammation, e.g., resulting from bacterial proliferation due to seborrhoeic retention and/or overproduction of sebum. Typically, the bacteria are diphtheroid anaerobic bacteria such as *Propionibacteria* (acnes, granulosum, avidum). In addition to inflammatory pathways, pathways involving HMG-CoA reductase may also be involved. For example, it is known in the art that cholesterol and the metabolites thereof play a role in cohesion of epidermal cells, particularly corneocytes (cells constituting the stratum corneum).

As another example, psoriasis is a chronic hyperproliferative skin condition wherein the subject exhibits inflammation, as well as excess proliferation of epidermal cells (scaling). The cause is thought to be an abnormal immune response to some element of the skin prompted by malfunctioning T cells. It is known in the art that multiple cellular events occur at the response site including increased cell adhesion molecule expression, upregulation of cytokines and growth factors, and penetration of the tissue by lymphocytes. It is also known in the art that HMG-CoA reductase inhibitors downregulate expression of cell adhesion molecules, inhibit the interaction between adhesion molecules required for leukocyte infiltration into inflammation sites, suppress the expression of T-helper-1 chemokine receptors on T cells, and inhibit the expression of proinflammatory cytokines. Namazi, M. R., Experimental Dermatology, 13:337–39 (2004). As another example, is known in the art that a form of eczema, atopic dermatitis, is mediated by the inflammatory mediators IFN-γ and/or TNF-α.

HMG-CoA reductase and/or MAP kinase may also play a role in muscoskeletal inflammatory conditions, such as arthritis, psoriatic arthritis, osteoarthritis, rheumatoid arthritis, and osteoporosis. For example, pathological bone resorption or erosion in osteoporosis and rheumatoid arthritis requires the activation of osteoclasts (large multinucleate cells formed from differentiated macrophages) and TNF-α, IFN-γ and IL-1 have been implicated in triggering excess osteoclast activity. Roux, S. Bone loss. Factors that regulate osteoclast differentiation: an update (review), Arthritis Res., 2(6):451-456 (2000); Evans et al., Nitric oxide and bone (review), J Bone Miner Res. March; 11(3):300–5 (1996).

HMG-CoA reductase and/or MAP kinase may also play a role in respiratory inflammatory conditions. For example, the inflammatory mediators IFN-γ and/or TNF-α are known in the art to mediate asthma and mucocutaneous inflammatory conditions such as allergic rhinitis.

HMG-CoA reductase and/or MAP kinase may also play a role in gastrointestinal and urinogenital inflammatory conditions. For example, gastrointestinal inflammatory conditons, such as inflammatory bowel disease (including ulcerative colitis and Crohn's disease), celiac disease, intestinal infections, enterocolitis, and gastritis, exhibit chronic spontaneous relapsing enteropathies mediated by IFN-γ and TNF-α. Further, it is known in the art that urogenital inflammatory disorders are mediated by IFN-γ and TNF-α.

HMG-CoA reductase and/or MAP kinase may also play a role in autoimmune diseases. For example, according to recent reports, HMG-CoA reductase inhibitors may have a beneficial effect on autoimmune disorders, such as multiple sclerosis (MS). Stuve, O., et al., The potential therapeutic role of statins in central nervous system autoimmune disorders (review), Cell Mol Life Sci. 2003 November; 60(11): 2483–91. Generally, MS is mediated by proinflammatory CD4 T (Th1) cells that recognize specific myelin proteins associated with MHC class II molecules on antigen presenting cells (APCs). It is known in the art that inhibitors of HMG-CoA reductase inhibit the production of iNOS, TNF-α, IL-1beta and IL-6 by microglia and astrocytes, both APCs. HMG-CoA reductase inhibitors also inhibit IFN-γ-inducible class II expression on APCs, e.g., by inhibiting transcription of the IFN-γ-inducible promoter, which may result in suppression of antigen presentation by APCs. Some HMG-CoA reductase inhibitors also bind lymphocyte function-associated antigen-1 (LFA-1), a beta2-integrin and prevent interaction with its ligand, ICAM-1, as well as T cell activation, suggesting a beneficial effect on MS independent of an inhibition of HMG-CoA reductase.

HMG-CoA reductase and/or MAP kinase may also play a role in graft rejection after organ or tissue transplantation. For example, HMG-CoA reductase inhibitors have been shown to significantly reduce the incidence of organ rejection, transplant vasculopathy, and natural killer (NK) cell cytotoxicity in recipients of heart transplants (Kobashigawa et al., Dual roles of HMG-CoA reductase inhibitors in solid organ transplantation: lipid lowering and immunosuppression (review), Kidney Int. Suppl., December; 52:S112–5 (1995)) and kidney transplants (Katznelson, S. et al., The effect of pravastatin on acute rejection after kidney transplantation—a pilot study (review), Transplantation, May 27; 61(10):1469–74 (1997)). Additionally, such inhibitors have been shown to decrease the progression of transplant vasculopathy and to increase patient survival (Wenke, K. et al., Simvastatin reduces graft vessel disease and mortality after heart transplantation: a four-year randomized trial, Circulation, September 2; 96(5):1398–402. (1997)), suggesting a possible drug class effect. It is known in the art that treatment of heart and kidney transplant patients with HMG-CoA reductase inhibitors significantly inhibits NK cell cytotoxicity beyond that obtained with the baseline regimen, consisting of prednisone, azathioprine, and cyclosporine. For example, it is known in the art that clinically relevant concentrations of simvastatin, which are not immunosuppressive themselves, significantly enhance inhibition of human T-cell responses by cyclosporin A in vitro. It has been suggested that synergism between the inhibitors and cyclosporin A could potentially be the basis for the immunosuppression uniquely observed in transplant patients. Katznelson, S. et al., Effect of HMG-CoA reductase inhibitors on chronic allograft rejection (Review), Kidney Int Suppl. 1999 July; 71:S117–21 (1999).

Accordingly, inhibition of HMG CoA reductase and/or MAP kinase, preferably inhibition of both, by a combination of compounds or forms of compounds of the present invention can also produce the aforementioned effects, in certain embodiments, as discussed in detail below.

In certain embodiments, the compositions of the present invention comprise compounds of formulas I and/or II, wherein I is a δ-lactone (cyclic ester) and II is a 3,5-dihydroxy carboxylic acid in protonated form (formula IIa) or deprotonated form (formula IIb).

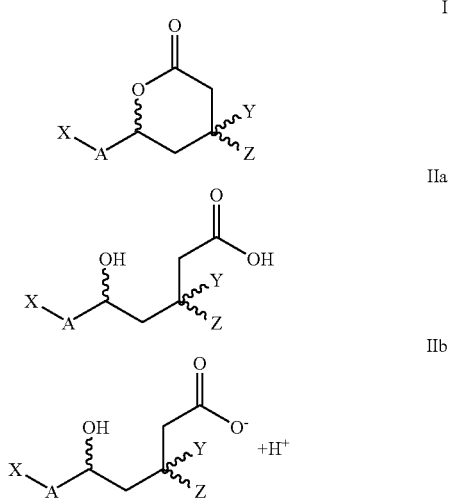

FIG. 3 illustrates the inter-conversion between δ-lactone and acid forms, where the δ-lactone ring opens to the acid form with (reversible) addition of water, and further equilibriates to the deprotonated form with the loss of a proton to give the corresponding carboxylate ion. It will be recognized by those in the art that a rapid equilibrium exists between the protonated form of a carboxylic acid and its deprotonated carboxylate form, and that the deprotonated form predominates at neutral and basic pH. The deprotonated form is equivalent to a salt form of the acid. Further, reference to "formula II" or "II" herein refers to both formula IIa and formula IIb, to the same extent as if the phrase "formula IIa and formula IIb" were used in place of "formula II" or "II." Similarly, a figure or structure illustrating either the IIa or IIb form also includes the corresponding other IIb or IIa form, to the same extent as if both structures had been illustrated. Moreover, the present invention encompasses both the protonated and deprotonated (i.e., salt) forms of the compounds disclosed herein.

In these formulas, X preferably comprises a lipophilic moiety. As used herein, a lipophilic moiety can refer to a molecular entity or a portion thereof having a tendency to dissolve in fat-like solvents, e.g., in a hydrocarbon solvent. Such moieties can also be referred to as hydrophobic moieties. Preferably, X comprises a lipophilic moiety bearing at least one aromatic substituent. A represents a covalent bond or a substituted or unsubstituted alkylene, alkenylene, or alkynylene linker of 2–6 carbons, optionally containing a heteroatom, such as O, N, or S. A is preferably a covalent bond, methylene, 1,2-oxamethylene, 1,2-ethylene, 1,2-ethynylene, 1,2-ethenylene, 1,3-propylene or 1,3-propenylene. More preferably, A is 1,2-ethylene or E-1,2-ethenylene. Y is hydrogen or a lower alkyl, preferably hydrogen. Z is a hydroxy (—OH) group or hydrogen, preferably a hydroxy group.

In FIG. 3a, the configurations at each of two stereogenic centers of formulas I and II are not specified. The present invention includes each of the four possible stereoisomers arising from the two possible absolute configurations at each of the two stereogenic centers of formulas I and II. Compounds useful in this invention can include mixtures of the various stereoisomers or a pure stereoisomeric form.

FIG. 3b illustrates an absolute configuration, designated (T,T), preferred in some embodiments of this invention. The designation (T,T) as used herein refers to the stereochemistry indicated, wherein wedge-shaped solid lines indicate bonds protruding above the plane of the illustration and dashed lines indicate bonds extending below the plane, so that the Y groups are above the plane, as are the ring oxygen of formula I and the corresponding hydroxy of formula II; while the Z groups are below the plane of the illustration. This (T,T) designation is used, rather than the conventional R or S designations, to reflect the fact that the actual absolute stereochemistry assignment will depend on the identity of A at one of the stereogenic centers, and the identity of Y and Z at the other stereogenic center. For example, the 5-position of the 3,5-dihydroxy carboxylic acid becomes R if A is ethylene, whereas the stereochemistry becomes S if A is ethenylene. Based on standard rules of nomenclature and priority of substituents at stereogenic centers, those of skill in the art can readily determine whether the stereochemistry is R or S at each of the sterogenic centers for each A, Y, and Z in the spatial arrangement depicted in FIG. 3b. In some embodiments, the (T,T) stereoisomer may comprise more than about 50%, more than about 70%, preferably more than about 90%, and more preferably more than about 98% of a mixture of more than one stereoisomer.

Further, those of skill in the art will recognize that certain compounds of the present invention may exhibit the phenomena of tautomerism, conformational isomerism, geometric isomerism and/or optical isomerism. It should be understood that the invention encompasses any tautomeric, conformational isomeric, optical isomeric and/or geometric isomeric forms of the MAP kinase and/or HMG-CoA reductase inhibitors described herein, as well as mixtures of these various different forms. For example, optically active compounds of the present invention may be administered in enantiomerically pure (or substantially pure) form or as a mixture of detrorotatory and levorotatory enantiomers, such as in a racemic mixture. It will also be appreciated that compounds disclosed herein can exist in different crystalline forms, including, e.g., polymorphs. The invention encompasses these different crystalline forms, mixtures of different crystalline forms, and pure or substantially pure crystalline forms.

A. Analogs of MAP Kinase Inhibitors

Figure 4:
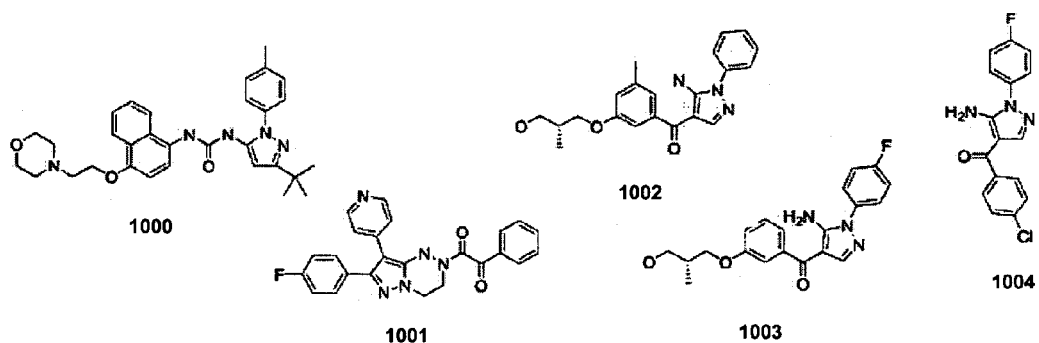
FIG. 4 illustrates one or more examples of each of twelve classes (a–l) of inhibitors of p38α MAP kinase.
Figure 4:
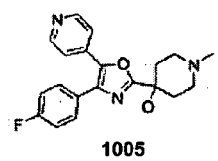
Figure 4:
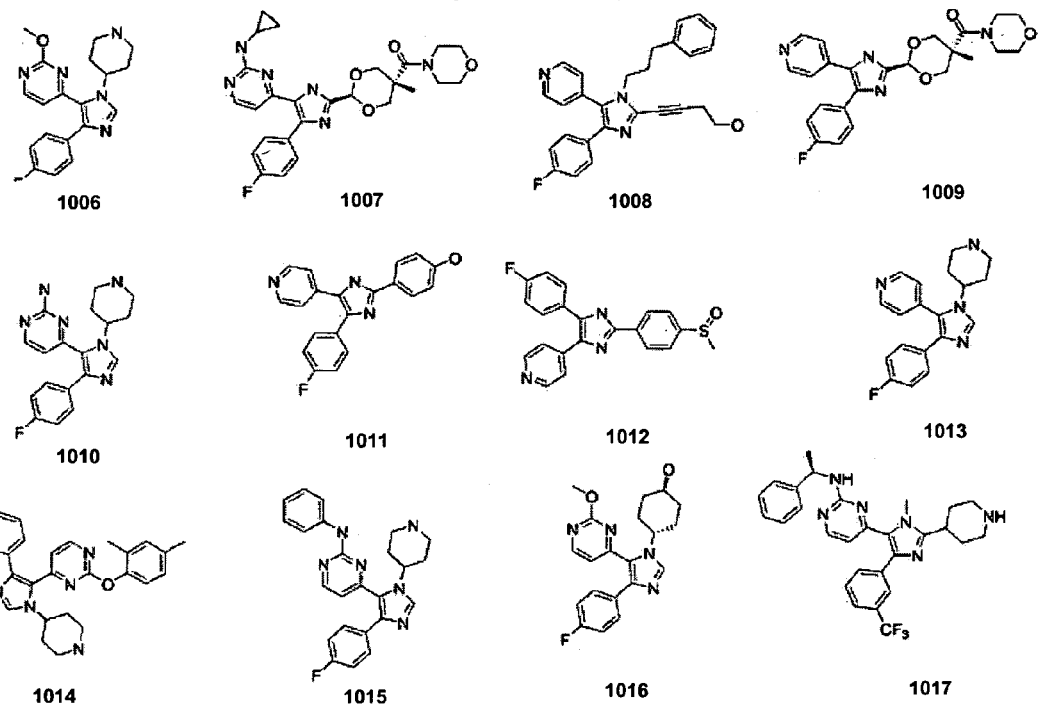
Figure 4:
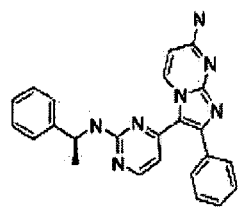
Figure 4:
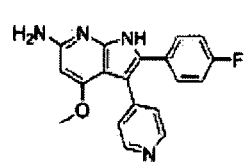
Figure 4:
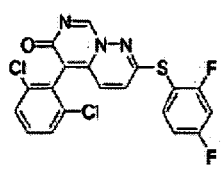
Figure 4:
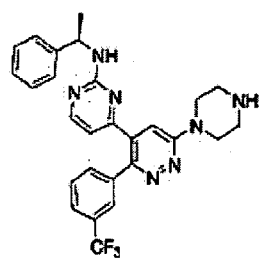
Figure 4:
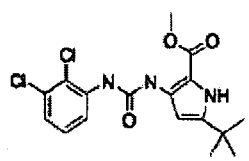
Figure 4:
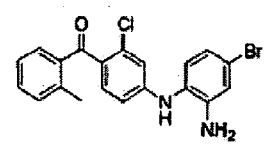
Figure 4:
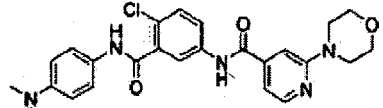
Figure 4:
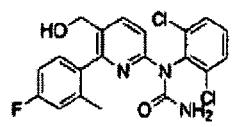
Figure 4:
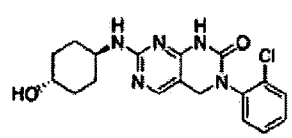
Figure 4:
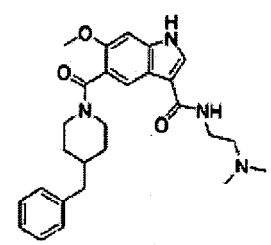

A subset of the compounds of formulas I and II are novel analogs of known inhibitors of MAP kinases, wherein X comprises a lipophilic MAP kinase inhibitor or a lipophilic moiety of a MAP kinase inhibitor. FIG. 4 illustrates one or more non-limiting examples of each of twelve classes (a–l) of inhibitors of p38α MAP kinase.

In some embodiments, preferred analogs include those derived from pyrazoles, such as compounds 1000–1004, illustrated in FIG. 4a. In some embodiments, preferred analogs include those derived form oxazoles, such as compound 1005, illustrated in FIG. 4b. In some embodiments, preferred analogs include derivatives of imidazoles, such as compounds 1006–1017, as illustrated in FIG. 4c.

In some embodiments, preferred analogs include derivatives of pyrrolo[2,3-b]pyrimidines, such as compounds 1018 and 1019, illustrated in FIG. 4d. In some embodiments, preferred analogs include those derived from diazaisoquinolinones, such as compound 1020, which is illustrated in FIG. 4e. In some embodiments, preferred analogs include those derived from 1,2-pyrazines, such as compound 1021, illustrated in FIG. 4f. In some embodiments, preferred analogs include derivatives of pyrroles, such as compound 1022, illustrated in FIG. 4g. In some embodiments, preferred analogs include derivatives of 4-aminobenzophenones, such as compound 1023, illustrated in FIG. 4h. In some embodiments, preferred analogs include those derived from 3-amidobenzamides, such as compound 1024, illustrated in FIG. 4i. In some embodiments, preferred analogs include those derived from pyridines, such as compound 1025, illustrated in FIG. 4j. In some embodiments, preferred analogs include those derived from pyrimidino[4,5-d]pyrimidinones, such as compound 1026, illustrated in FIG. 4k. In some embodiments, preferred analogs include those derived from indoles, such as compound 1027, illustrated in FIG. 4l.

The present invention includes all stereoisomers arising from the possible absolute configurations at any stereogenic center of novel analogs of MAP kinase inhibitors of formula I and/or II, e.g., wherein X comprises a lipophilic MAP kinase inhibitor or a lipophilic moiety of a MAP kinase inhibitor. Mixtures of the various stereoisomers or pure or substantially pure stereoisomeric forms may be used in various embodiments of the instant invention.

Figure 5:
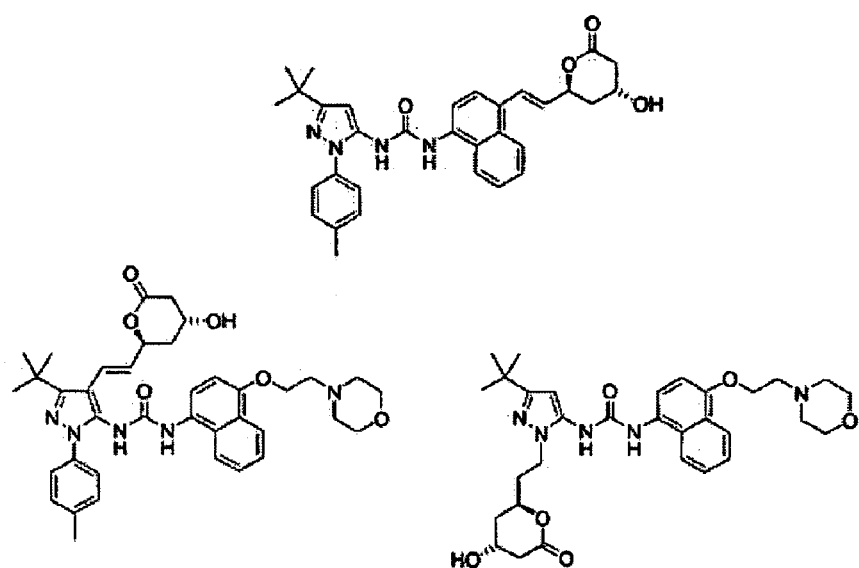
FIG. 5 illustrates lactone derivatives of one example each of twelve classes (a–l) of inhibitors of p38α MAP kinase.
Figure 5:
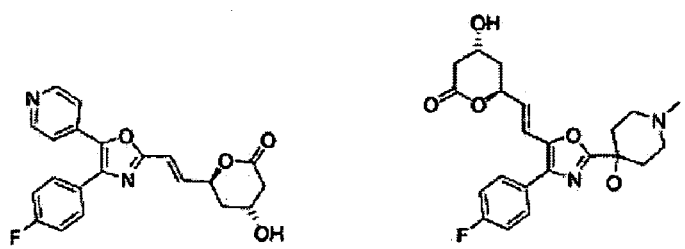
Figure 5:
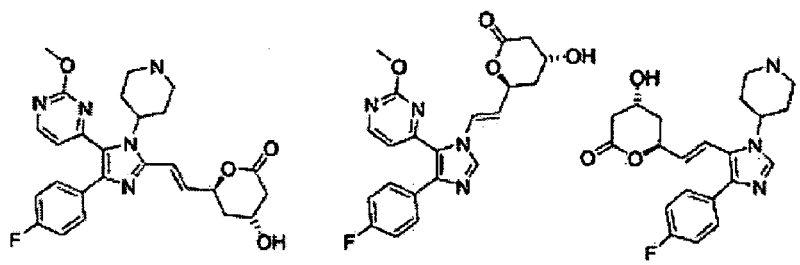
Figure 5:
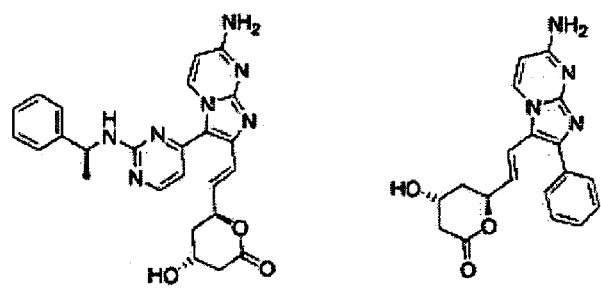
Figure 5:
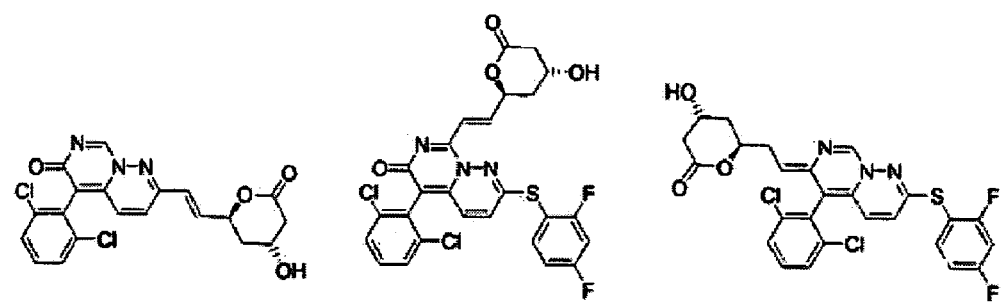
Figure 5:
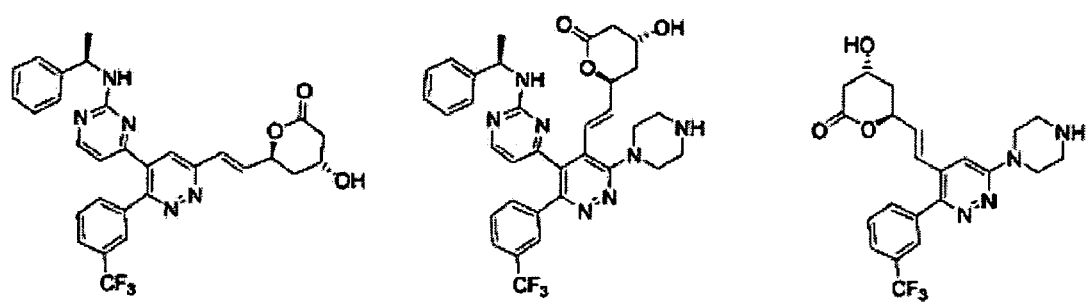
Figure 5:
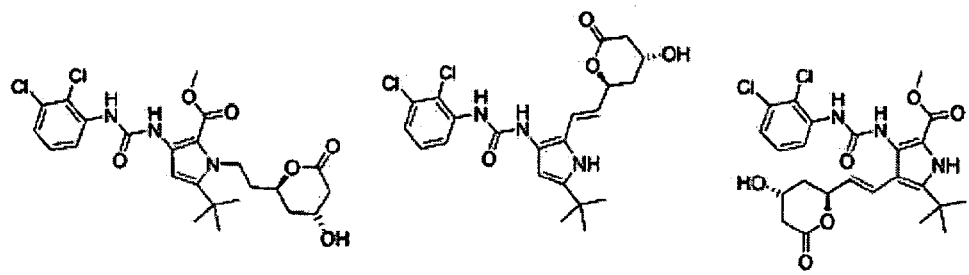
Figure 5:
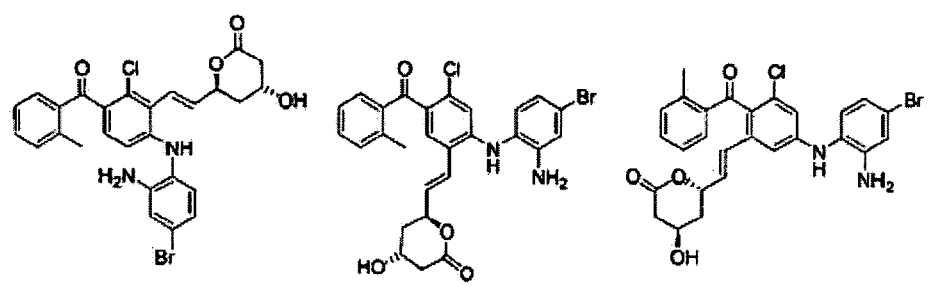
Figure 5:
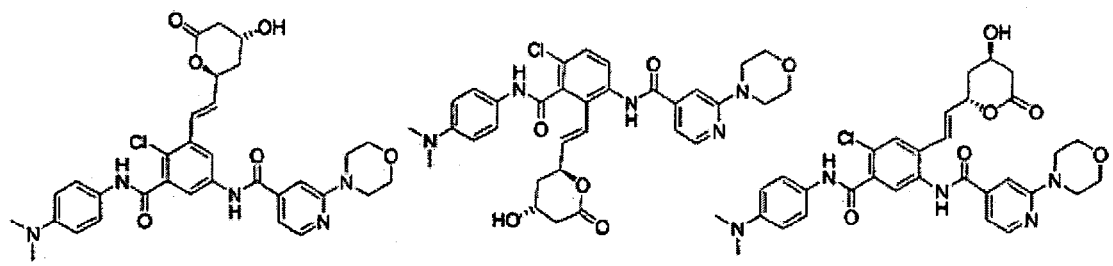
Figure 5:
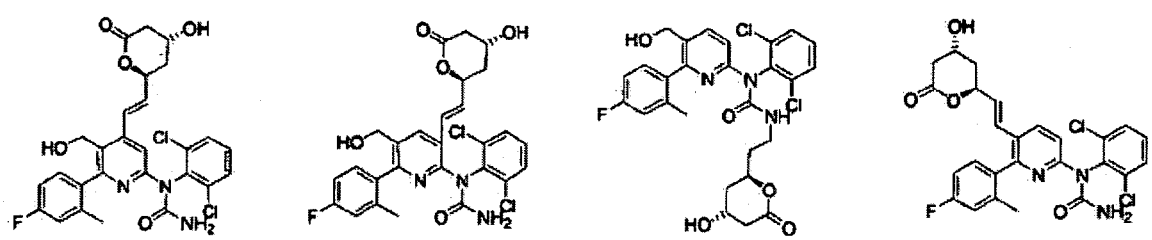
Figure 5:
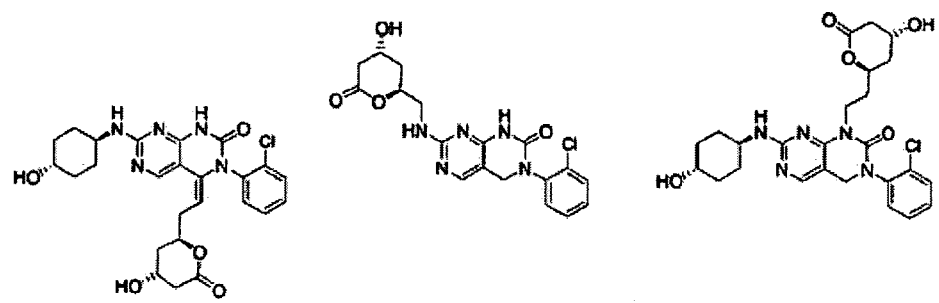
Figure 5:
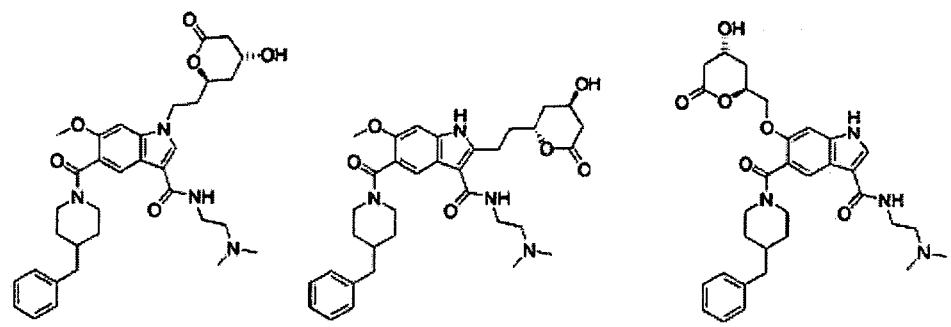

In certain embodiments, lipophilic MAP kinase inhibitors are substituted or appended with A-lactone or A-acid moieties of formulas I and II, respectively, to form novel compounds of the present invention. FIG. 5 illustrates lactone (formula I) derivatives of one example of each of the twelve classes of inhibitors of p38α MAP kinase illustrated in FIG. 4. It is to be understood that these represent examples of certain embodiments, and that other kinase inhibitors, attachment points, linking moieties (A), stereochemistries, etc., are expressly contemplated and included as other embodiments of the present invention. Further, the acid forms (formula II) of each and any of these examples are also a contemplated embodiment of the present invention.

FIG. 5a illustrates some preferred compounds of formula I wherein X comprises the pyrazole MAP kinase inhibitor compound 1000 or a lipophilic moiety thereof substituted or appended at three different positions with the A-lactone moiety, and wherein A is 1,2-ethenylene or 1,2-ethylene and Y is hydrogen.

FIG. 5b illustrates some preferred compounds of formula I wherein X comprises a lipophilic moiety of the oxazole MAP kinase inhibitor compound 1005, and wherein A is 1,2-ethenylene and Y is hydrogen. In each of the two structures illustrated, one of compound 1005's appendages on the oxazole ring has been substituted by the A-lactone moiety of formula I. The two structures illustrated in FIG. 5b are preferred compounds in some embodiments.

FIG. 5c illustrates some preferred compounds of formula I wherein X comprises the imidazole MAP kinase inhibitor compound 1006 or a lipophilic moiety thereof, A is 1,2-ethenylene and Y is hydrogen. In one of the three illustrated examples, the lipophilic moiety comprises all of compound 1006 except the 4-piperidyl moiety, which has been replaced with the A-lactone moiety of formula I. In another of the illustrated examples, the lipophilic moiety comprises all of compound 1006 except the 2-methoxy-4-pyrimidinyl group, which has been replaced. The three structures illustrated in FIG. 5c are preferred compounds in some embodiments of the present invention.

FIG. 5d illustrates some preferred compounds of formula I wherein X comprises a lipophilic moiety of pyrrolo[2,3-b]pyrimidine MAP kinase inhibitor compound 1018, A is 1,2-ethenylene, and Y is hydrogen. In the illustrated examples, the lipophilic moieties each comprise all but one of the aromatic substituents of compound 1018 in that the A-lactone moiety of formula I has been substituted for one of these substituents. The two structures illustrated in FIG. 5d are preferred compounds in some embodiments.

FIG. 5e illustrates some preferred compounds of formula I wherein X comprises the diazaisoquinolinone MAP kinase inhibitor compound 1020 or a lipophilic moiety thereof, A is 1,2-ethenylene or 1,2-methenomethylene and Y is hydrogen. In two of the illustrated examples, the lipophilic moiety comprises all but a thioaryl substituent, or all but one carbonyl oxygen substituents, of compound 1020 in that the A-lactone moiety of formula I has been substituted for one of each of these substituents.

FIG. 5f illustrates some preferred compounds of formula I wherein X comprises the 1,2-pyrazine MAP kinase inhibitor compound 1021 or a loipihilic moiety thereof, A is 1,2-ethenylene and Y is hydrogen. In the illustrated examples, the lipophilic moiety comprises all but one aromatic substituent, or all but a benzene ring, or all but a piperazine ring of compound 1021 in that the A-lactone moiety of formula I has been substituted for one of each of these substituents.

FIG. 5g illustrates some preferred compounds of formula I wherein X comprises the pyrrole MAP kinase inhibitor compound 1022 or a lipophilic moiety thereof, A is 1,2-ethylene or 1,2-ethenylene, and Y is hydrogen. In one of the illustrated examples, the lipophilic moiety comprises all but a carboxymethyl group of compound 1022 in that the A-lactone moiety of formula I has been substituted for this substituent. The three structures illustrated in FIG. 5g represent preferred compounds in some embodiments.

FIG. 5h illustrates some preferred compounds of formula I wherein X comprises the 4-aminobenzophenone MAP kinase inhibitor compound 1023, A is 1,2-ethenylene, and Y is hydrogen. In the illustrated examples, the compound 1023 structure is appended at three different positions with the A-lactone moiety of formula I. The three structures illustrated in FIG. 5h represent preferred compounds in some embodiments.

FIG. 5i illustrates some preferred compounds of formula I wherein X comprises the 3-amidobenzamide MAP kinase inhibitor compound 1024, A is 1,2-ethenylene, and Y is hydrogen. In the illustrated examples, the compound 1024 structure is appended at three different positions with the A-lactone moiety of formula I.

FIG. 5j illustrates some preferred compounds of formula I wherein X comprises the pyridine MAP kinase inhibitor compound 1025 or a lipophilic moiety thereof, A is 1,2-ethylene or 1,2-ethenylene, and Y is hydrogen. In one of the illustrated examples, the lipophilic moiety comprises all but a hydroxymethyl group of compound 1025 in that the A-lactone moiety of formula I has been substituted for this substituent. The first and fourth structures illustrated in FIG. 5j are preferred compounds in some embodiments.

FIG. 5k illustrates some preferred compounds of formula I wherein X comprises the pyrimidino[4,5-d]pyrimidinone MAP kinase inhibitor compound 1026 or a lipophilic moiety thereof, A is 1,2-methenomethylene, methylene, or 1,2-ethylene, and Y is hydrogen. In one of the illustrated examples, the lipophilic moiety comprises all but the 4-hydroxycylohexyl moiety of compound 1026 in that the A-lactone moiety of formula I has been substituted for this substituent.

FIG. 5l illustrates some preferred compounds of formula I wherein X comprises the indole MAP kinase inhibitor compound 1027, A is methylene or 1,2-ethylene, and Y is hydrogen. In the illustrated examples, the compound 1027 structure is appended at three different positions with the A-lactone moiety. The second structure illustrated in FIG. 5l is preferred in some embodiments.

The compounds disclosed in this invention can be produced by methods known in the art as they are derivatives of classes of compounds known in the art.

The present invention relates to these compounds, to pharmaceutical formulations comprising one of more of these compounds, e.g., in combination formulations, and to the use of such compounds and/or the corresponding acids of formula II in treating MAP kinase-related and/or HMG-CoA reductase-related conditions, as described in more detail below.

B. Analogs of HMG-CoA Reductase Inhibitors

A subset of the compounds of formulas I and II are novel analogs of known inhibitors of HMG-CoA reductase, wherein X comprises a lipophilic HMG-CoA reductase inhibitor, e.g., a statin, or a lipophilic moiety of an HMG-CoA reductase inhibitor. A statin can refer to any compound that can inhibit HMG-CoA reductase, generally comprising formula I or II. Known lipophilic inhibitors of HMG-CoA reductase include, for example, mevasatin, lovastatin, simvastatin, pravastatin, fluvastatin, atorvastatin, cerivastatin, rosuvastatin, pitavastatin, glenvastatin, bervastatin, dalvastatin, eptastatin, dihydroeptastatin, itavastatin, L-154819, advicor, L-654969, and other statin drugs used to treat disorders such as hypercholesterolemia.

Statins are classified in the art as natural or synthetic statins depending on their origin. Natural stains include, for example, mevastatin, lovastatin, simvastatin, pravastatin, and the like. Synthetic statins include, for example, atorvastatin, fluvastatin, cerivastatin, rosuvastatin, pitavastatin, and glenvastatin.

FIG. 6 illustrates an example of each of twelve known classes (a–l) of statin inhibitors of HMG-CoA reductase in the lactone form of formula I. FIG. 6a illustrates fluvastatin lactone, derivatives of which are preferred in certain embodiments of the invention. FIG. 6b illustrates atorvastatin lactone, derivatives of which are preferred in certain embodiments of the invention. FIG. 6c illustrates pitavastatin lactone, derivatives of which are preferred in certain preferred embodiments. FIG. 6d illustrates cerivastatin lactone, derivatives of which are preferred in certain embodiments of the invention. FIG. 6e illustrates rosuvastatin lactone, derivatives of which are preferred in certain embodiments of the invention. FIG. 6f illustrates glenvastatin lactone, derivatives of which are preferred in certain embodiments of the invention. FIG. 6g illustrates simvastatin lactone, derivatives of which are preferred in certain embodiments of the invention. FIG. 6h illustrates lovastatin lactone, derivatives of which are preferred in certain embodiments of the invention. FIG. 6i illustrates pravastatin lactone, derivatives of which are preferred in certain embodiments of the invention. FIG. 6j illustrates mevastatin lactone, derivatives of which are preferred in certain embodiments of the invention. FIG. 6k illustrates bervastatin lactone, derivatives of which are preferred in certain embodiments of the invention. FIG. 6l illustrates dalvastatin lactone, derivatives of which are preferred in certain embodiments of the invention. In particular, more preferred statin lactones are those derived from synthetic statins, and even more preferred stain lactones are those derived from atorvastatin, fluvastatin, rosuvastatin, cerivastatin, pitavastatin and glenvastatin.

Figure 7A:
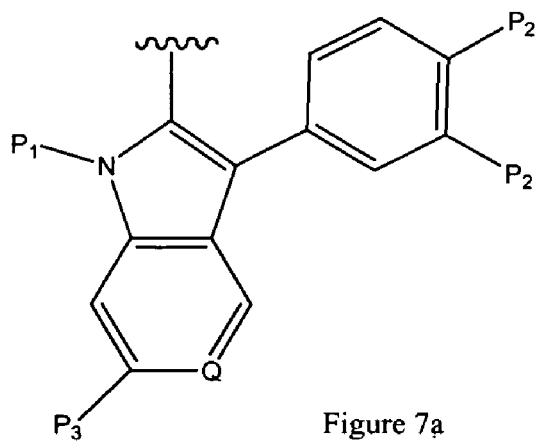
FIG. 7 illustrates examples of lipophilic moieties of six classes (a–f) of synthetic statin inhibitors of HMG-CoA reductase and their substituents.
Figure 7B:
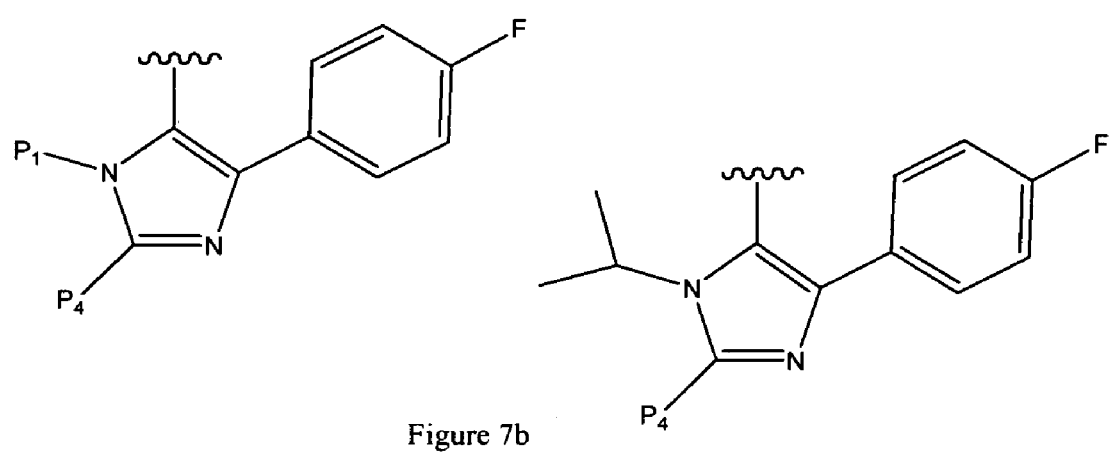
Figure 7C:
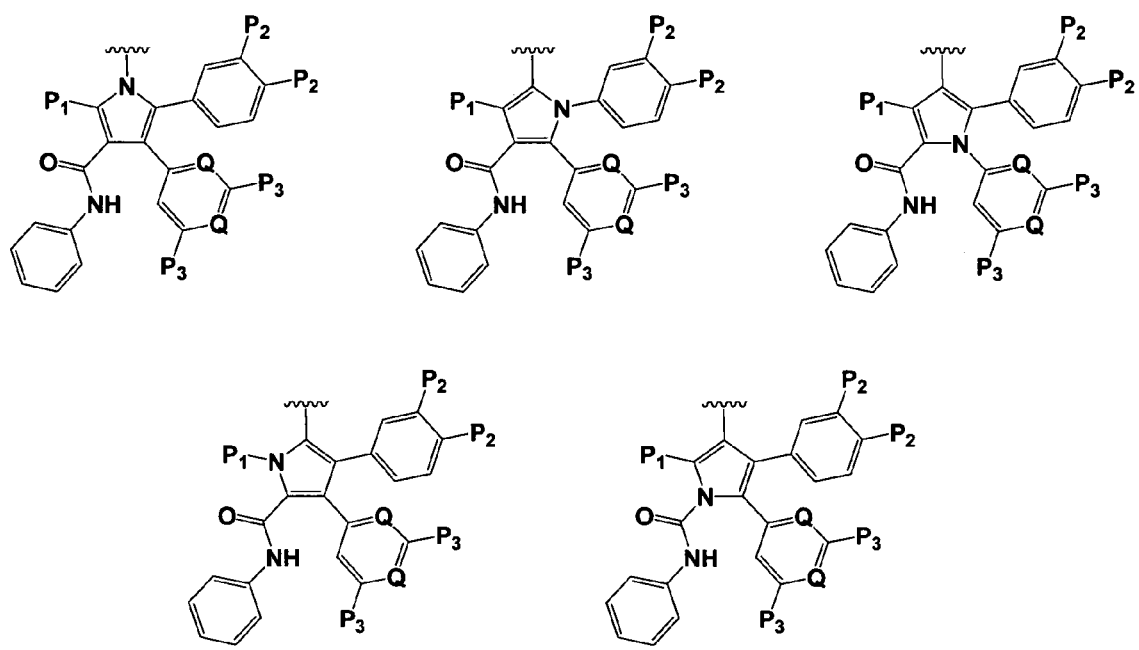
Figures 7, 7F:
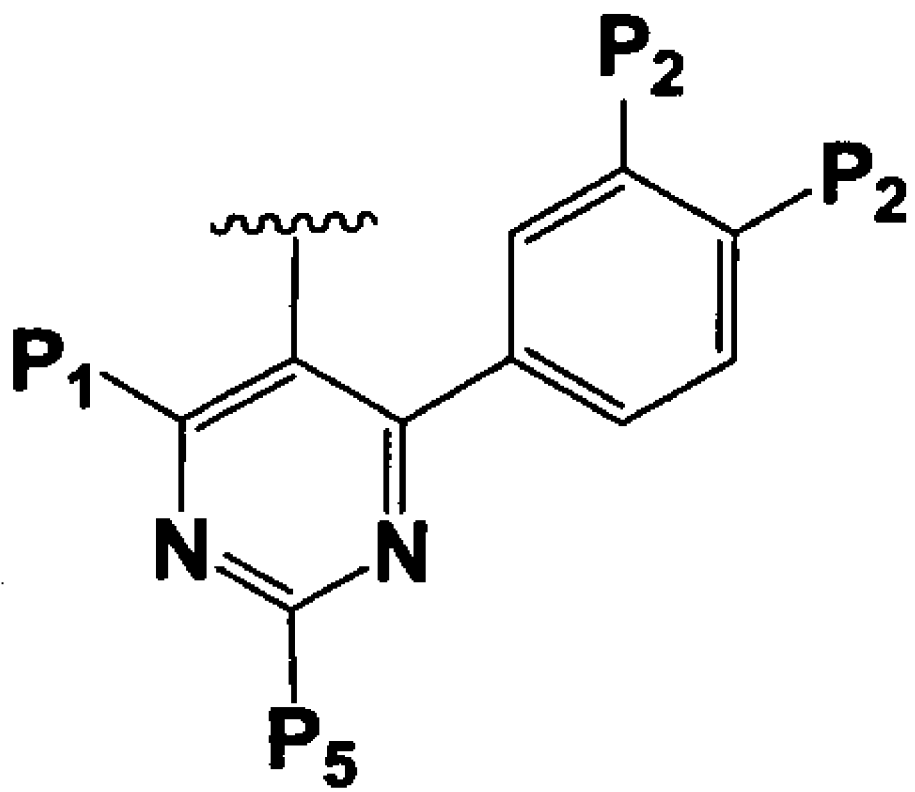

FIG. 7, for example, illustrates more specific examples of lipophilic moieties (X) derived from six classes (a–f) of synthetic statins and their substituents. In each case independently, $P_1$ is tert-butyl, iso-propyl, cyclopropyl, 2-hydroxy-2-propyl, 1-hydroxycyclopropyl; $P_2$ is hydrogen, fluorine, or -trifluoromethyl; $P_3$ is hydrogen, cyano, methoxy, phenoxy, anilino, phenylmethylamino, or amino; $P_4$ is hydrogen, phenyl or phenylcarbamoyl; $P_5$ is hydrogen, aryl, substituted aryl, heteroaryl, substituted heteroaryl, aniline, substituted aniline, phenyl ether, substituted phenyl ether, N-alkyl alkyl sulfonamido, N-alkyl aryl sulfonamide, N-alkyl alkanamido, or N-alkyl arylamido; and Q is —CH, nitrogen, or nitrogen oxide.

FIG. 7a illustrates an example of an indole-based lipophilic moiety related to fluvastatin, preferred in some embodiments. FIG. 7b illustrates two examples of imidazole-based lipophilic moieties related to atorvastatin, which are preferred in some embodiments. FIG. 7c illustrates five examples of pyrrole-based lipophilic moieties related to atorvastatin, which are preferred in certain embodiments. FIG. 7d illustrates three examples of quinoline-based lipophilic moieties related to pitavastatin, preferred in some embodiments. FIG. 7e illustrates four examples of pyridine-based lipophilic moieties related to cerivastatin, preferred in some embodiments. FIG. 7f illustrates an example of a pyrimidine-based lipophilic moiety related to rosuvastatin, which is preferred in some embodiments.

In certain embodiments, lipophilic derivatives of statins, including, for example the lipophilic moieties of FIG. 7, are substituted or appended with A-lactone or A-acid moieties of formulas I and II, respectively, to form novel compounds of the present invention. FIG. 8, for example, illustrates specific examples of lactone (formula I) derivatives of each of the four classes (a–d) of statins represented in FIG. 7 and wherein each of $P_1$, $P_2$, $P_3$, $P_4$, $P_5$, and Q have been selected to give compounds preferred in some embodiments of the present invention. It is to be understood that these represent examples of certain embodiments, and that other statins, attachment points, linking moieties (A), stereochemistries, etc., are expressly contemplated and included as other embodiments of the present invention. Further, the acid form (formula II) of each and any of these examples is also a contemplated embodiment of the present invention.

Figure 8A:
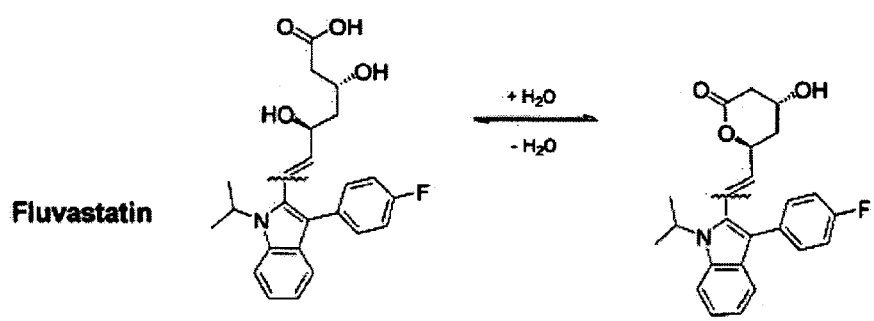
FIG. 8 illustrates specific examples of lactone derivatives of each of four classes (a–d) of statin inhibitors of HMG-CoA reductase.
Figure 8A:
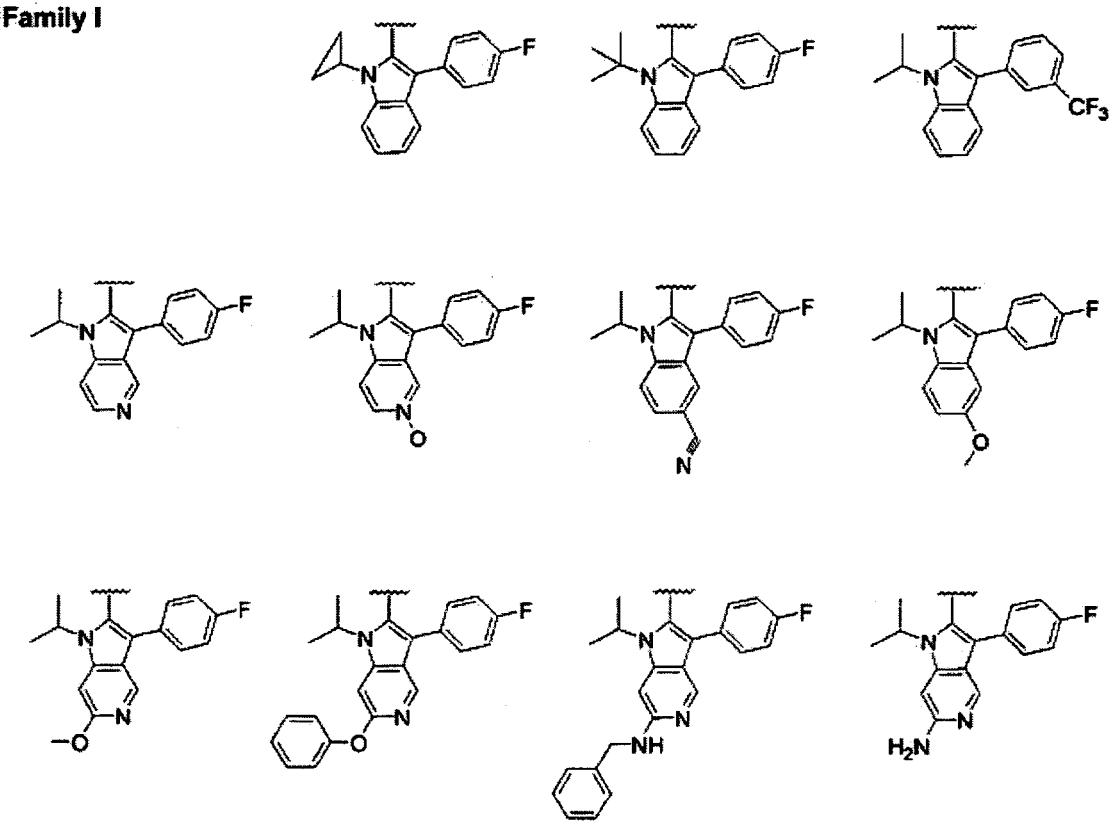
Figure 8B:
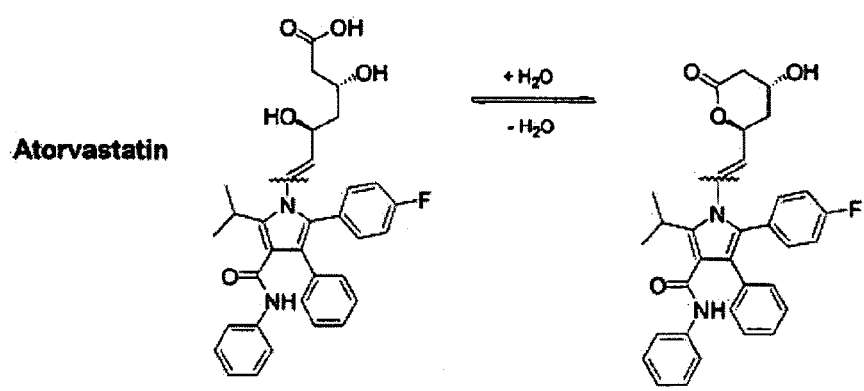
Figure 8B:
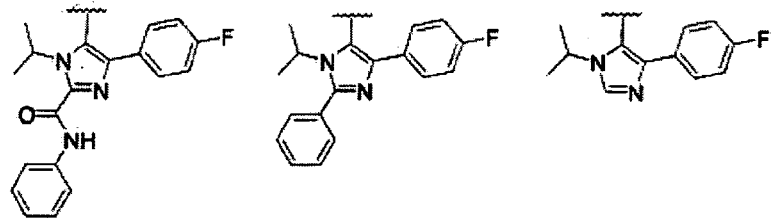
Figure 8C:
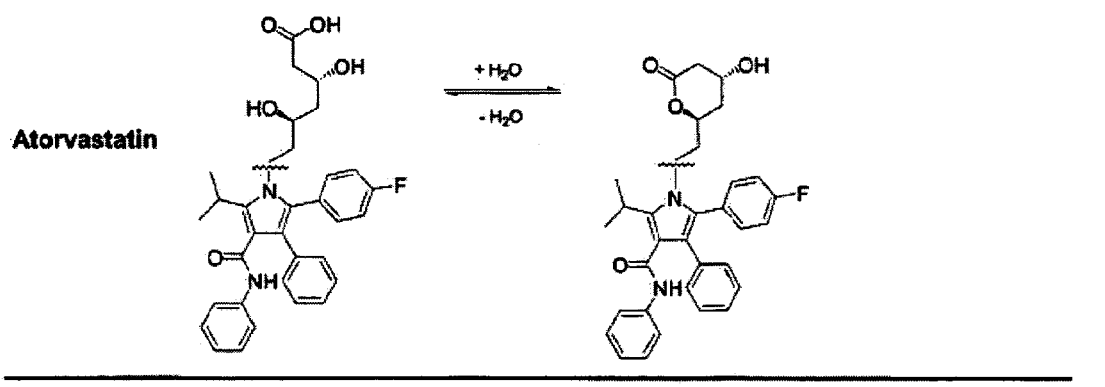
Figure 8C:
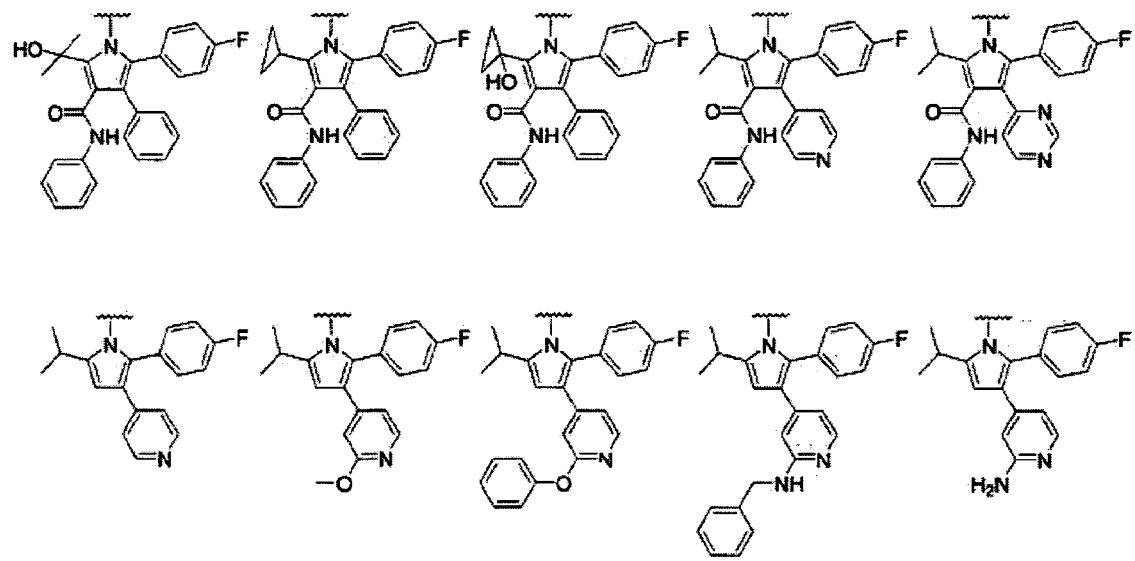
Figure 8D:
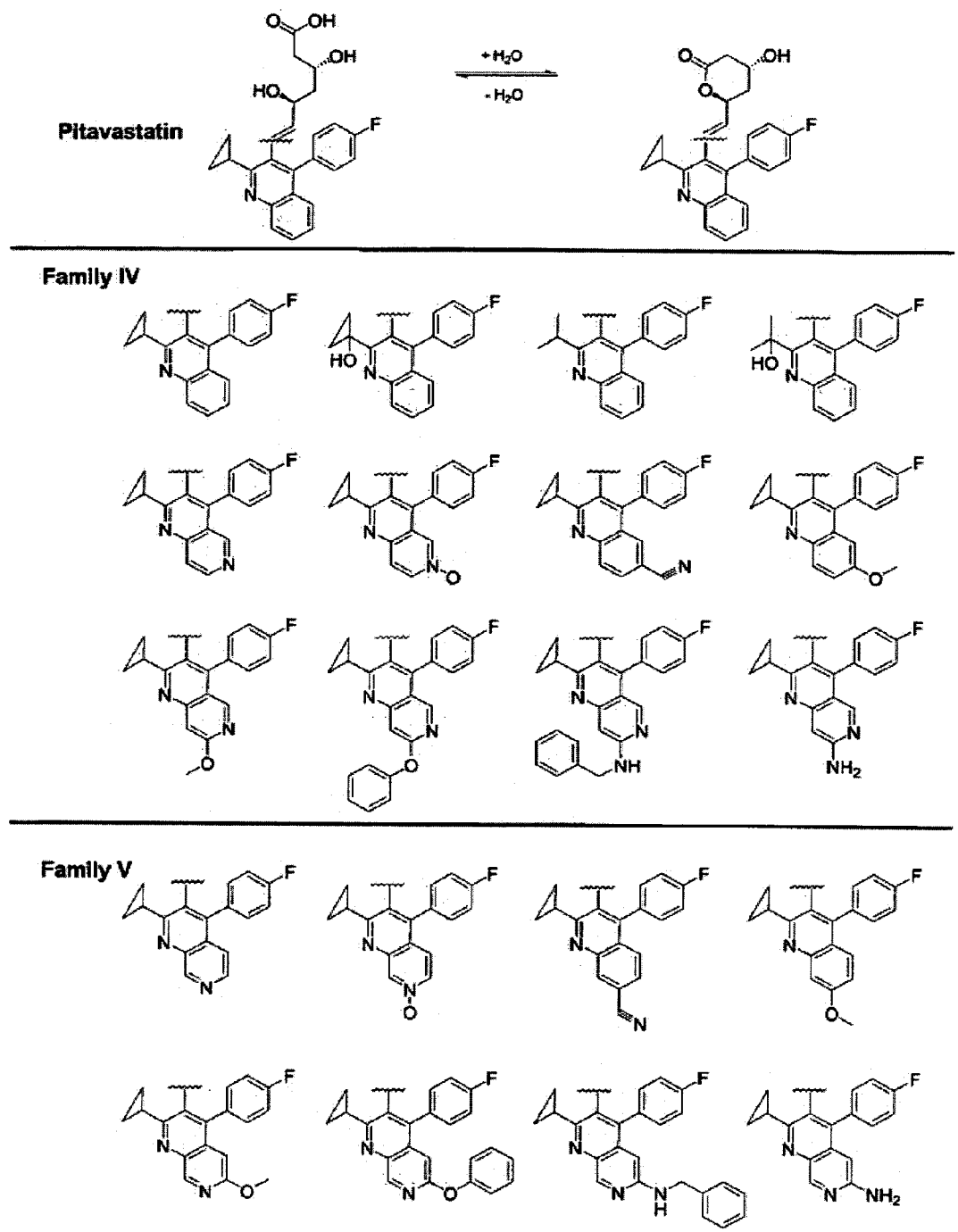
Figure 8E:
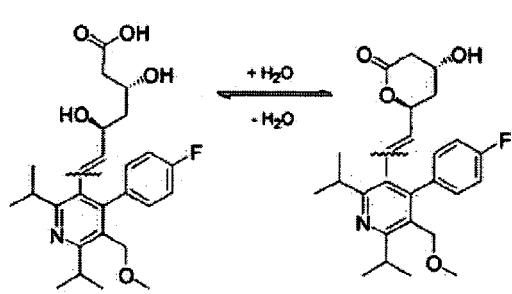
Figure 8E:
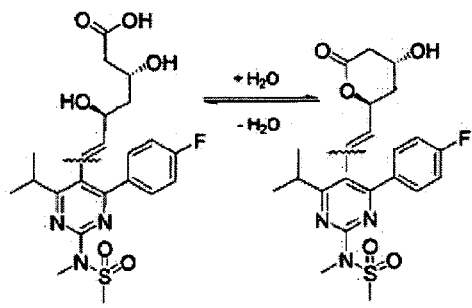
Figure 8E:
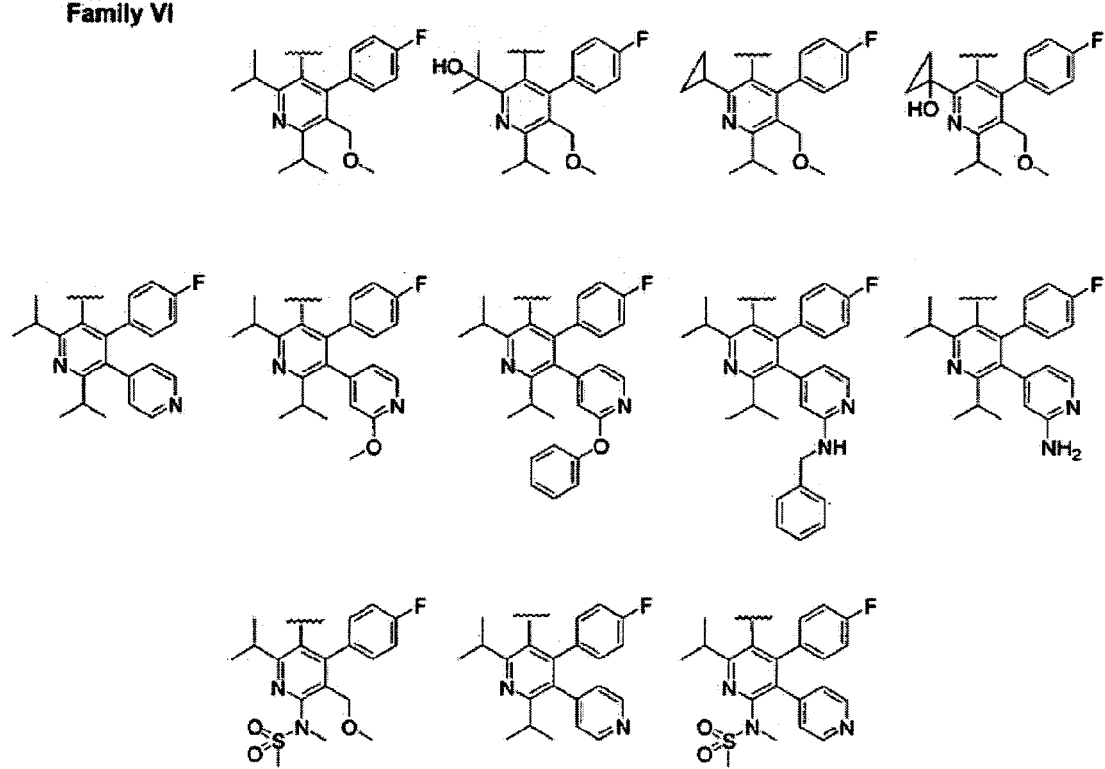

FIG. 8a illustrates selected indole-based lipophilic moieties related to fluvastatin, which are preferred in some embodiments (Family I). FIG. 8b illustrates selected imidazole-based lipophilic moieties derived from atorvastatin, which are preferred in some embodiments (Family II). FIG. 8c illustrates selected pyrrole-based lipophilic moieties derived from atorvastatin, which are preferred in some embodiments (Family III). FIG. 8d illustrates selected quinoline-based lipophilic moieties related to pitavastatin, which are preferred in some embodiments, divided amongst two families, Family IV and Family V. FIG. 8e illustrates selected pyridine-based lipophilic moieties related to cerivastatin, which are preferred in some embodiments (Family VI).

The present invention includes all stereoisomers arising from the possible absolute configurations at any stereogenic center of novel analogs of HMG CoA reductase inhibitors of formula I and/or II, e.g., wherein X comprises a lipophilic HMG-CoA reductase inhibitor, e.g., a statin, or a lipophilic moiety of an HMG-CoA reductase inhibitor. Mixtures of the various stereoisomers or pure or substantially pure stereoisomeric forms may be used in various embodiments of the instant invention.

The compounds disclosed in this invention can be produced by methods known in the art as they are derivatives of classes of compounds known in the art. For example, the synthesis of statins is described in Roth et al., *J. Med. Chem.*, 34:357–366 (1991); Krause et al., *J. Drug Dev.*, 3(Suppl. 1):255–257 (1990); and Karanewsky, et al.; *J. Med. Chem.* 33:2952–2956 (1990). Examples are also provided in the Examples below. Further, specific examples of the present invention can be made by variations of methods known to those of skill in the art and provided herein, for example, where starting materials, solvents, and other reaction conditions are varied to optimize yields.

In certain embodiments, the compounds of the present invention can be made using commercially available compounds as starting materials. For example, lactones of formula I can be prepared from commercially available salts of HMG-CoA reductase inhibitors. For instance, commercially available calcium or sodium salts of atorvastatin, fluvastatin and rosuvastatin may be converted to their protonated free acid forms by extracting the salt forms from weakly acidic aqueous media into an aprotic organic solvent such as ethyl acetate. By stirring the free acid forms in this or another aprotic organic solvent (such as toluene) approximately at or above room temperature, spontaneous conversion to the lactone form occurs over a timeframe of about hours to about days. The lactone forms may be conveniently purified by any methods known in the art, including by column, preparative thin-layer, rotating, or high-pressure chromatography on silica gel columns using standard eluting solvent systems such as about 5:1 (v:v) acetone:ethyl acetate.

In other embodiments, compounds of the present invention can be made from modifying intermediates of synthesis pathways of known statins. For example, a group can be replaced by reactive groups such as an amino, halogen, or hydroxy group, or a metal derivative such as sodium, magnesium, or lithium, and these groups further reacted. Further, those skilled in art will recognize that compounds of the present invention synthesized by various art-known methods will give cis/trans isomers, E/Z forms, diastereomers, and optical isomers, all of which are included in the present invention.

Details for synthesizing the side chain of formula II are provided in Example 9 below.

The present invention relates to these compounds, to pharmaceutical formulations comprising one of more of these compounds, e.g., in combination formulations, and to the use of such compounds and/or the corresponding acids of formula II in treating MAP kinase-related and/or HMG-CoA reductase-related conditions.

Another aspect of the present invention relates to analogs of known lipophilic MAP kinase and/or HMG-CoA reductase inhibitors, e.g. statins, having structures modified to favor and/or enforce a closed ring structure, for example, a ring structure or cyclic form that is not hydrolyzed or not substantially hydrolyzed to its carboxylic acid or carboxylate forms. "Not hydrolyzed" and "not substantially hydrolyzed," along with their grammatical conjugations, include situations where some of the compound is hydrolyzed while some is not hydrolyzed. Preferably, at least about 50%, at least about 75%, at least about 90%, and more preferably at least about 95% of the compound is in a ring structure of cyclic form at equilibrium, in situations where the compound is not substantially hydrolyzed. Preferably, at least about 70%, at least about 80%, at least about 90%, and more preferably at least about 95%, and even more preferably at least about 98% of the compound is in a ring structure or cyclic form at equilibrium, in situations where the compound is not hydrolyzed.

FIG. 9 illustrates two examples of modified closed ring structures that are analogs of a δ-lactone; FIG. 9a represents a des-oxo-form (formula III), where the carbonyl oxygen is removed, thereby inhibiting hydrolytic ring opening. FIG. 9b represents a δ-lactam form (formula IV), where a nitrogen replaces an oxygen in the ring, which increases the hydrolytic stability of the cyclic form. In these formulas, X comprises a lipophilic moiety. In some preferred embodiments, X comprises a lipophilic MAP kinase inhibitor or a lipophilic moiety of a MAP kinase inhibitor, for example, the MAP kinase inhibitors of FIG. 4, as well as lipophilic moieties of analogs of MAP kinase inhibitors, such as those of FIG. 5. In some preferred embodiments, X comprises a lipophilic moiety of a statin, including, for example, the statins of FIG. 6, as well as lipophilic moieties of statin analogs, such as those of FIGS. 7 and 8. Preferably, X comprises a lipophilic moiety bearing at least one aromatic substituent, more preferably an aromatic moiety of a synthetic statin. A represents a covalent bond or a substituted or unsubstituted alkylene, alkenylene, or alkynylene linker of 2–6 carbons, optionally containing a heteroatom, such as O, N, or S. A is preferably a covalent bond, methylene, 1,2-oxamethylene, 1,2-ethylene, 1,2-ethynylene, 1,2-ethenylene, 1,3-propylene or 1,3-propenylene. More preferably, A is 1,2-ethylene or E-1,2-ethenylene. Y is hydrogen or a lower alkyl, preferably hydrogen. Z is a hydroxy (—OH) group or hydrogen, preferably a hydroxy group. And $P_6$ is hydrogen, aryl, substituted aryl, heteroaryl, substituted heteroaryl, alkaryl, substituted alkaryl, benzyl, substituted benzyl, napthylmethylene, or substituted napthlymethylene. Preferably, $P_6$ is alkaryl or substituted alkaryl; more preferably $P_6$ is benzyl, substituted benzyl, napthylmethylene, or substituted napthlymethylene.

Further, each of the four possible stereoisomers, arising from the two possible absolute configurations at each of the two stereogenic centers of formulas III and IV, are contemplated embodiments of the invention. In particular, an absolute configuration as illustrated in FIG. 3b, depicted as (T,T), is preferred in some embodiments. Also, des-oxo and δ-lactam forms derived from synthetic statins, including, for example, atorvastatin, fluvastatin, rosuvastatin, cerivastatin, pitavastatin, and glenvastatin, are particularly preferred in some embodiments.

Some embodiments are componds comprising novel series of substituted imidazoles, substituted pyrazoles, substituted pyrroles, substituted indoles, substituted pyridines, substituted pyrimidines, or substitued quinolines, some embodiments of which are discussed in more detail below.

The present invention relates to these compounds, to pharmaceutical formulations comprising one of more of these compounds, e.g., in combination formulations, and to the use of such compounds and/or the corresponding acids of formula II in treating MAP kinase-related and/or HMG-CoA reductase related conditions, as described in more detail below.

C. Substituted Imidazole Series

In some aspects of the invention, methods described herein employ a subset of the compounds of formulas I and II that are substituted imidazoles of formula V

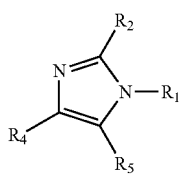

Formula V where $R_1$ is

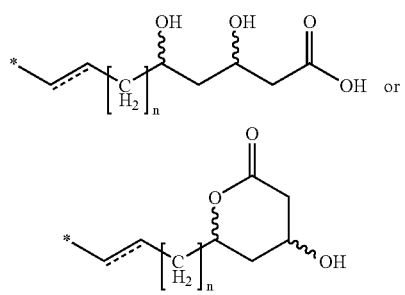

in which n is 0 or any integer;
$R_2$ is optionally substituted alkyl, aryl, or heteroaryl;
$R_4$ is optionally substituted

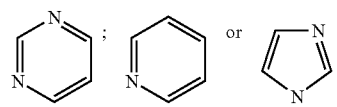

and $R_5$ is optionally substituted aryl or heteroaryl, or a salt thereof.

The dotted line in the bridging group of $R_1$ is meant to indicate that the bridging group may be either an ethyl (i.e., is —$CH_2$—$CH_2$—) or ethenyl (i.e., —CH=CH—) group. Also contemplated as falling within the scope of formula V are salts, solvates, esters, tautomers, polymorphs, metabolites, prodrugs, N-oxides, sulfoxides or sulfones thereof. Preferred salts include those of calcium, sodium and potassium.

In some embodiments, the N at the 3-position of the imidazole ring is protonated (e.g., reversibly protonated) or optionally substituted. Also contemplated within the scope of Formula V are compounds where the $R_4$ pyrimidinyl, pyridinyl or imidazolyl ring is attached via any available carbon or nitrogen atom of the ring.

In choosing compounds of the present invention, one of ordinary skill in the art will recognize that the various substituents, i.e. $R_1$, $R_2$, etc., are to be chosen in conformity with well-known principles of chemical structure connectivity.

The term "substituted" can include multiple degrees of substitution by a named substitutent. Where multiple substituent moieties are disclosed or claimed, the substituted compound can be independently substituted with one or more of the disclosed or claimed substituent moieties, singly or pluraly.

"Alkyl", as well as other groups having the prefix "alk", such as alkoxy, alkanoyl, can refer to optionally substituted carbon chains which may be linear or branched or combinations thereof. Examples of alkyl groups include, e.g., methyl, ethyl, n-propyl, isopropyl, n-butyl, iso- sec- and tert-butyl, pentyl, hexyl, heptyl, octyl, nonyl, and the like.

"Aryl" can refer to optionally substituted mono- or bicyclic aromatic rings containing only carbon atoms. The term can also include aryl group fused to a monocyclic cycloalkyl or monocyclic cycloheteroalkyl group in which the point of attachment is on an aromatic portion. Examples of aryl groups include, e.g., phenyl, naphthyl, indanyl, indenyl, tetrahydronaphthyl, 2,3-dihydrobenzofuranyl, dihydrobenzopyranyl, 1,4-benzodioxanyl, and the like.

"Heteroaryl" can refer to an optionally substituted mono- or bicyclic aromatic ring containing at least one heteroatom (an atom other than carbon), such as N, O and S, with each ring containing about 5 to about 6 atoms. Examples of heteroaryl groups include, e.g., pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Halogen" can include fluorine, chlorine, bromine and iodine.

As used herein, R, R', etc., generally refer to any non-aromatic group, including, e.g., substituted or unsubstituted alkyl groups, unless specifically defined otherwise. Ar, Ar', etc., generally refer to substituted or unsubstituted aromatic groups, including, e.g., aryls and heteroaryls.

Compounds of formula V contain one or more asymmetric centers and can thus occur as racemates and racemic mixtures, pure or substantially pure isomeric forms, single enantiomers, diastereomeric mixtures and individual diastereomers. The present invention is meant to comprehend all such isomeric forms of the compounds of formula V.

In some preferred embodiments, n is 0 1, 2 or 3. In some preferred embodiments, $R_1$ has the following stereochemistry:

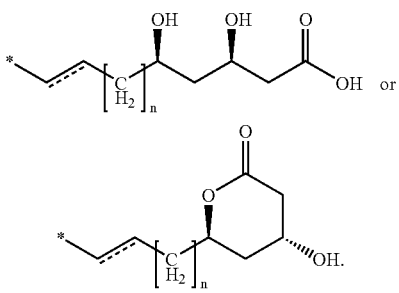

Some of the compounds described herein contain olefinic double bonds, and unless specified otherwise, are meant to include both E and/or Z geometric isomers. In some embodiments, the E geometric isomer is preferred.

Some of the compounds described herein may exist with different points of attachment of hydrogen, referred to as tautomers. Such an example may be a ketone and its enol form known as keto-enol tautomers. The individual tautomers as well as mixtures thereof are encompassed within compounds of formula V.

In preferred embodiments, the compounds of formula V are MAP kinase inhibitors and/or are used in the methods wherein an inhibition of MAP kinase is desired, e.g., in the treatment of MAP kinase-related conditions.

In more preferred embodiments, a novel subset of compounds (or salts thereof) of formula V are provided wherein $R_1$ is

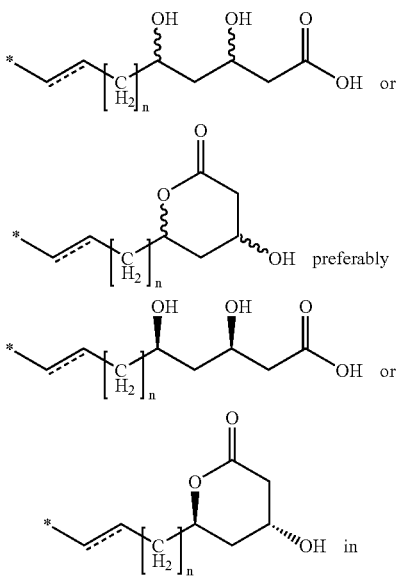

which n is 0 or any integer, preferably 0, 1 or 2; and $R_4$ is optionally substituted

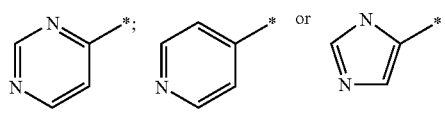

with the proviso that when $R_4$ is the pyridinyl ring optionally substituted with one or more substituents selected from halogen atoms and hydroxyl, $C_{1-3}$ alkyl, $C_{1-3}$ alkoxy and trifluoromethyl groups, then the bridging group of $R_1$ is —$CH_2$—$CH_2$—.

$R_4$ substituents may be present on one or more vacant positions of a carbon and/or heteroatom of the pyrimidinyl, pyridinyl or imidazolyl rings. Examples of suitable substituents include, but are not limited to, oxygen, fluorine, chlorine, bromine or iodine atoms or methyl, ethyl, n-propyl, isopropyl, methoxy, ethoxy, n-propoxy, isopropoxy, trifluoromethyl, hydroxy, or optionally substituted amino groups. For example, in some embodiments, $R_4$ is the pyridinyl ring substituted with one or more optionally substituted amino groups, and the bridging group of $R_1$ is either —$CH_2$—$CH_2$— or —CH=CH—. Particularly preferred $R_4$ substitutents include —NH-phenyl, —NH—$CH_3$, and $NH_2$ groups.

In still some embodiments, $R_4$ substitutents include N-oxides, for example:

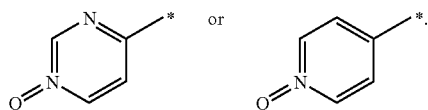

In still some embodiments, $R_4$ can be

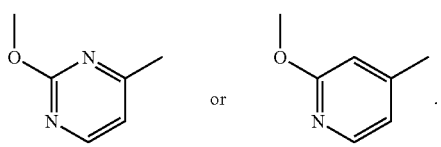

A particularly preferred group of compounds of formula V are those wherein $R_2$ is a $C_{1-6}$ alkyl group optionally substituted with one to three halogen atoms for example a trifluoromethyl or a $C_{1-4}$ alkyl group, more particularly a $C_{3-4}$ branched alkyl group, e.g., 1-methylpropyl. In even more preferred embodiments, $R_2$ is isopropyl, t-butyl, —$CF_3$, phenyl,

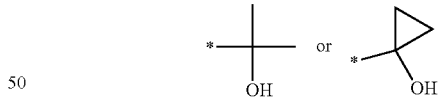

In some embodiments within this particularly preferred group, compounds wherein $R_5$ is an optionally substituted phenyl group are especially preferred.

When $R_5$ is a substituted phenyl group then these preferably contain from 1 to 3 substituents. Examples of suitable $R_5$ substituents include halogen atoms e.g. fluorine, bromine, chlorine, methoxy, methyl, ethyl, hydroxy or trifluoromethyl groups. Preferred substituted $R_5$ substituents include halophenyl such as 4-fluorophenyl, 4-chlorophenyl, 3-chlorophenyl, 3-bromophenyl, 3,5-dibromophenyl, 3,5-dichlorophenyl, alkyl-halophenyl such as 5-chloro-2-methylphenyl, 4-fluoro-2-methylphenyl, 3,5-dimethyl-4-fluorophenyl, 4-chloro-3,5-dimethylphenyl and 3,5-diethyl-4-fluorophenyl, alkylphenyl such as 4-methylphenyl, 3,5-dimethylphenyl, hydroxyphenyl, methoxyphenyl or 3-trifluoromethylphenyl. Particularly preferred is 4-fluorophenyl or 3-trifluoromethylphenyl.

A particularly preferred group of compounds are those wherein $R_2$ is a phenyl, trifluoromethyl, t-butyl or more especially an isopropyl group; $R_5$ is a phenyl, 3-chlorophenyl, 3-trifluoromethylphenyl, 4-chlorophenyl, 4-fluorophenyl, 4-fluoro-2-methylphenyl, 3,5-diethyl-4-fluorophenyl or 3,5-dimethyl-4-fluorophenyl group; and $R_4$ comprises a 4-pyridinyl group, a 4-pyrimidinyl group, or a 4-imidazolyl group, a 2-aminophenyl-4-pyridinyl group, a 2-aminophenyl-4-pyrimidinyl group, a 2-aminomethyl-4-pyridinyl group, or a 2-aminomethyl-4-pyrimidinyl group, especially 4-pyrimidinyl, 4-pyridinyl, 2-aminophenyl-4-pyrimidinyl, 2-aminomethyl-4-pyrimidinyl, 2-amino-4-pyridinyl, or 2-aminomethyl-4-pyridinyl. Within this particularly preferred group of compounds, those in which $R_5$ is a 4-fluorophenyl group are especially preferred.

A preferred group of compounds of formula V are compounds of formula Va

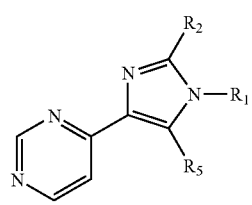

Formula Va wherein $R_1$ is

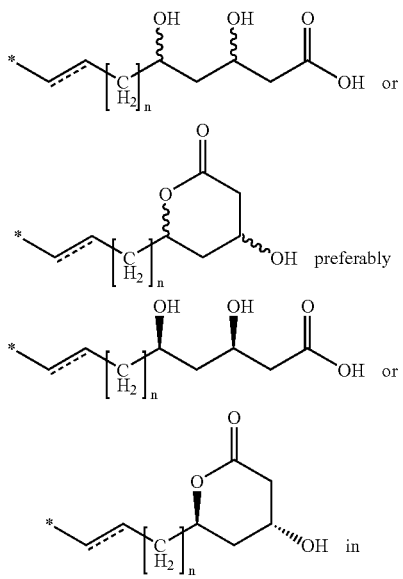

which n is 0 or any integer, preferably 0, 1 or 2;
$R_2$ is optionally substituted alkyl, aryl, or heteroaryl;
the pyrimidinyl ring is optionally substituted;
and $R_5$ is optionally substituted aryl or heteroaryl, or a salt thereof.

In some embodiments, the pyrimidinyl ring is unsubstituted. In other emobdiments, the pyrimidinyl ring is substituted, e.g., with optionally substituted amino groups, especially —NH—CH$_3$ or —NH-phenyl; or with —O—CH$_3$.

Another preferred group of compounds of formula V are compounds of formula Vb

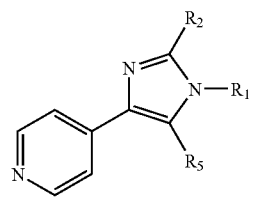

Formula Vb wherein $R_1$ is

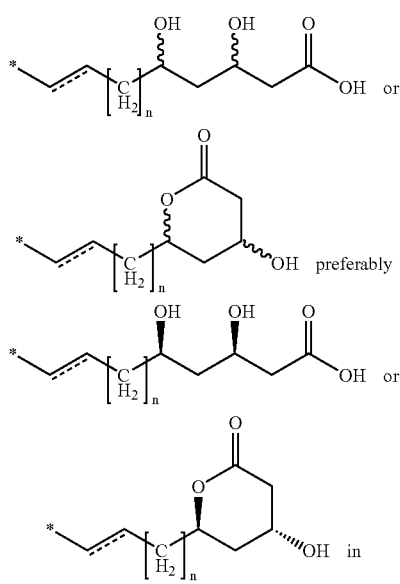

which n is 0 or any integer, preferably 0, 1 or 2;
$R_2$ is optionally substituted alkyl, aryl, or heteroaryl;
the pyridinyl ring is optionally substituted, with the proviso that when the pyridinyl ring is unsubstituted or substituted with one or more substituents selected from halogen atoms and hydroxyl, C1–3 alkyl, C1–3 alkoxy and trifluoromethyl groups, then the bridging group of $R_1$ is —CH$_2$—CH$_2$—;
and $R_5$ is optionally substituted aryl or heteroaryl, or a salt thereof.

In some embodiments, the pyridinyl ring is unsubstituted. In other emobdiments, the pyridinyl ring is substituted, e.g., with optionally substituted amino groups, especially, —NH$_2$ or —NH—CH$_3$.

Particularly preferred examples of compounds of the present invention include, but are not limited to, the following:

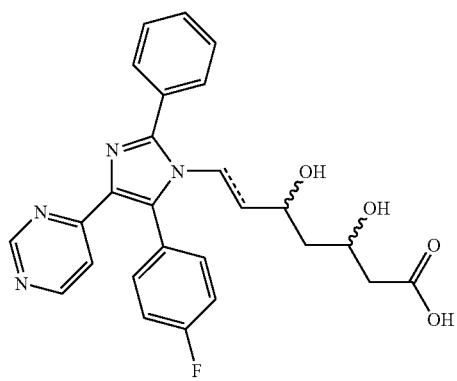

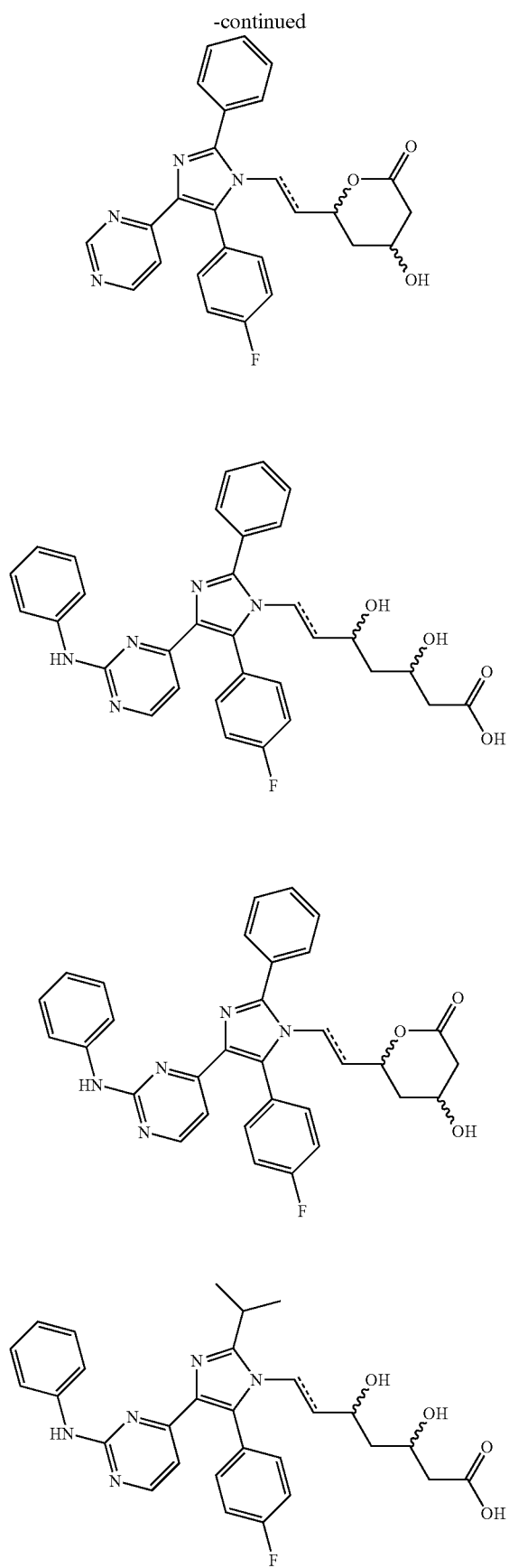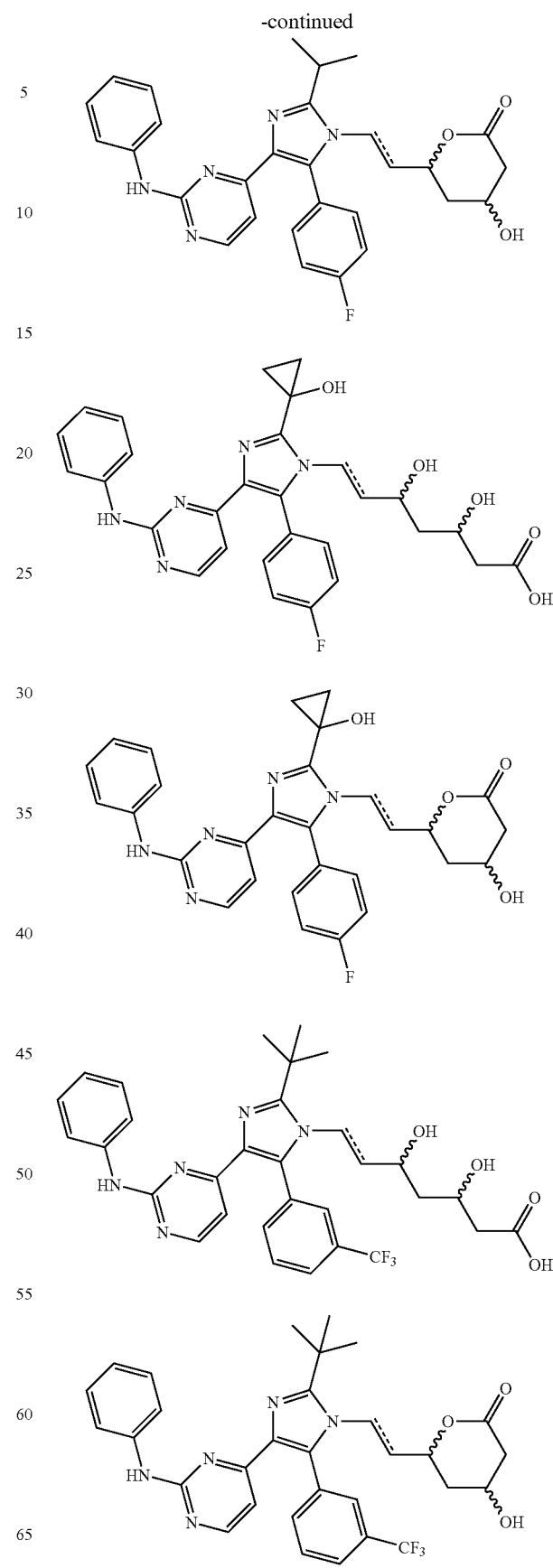

-continued
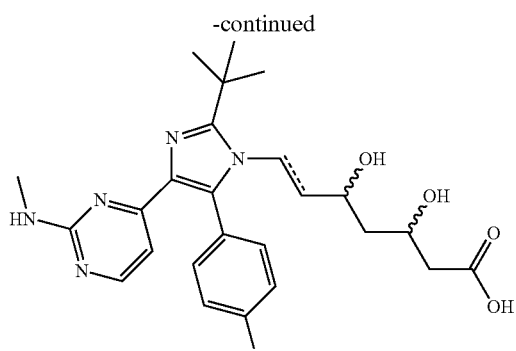
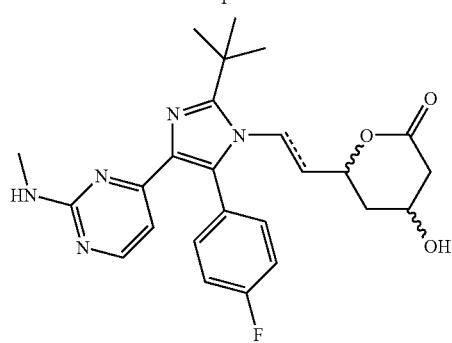
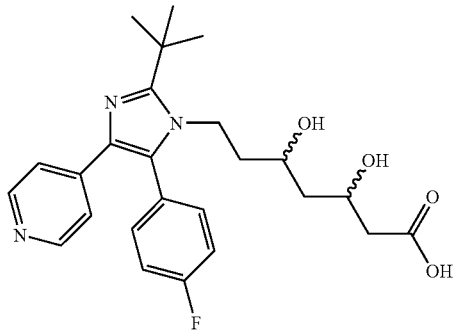
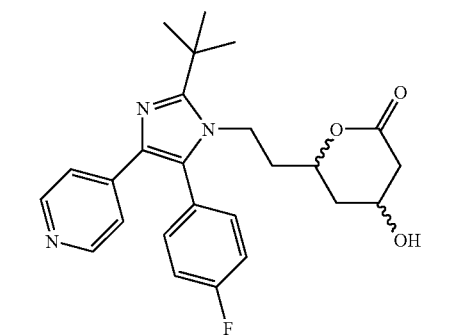
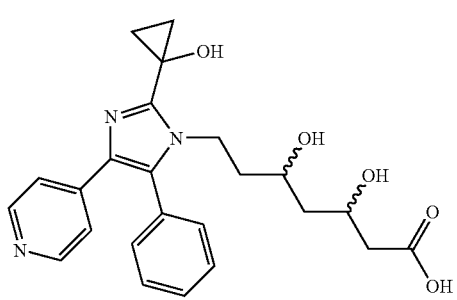
-continued
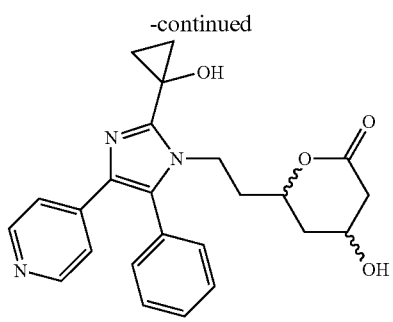
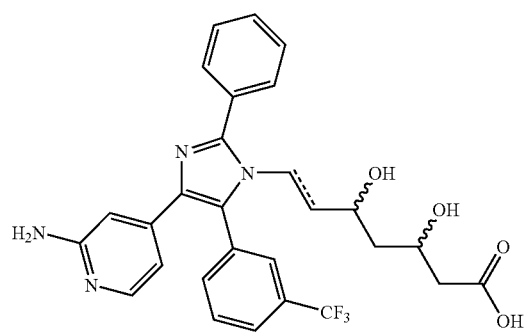
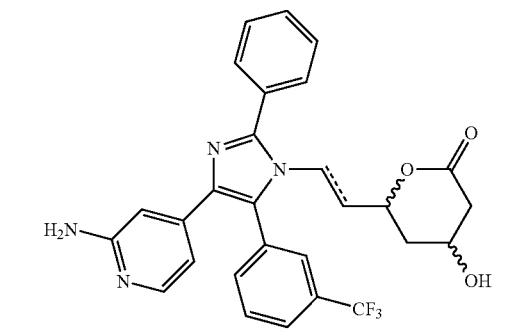
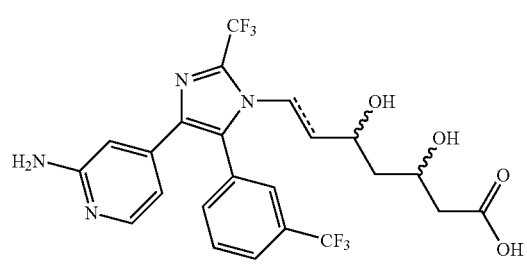
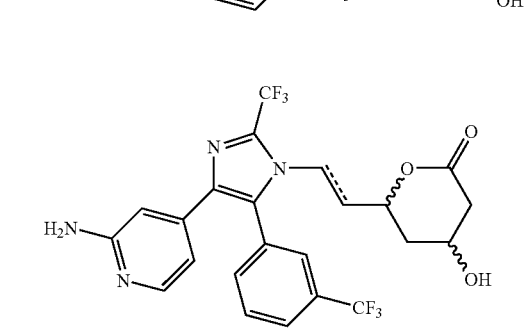

-continued
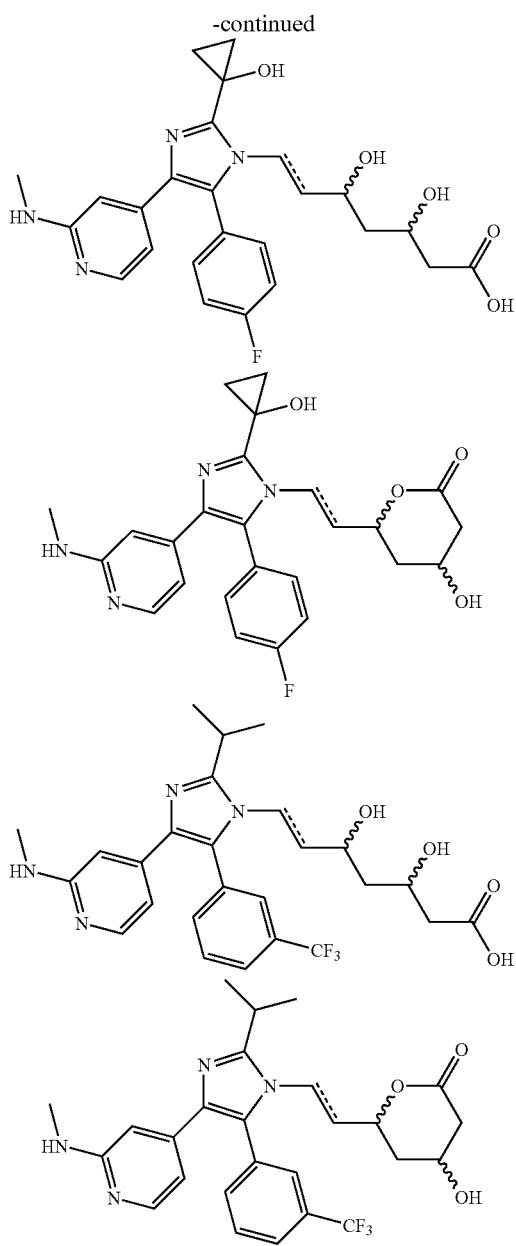
More particularly preferred examples of compounds of the present invention include, but are not limited to, the following:
-continued
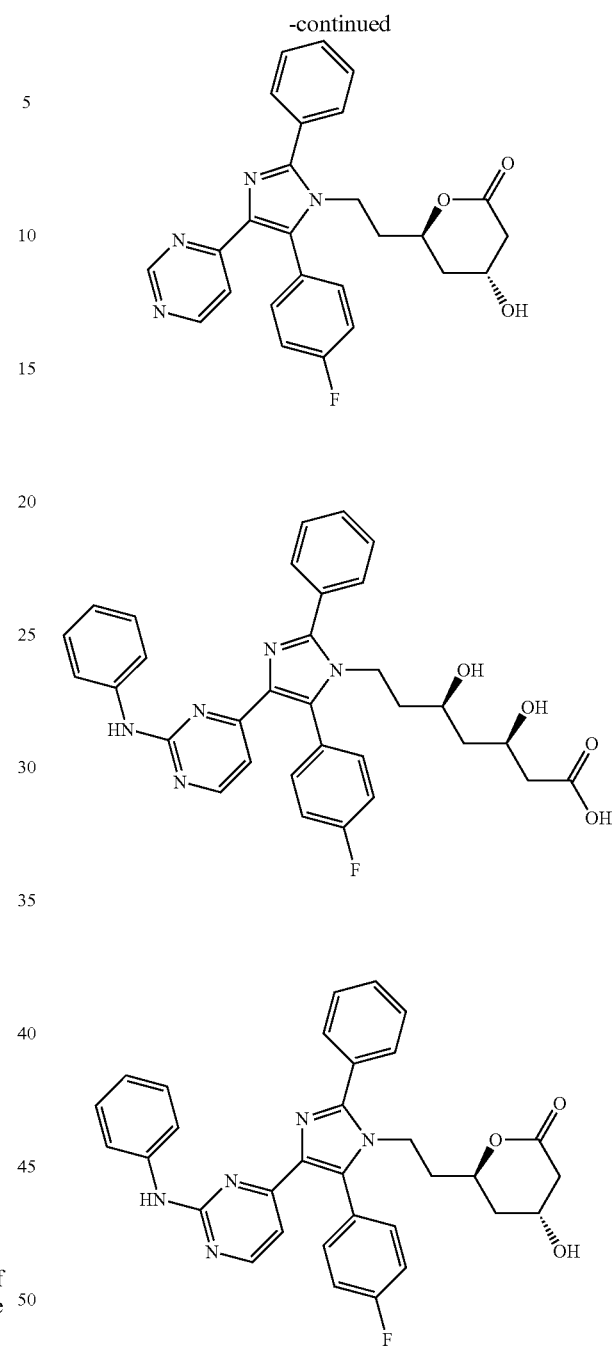
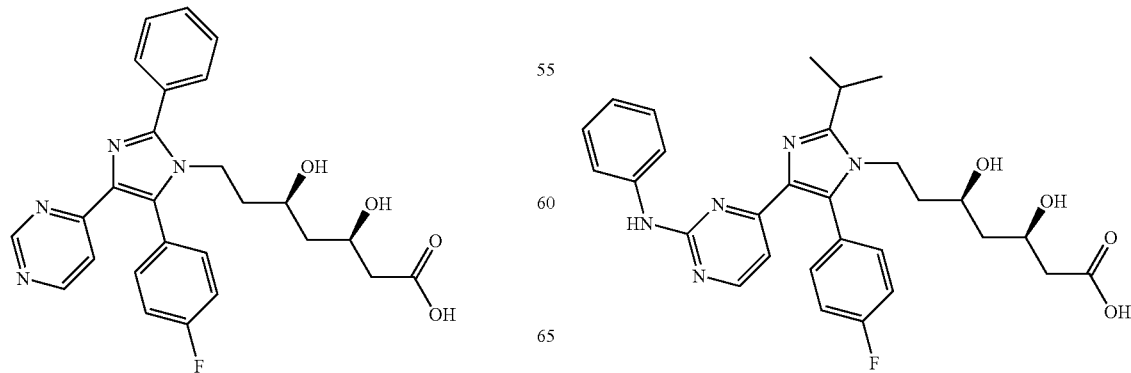

-continued
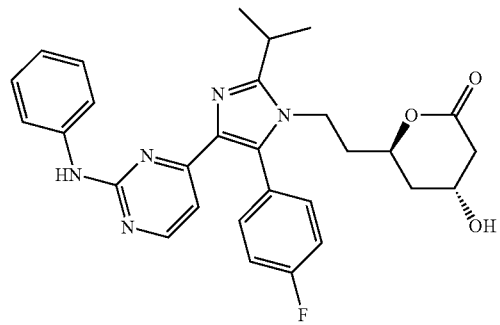
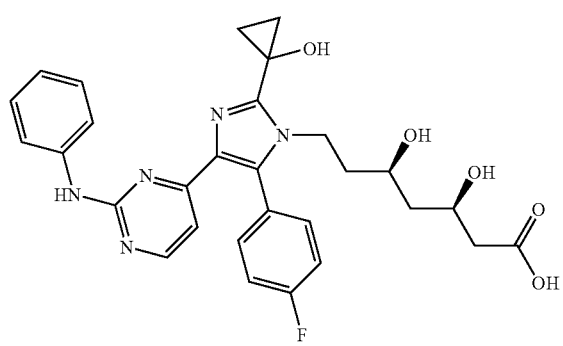
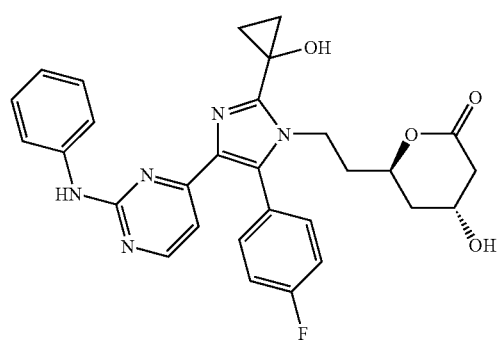
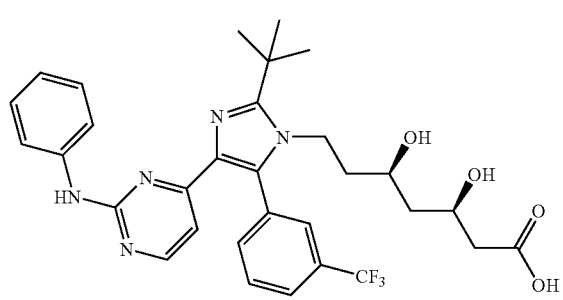
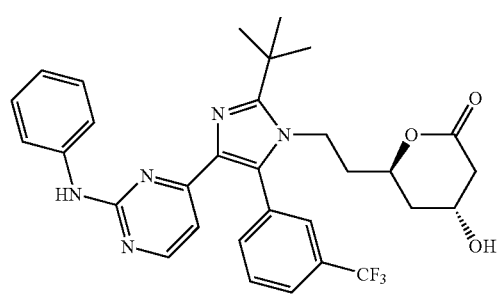
-continued
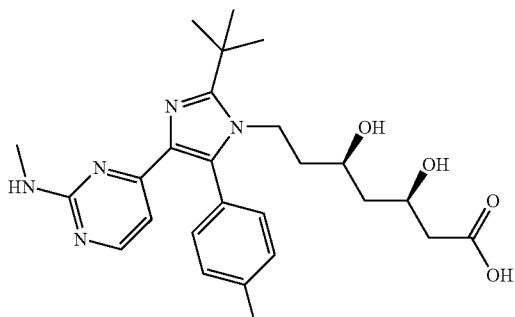
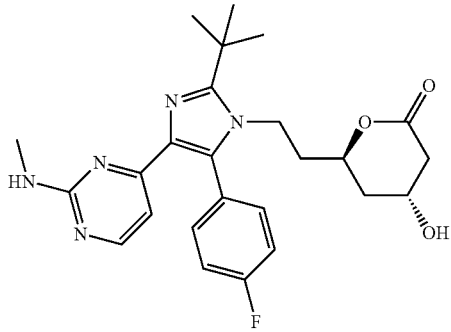
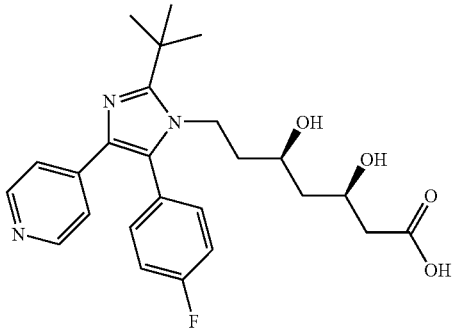
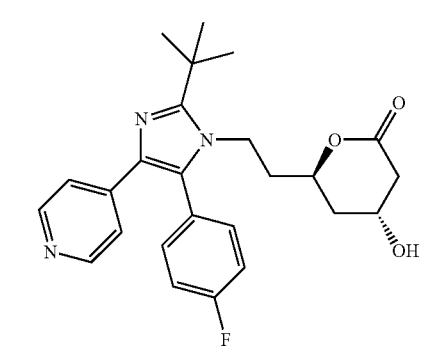
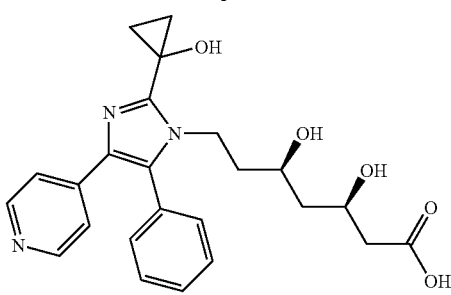

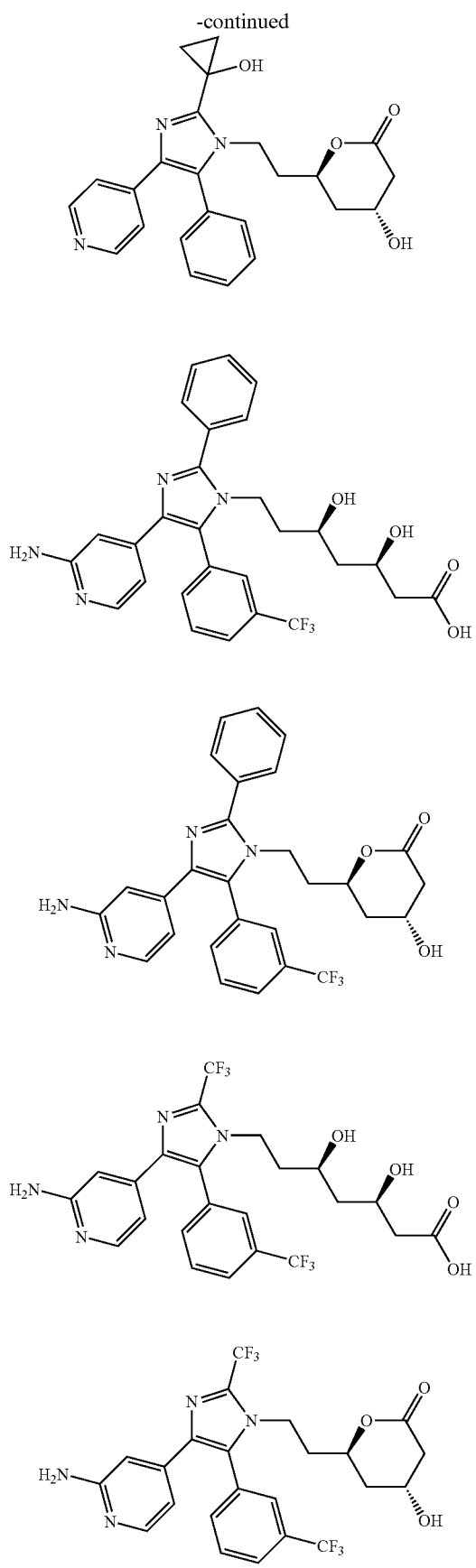
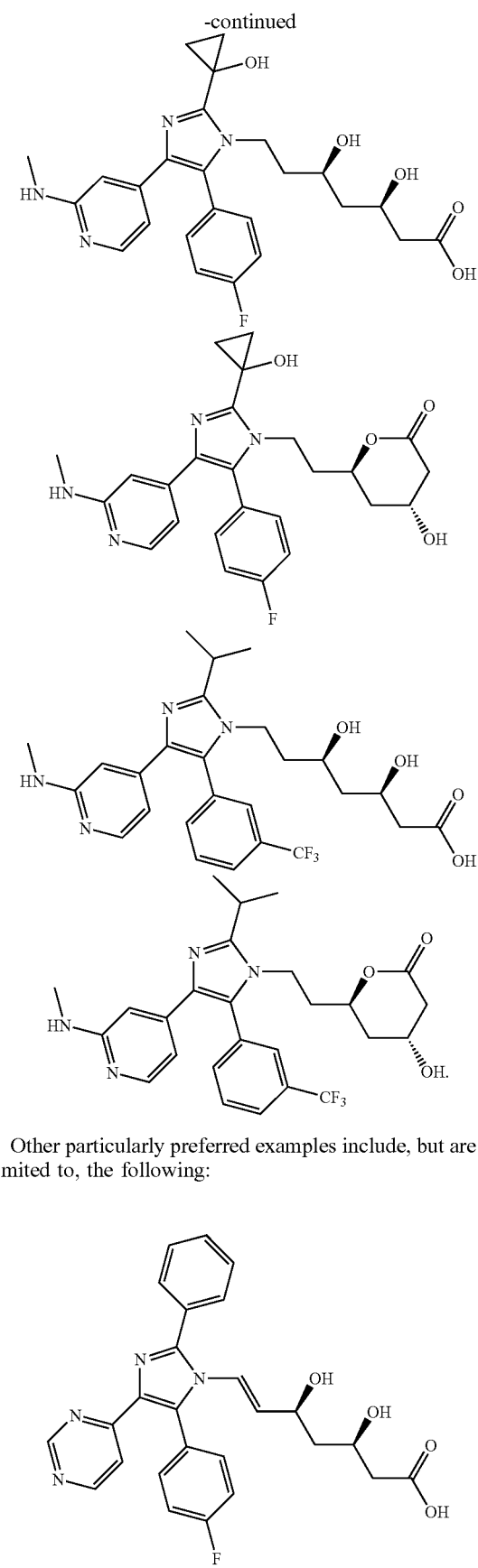
Other particularly preferred examples include, but are not limited to, the following:
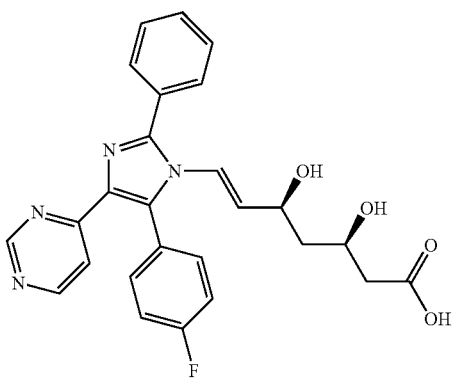

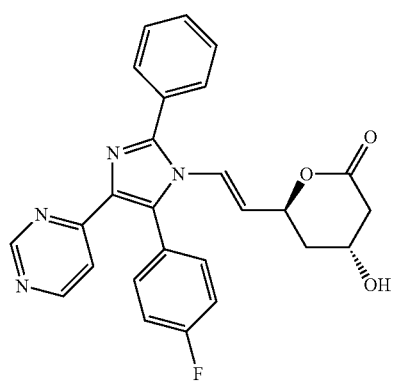
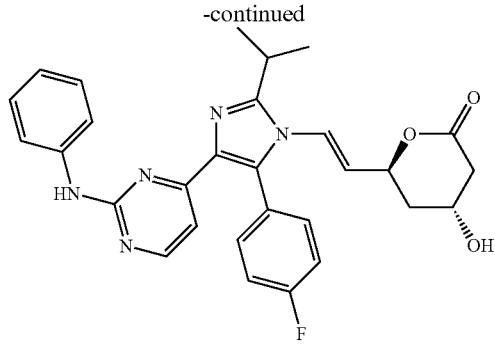
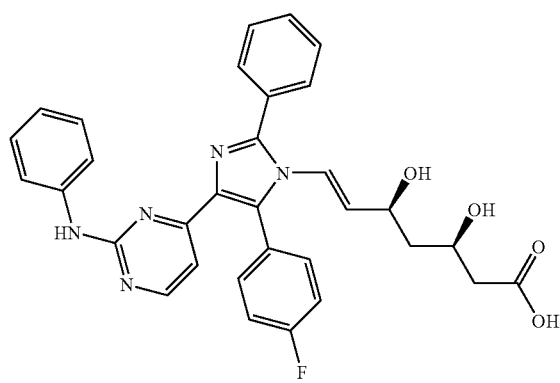
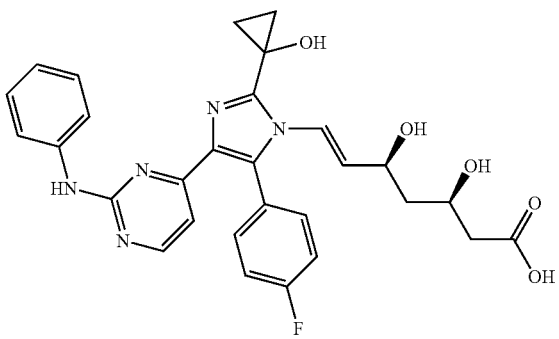
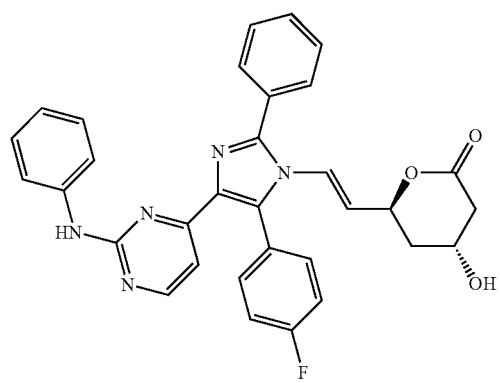
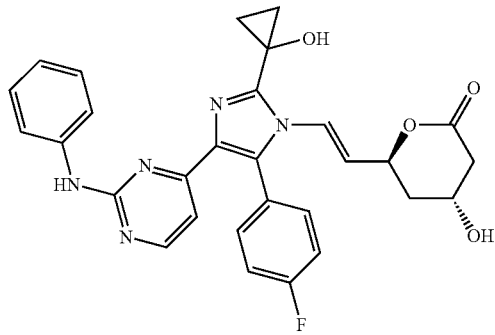
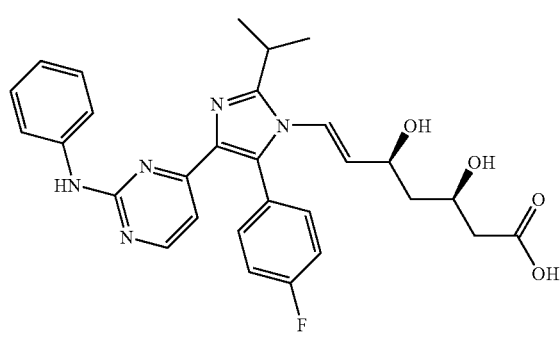
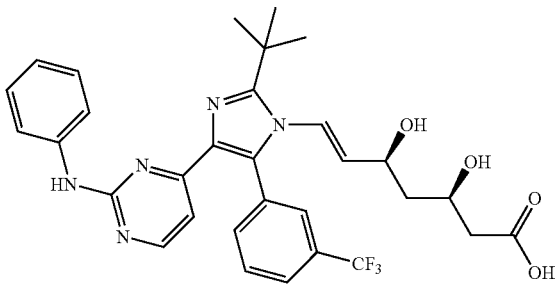
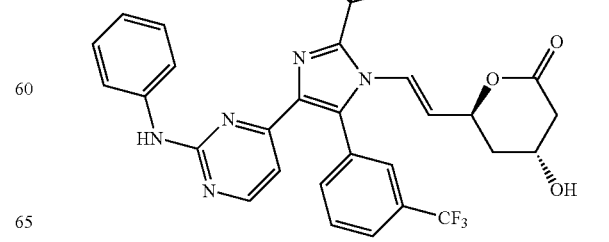

-continued
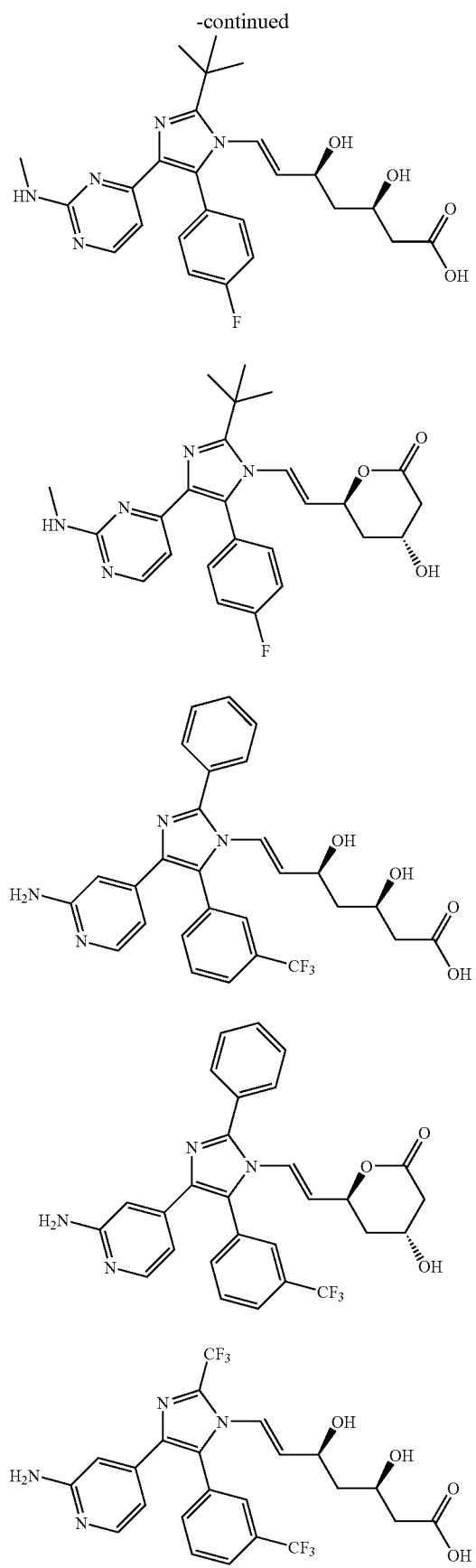
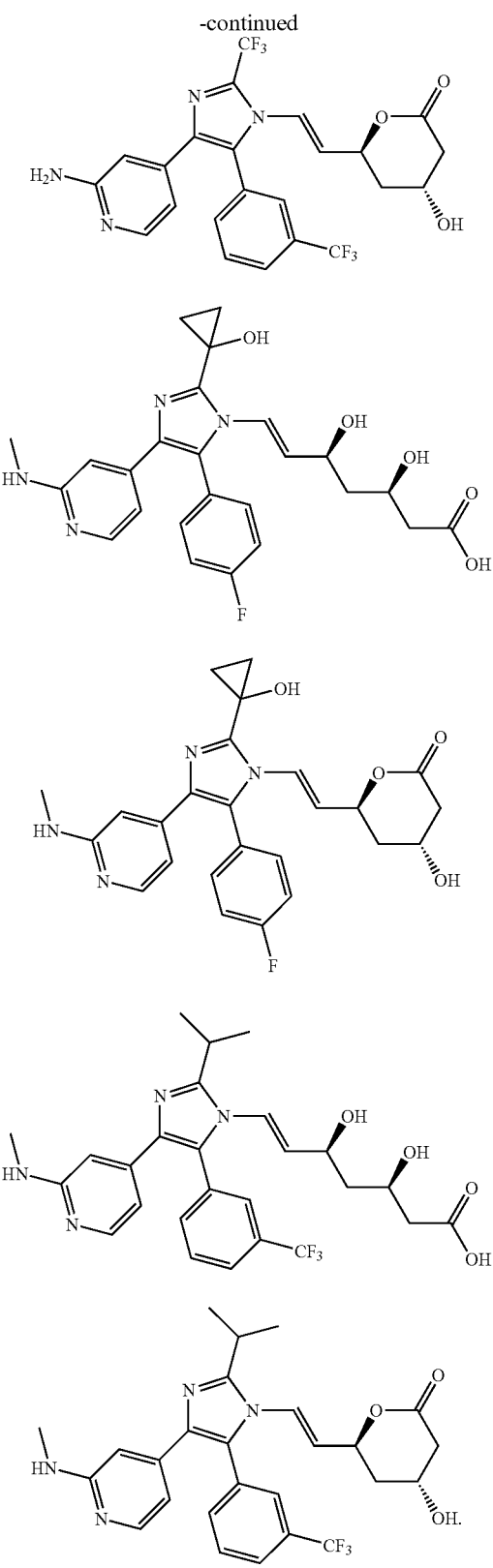
Compounds of the formula V may be separated into diastereoisomeric pairs of enantiomers by, for example, fractional crystallization from a suitable solvent, for example MeOH or ethyl acetate or a mixture thereof. The pair of enantiomers may be separated into individual stereoisomers by, for example the use of an optically active amine as a resolving agent or on a chiral HPLC column. Racemic mixtures can be separated into their individual enantiomers by any of a number of conventional methods. These include chiral chromatography, derivatization with a chiral auxillary followed by separation by chromatography or crystallization, and fractional crystallization of diastereomeric salts.

Alternatively, any enantiomer of a compound of the general formula V may be obtained by stereospecific synthesis using optically pure starting materials or reagents of known configuration. In preferred embodiments, compounds of formula V are administered as enantiomerically pure (or substantially enantiomerically pure) formulations.

Details for synthesizing imidazoles of formula V of the invention are provided in Examples 13 and 14 below. Specifically, Example 13 provides examples of synthesizing (3R,5R)-7-(2,5-diphenyl-4-(pyridin-4-yl)-1H-imidazol-1-yl)-3,5-dihydroxyheptanoic acid, calcium salt and (3R,5R)-7-(5-(4-fluorophenyl)-2-phenyl-4-(pyridin-4-yl)-1H-imidazol-1-yl)-3,5-dihydroxyheptanoic acid, calcium salt, via sidechain condensation. Example 14 provides examples of synthesizing (3S,5S), (3R,5R)-6-(5-(4-fluorophenyl)-2-phenyl-4-(pyrimidin-4-yl)-1H-imidazol-1-yl)-3,5-dihydroxyhexanoic acid, calcium salt via an N-alkylation.

D. Substituted Pyrazole Series

In some aspects of the invention, methods described herein employ a subset of the compounds of formulas I and II that are substituted pyrazoles of formula VI

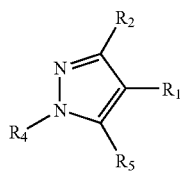

Formula VI where $R_1$ is

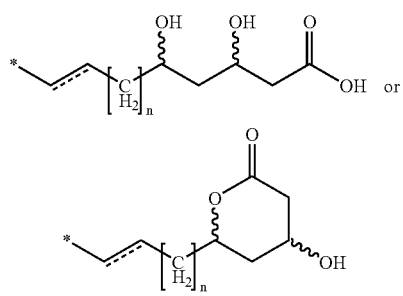

in which n is 0 or any integer;
$R_2$ is optionally substituted alkyl, aryl, or heteroaryl;
$R_4$ is optionally substituted

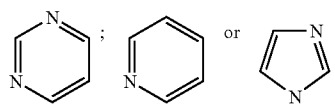

and $R_5$ is optionally substituted aryl or heteroaryl, or a salt thereof.

The dotted line in the bridging group of $R_1$ is meant to indicate that the bridging group may be either an ethyl (i.e., is —CH$_2$—CH$_2$—) or ethenyl (i.e., —CH=CH—) group. Also contemplated as falling within the scope of formula VI are salts, solvates, esters, tautomers, polymorphs, metabolites, prodrugs, N-oxides, sulfoxides or sulfones thereof. Preferred salts include those of calcium, sodium and potassium.

In some embodiments, the N at the 2-position of the pyrazole ring is protonated (e.g., reversibly protonated) or optionally substituted. Also contemplated within the scope of Formula VI are compounds where the $R_4$ pyrimidinyl, pyridinyl or imidazolyl ring is attached via any available carbon or nitrogen atom of the ring.

In choosing compounds of the present invention, one of ordinary skill in the art will recognize that the various substituents, i.e. $R_1$, $R_2$, etc., are to be chosen in conformity with well-known principles of chemical structure connectivity.

The term "substituted" can include multiple degrees of substitution by a named substitutent. Where multiple substituent moieties are disclosed or claimed, the substituted compound can be independently substituted with one or more of the disclosed or claimed substituent moieties, singly or pluraly.

Compounds of formula VI contain one or more asymmetric centers and can thus occur as racemates and racemic mixtures, pure or substantially pure isomeric forms, single enantiomers, diastereomeric mixtures and individual diastereomers. The present invention is meant to comprehend all such isomeric forms of the compounds of formula VI.

In some preferred embodiments, n is 0, 1, 2 or 3. In some preferred embodiments, $R_1$ has the following stereochemistry:

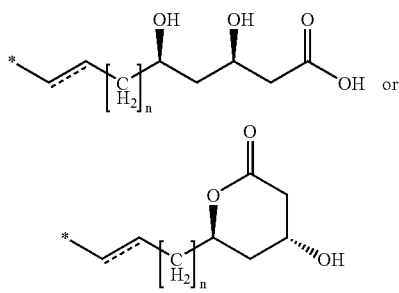

Some of the compounds described herein contain olefinic double bonds, and unless specified otherwise, are meant to include both E and/or Z geometric isomers. In some embodiments, the E geometric isomer is preferred.

Some of the compounds described herein may exist with different points of attachment of hydrogen, referred to as tautomers. Such an example may be a ketone and its enol form known as keto-enol tautomers. The individual tautomers as well as mixtures thereof are encompassed within compounds of formula VI.

In preferred embodiments, the compounds of formula VI are MAP kinase inhibitors and/or are used in the methods wherein an inhibition of MAP kinase is desired, e.g., in the treatment of MAP kinase-related conditions.

In more preferred embodiments, a novel subset of compounds (or salts thereof) of formula VI are provided wherein $R_1$ is

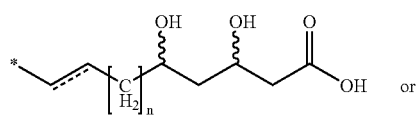 or preferably

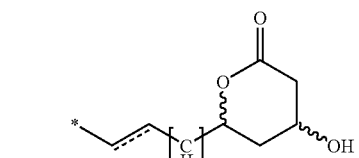

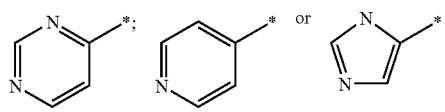 or

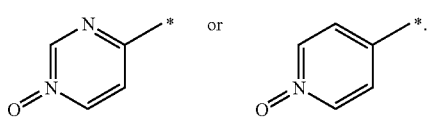

or a salt thereof in which n is 0 or any integer, preferably 0, 1 or 2; and $R_4$ is optionally substituted

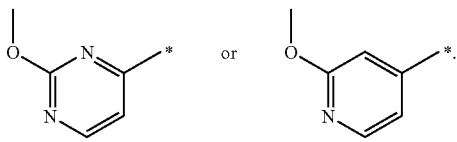

with the proviso that when $R_2$ is an alkyl from 1–3 carbon atoms, trifluoromethyl, diakylamino in which alkyl is 1–4 carbon atoms, pyrrolidino, piperidino, morpholino or piperazino, then $R_4$ is substituted.

$R_4$ substituents may be present on one or more vacant positions of a carbon and/or heteroatom of the pyrimidinyl, pyridinyl or imidazolyl rings. Examples of suitable substituents include, but are not limited to, oxygen, fluorine, chlorine, bromine or iodine atoms or methyl, ethyl, n-propyl, isopropyl, methoxy, ethoxy, n-propoxy, isopropoxy, trifluoromethyl, hydroxy, or optionally substituted amino groups. Particularly preferred $R_4$ substitutents include —$OCH_3$ and —NH-phenyl groups.

In still some embodiments, $R_4$ substitutents include N-oxides, for example:

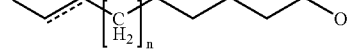

In still some embodiments, $R_4$ can be

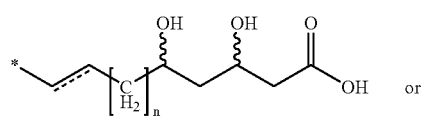

Particularly preferred $R_2$ groups include lower alkyl, e.g., an alkyl from one to four carbon atoms, dimethylamino, or 1-methylpropyl, and especially isopropyl, phenyl, or hydrogen.

In still some preferred embodiments, $R_5$ is phenyl which is monosubstituted with alkyl of from one to three carbon atoms, fluorine, chlorine, or trifluoromethyl; or phenyl which is disubstituted with two groups independently selected from alkyl of from one to three carbon atoms, fluorine, chlorine, or trifluoromethyl. Particularly preferred is 4-fluorophenyl or 3-trifluoromethylphenyl.

A particularly preferred group of compounds are those wherein $R_2$ is a hydrogen, phenyl, or isopropyl group; $R_5$ is a 3-trifluoromethylphenyl or 4-fluorophenyl group; and $R_4$ comprises a 4-pyridinyl group, a 4-pyrimidinyl group, or a 4-imidazolyl group, especially 2-methoxy-4-pyrimidinyl, 2-aminophenyl-4-pyrimidinyl, or 2-aminophenyl-4-pyridinyl. Within this particularly preferred group of compounds, those in which $R_5$ is a 3-trifluoromethylphenyl group are especially preferred A preferred group of compounds of formula VI are compounds of Formula VIa Formula VIa

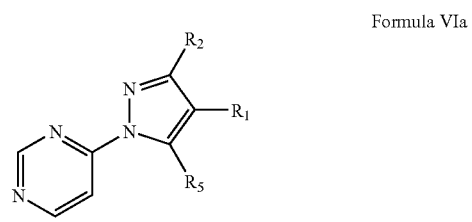

wherein $R_1$ is

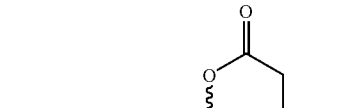 or preferably

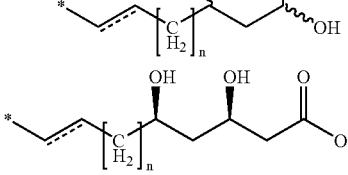 or

-continued

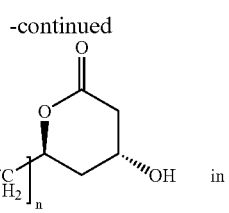 in which n is 0 or any integer, preferably 0, 1 or 2;
$R_2$ is optionally substituted alkyl, aryl, or heteroaryl;
the pyrimidinyl ring is optionally substituted;
and $R_5$ is optionally substituted aryl or heteroaryl, or a salt thereof, with the proviso that when $R_2$ is an alkyl from 1–3 carbon atoms, trifluoromethyl, diakylamino in which alkyl is 1–4 carbon atoms, pyrrolidino, piperidino, morpholino or piperazino, then $R_4$ is substituted.

In some embodiments, the pyrimidinyl ring is unsubstituted. In other emobdiments, the pyrimidinyl ring is substituted, e.g., with optionally substituted amino groups, especially —NH-phenyl, or with optionally substituted alkoxy groups, especially —O—$CH_3$.

Another preferred group of compounds of formula VI are compounds of formula VIb

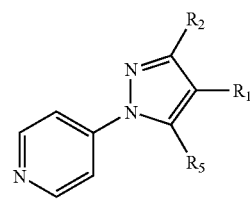

Formula VIb wherein $R_1$ is

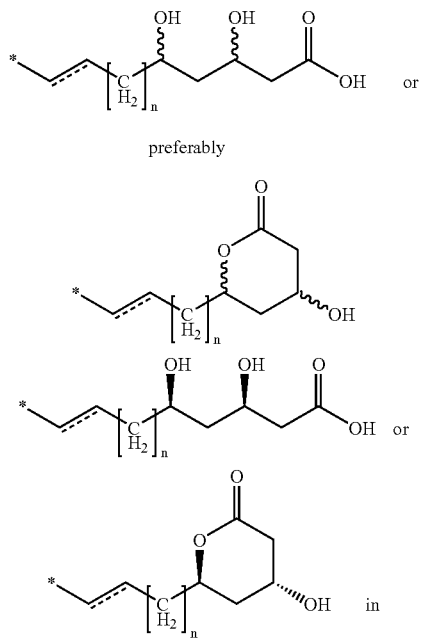

which n is 0 or any integer, preferably 0, 1 or 2;
$R_2$ is optionally substituted alkyl, aryl, or heteroaryl;
the pyridinyl ring is optionally substituted;
and $R_5$ is optionally substituted aryl or heteroaryl, or a salt thereof, with the proviso that when $R_2$ is an alkyl from 1–3 carbon atoms, trifluoromethyl, diakylamino in which alkyl is 1–4 carbon atoms, pyrrolidino, piperidino, morpholino or piperazino, then $R_4$ is substituted.

In some embodiments, the pyridinyl ring is unsubstituted. In other emobdiments, the pyridinyl ring is substituted, e.g., with optionally substituted amino groups, especially, —NH-phenyl.

Particularly preferred examples of compounds of the present invention include, but are not limited to, the following:

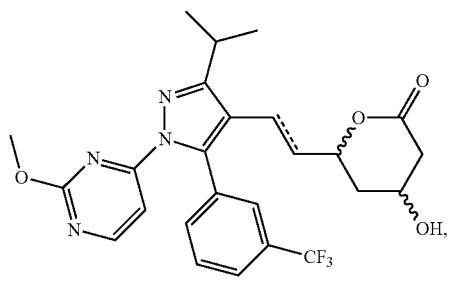

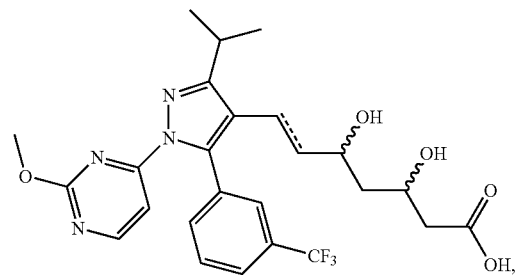

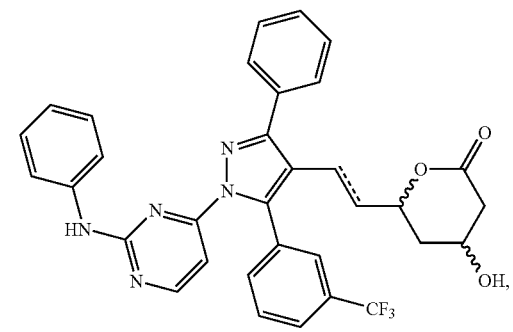

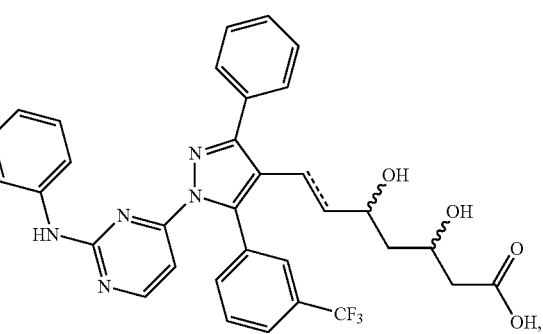

-continued
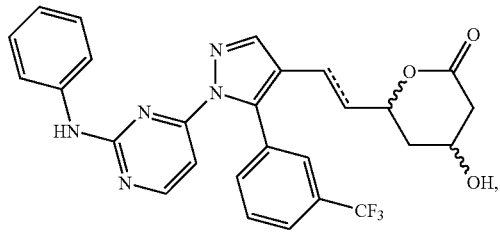
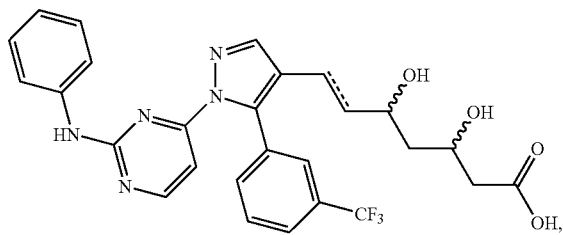
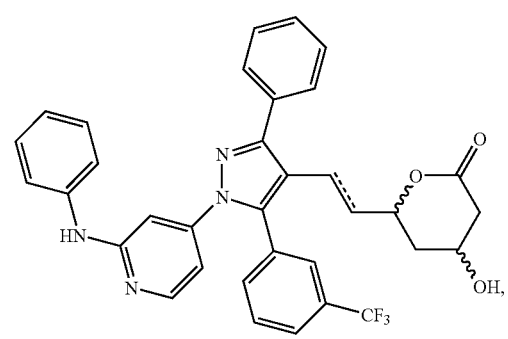
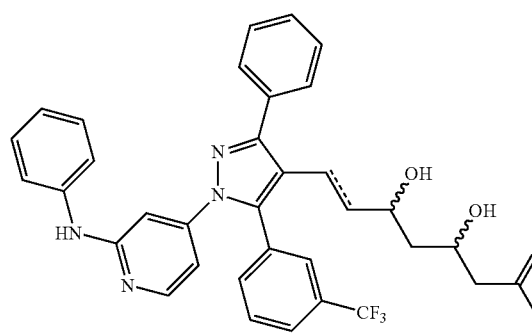
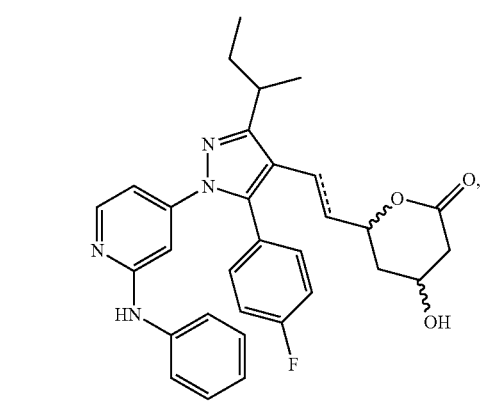
-continued
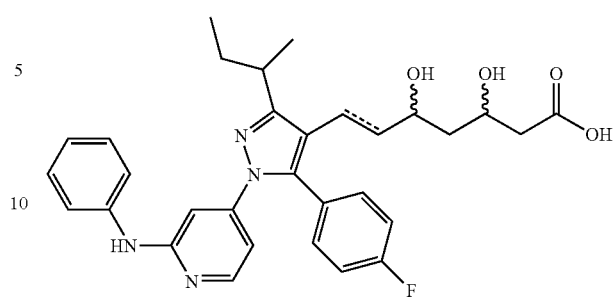
More particularly preferred examples of compounds of the present invention include, but are not limited to, the following:
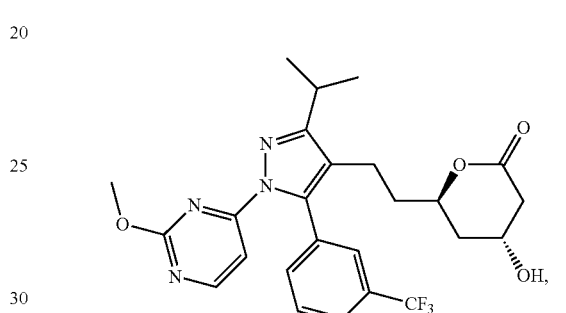
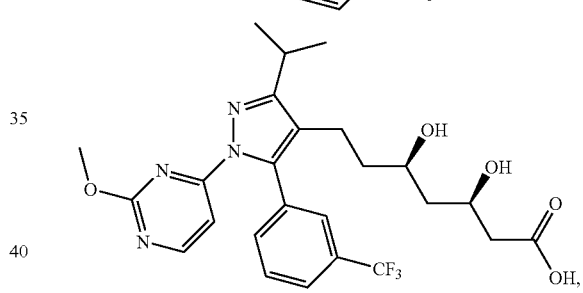
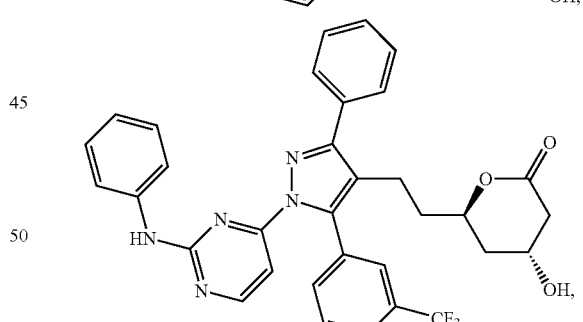
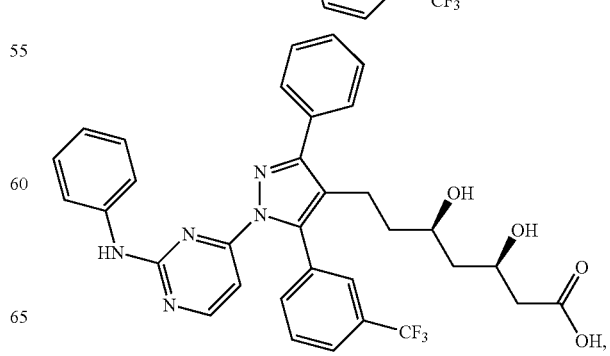

-continued
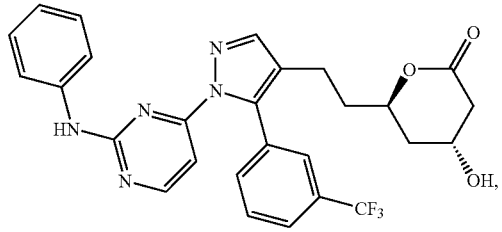
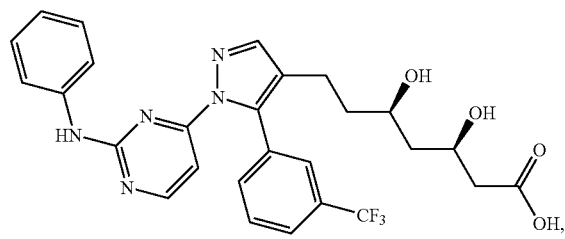
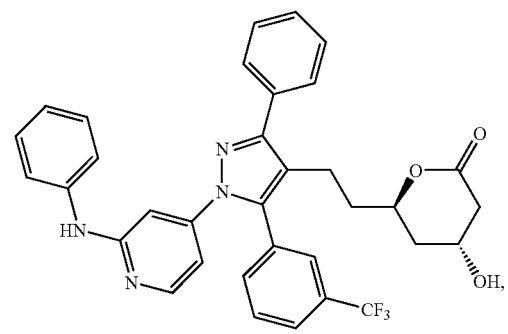
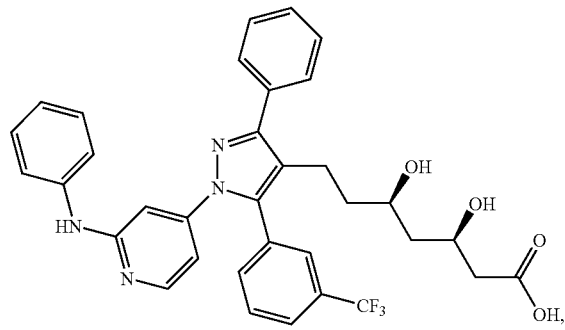
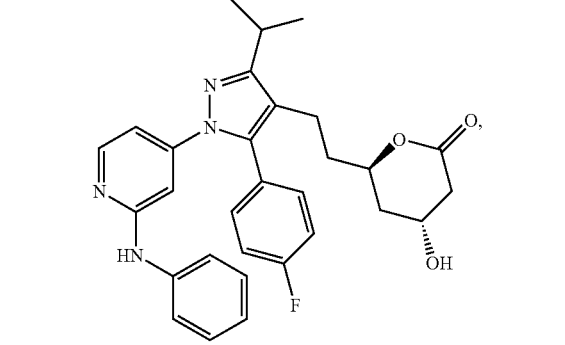
-continued
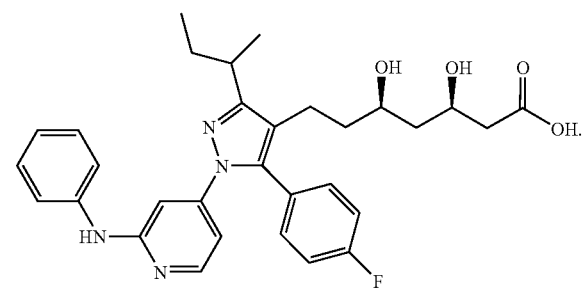
Other particularly preferred examples include, but are not limited to, the following:
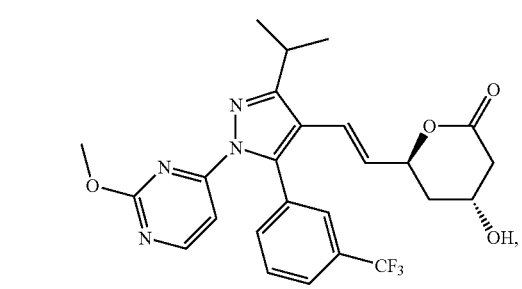
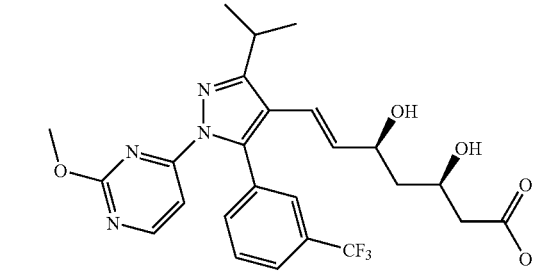
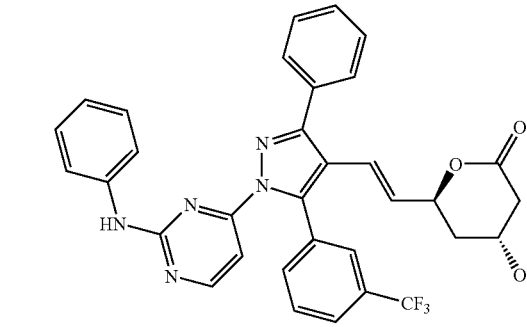
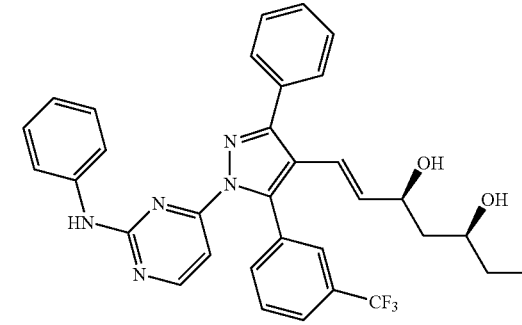

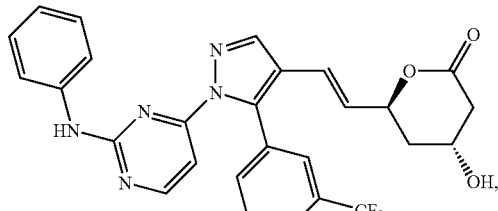

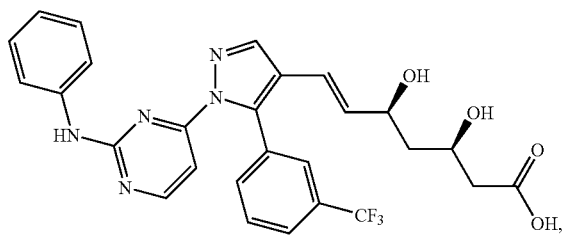

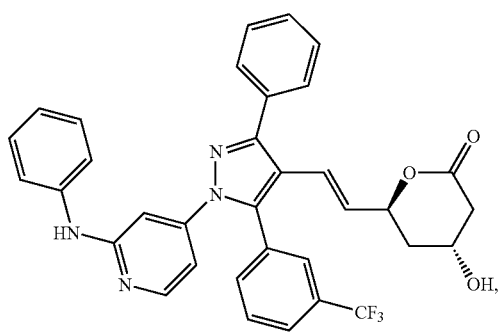

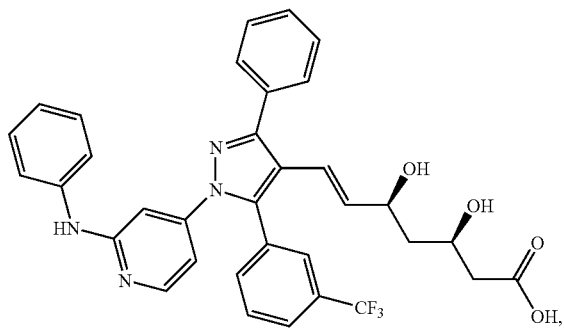

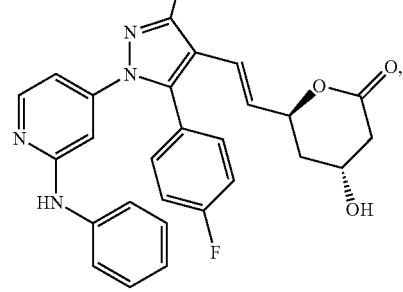

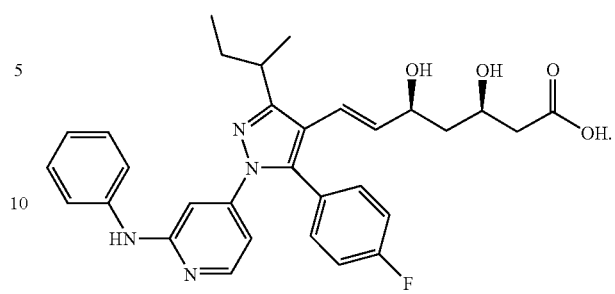

Compounds of the formula VI may be separated into diastereoisomeric pairs of enantiomers by, for example, fractional crystallization from a suitable solvent, for example MeOH or ethyl acetate or a mixture thereof. The pair of enantiomers may be separated into individual stereoisomers by, for example the use of an optically active amine as a resolving agent or on a chiral HPLC column. Racemic mixtures can be separated into their individual enantiomers by any of a number of conventional methods. These include chiral chromatography, derivatization with a chiral auxillary followed by separation by chromatography or crystallization, and fractional crystallization of diastereomeric salts.

Alternatively, any enantiomer of a compound of the general formula VI may be obtained by stereospecific synthesis using optically pure starting materials or reagents of known configuration. In preferred embodiments, compounds of formula VI are administered as enantiomerically pure (or substantially enantiomerically pure) formulations.

Details for synthesizing pyrazoles of formula VI of the invention are provided in Examples 10 and 11 below. Specifically, Example 10 provides examples of synthesizing four N-pyridyl pyrazoles and Example 11 provides examples of synthesizing eight N-pyrimidinyl pyrazoles.

E. Substituted Pyrrole Series

In some aspects of the invention, methods described herein employ a subset of the compounds of formulas I and II that are substituted pyrroles of formula VII

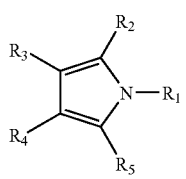

Formula VII where $R_1$ is

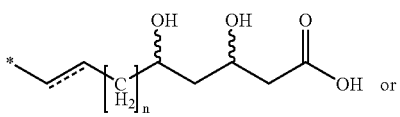

-continued

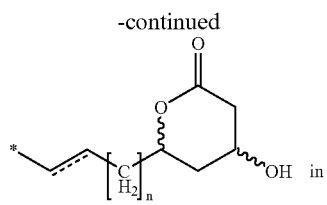

which n is 0 or any integer;

$R_2$ is optionally substituted alkyl, aryl or heteroaryl;

$R_3$ is any substituent;

$R_4$ is optionally substituted

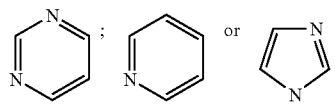

and $R_5$ is optionally substituted aryl or heteroaryl, or a salt thereof.

The dotted line in the bridging group of $R_1$ is meant to indicate that the bridging group may be either an ethyl (i.e., is —$CH_2$—$CH_2$—) or ethenyl (i.e., —CH=CH—) group. Also contemplated as falling within the scope of formula VII are salts, solvates, esters, tautomers, polymorphs, metabolites, prodrugs, N-oxides, sulfoxides or sulfones thereof. Preferred salts include those of calcium, sodium and potassium.

Also contemplated within the scope of Formula VII are compounds where the $R_4$ pyrimidinyl, pyridinyl or imidazolyl ring is attached via any available carbon or nitrogen atom of the ring.

In choosing compounds of the present invention, one of ordinary skill in the art will recognize that the various substituents, i.e. $R_1$, $R_2$, etc., are to be chosen in conformity with well-known principles of chemical structure connectivity.

The term "substituted" can include multiple degrees of substitution by a named substitutent. Where multiple substituent moieties are disclosed or claimed, the substituted compound can be independently substituted with one or more of the disclosed or claimed substituent moieties, singly or pluraly.

Compounds of formula VII contain one or more asymmetric centers and can thus occur as racemates and racemic mixtures, pure or substantially pure isomeric forms, single enantiomers, diastereomeric mixtures and individual diastereomers. The present invention is meant to comprehend all such isomeric forms of the compounds of formula VII.

In some preferred embodiments, n is 0, 1, 2 or 3. In some preferred embodiments, $R_1$ has the following stereochemistry:

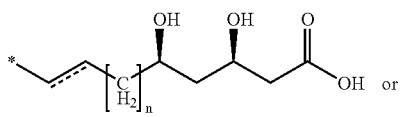

-continued

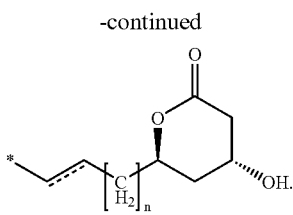

Some of the compounds described herein contain olefinic double bonds, and unless specified otherwise, are meant to include both E and/or Z geometric isomers. In some embodiments, the E geometric isomer is preferred.

Some of the compounds described herein may exist with different points of attachment of hydrogen, referred to as tautomers. Such an example may be a ketone and its enol form known as keto-enol tautomers. The individual tautomers as well as mixtures thereof are encompassed within compounds of formula VII.

In preferred embodiments, the compounds of the formula VII are MAP kinase inhibitors and/or are used in the methods wherein an inhibition of MAP kinase is desired, e.g., in the treatment of MAP kinase-related conditions.

In more preferred embodiments, a novel subset of compounds (or salts thereof) of formula VII are provided wherein $R_1$ is wherein $R_1$ is

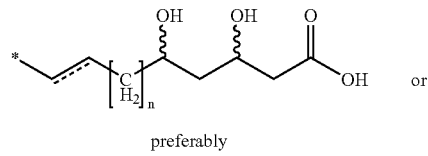

preferably

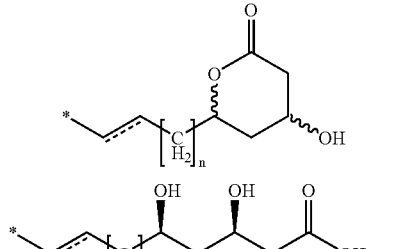

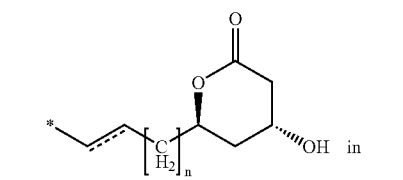

which n is 0 or any integer, preferably 0, 1 or 2; and $R_4$ is optionally substituted

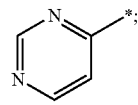

optionally substituted

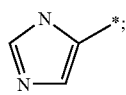

or substituted

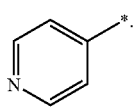

R$_4$ substituents may be present on one or more vacant positions of a carbon and/or heteroatom of the pyrimidinyl, pyridinyl or imidazolyl rings. Examples of suitable substituents include, but are not limited to, oxygen, methyl, ethyl, n-propyl, isopropyl, methoxy, ethoxy, n-propoxy, isopropoxy, trifluoromethyl, hydroxy, or optionally substituted amino groups. For example, in some embodiments, R$_4$ is the pyridinyl ring substituted with one or more optionally substituted amino groups. Particularly preferred R$_4$ substitutents include —OCH$_3$, —NH$_2$, —NH—CH$_3$, and —NH-Phenyl.

In still some embodiments, R$_4$ substitutents include N-oxides, for example:

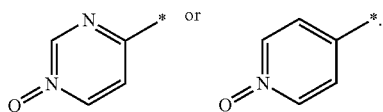

In still some embodiments, R$_4$ can be

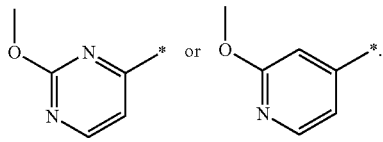

A particularly preferred group of compounds of formula VII are those wherein R$_2$ is a branched alkyl group such as isopropyl or isobutyl. Particularly preferred is isopropyl.

Another preferred class of compounds of formula VII are those compounds wherein R$_5$ is a substituted phenyl group and preferably contains from 1 to 3 substituents. Examples of suitable R$_5$ substituents include halogen atoms e.g. fluorine, bromine, chlorine, methoxy, methyl, ethyl, hydroxy, fluorophenyl or trifluoromethyl groups. Particularly preferred is 4-fluorophenyl or 3-trifluoromethylphenyl.

Another preferred class of compounds of formula VII are those compounds wherein R$_3$ is —CONH—W, where W is optionally substituted phenyl. Examples of suitable substituents include, but are not limited to, fluorine, chlorine, bromine or iodine atoms or methyl, ethyl, n-propyl, isopropyl, methoxy, ethoxy, n-propoxy, isopropoxy, trifluoromethyl, hydroxy, or optionally substituted amino groups. Particularly preferred are compounds in which W is unsubstituted phenyl.

A particularly preferred group of compounds are those wherein R$_2$ is isopropyl; R$_5$ is 4-fluorophenyl; R$_3$ is —CONH-phenyl; and R$_4$ comprises a 4-pyrimidinyl group, 2-methyl-4-pyridinyl group, a 2-amino-4-pyridinyl group, a 2-aminophenyl-4-pyridinyl group, a 2-aminomethyl-4-pyrimidinyl group, a 2-aminomethyl-4-pyridinyl group, or a 4-imidazolyl group, especially 4-primidinyl, 2-methoxy-4-pyrimidinyl, 2-amino-4-pyrimidinyl, or 2-aminophenyl-4-pyrimidinyl.

A preferred group of compounds of formula VII are compounds of formula VIIa

Formula VIIa

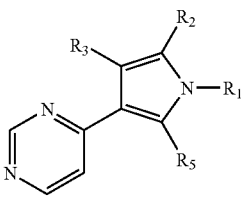

wherein R$_1$ is

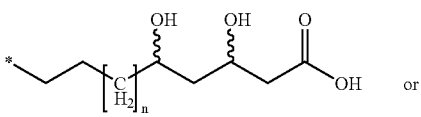

preferably

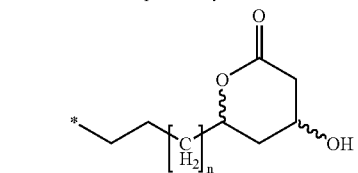

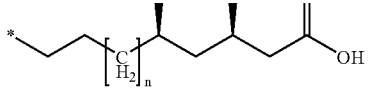

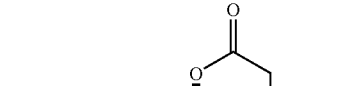

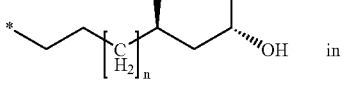

in which n is 0 or any integer, preferably 0, 1 or 2;

R$_2$ is optionally substituted alkyl, aryl, or heteroaryl;

the pyrimidinyl ring is optionally substituted;

and R$_5$ is optionally substituted aryl or heteroaryl, or a salt thereof.

In some embodiments, the pyrimidinyl ring is unsubstituted. In other emobdiments, the pyrimidinyl ring is substituted, e.g., with optionally substituted amino groups, especially —NH$_2$ or —NH-phenyl, or with optionally substituted alkoxy groups, especially —O—CH$_3$.

Another preferred group of compounds of formula VI are compounds of formula VIIb

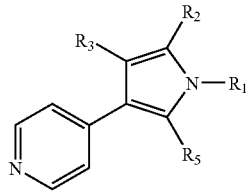

Formula VIIb wherein R₁ is

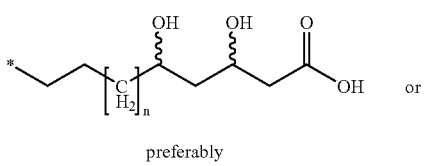

preferably

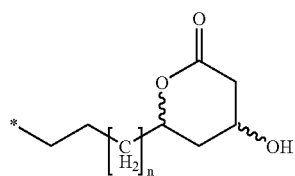

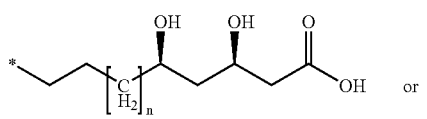 or

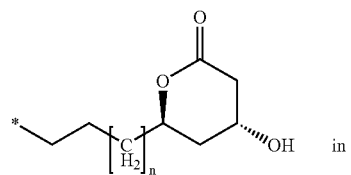 in which n is 0 or any integer, preferably 0, 1 or 2;
R₂ is optionally substituted alkyl, aryl, or heteroaryl;
the pyridine ring is substituted;
and R₅ is optionally substituted aryl or heteroaryl, or a salt thereof.

Particularly preferred examples of compounds of the present invention include, but are not limited to, the following:

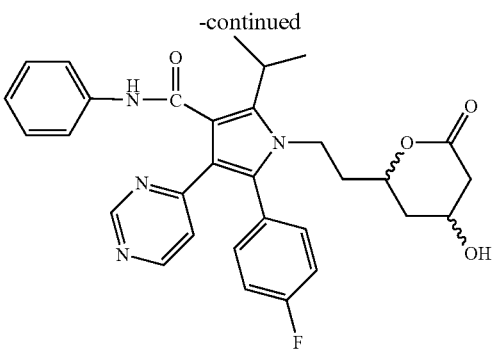

-continued

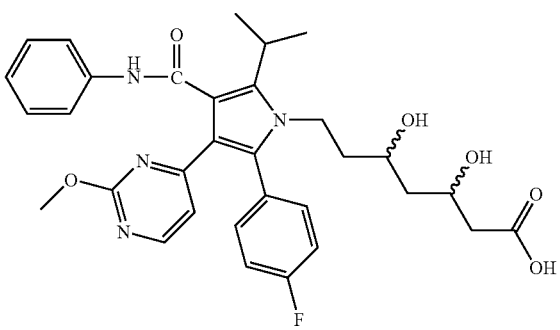

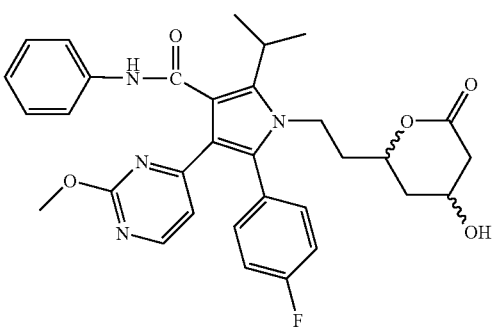

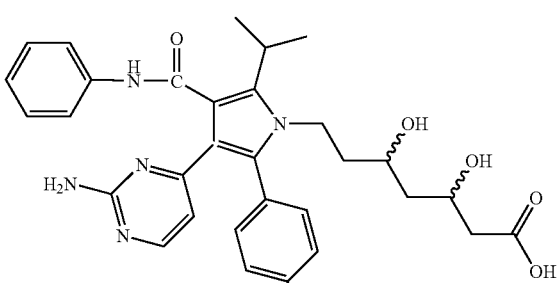

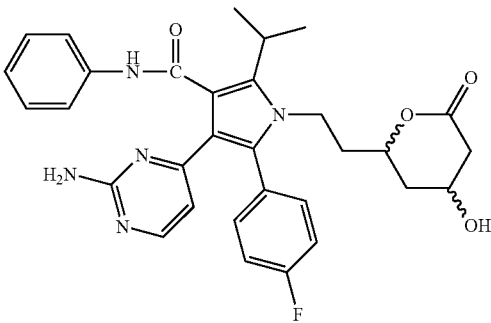

-continued
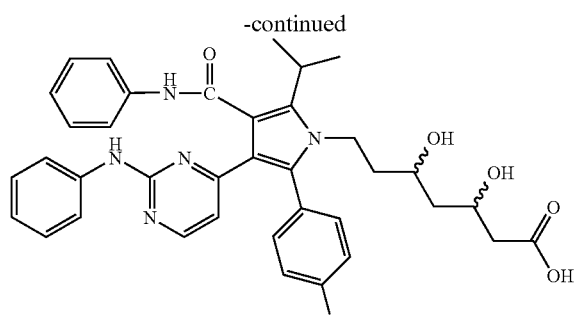
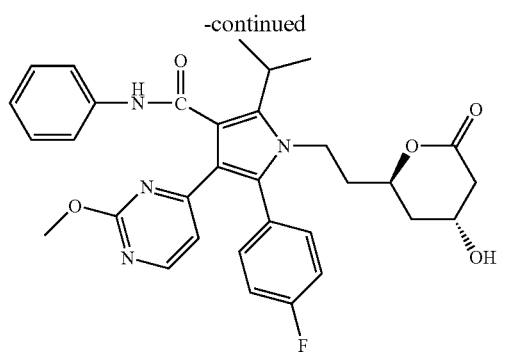
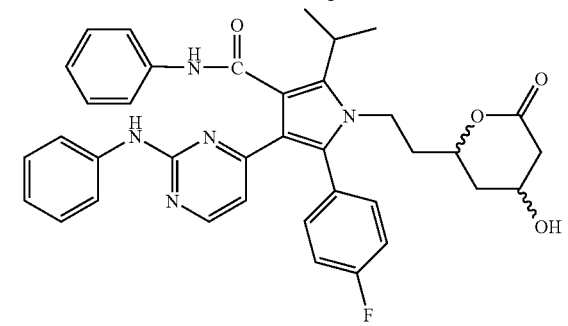
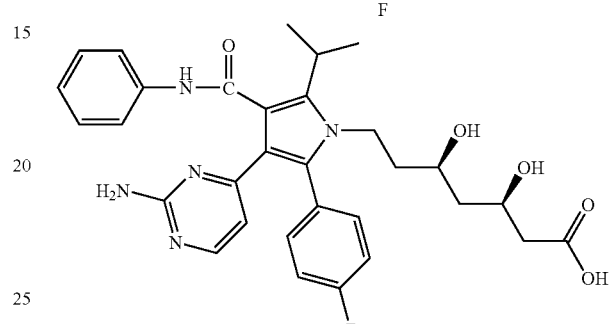
More particularly preferred examples of compounds of the present invention include, but are not limited to, the following:
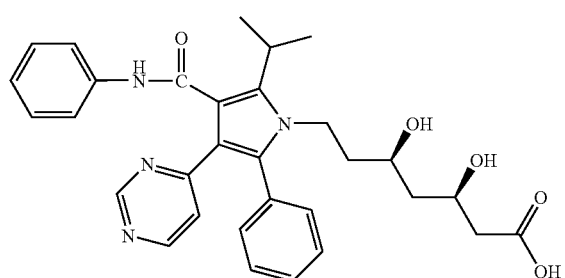
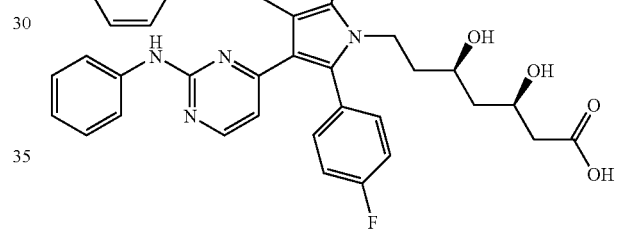
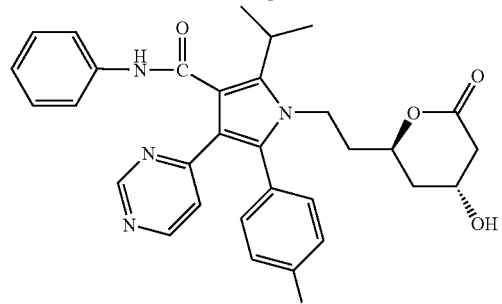
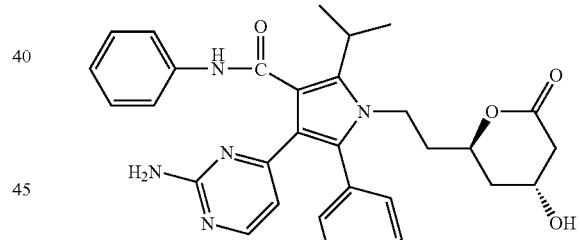
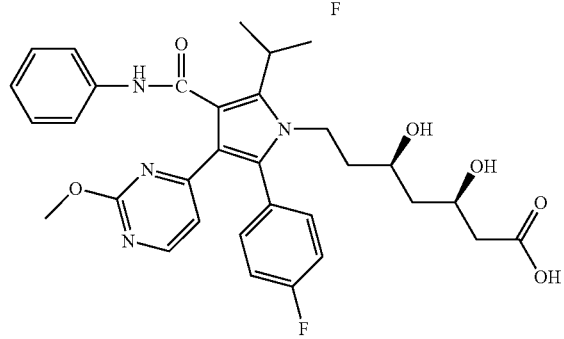
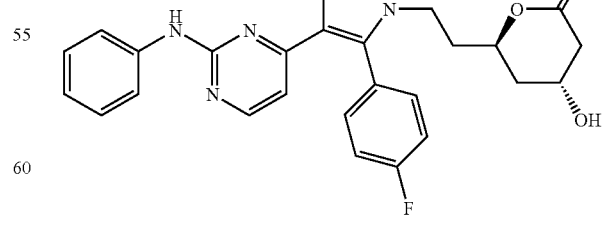
Compounds of the formula VII may be separated into diastereoisomeric pairs of enantiomers by, for example, fractional crystallization from a suitable solvent, for example MeOH or ethyl acetate or a mixture thereof. The pair of enantiomers may be separated into individual stereoisomers by, for example the use of an optically active amine as a resolving agent or on a chiral HPLC column. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Alternatively, any enantiomer of a compound of the general formula VII may be obtained by stereospecific synthesis using optically pure starting materials or reagents of known configuration. In preferred embodiments, compounds of formula VII are administered as enantiomerically pure (or substantially enantiomerically pure) formulations.

Details for synthesizing pyrroles of formula VII of the invention are provided in Example 12 below.

F. Combinations of a Statin Lactone and Another Active Agent

In another aspect, the present invention provides compositions comprising combinations of a statin lactone with one or more additional active agents, preferably a pharmacologically active agent. Some embodiments include combinations comprising two or more statin lactones; two or more hydroxy acid forms of a statin; two or more non-statin anti-inflammatory agents; a statin lactone and a hydroxy acid form of a statin; a non-statin anti-inflammatory agent and a statin lactone; and a non-statin anti-inflammatory agent and a hydroxy acid form of a statin. In some embodiments, such combinations have molar ratios of about 99:1 to about 1:99. Preferably, the range of molar ratios is selected from about 80:20 to about 20:80; about 75:25 to about 25:75, about 70:30 to about 30:70, about 66:33 to about 33:66; about 60:40 to about 40:60; about 50:50; and about 90:10 to about 10:90. More preferably the molar ratio is about 1:9, and most preferably about 1:1.

In some embodiments, a statin lactone is combined with the hydroxy acid form of the same or a different statin, or a pharmaceutically acceptable salt thereof. In some embodiments, the statin lactone and hydroxy acid (or salt) forms may be combined in molar ratios of about 99:1 to about 1:99. Preferably, the range of molar ratios of statin lactone: hydroxy acid (or salt) is selected from about 80:20 to about 20:80; about 75:25 to about 25:75, about 70:30 to about 30:70; about 66:33 to about 33:66; about 60:40 to about 40:60; about 50:50; and about 90:10 to about 10:90. More preferably the molar ratio of statin lactone: hydroxy acid (or salt) is about 1:9, and most preferably about 1:1.

The statin lactone is preferably at least one lactone selected from fluvastatin lactone, simvastatin lactone, lovastatin lactone, rosuvastatin lactone, pitavastatin lactone, glenvastatin lactone, cerivastatin lactone, pravastatin lactone, mevastatin lactone, bervastatin lactone and dalvastatin lactone, and most preferably is atorvastatin lactone. The statin hydroxy acid (or salt) is preferably at least one acid (or salt) selected from fluvastatin, simvastatin, lovastatin, rosuvastatin, pitavastatin, glenvastatin, cerivastatin, pravastatin, mevastatin, bervastatin and dalvastatin, and most preferably is atorvastatin and/or pitavastatin. For example, in some embodiments, the calcium salt of atorvastatin and/or the sodium salt of pitavastatin may be used. Still some embodiments use the sodium salt of cerivastatin, also known as rivastatin; the sodium salt of fluvastatin; and/or nisvastatin, also referred to as NK-104. See, e.g., Drugs of the Future, 1999, 24(5), pp. 511–513.

Additional details of compositions comprising a statin lactone combined with a hydroxy acid (or salt) form of a statin are provided in Example 4. Specifically, Example 4a describes a gel formulation comprising atorvastatin lactone and atorvastatin calcium, at a ratio of 1:1. Example 4b describes a tablet formulation comprising atorvastatin lactone and atorvastatin calcium, at a ratio of 1:1. Example 4c describes a tablet formulation comprising atorvastatin lactone and pitavastatin calcium, at a ratio of 1:1.

In some embodiments, a statin lactone is combined with a non-statin anti-inflammatory agent. For example, the statin lactone and non-statin anti-inflammatory agent may be combined in molar ratios of about 99:1 to about 1:99. Preferably, the range of molar ratios of statin lactone: non-statin anti-inflammatory agent is selected from about 80:20 to about 20:80; about 75:25 to about 25:75, about 70:30 to about 30:70, about 66:33 to about 33:66; about 60:40 to about 40:60; about 50:50; and about 90:10 to about 10:90. More preferably the molar ratio of statin lactone: non-statin anti-inflammatory agent is about 1:9, and most preferably about 1:1. The statin lactone is preferably at least one lactone selected from fluvastatin lactone, simvastatin lactone, lovastatin lactone, rosuvastatin lactone, pitavastatin lactone, glenvastatin lactone, cerivastatin lactone, pravastatin lactone, mevastatin lactone, bervastatin lactone and dalvastatin lactone, and most preferably is atorvastatin lactone.

A non-statin anti-inflammatory agent can be any agent that is not a statin lactone or a hydroxy acid form of a statin or salt thereof. Preferably, the non-statin anti-inflammatory agent can be selected from among immunosuppressive agents, steroidal anti-inflammatory agents, anti-histamines, mast cell stabilizers and anti-autocoids, protein kinase inhibitors, MAP kinase inhibitors, p38 MAP kinase inhibitors, disease-modifying anti-rheumatic drugs (DMARDs) and, more preferably, non-steroidal anti-inflammatory agents (NSAIDs).

Preferred immunosuppressive agents include, e.g., mycophenolate mofetil, cyclosporine, azathioprine, tacrolimus, pimecrolimus, sirolimus, and the like. Preferred steroidal anti-inflammatory agents include, e.g., prescription and non-prescription topical and aerosol corticosteroids, cortisone, cortisone acetate, hydrocortisone, dexamethasone, dexamethasone phosphate salts, prednisone, prednisolone phosphate salts, prednisolone, methyprednisolone, methylprednisolone acetate, beclomethasone, beclomethasone dipropionate, budesonide, ciclesonide, flunisolide, triamcinolone acetonide, and the like.

Preferred non-steroidal anti-inflammatory agents (NSAIDs) include, e.g., salicylates, acetyl salicylic acid, sodium salicylate, colchicine, choline magnesium trisalicylate, salsalate, diflunisal, salicylsalicylic acid, sulfasalazine, olsalazine, indomethacin, sulindac, etodolac, macrolide immunosuppressives, tolmetin, clobetasol, dapsone, diflorasone, halobetasol, diclofenac, ketorolac, ibuprofen, naproxen, flurbiprofen, ketoprofen, fenoprofen, oxaprozin, mefanamic acid, meclofenamic acid, para-aminophenols, propionic acids, piroxicam, tenoxicam, meloxicam, nimesulide, phenylbutazone, oxyphenthatrazone, nabumetone, darbufelone, licofelone, rofecoxib, celecoxib, etoricoxib, valdecoxib, lumiracoxib, cimicoxib, parecoxib, BMS-347070, LAS-34475, GW-406,381, CS-501, P-54, FK-3311, S-2474, ajulemic acid, and the like, as well as pharmaceutically acceptable salts thereof. Other preferred NSAIDs include, e.g., prostaglandins, leukotrienes and thromboxanes, and other agents which inhibit cyclooxygenase enzymes, especially, specific cyclooxygenase inhibitors.

Additional details of compositions comprising a statin lactone combined with a non-statin anti-inflammatory agent are provided in Example 4. Specifically, Example 4d describes an ointment comprising atorvastatin lactone and the non-statin anti-inflammatory agent naproxen sodium, at a ratio of 1:1. Example 4e describes an ointment comprising atorvastatin lactone and the non-statin anti-inflammatory agent diclofenac, at a ratio of 1:1. Example 4f describes a rectal suppository comprising atorvastatin lactone and the non-statin anti-inflammatory agent aminosalicylic acid, at a ratio of 1:9. Examples 4g, 4h, and 4i describe an ointment, a gel and a cream, respectively, each comprising atorvastatin lactone and the non-statin anti-inflammatory indomethacin, each at a ratio of 1:1.

In some embodiments of the present invention, a composition comprising two or more of the aforementioned compounds, forms, and/or agents provides a synergistic effect. A synergistic effect can refer to one in which two or more compounds, forms and/or agents work together to produce a total effect superior to and/or greater than that of any one compound, form and/or agent alone. For example, the total effect may be a greater percentage increase in inhibition of a MAP kinase and/or a greater percentage increase in the inhibition of a MAP kinase-related in vitro and/or in vivo effect and/or a greater percentage increase in effectiveness in treating a MAP kinase-related condition. For example, a synergistic effect may be at least about a 5%, at least about a 10%, at least about a 15%, at least about a 20%, at least about a 30%, at least about a 40%, at least about a 50%, at least about a 60%, at least about a 70%, or at least about an 80% greater increase.

In preferred embodiments, combinations of a statin lactone and one or more other active agents show a synergistic effect on reducing or inhibiting inflammation. For example, use of a combination of the present invention may provide a greater percentage decrease in swelling due to inflammation compared to the effect using one or other of components of the combination alone. For example, in some embodiments, a combination of atorvastatin lactone with atorvastatin hydroxy acid (or salt); atorvastatin lactone with pitavastatin hydroxy acid (or salt); or atorvastatin lactone with indomethacin produce synergistic effects on reducing or inhibiting inflammation, compared to the effect using atorvastatin lactone alone, atorvastatin hydroxy acid (or salt) alone, pitavastatin hydroxy acid (or salt) alone, and/or indomethacin alone. Without being limited to a given hypotheis, theory and/or mechanism of action, the atorvastatin lactone may act by inhibiting p38α MAP kinase, centrally involved in inflammatory signaling cascades as discussed above. Additional details or such combinations providing synergistic effects on inflammation reduction or inhibition are provided in Example 8 below, e.g., where treatment with formulations comprising a combination of atorvastatin lactone and the non-statin anti-inflammatory agent indomethacin provides synergistic inhibitory effects on inflamamtion.

II. Methods of Treatment

Another aspect of the present invention relates to methods of using pharmaceutical compositions and kits comprising compounds described herein to treat kinase-related and/or reductase-related compounds, preferably MAP kinase-related and/or HMG-CoA reductase-related conditions, as well as novel uses of known compounds for the treatment of MAP kinase-related conditions, and novel combinations for the treatment of MAP kinase- and/or HMG CoA reductase-related conditions, especially inflammatory conditions.

The present invention provides methods, pharmaceutical compositions, and kits for the treatment of animal subjects. The term "animal subject" as used herein includes humans as well as other mammals. The term "treating" as used herein includes achieving a therapeutic benefit and/or a prophylactic benefit. By therapeutic benefit is meant eradication or amelioration of the underlying disorder being treated. For example, in an arthritic patient, therapeutic benefit includes eradication or amelioration of the underlying arthritis. Also, a therapeutic benefit is achieved with the eradication or amelioration of one or more of the physiological symptoms associated with the underlying disorder such that an improvement is observed in the patient, notwithstanding the fact that the patient may still be afflicted with the underlying disorder. For example, a MAP kinase inhibitor of the present invention provides therapeutic benefit not only when rheumatoid arthritis is eradicated, but also when an improvement is observed in the patient with respect to other disorders or discomforts that accompany rheumatoid arthritis, like stiffness or swelling in the joints. Similarly, compositions of the present invention can provide therapeutic benefit in ameliorating other symptoms associated with MAP kinase-related conditions, e.g., inflammatory and/or autoimmune conditions, including redness, rashes, swelling, itching, irritation, dryness, scaling, flaking, pain, temperature increase, loss of normal function, and the like.

For prophylactic benefit, a pharmaceutical composition of the invention may be administered to a patient at risk of developing a MAP kinase-related condition and/or a HMG-CoA reductase-related condition, or to a patient reporting one or more of the physiological symptoms of such conditions, even though a diagnosis of the condition may not have been made. Administration may prevent the condition from developing, or it may reduce, lessen, shorten and/or otherwise ameliorate the condition that develops.

A. Treatment of MAP Kinase-Related Conditions

The term "MAP kinase-related condition" as used herein refers to a condition in which directly or indirectly reducing the activity of a protein kinase involved in signaling cascades of an allergic, inflammatory and/or an autoimmune response is desirable, and/or directly or indirectly reducing the production and/or effects of one or more products of the protein kinase is desirable. For example, a MAP kinase-related condition may involve over-production or unwanted production of one or more pro-inflammatory cytokines, such as tumor necrosis factor-α (TNF-α), interleukin-1β (IL-1β), or other chemical messengers of signal transduction pathways associated with inflammation (including responses to and expression of TNF-α and IL-1β), apoptosis, growth and differentiation.

Examples of MAP kinase-related conditions include but are not limited to allergic, inflammatory and autoimmune conditions, such as, for example, ocular allergic, ocular inflammatory and/or ocular autoimmune conditions; allergic, inflammatory and/or autoimmune conditions of the ear; allergic, inflammatory and/or autoimmune conditions of the skin and skin structures; gastrointestinal allergic, gastrointestinal inflammatory and/or gastrointestinal autoimmune conditions; respiratory allergic, respiratory inflammatory and/or respiratory autoimmune conditions; as well as arthritis, rheumatoid arthritis, and/or other inflammatory/autoimmune diseases of the musculoskeletal system; osteoarthritis; vascular inflammatory conditions, vasculitis, inflammatory bowel disease (including ulcerative colitis and Crohn's disease), Celiac sprue, acne, psoriasis (as well as other papulosquamous disorders such as lichen planus), topical dermatitis; atopic dermatitis (including eczema), irritant contact dermatitis, endotoxemia, restenosis, sepsis, and toxic shock syndrome, as well as transplant rejection. Other MAP kinase-related conditions include ageing, photoageing, cachexia, leprosy, Leishmaniasis, asthma, chronic pelvic pain, inflammatory muscle disease, allergic rhinitis (hay fever), gastritis, vaginitis, conjunctivitis, interstitial cystitis, chronic fatigue syndrome, osteoporosis, scleroderma, and the like. MAP-kinase related conditions can also include diabetes, chronic obstructive pulmonary disease, as well as cardiovascular-related conditions such as atherosclerosis, myocardial infarction, congestive heart failure, ischemic-reperfusion injury and other vascular inflammatory conditions. MAP-kinase related conditions can also include proliferative disorders, including cancers, e.g., multiple myeloma, fibrotic disorders, mesangial cell proliferative disorders, such as glomerulonephritis, diabetic nephropathy malignant nephrosclerosis, thrombotic microangiopathy syndromes, organ transplant rejection and glomerulopathies. MAP-kinase related condition can also include neurodegenerative diseases, e.g. Alzheimer's and pain sensation, as well as infectious diseases such as viral, bacterial, and fungal infections.

Other conditions treatable with compositions, kits, and methods of the present invention include those currently treated with soluble TNF receptors, anti-TNF antibodies, IL-1 receptor antagonists, TNF-α converting enzyme inhibitors, inhibitors of protein-tyrosine kinases and/or inhibitors of protein serine/threonine kinases of the MAP kinase family, preferably including conditions currently treated with inhibitors of p38 MAP kinases and/or the stress-activated protein kinases/Jun N-terminal kinases (SAPKs/JNKs). Most preferably, conditions treatable with the practice of this invention include those relating to p38α MAP kinase, e.g, conditions currently treated by inhibition of p38α MAP kinase activity.

Reducing the activity of a protein kinase, e.g. a MAP kinase, is also referred to as "inhibiting" the kinase. The term "inhibits" and its grammatical conjugations, such as "inhibitory," do not require complete inhibition, but refer to a reduction in kinase activity. Such reduction is preferably by at least about 50%, at least about 75%, at least about 90%, and more preferably by at least about 95% of the activity of the enzyme in the absence of the inhibitory effect, e.g., in the absence of an inhibitor. Conversely, the phrase "does not inhibit" and its grammatical conjugations refer to situations where there is less than about 20%, less than about 10%, and preferably less than about 5%, of reduction in enzyme activity in the presence of the compound. Further the phrase "does not substantially inhibit" and its grammatical conjugations refer to situations where there is less than about 30%, less than about 20%, and preferably less than about 10% of reduction in enzyme activity in the presence of the compound.

The ability to reduce enzyme activity is a measure of the potency or the activity of a compound, or combination of compounds, towards or against the enzyme. Potency is preferably measured by cell free, whole cell and/or in vivo assays in terms of IC50, $K_i$ and/or ED50 values. An IC50 value represents the concentration of a compound required to inhibit enzyme activity by half (50%) under a given set of conditions. A $K_i$ value represents the equilibrium affinity constant for the binding of an inhibiting compound to the enzyme. An ED50 value represents the dose of a compound required to effect a half-maximal response in a biological assay. Further details of these measures will be appreciated by those of ordinary skill in the art, and can be found in standard texts on biochemistry, enzymology, and the like.

In some embodiments, compounds in one or more forms represented by formulas I, II, III, and IV inhibit a MAP kinase. These compounds can exert anti-inflammatory effects in vitro and/or in vivo and can form the basis for pharmaceutical compositions useful in the treatment of MAP kinase-related conditions, e.g., allergic, inflammatory and/or autoimmune diseases, in humans and other mammals. In certain embodiments, for example, these compositions reduce production of, and signaling pathways involving, TNF-α and IL-1β.

As noted above, a subset of the compounds of formulas I and II are novel analogs of known inhibitors of MAP kinases, wherein X comprises a lipophilic MAP kinase inhibitor or a lipophilic moiety or analog thereof. Some of these analogs retain MAP kinase inhibitory activity in the lactone and/or acid forms, and are useful in the practice of this invention, e.g. in a method of treating a MAP kinase-related condition by administering to a subject an effective amount of at least one of such compounds. For example, certain lactone derivatives illustrated in FIG. 5 are preferred in some embodiments, as described in detail above.

Also as noted above, a subset of the compounds of formulas I and II are novel analogs of known inhibitors of HMG-CoA reductase, wherein X comprises a lipophilic moiety of an HMG-CoA reductase inhibitor, e.g., a statin, a synthetic statin, or an analog thereof. Some of these analogs display MAP kinase inhibitory activity in the lactone and/or acid forms, and are useful in the practice of this invention, e.g. in a method of treating a MAP kinase-related condition by administering to a subject an effective amount of at least one of such compounds. For example, certain lactone derivatives illustrated in FIG. 7 are preferred in some embodiments, as described in detail above, while the specific lactone derivatives illustrated in FIG. 8 are even more preferred. In some embodiments, the acid forms of such compounds also display MAP kinase inhibitory activity. In some preferred embodiments, MAP kinase inhibition is not reversed by addition of farnesyl pyrophosphate, geranyl geranyl pyrophosphate, mevalonate or any downstream product of mevalonate. In some embodiments, the lactone form does not inhibit or does not substantially inhibit HMG-CoA reductase. In some preferred embodiments, a lactone form may be formulated into solutions, suspensions, ointments and/or suppositories for topical application and/or rectal administration. The formulation may be applied to regions of inflammation, e.g., to exert a local effect, as described in more detail below. Preferably, in such embodiments, little or no systemic effects are observed Another subset of the compounds of formula I are known inhibitors of HMG-CoA reductase, including mevasatin, lovastatin, simvastatin, pravastatin, fluvastatin, atorvastatin, cerivastatin, rosuvastatin, pitavastatin, glenvastatin, bervastatin, dalvastatin, eptastatin, dihydroeptastatin, itavastatin, L-154819, advicor, L-654969, and other statin drugs used to treat disorders such as hypercholesterolemia.

In the case of these compounds, the present invention relates to the use of the corresponding lactones of formula I in treating MAP kinase-related conditions, e.g., inflammatory diseases, in particular conditions where inhibiting p38α MAP kinase activity is desirable and where a synthetic statin lactone is used. For instance, such compounds find use in treating an inflammatory condition by administering an effective amount of a statin lactone to a subject where the lactone inhibits a MAP kinase. For example, the statin lactones illustrated in FIG. 6 are preferred in some embodiments for treating MAP kinase-related conditions. More preferred statin lactones are those derived from atorvastatin, fluvastatin, rosuvastatin, cerivastatin, pitavastatin and glenvastatin. In some preferred embodiments, MAP kinase inhibition is not reversed by addition of farnesyl pyrophosphate, geranyl geranyl pyrophosphate, mevalonate or any downstream product of mevalonate. In some preferred embodiments, the lactone is not hydrolyzed, or not substantially hydrolyzed, to an acid form. In some such embodiments, the lactone does not inhibit or does not substantially inhibit HMG-CoA reductase. In some of these preferred embodiments, a lactone form may be formulated into solutions, suspensions, ointments and/or suppositories for topical application and/or rectal administration. The formulation may be applied to regions of inflammation, e.g., to exert a local effect, as described in more detail below. Preferably, in such embodiments, little or no systemic effects are observed. In some embodiments, the acid forms of such compounds also display MAP kinase inhibitory activity.

Table I illustrates in vitro inhibition of p38α MAP kinase activity by lactone derivatives of each of two classes of statins.

TABLE I

| Compound | IC50 p38α |
|---|---|
| Atorvastatin calcium | >100 μM |
| Atorvastatin lactone | 20 μM |
| Fluvastatin sodium | 34 μM |
| Fluvastatin lactone | 45 μM |
| Rosuvastatin calcium | 92 μM |
| Rosuvastatin lactone | >100 μM |
| Simvastatin sodium | >100 μM |

The δ-lactone forms of atorvastatin and fluvastatin show inhibitory activity against human p38α MAP kinase. Atorvastatin lactone gave an IC50 of about 20 μM, while fluvastatin lactone exhibited an IC50 value of about 45 μM in some embodiments. Also, the acid/salt form of fluvastain (e.g., fluvastatin sodium) inhibits p38α MAP kinase, showing an IC50 of about 34 μM in some embodiments.

Further, certain lipophilic MAP kinase inhibitors as well as lipophilic moieties and analogs thereof, having structures that favor a closed ring structure or cyclic form, including compounds of formulas III and IV described above, can also display MAP kinase inhibitory activity. Structures comprising a lipophilic MAP kinase inhibitor or a lipophilic moiety thereof, for example the MAP kinase inhibitors of FIG. 4, as well as lipophilic moieties or analogs thereof, such as those of FIG. 5, are preferred in some embodiments.

Further, certain analogs of known lipophilic HMG-CoA reductase inhibitors having structures modified to favor a closed ring structure or cyclic form, including compounds of formulas III and IV described above, can also display MAP kinase inhibitory activity. Such structures can be useful in the practice of this invention, e.g., in a method of treating a MAP kinase-related condition by administering to a subject an effective amount of at least one of such compounds. In some embodiments, a compound of formula III or IV does not inhibit or does not substantially inhibit HMG-CoA reductase. Structures comprising a statin or a lipophilic moiety of a statin, for example, the statins of FIG. 6, as well as lipophilic moieties of statin analogs, such as those of FIGS. 7 and 8, are preferred in some embodiments. More preferred embodiments include des-oxo and δ-lactam derivatives from a synthetic statin, or des-oxo and δ-lactam derivatives from atorvastatin, fluvastatin rosuvastatin, cerivastatin, pitavastatin and glenvastatin, as described above.

The present invention also includes kits that can be used to treat a MAP kinase-related conditions. These kits comprise a compound or combination of compounds described herein and preferably instructions teaching the use of the kit according to the various methods and approaches described herein. Such kits also include information, such as scientific literature references, package insert materials, clinical trial results, and/or summaries of these and the like, which indicate or establish the activities and/or advantages of the compound. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like.

B. Treatment of HMG-CoA Reductase-Related Conditions

The term "HMG-CoA reductase-related condition" as used herein refers to a condition in which directly or indirectly reducing the activity of HMG-CoA reductase is desirable and/or directly or indirectly reducing the production and/or effects of one or more products of HMG-CoA reductase is desirable. For example, an HMG-CoA reductase-related condition may involve elevated levels of cholesterol, in particular, non-HDL cholesterol in plasma, such as elevated levels of LDL cholesterol. Typically, a patient is considered to have high or elevated cholesterol levels based on a number of criteria, for example, see Pearlman, *Postgrad. Med.* 112(2):13–26 (2002), incorporated herein by reference. Guidelines include serum lipid profiles, such as LDL compared with HDL levels.

Examples of HMG-CoA reductase-related conditions include hypercholesterolemia, lipid disorders such as hyperlipidemia, and atherogenesis and its sequelae of cardiovascular diseases, including atherosclerosis, other vascular inflammatory conditions, myocardial infarction, ischemic stroke, occlusive stroke, and peripheral vascular diseases, as well as other conditions in which decreasing cholesterol and/or other products of the cholesterol biosynthetic pathways can produce a benefit. Other HMG-CoA reductase-related conditions treatable with compositions, kits, and methods of the present invention include those currently treated with statins.

Reducing the activity of HMG-CoA reductase, is also referred to as "inhibiting" the enzyme. The term "inhibits" and its grammatical conjugations, such as "inhibitory," do not require complete inhibition, but refer to a reduction in HMG-CoA reductase activity. Such reduction is preferably by at least about 50%, at least about 75%, at least about 90%, and more preferably by at least about 95% of the activity of the enzyme in the absence of the inhibitory effect, e.g., in the absence of an inhibitor. Conversely, the phrase "does not inhibit" and its grammatical conjugations refer to situations where there is less than about 20%, less than about 10%, and preferably less than about 5% of reduction in enzyme activity in the presence of the compound. Further the phrase "does not substantially inhibit" and its grammatical conjugations refer to situations where there is less than about 30%, less than about 20%, and preferably less than about 10% of reduction in enzyme activity in the presence of the compound.

The ability to reduce enzyme activity is a measure of the potency or the activity of the compound or combination of componds towards or against the enzyme. Potency is preferably measured by cell free, whole cell and/or in vivo assays in terms of IC50 or ED50 values. An IC50 value represents the concentration of a compound required to inhibit the enzyme activity by half (50%) under a given set of conditions. A Ki value represents the equilibrium affinity constant for the binding of an inhibiting compound to the enzyme. An ED50 value represents the dose of a compound required to effect a half-maximal response in a biological assay. Further details of these measures will be appreciated by those of ordinary skill in the art, and can be found in standard texts on biochemistry, enzymology, and the like.

In some embodiments, compounds in one or more forms represented by formulas I, II, III, and IV inhibit HMG-CoA reductase. In many embodiments, compounds of formula II inhibit HMG-CoA reductase. Such compounds find use in the practice of this invention e.g., in a method of treating an HMG-CoA reductase-related condition by administering to a subject an effective amount of at least one of such compounds. These compounds can lower cholesterol levels in vitro and in vivo, and/or increase HDL, thereby forming the basis for pharmaceutical compositions useful in the treatment of HMG-CoA reductase-related conditions, e.g., hypercholesterolemia and atherosclerosis, in humans and other mammals.

As noted above, a subset of the compounds of formulas I and II are novel analogs of known inhibitors of MAP kinases, wherein X comprises a lipophilic MAP kinase inhibitor or a lipophilic moiety or analog thereof. Some of these analogs display HMG-CoA reductase inhibitory activity, for example, in the acid form (formula II), and are useful in the practice of this invention, e.g., in a method of treating an HMG-CoA reductase-related condition by administering to a subject an effective amount of at least one of such compounds. For example, acid forms, in particular the carboxylate forms, of certain lactone derivatives illustrated in FIG. 5 are preferred in some embodiments for the treatment of HMG-CoA reductase-related conditions.

Also as noted above, a subset of the compounds of formulas I and II are novel analogs of known inhibitors of HMG-CoA reductase, wherein X comprises a lipophilic moiety of an HMG-CoA reductase inhibitor, e.g., a statin, or an analog thereof. Some of these analogs retain HMG-CoA reductase inhibitory activity in the lactone and/or acid form, in particular, in the acid carboxylate form, and are useful in the practice of this invention, e.g., in a method of treating an HMG-CoA reductase-related condition by administering to a subject an effective amount of at least one of such compounds. For example, acid carboxylate forms of certain lactone derivatives illustrated in FIG. 7 are preferred in some embodiments.

Also as noted above, in some embodiments, a compound of the instant invention, or a composition comprising one or more such compounds, can be used in treating an HMG-CoA reductase-related condition by increasing HDL levels. Higher levels of HDL are believed to protect against, e.g., atherosclerosis, whereas low HDL is recognized as an independent risk factor for cornary artery disease. For example, an HDL level below about 40 mg/DL can be considered in need of treatment. Without being limited to a particular theory and/or hypothesis, compounds of the instant invention can bring about an upregulation of HDL in treating an HMG Co-A reductase related condition, such as artherosclerosis.

Upregulating HDL is also referred to as "increasing" HDL or HDL levels. The term "increases" and its grammatical conjugations can refer to a small, significant and/or substantial increase, preferably an increase sufficient to decrease a risk of an HMG-CoA reductase-related condition in a subject being treated. Such increase is preferably by at least about 10%, at least about 20%, at least about 30%, and more preferably by at least about 50% of HDL levels in the absence of treatment. In preferred embodiments, atorvastatin and analogs of atorvastatin are used to increase HDL.

The present invention also includes kits that can be used to treat an HMG-CoA reductase-related condition. These kits comprise a compound or combination of compounds described herein, and preferably instructions teaching the use of the kit according to the various methods and approaches described herein. Such kits also include information, such as scientific literature references, package insert materials, clinical trial results, and/or summaries of these and the like, which indicate or establish the activities and/or advantages of the compound(s). Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like.

C. Treatment of Both MAP Kinase- and HMG-CoA Reductase-Related Conditions

One of the purposes of this invention is to describe compounds or combinations of compounds which inhibit both MAP kinase and HMG-CoA reductase. Such compounds or combinations can exert concomitant anti-inflammatory and cholesterol-lowering effects in vitro and/or in vivo. In certain embodiments, for example, these compounds or combinations reduce production of, and signaling pathways involving, TNF-α and IL-1β, as well as inhibiting production of cholesterol and/or other downstream products of mevalonate, including mevalonate pyrophosphate, isopentyl pyrophosphate, geranyl pyrophosphate, farnesyl pyrophosphate, dolichols, farnesylated proteins, trans-trans geranylgeranyl pyrophosphate, ubiquinone, geranyl-geranylated proteins, squalene, and the like. Further, in some embodiments, these compounds or combinations can exert superior anti-atherogenesis and/or anti-inflammatory effects in vivo.

Such compounds or combinations can form the basis for pharmaceutical compositions, kits, and methods for treating both MAP kinase-related conditions and HMG-CoA reductase-related conditions in humans and other animals. Moreover, such compositions can provide superior benefits in treating HMG-CoA reductase-related conditions, such as cardiovascular disease, compared with treatments that inhibit HMG-CoA reductase but do not inhibit or do not substantially inhibit MAP kinase. Also, compositions of the present invention can provide superior benefits in treating MAP kinase-related conditions, such as inflammatory conditions, compared with treatments that inhibit MAP kinases but do not inhibit or do not substantially inhibit HMG-CoA reductase.

Figure 10:
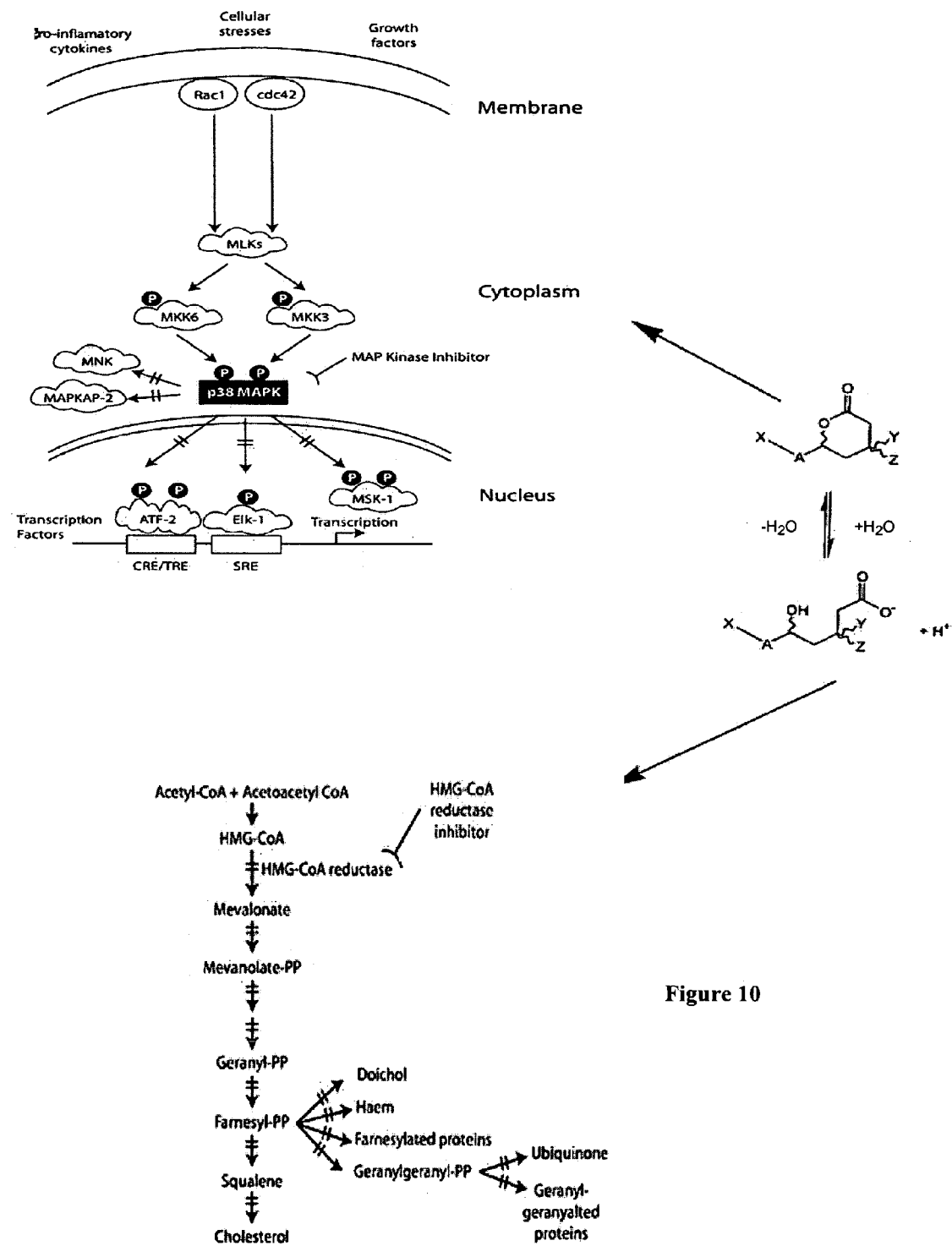
FIG. 10 illustrates a treatment approach in which compositions of the present invention produce a benefit in both MAP kinase-related and HMG-CoA reductase-related conditions.

FIG. 10, for example, illustrates a treatment approach in which compositions of the present invention produce a benefit in both MAP kinase- and HMG-CoA reductase-related conditions. This figure serves only as an example, and is in no way intended to be limiting with respect to the present invention. For example, those skilled in the art will readily appreciate variations and modifications of the scheme illustrated, and such variations and modifications are also contemplated as being contained within the scope of the invention.

As FIG. 10 illustrates, the δ-lactone form (formula I) of a compound of this invention can inhibit a MAP kinase, and the acid form (formula II), in particular the deprotonated carboxylate form (formula IIb), can inhibit HMG-CoA reductase. Accordingly, this treatment approach can provide a benefit in both a HMG-CoA reductase-related condition and a MAP kinase-related condition, for instance, in a method comprising administering to a subject an effective amount of at least one of such compounds, e.g., reducing pro-inflammatory cytokine production, in the treatment of a MAP kinase-related condition, such as an allergic, inflammatory and/or autoimmune condition, and reducing cholesterol production in the treatment of a HMG-CoA reductase-related condition, such as cardiovascular disease. This reduction in pro-inflammatory cytokine production by inhibition of a MAP kinase, e.g., p38α MAP kinase, may be in addition to other immunomodulatory effects of some HMG-CoA reductase inhibitors that may, for example, produce immunomodulatory responses though the action of metabolites such as farnesyl pyrophosphate and/or geranylgeranyl pyrophosphate. Moreover, in some embodiments, the role of a compound of the present invention in a MAP kinase-related pathway is distinct from the anti-inflammatory effects of some statins through metabolite products such as geranylgeranyl pyrophosphate and/or farnesyl pyrophosphate. For example, the inhibitory activity of some compounds of this invention on a MAP kinase and on MAP-kinase related conditions need not be reversed by exogenous addition of mevalonate (e.g., sodium mevalonate), geranylgeranyl pyrophosphate, farnesyl pyrophosphate, and/or other downstream product of mevalonate.

Furthermore, the interplay between inflammatory and HMG-CoA reductase-related disorders means that compositions regulating both a MAP kinase and HMG-CoA reductase pathways can be particularly beneficial. Inhibition of HMG-CoA reductase can lead to improved serum lipid profiles, such as decreased LDL and increased HDL levels, which in turn can lead to a reduction in the rate of atherogenesis. On the other hand, initiation of atherogenic plaque deposition (e.g., via foam cells) is reduced by the anti-inflammatory effects, including those which derive from inhibition of a MAP kinase. Inhibition of a MAP kinase can also antagonize inflammatory processes which contribute to the disruption of atherogenic plaques and which, in turn, can lead to arterial thrombosis, blockade, etc. Consequently, pharmaceutical compositions including a compound of formula I/II and having inhibitory activity against both a MAP kinase and HMG-CoA reductase can be superior, preferably differentially superior, to drugs targeting only HMG-CoA reductase. In some preferred embodiments, such compositions can provide a differentially superior benefit in treating cardiovascular disease related to atherogenesis, including formation and disruption of atherosclerotic plaques. Further, pharmaceutical compositions including a compound or combination of compounds of formula I and/or formula II having inhibitory activity against both a MAP kinase and HMG-CoA reductase can be superior, preferably differentially superior, to drugs targeting only a MAP kinase in terms of treating a MAP kinase-related condition, such as inflammation, again due to the interplay between inflammatory and cardiovascular conditions.

In some embodiments, a compound of formula I inhibits or is more potent against a MAP kinase while the corresponding compound of formula II, with equivalent X, Y, Z, A and stereochemistry, inhibits or is more potent against HMG-CoA reductase. In some preferred embodiments, the activities or potencies of a compound of formula I and the corresponding compound of formula II are similar towards a MAP kinase and HMG-CoA reductase. In preferred embodiments, the potencies of these forms against their respective targets differs by no more than a factor of about 1000, more preferably about 100, and most preferably about 10. In a preferred embodiment, compounds of formulas I and II have absolute configuration as illustrated in FIG. 3b and designated as (T,T) absolute configuration, as defined above.

In other preferred embodiments, the potency of a compound of formula I and/or II against a MAP kinase is greater than its potency against HMG-CoA reductase. In such embodiments, potencies with respect to a MAP kinase and HMG-CoA reductase differ by at least a factor of about 10. More preferably, potencies can differ by more than a factor of about 100. Most preferably, potencies can differ by more than a factor of about 1000. In yet other preferred embodiments, the potency of a compound of formula I and/or II against HMG-CoA reductase is greater than its potency against a MAP kinase. In such embodiments, potencies with respect to HMG-CoA reductase and a MAP kinase differ by at least a factor of about 10. More preferably, potencies can differ by more than a factor of about 100. Most preferably, potencies can differ by more than a factor of about 1000.

In some embodiments, a compound of formula I inhibits both a MAP kinase and HMG-CoA reductase. In some embodiments, a compound of formula II inhibits both a MAP kinase and HMG-CoA reductase. In other embodiments, a compound of formula III inhibits both a MAP kinase and HMG-CoA reductase; in still other embodiments, a compound of formula IV inhibits both a MAP kinase and HMG-CoA reductase. In nearly all preferred embodiments, compounds of formula II inhibit HMG-CoA reductase.

As noted above, a subset of the compounds of formulas I and II are novel analogs of known inhibitors of MAP kinases, wherein X comprises a lipophilic MAP kinase inhibitor or a lipophilic moiety or analog thereof. Some of these analogs retain MAP kinase inhibitory activity in the lactone and/or acid forms while also exhibiting HMG-CoA reductase inhibitory activity in the acid and/or lactone forms. In some preferred embodiments, a MAP kinase analog of the present invention inhibits a MAP kinase in the lactone form of formula I and inhibits HMG-CoA reductase in the corresponding acid form of formula II, in particular the carboxylate form of formula IIb. In preferred embodiments, such compounds are useful in the present invention, e.g., in a method comprising administering to a subject an effective amount of at least one of such compounds to treat a MAP kinase-related condition and additionally treating an HMG-CoA reductase-related condition. MAP kinase analogs illustrated in FIG. 5 can provide examples of such preferred embodiments. In other embodiments, the lactone form inhibits both a MAP kinase and HMG-CoA reductase; in still other embodiments, the acid form inhibits both a MAP kinase and HMG-CoA reductase.

Also as noted above, a subset of the compounds of formulas I and II are novel analogs of known inhibitors of HMG-CoA reductase, wherein X comprises a lipophilic moiety of an HMG-CoA reductase inhibitor, e.g., a statin, a synthetic statin, or an analog thereof. Some of these analogs retain HMG-CoA reductase inhibitory activity in the acid and/or lactone forms while also exhibiting MAP kinase inhibitory activity in the lactone and/or acid forms. In some preferred embodiments, a statin analog of the present invention inhibits HMG-CoA reductase in the acid form of formula II (in particular, in the carboxylate form of formula IIb) and inhibits a MAP kinase in the corresponding lactone form of formula I. In preferred embodiments, such compounds find use in the practice of the invention, e.g., in a method comprising administering to a subject an effective amount of at least one of such compounds to treat a MAP kinase-related condition and additionally treating an HMG-CoA reductase-related condition. Statin analogs illustrated in FIG. 7 can provide examples of such preferred embodiments, and the specific examples illustrated in FIG. 8 can provide even more preferred embodiments. In other embodiments, the lactone form inhibits both a MAP kinase and HMG-CoA reductase; in still other embodiments, the acid form inhibits both a MAP kinase and HMG-CoA reductase.

The present invention also includes kits that can be used to treat MAP kinase- and HMG-CoA reductase-related conditions, in particular cardiovascular disease related to atherogenesis. These kits can comprise a compound or combination of compounds described herein, including compounds of formula I and/or II which have inhibitory activity against both a MAP kinase and HMG-CoA reductase, and preferably instructions teaching the use of the kit according to the various methods and approaches described herein.

Such kits also include information, such as scientific literature references, package insert materials, clinical trial results, and/or summaries of these, and the like, which indicate or establish the multiple activities of the compounds or combination and indicate and/or establish how its use provides advantages and/or differential superiority in treating an HMG-CoA reductase- and/or a MAP kinase-related condition, preferably in treating cardiovascular disease. Such information may be based on the results of various studies, for example, studies using experimental animals involving in vivo models and studies based on human clinical trials. Kits of the present invention may also include materials comparing the approaches of the present invention with other therapies, which do not display a combination of MAP kinase plus HMG-CoA reductase inhibitory activities. Kits described herein can be provided, marketed and/or promoted to health providers, including physicians, nurses, pharmacists, formulary officials, and the like.

D. Treatment of Inflammatory Conditions

Another aspect of the present invention relates to methods of using pharmaceutical compositions and kits comprising combinations of compounds, forms and/or agents described herein to treat MAP kinase-related and/or HMG-CoA reductase-related conditions that are inflammatory conditons. Inflammatory conditions, as used herein, can refer to inflammatory diseases or disorders associated with inflammation due to relatedness to MAP kinase-, HMG CoA reductase- and/or other pathways. Inflammatory conditions treatable using some embodiments of the instant invention can involve different organ systems, and can vary in severity from trivial to lethal.

For example, inflammatory conditions of the skin can be treated in some embodiments of the instant invention, including, but not limited to, atopic dermatitis, age-related effects, acne, eczema, psoriasis and skin cancer. Various types of acne can be treated uisng some embodiments of the instant invention, including, e.g., acne atrophica, bromide or chlorine acne, common acne (acne vulgaris), acne conglobata, contact acne, contagious acne of horses, acne cosmetica, cystic acne, acne detergicans, epidemic acne, acne estivalis, excoriated acne, acne frontalis, acne fulminans, halogen acne, acne indurata, infantile acne, iodide acne, acne keloid, acne mechanica, acne necrotica miliaris, neonatal acne, acne papulosa, picker's acne, pommade acne, premenstrual acne, acne pustulosa, acne rosacea, acne scorbutica, acne scrofulosorum, acne tropicalis, acne urticata, acne varioliformis, acne venenata, and the like.

Various types of eczema can be treated in some embodiments of the instant invention, including, e.g., eczematous dermatitis, such as atopic dermatitis, the most common form of eczema, generally seen in infants and young adults. Eczema can present as a red, itchy, non-contagious inflammation of the skin that can be acute or chronic, possibly accompanied by red skin patches, pimples, crusts, scabs, and watery discharge.

Various effects of ageing can be treated in some embodiments of the instant invention, including, e.g., skin-related inflammatory diseases attributable to ageing. Such effects can include formation of wrinkles and fine lines, slackening of cutaneous and subcutaneous tissue, loss of skin elasticity, reduction in skin tone and texture and/or yellowing. Loss of elasticity can result form atrophy of the epidermis, beginning on a small scale and eventually decreasing the number of cells in the dermis. Capillaries can become more susceptible to bruising, collagen metabolism may slow, and/or the concentration of the cell surface molecule glycosaminoglycan (believed to have a role in the recognition of other cells and substrates) may decrease. With ageing, skin may exhibit chronic inflammation with enlarged fibroblasts. Effects of ageing aggravated with sun exposuse can also be treated in some embodiments, e.g., pigmentation marks, telangiectasias, elastosis, and/or other skin photo-damage, as well as benign, premalignant and/or malignant neoplasms (e.g., caused by prolonged sun exposure). Ageing itself, e.g., can be considered as an inflammatory condition, e.g., as the ability to mount an inflammatory response decreases and healing time for injuries increases with age.

Inflammatory conditions of the skin that can be treated in some embodiments of the instant invention include skin cancers and other hyperproliferative skin disorders, including, e.g., without being not limited to, basal cell carcinoma, squamous cell carcinoma (Bowen's disease), keratosis (such as actinic or seborrheic keratosis), and/or disorders of keratinization (such as ichthyosis and keratoderma).

Inflammatory conditions of the respiratory system can be treated in some embodiments of the instant invention, including, but not limited to, allergic rhinitis, chronic obstructive pulmonary disease, adult respiratory distresss syndrome, asthma, and the like. Allergic asthma can include atopic, chronic diseases of the lung characterized by inflammation of the air passages. Allergic rhinitis or hay fever can include conditions that affect mucous membranes characterized by seasonal or perennial nasal inflammation, e.g., in response to an allergen. Other mucous inflammatory conditions treatable using some embodiments of the instant invention can include lamellar ichthyosis, acne, rosacea, and the like.

Inflammatory conditions of the urogenital tract can be treated in some embodiments of the instant invention, including, but not limited to, vaginitis and interstitial cystitis, and other conditions characterized by inflammation of the urogenital epithelium and/or the urinary bladder. Interstitial cystitis also can include other conditions associated with a dysfunctional bladder glycosaminoglycan protective layer and/or increased numbers of activated bladder mast cells.

Inflammatory conditions of the gastrointestinal tract can be treated in some embodiments of the instant invention, including, but not limited to, celiac diseases, e.g., celiac sprue, inflammatory bowel disease (including ulcerative colitis and Crohn's disease), intestinal infections, enterocolitis, gastritis, and the like.

Inflammatory conditons of the musculoskeletal system can be treated in some embodiments of the instant invention, including, but not limited to, inflammatory muscle pain, arthritis, rheumatoid arthritis, psoriatic arthritis, osteoarthritis, osteoporosis, and the like. Osteoporosis can include conditions characterized by decreased bone mass, increased fragility of the remaining bone, and/or increased incidence of fractures.

Inflammatory conditions of the vascular system an be treated in some embodiments of the instant invention, including, but not limited to hypercholesterolemia, hyperlipidemia, atherogenesis and associated cardiovascular risks of atherosclerosis, thrombosis, myocardial infarction, ischemic stroke, ischemic-reperfusion injury, peripheral vascular disease, e.g., peripheral occlusive disease, and the like. Inflammatory conditions of the systemic circulation also include endotoxemia, lupus erythrematosus, sepsis, toxic shock syndrome and transplant rejection, and may also be treated in some embodiments.

Inflammatory conditions of the central nervous system can be treated in some embodiments of the instant invention, including, but not limited to, neurogenic inflammation and neurodegenerative diseases, such as Alzheimer's disease, and the like.

In some embodiments, compositions comprisng combinations of compounds, forms and/or agents described herein provide treatments for autoimmune conditions. Autoimmune conditions as used herein can include organ or tissue-specific autoimmune conditions, as well as those which affect the whole body. Organ or tissue-specific autoimmune conditions that can be treated in some embodiments of the instant invention include, e.g., type I diabetes mellitus, multiple sclerosis, primary billiary cirrhosis, Hashimotos thyroiditis, pernicious anemia, Crohn's disease, Addison's disease, myasthenia gravis, rheumatoid arthritis, uveitis, psoriasis, Guillain-Barre Syndrome, Graves' disease, and the like. Systemic autoimmune conditions that can be treated in some embodiments include, e.g., systemic lupus erythematosus, ermatomyositis, and the like.

As detailed above, in some embodiments, combinations comprising a statin lactone and one or more additional active agents can be used in treating one or more of the inflammatory conditions provided herein. Preferred combinations can depend on the affected system. For example, combinations comprising a statin lactone and a salt form of a hydroxy acid statin are preferred in the treatment of inflammatory conditions of the vascular system and central nervous system, especially Alzheimer's disease, as well as inflammatory conditions of the skin, especially eczema, psoriasis, acne and the effects of ageing. Also as detailed above, preferred combinations comprise atorvastatin lactone with a salt of either atorvastatin or pitavastatin in a molar ratio of about 90:10 to about 10:90. In other embodiments, combinations comprising a statin lactone and a non-statin anti-inflammatory agent are preferred, e.g., where combinations comprising atorvastatin lactone and a non-steroidal anti-inflammatory drug are used in a molar ratio of about 90:10 to about 10:90.

One of the purposes of this invention is to teach combinations of compounds that can produce synergistic effects in treating an inflammatory condition, e.g., one or more of the inflammatory conditions provided herein. For example, in some prefered embodiments, a combination of a statin lactone and another active agent provides a synergistic effect in treating an inflammatory condition, as detailed above. Additional details of combinations providing synergistic inhibitory effects in treating inflammation are provided in Example 8 below.

III. Formulations, Routes of Administration, and Effective Doses

Yet another aspect of the present invention relates to formulations, routes of administration and effective doses for pharmaceutical compositions comprising a compound or combination of compounds of the instant invention. Such pharmaceutical compositions can be used to treat inflammatory, MAP kinase-related, and/or HMG-CoA reductase-related conditions, as described in detail above.

The compounds of formula I/II may be provided in a either the lactone or acid form, and/or may be allowed to interconvert in vivo after administration. That is, either the δ-lactone or hydroxy carboxylic acid form, or pharmaceutically acceptable salts, esters or amides thereof, may be used in developing a formulation for use in the present invention. Further, in some embodiments, the compound may be used in combination with one or more other compounds or with one or more other forms. For example a formulation may comprise both the lactone and acid forms in particular proportions, depending on the relative potencies of the lactone and acid forms and the intended indication. For example, in compositions for treating both MAP kinase- and HMG-CoA reductase-related conditions where the lactone form inhibits MAP kinase and the acid (carboxylate) form inhibits HMG-CoA reductase, and where potencies are similar, about a 1:1 ratio of lactone to acid forms may be used. The two forms may be formulated together, in the same dosage unit e.g. in one cream, suppository, tablet, capsule, or packet of powder to be dissolved in a beverage; or each form may be formulated in a separate unit, e.g., two creams, two suppositories, two tablets, two capsules, a tablet and a liquid for dissolving the tablet, a packet of powder and a liquid for dissolving the powder, etc.

Similarly, compounds of formula III and IV, or their pharmaceutically acceptable salts, esters, or amides thereof, may be used alone, together, or in combination with the corresponding or other compounds of formula I and II, described above. For example, a compound of formula IV (closed δ-lactam ring) may be co-administered with a compound of formula II (open acid form), where the compounds have equivalent X, Y, Z, A and stereochemistries. Such administration may be useful for treating both MAP kinase- and HMG-CoA reductase-related conditions, for example, where the lactam form inhibits MAP kinase and the acid (carboxylate) form inhibits HMG-CoA reductase. The two forms may be formulated together, in the same dosage unit e.g. in one cream, suppository, tablet, capsule, or packet of powder to be dissolved in a beverage; or each form may be formulated in separate units, e.g, two creams, suppositories, tablets, two capsules, a tablet and a liquid for dissolving the tablet, a packet of powder and a liquid for dissolving the powder, etc.

The term "pharmaceutically acceptable salt" means those salts which retain the biological effectiveness and properties of the compounds used in the present invention, and which are not biologically or otherwise undesirable. For example, a pharmaceutically acceptable salt does not interfere with the beneficial effect of a compound of the invention in inhibiting MAP kinase and/or HMG-CoA reductase, e.g., in treating an inflamatory, MAP kinase-related and/or HMG-CoA reductase related conditon.

Typical salts are those of the inorganic ions, such as, for example, sodium, potassium, calcium, magnesium ions, and the like. Such salts include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid. In addition, if the compound(s) contain a carboxy group or other acidic group, it may be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine, triethanolamine, and the like.

A pharmaceutically acceptable ester or amide refers to those which retain biological effectiveness and properties of the compounds used in the present invention, and which are not biologically or otherwise undesirable. For example, the ester or amide does not interfere with the beneficial effect of a compound of the invention in inhibiting MAP kinase and/or HMG-CoA reductase, e.g., in treating an inflamatory, MAP kinase-related and/or HMG-CoA reductase related conditon. Typical esters include ethyl, methyl, isobutyl, ethylene glycol, and the like. Typical amides include unsubstituted amides, alkyl amides, dialkyl amides, and the like.

In some embodiments, a compound may be administered in combination with one or more other compounds, forms, and/or agents, e.g., as described above. Pharmaceutical compositions comprising combinations of a statin lactone with one or more other active agents can be formulated to comprise certain molar ratios. For example, molar ratios of about 99:1 to about 1:99 of statin lactone to the other active agent can be used. Preferably, the range of molar ratios of statin lactone: other active agent is selected from about 80:20 to about 20:80; about 75:25 to about 25:75, about 70:30 to about 30:70, about 66:33 to about 33:66, about 60:40 to about 40:60; about 50:50; and about 90:10 to about 10:90. More preferably, the molar ratio of statin lactone: other active agent is about 1:9, and most preferably about 1:1. The two compounds, forms and/or agents may be formulated together, in the same dosage unit e.g. in one cream, suppository, tablet, capsule, or packet of powder to be dissolved in a beverage; or each compound, form, and/or agent may be formulated in separate units, e.g, two creams, suppositories, tablets, two capsules, a tablet and a liquid for dissolving the tablet, a packet of powder and a liquid for dissolving the powder, etc.

If necessary or desirable, the compounds and/or combinations of compounds may be administered with still other agents. The choice of agents that can be co-administered with the compounds and/or combinations of compounds of the instant invention can depend, at least in part, on the condition being treated. Agents of particular use in the formulations of the present invention include, for example, any agent having a therapeutic effect for kinase-related and/or HMG-CoA reductase-related conditions, including, e.g., drugs used to treat inflammatory conditions. For example, in treatments for acne, formulations of the instant invention may additionally contain one or more conventional acne treatments, such as keratolytic agents, e.g., retinoids, particularly retinoic acid; anti-inflammatory agents, such as peroxides, particularly benzoyl peroxide; and antiseborrhoeic agents. In treamtents for osteoporosis, as another example, formulations may additionally contain one or more supplements, such as vitamin D and/or calcium, and/or one or more biphosphonate medications, e.g., which block bone resorption.

In still other embodiments, compounds and/or combinations of compounds described herein can be co-formulated and/or co-administered with agents useful for the prevention and/or treatment of atherosclerosis and its sequelae. These agents include, but are not limited to, e.g., inhibitors of cholesterol ester transferase protein (CETP) (e.g., JTT-705, torcetrapib); inhibitors of sterol acyl-CoA-acyl transferase (ACAT) (e.g., pactimibe, SMP-797, K-604); inhibitors of microsomal triglyceride transferase protein (MTTP) (e.g., implitipide, JTT-130); modulators of peroxisome proliferators activated receptors (PPARs) (e.g., binifibrate, gemfibrozil, clinofibrate, ronifibrate, fenofibrate, bezafibrate, LY-929, GW-516, GW-590735, NS-220, LY-674, DRF-10945, SB-641597, AVE-8134, AVE-0847, ciglitazone, pioglitazone, darglitazone, rosiglitazone, isaglitazone, reglitazar, farglitazar, tesaglitazar, balaglitazone, ragaglitazar, rivoglitazone, imiglitazar, edaglitazone, oxeglitazar, muraglitazar); inhibitors of cholesterol absorption (e.g., ezetimibe, colesevelam hydrochloride, cholestyramine, colestimide, colestipol hydrochloride, BTG-511); vitamins (e.g., niacin); inhibitors of platelet aggregation (e.g., aspirin, clopidogrel, D-003); inhibitors of ileal bile acid transport (IBAT) (e.g., S-8921, BARI-1741); inhibitors of lipoprotein-associated phospholipase A2 (Lp-PLA2) (e.g., SB-480848, SB-659032, SB-677116); inhibitors of squalene synthase (e.g., TAK-475); antagonists of chemokine CCR2 receptor (e.g., INCB-3284, C-8834, C-1602).

The compound(s) (or pharmaceutically acceptable salts, esters or amides thereof) may be administered per se or in the form of a pharmaceutical composition wherein the active compound(s) is in an admixture or mixture with one or more pharmaceutically acceptable carriers. A pharmaceutical composition, as used herein, may be any composition prepared for administration to a subject. Pharmaceutical compositions for use in accordance with the present invention may be formulated in conventional manner using one or more physiologically acceptable carriers, comprising excipients, diluents, and/or auxiliaries, e.g., which facilitate processing of the active compounds into preparations that can be administered. Proper formulation may depend at least in part upon the route of administration chosen. The compound(s) useful in the present invention, or pharmaceutically acceptable salts, esters, or amides thereof, can be delivered to a patient using a number of routes or modes of administration, including oral, buccal, topical, rectal, transdermal, transmucosal, subcutaneous, intravenous, and intramuscular applications, as well as by inhalation.

For oral administration, the compounds can be formulated readily by combining the active compound(s) with pharmaceutically acceptable carriers well known in the art. Such carriers enable the compounds of the invention to be formulated as tablets, including chewable tablets, pills, dragees, capsules, lozenges, hard candy, liquids, gels, syrups, slurries, powders, suspensions, elixirs, wafers, and the like, for oral ingestion by a patient to be treated. Such formulations can comprise pharmaceutically acceptable carriers including solid diluents or fillers, sterile aqueous media and various non-toxic organic solvents. Generally, the compounds of the invention will be included at concentration levels ranging from about 0.5%, about 5%, about 10%, about 20%, or about 30% to about 50%, about 60%, about 70%, about 80% or about 90% by weight of the total composition of oral dosage forms, in an amount sufficient to provide a desired unit of dosage.

Aqueous suspensions for oral use may contain compound(s) of this invention with pharmaceutically acceptable excipients, such as a suspending agent (e.g., methyl cellulose), a wetting agent (e.g., lecithin, lysolecithin and/or a long-chain fatty alcohol), as well as coloring agents, preservatives, flavoring agents, and the like.

In some embodiments, oils or non-aqueous solvents may be required to bring the compounds into solution, due to, for example, the presence of large lipophilic moieties. Alternatively, emulsions, suspensions, or other preparations, for example, liposomal preparations, may be used. With respect to liposomal preparations, any known methods for preparing liposomes for treatment of a condition may be used. See, for example, Bangham et al., *J. Mol. Biol.* 23: 238–252 (1965) and Szoka et al., *Proc. Natl. Acad. Sci. USA* 75: 4194–4198 (1978), incorporated herein by reference. Ligands may also be attached to the liposomes to direct these compositions to particular sites of action. Compounds of this invention may also be integrated into foodstuffs, e.g, cream cheese, butter, salad dressing, or ice cream to facilitate solubilization, administration, and/or compliance in certain patient populations.

Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; flavoring elements, cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents may be added, such as the cross-linked polyvinyl pyrrolidone, agar, or alginic acid or a salt thereof such as sodium alginate. The compounds may also be formulated as a sustained release preparation.

Dragee cores can be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compounds.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for administration.

In some preferred embodiments, oral formulations are used to treat Alzheimer's and/or other inflammatory conditons of the central nervous system. In some preferred embodiments, oral formulations are used to treat arthritis, rheumatoid arthritis and/or other inflammatory conditions of the musculoskeletal system. As detailed above, preferred compositions in such embodiments are those comprising a statin lactone and a non-statin anti-inflammatory agent.

In some preferred embodiments, oral formulations are used to treat inflammatory conditions of the vascular system especially hypercholesterolemia, hyperlipidemia, atherosclerosis, peripheral occlusive disease, myocardial infarction, and stroke. Preferred compositions in such embodiments are those comprising a statin lactone and a salt form of a hydroxy acid statin. More preferred are combinations of atorvastatin lactone with a salt of either atorvastatin or pitavastatin, even more preferably in a molar ratio of about 90:10 to about 10:90. Additional details of such preferred embodiments for oral formulations are provided in Example 4, as outlined above. Specifically, Example 4b describes a coated tablet formulation comprising atorvastatin lactone and atorvastatin calcium, at a ratio of 1:1. Example 4c describes a coated tablet formulation of enteric-coated granules comprising atorvastatin lactone and pitavastatin calcium, at a ratio of 1:1.

For injection, the compounds of the present invention may be formulated in aqueous solutions, preferably in physiologically compatible buffers such as Hank's solution, Ringer's solution, or physiological saline buffer. Such compositions may also include one or more excipients, for example, preservatives, solubilizers, fillers, lubricants, stabilizers, albumin, and the like. Methods of formulation are known in the art, for example, as disclosed in Remington's Pharmaceutical Sciences, latest edition, Mack Publishing Co., Easton P.

In addition to the formulations described previously, the compounds may also be formulated as a depot preparation. Such long acting formulations may be administered by implantation or transcutaneous delivery (for example subcutaneously or intramuscularly), intramuscular injection or use of a transdermal patch. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In some embodiments, pharmaceutical compositions comprising one or more compounds of the present invention exert local and regional anti-inflammatory effects when administered topically or injected at or near particular sites of inflammation. Direct topical application, e.g., of a viscous liquid, gel, jelly, cream, lotion, ointment, suppository, foam, or aerosol spray, may be used for local administration, to produce for example local and/or regional effects. Pharmaceutically appropriate vehicles for such formulation include, for example, lower aliphatic alcohols, polyglycols (e.g., glycerol or polyethylene glycol), esters of fatty acids, oils, fats, silicones, and the like. Such preparations may also include preservatives (e.g., p-hydroxybenzoic acid esters) and/or antioxidants (e.g., ascorbic acid and tocopherol). See also Dermatological Formulations: Percutaneous absorption, Barry (Ed.), Marcel Dekker Incl, 1983. In some preferred embodiments, local/topical formulations comprising a statin lactone and a non-statin anti-inflammatory agent are used to treat inflammatory conditions. Preferred compositions in such embodiments are those comprising atorvastatin lactone and a non-steroidal anti-inflammatory drug, even more preferably in a molar ratio of about 90:10 to about 10:90.

In some preferred embodiments, local/topical formulations are used to treat allergic, inflammatory and/or autoimmune conditions of the skin or skin structures, especially for treating eczema, psoriasis, acne and the effects of aging. For example, for treating inflammatory and/or autoimmune conditions, a cream comprising a compound of the invention in formula I, II, III, or IV may be topically applied to the affected site, for example, sites displaying red plaques or dry scales in psoriasis, or areas of irritation and dryness in dermatitis. Preferred compositions in such embodiments are those comprising a statin lactone and a salt form of a hydroxy acid statin. More preferred are combinations of atorvastatin lactone with a salt of either atorvastatin or pitavastatin, even more preferably in a molar ratio of about 90:10 to about 10:90.

Pharmaceutical compositions of the present invention may contain a cosmetically or dermatologically acceptable carrier. Such carriers are compatible with skin, nails, mucous membranes, tissues and/or hair, and can include any conventionally used cosmetic or dermatological carrier meeting these requirements. Such carriers can be readily selected by one of ordinary skill in the art. In formulating skin ointments, a compound or combination of compounds of the instant invention may be formulated in an oleaginous hydrocarbon base, an anhydrous absorption base, a water-in-oil absorption base, an oil-in-water water-removable base and/or a water-soluble base.

The compositions according to the present invention may be in any form suitable for topical application, including aqueous, aqueous-alcoholic or oily solutions, lotion or serum dispersions, aqueous, anhydrous or oily gels, emulsions obtained by dispersion of a fatty phase in an aqueous phase (O/W or oil in water) or, conversely, (W/O or water in oil), microemulsions or alternatively microcapsules, microparticles or lipid vesicle dispersions of ionic and/or nonionic type. These compositions can be prepared according to conventional methods. Other than the compounds of the invention, the amounts of the various constituents of the compositions according to the invention are those conventionally used in the art. These compositions in particular constitute protection, treatment or care creams, milks, lotions, gels or foams for the face, for the hands, for the body and/or for the mucous membranes, or for cleansing the skin. The compositions may also consist of solid preparations constituting soaps or cleansing bars.

Compositions of the present invention may also contain adjuvants common to the cosmetic and dermatological fields, such as hydrophilic or lipophilic gelling agents, hydrophilic or lipophilic active agents, preserving agents, antioxidants, solvents, fragrances, fillers, sunscreens, odor-absorbers and dyestuffs. The amounts of these various adjuvants are those conventionally used in the fields considered and, for example, are from about 0.01% to about 20% of the total weight of the composition. Depending on their nature, these adjuvants may be introduced into the fatty phase, into the aqueous phase and/or into the lipid vesicles.

Preferred embodiments of ointment formulations are described in Example 4. Example 4a describes a gel formulation comprising atorvastatin lactone and atorvastatin calcium. Example 4d describes a hydrophilic ointment comprising atorvastatin lactone and naproxen sodium. Example 4e describes a polyethylene glycol ointment comprising atorvastatin lactone and diclofenac. Example 4g describes an ointment comprising atorvastatin lactone and indomethacin. Example 4h describes a gel formulation including atorvastatin lactone and indomethacin. Example 4i describes a cream formulation comprising atorvastatin lactone and indomethacin. Example 4j describes a skin ointment comprising atorvastatin lactone and petrolatum USP. Example 4k describes a skin ointment comprising fluvastatin lactone and white petrolatum. Example 4l describes a skin ointment comprising cerivastatin lactone. Example 4m describes a skin ointment comprising pitavastatin lactone and polyethylene glycol. In more preferred embodiments, the ointment, gel, and/or cream formulations described in Examples 4g, 4h, and 4i, respectively, provide synergistic inhibitory effects in treating inflammation, e.g., as detailed in Example 8 below.

In some embodiments, ocular allergic, inflammatory and/or autoimmune conditions can be effectively treated with ophthalmic solutions, suspensions, ointments or inserts comprising a compound or combination of compounds of the present invention. Preferred embodiments of formulations for ocular use are provided in Example 4. Specifically, Example 4n describes an isotonic solution comprising rosuvastatin; Example 4o describes an ointment comprising cerivastatin lactone; and Example 4p describes an ointment comprising atorvastatin lactone, each of which can be used for ocular application.

In some embodiments, allergic, inflammatory and/or autoimmune conditions of the ear can be effectively treated with otic solutions, suspensions, ointments or inserts comprising a compound or combination of compounds of the present invention. Preferred embodiments of formulations for otic use are provided in Example 4. Specifically, Example 4q describes a solution comprising fluvastatin sodium and glycerin for otic use.

In some preferred embodiments, the compounds of the present invention are delivered in soluble rather than suspension form, which allows for more rapid and quantitative absorption to the sites of action. In general, formulations such as jellies, creams, lotions, suppositories and ointments can provide an area with more extended exposure to the compounds of the present invention, while formulations in solution, e.g., sprays, provide more immediate, short-term exposure.

In some embodiments relating to topical/local application, the pharmaceutical compositions can include one or more penetration enhancers. For example, the formulations may comprise suitable solid or gel phase carriers or excipients that increase penetration or help delivery of compounds or combinations of compounds of the invention across a permeability barrier, e.g., the skin. Many of these penetration-enhancing compounds are known in the art of topical formulation, and include, e.g., water, alcohols (e.g., terpenes like methanol, ethanol, 2-propanol), sulfoxides (e.g., dimethyl sulfoxide, decylmethyl sulfoxide, tetradecylmethyl sulfoxide), pyrrolidones (e.g., 2-pyrrolidone, N-methyl-2-pyrrolidone, N-(2-hydroxyethyl)pyrrolidone), laurocapram, acetone, dimethylacetamide, dimethylformamide, tetrahydrofurfuryl alcohol, L-α-amino acids, anionic, cationic, amphoteric or nonionic surfactants (e.g., isopropyl myristate and sodium lauryl sulfate), fatty acids, fatty alcohols (e.g., oleic acid), amines, amides, clofibric acid amides, hexamethylene lauramide, proteolytic enzymes, α-bisabolol, d-limonene, urea and N,N-diethyl-m-toluamide, and the like Additional examples include humectants (e.g., urea), glycols (e.g., propylene glycol and polyethylene glycol), glycerol monolaurate, alkanes, alkanols, ORGELASE, calcium carbonate, calcium phosphate, various sugars, starches, cellulose derivatives, gelatin, and/or other polymers. In some embodiments, the pharmaceutical compositions will include one or more such penetration enhancers.

In some embodiments, the pharmaceutical compositions for local/topical application can include one or more antimicrobial preservatives such as quaternary ammonium compounds, organic mercurials, p-hydroxy benzoates, aromatic alcohols, chlorobutanol, and the like.

Gastrointestinal allergic, inflammatory and/or autoimmune conditions can be effectively treated with orally- or rectally delivered solutions, suspensions, ointments, enemas and/or suppositories comprising a compound or combination of compounds of the present invention. Local/topical formulations are preferred for therapy of Crohn's colitis and other allergic, inflammatory and/or autoimmune diseases of the gastrointestinal system.

In treating inflammatory bowel disease, for example, a suppository formulation of a compound or combination of compounds disclosed herein can be used. In such embodiments, the active ingredient can produce a benefit locally at or near the site of application, rather than systemically, by inhibiting a MAP kinase inhibitor, e.g., p38α MAP kinase. In some preferred embodiments, a lactone form (formula I) of a known statin is used in formulations for topical inhibition of MAP kinase. In more preferred embodiments, the statin lactone used topically is a synthetic statin lactone, such as atorvastatin, cerivastatin, fluvastatin, pitavastatin, glenvastatin, and/or rosuvastatin, including, for example, structures provided in FIGS. 7 and 8. In some preferred embodiments, compounds modified to favor a closed ring structure, such as formulas III and IV of FIG. 9, are used in formulations for topical inhibition of MAP kinase. In more preferred embodiments, the modified compound is derived from a synthetic statin lactone, such as atorvastatin, cerivastatin, fluvastatin, pitavastatin, glenvastatin, and/or rosuvastatin.

Details of preferred embodiments for enema and suppository formulations are described in Example 4. Specifically, Example 4r describes a retention enema comprising cerivastatin sodium; Example 4s describes a retention enema comprising pitavastatin lactone; Example 4t describes a rectal suppository comprising fluvastatin lactone; Example 4u describes a rectal suppository comprising atorvastatin lactone; and Example 4f describes a rectal suppository comprising atorvastatin lactone and aminosalicylic acid.

Respiratory allergic, inflammatory and/or autoimmune conditions can be effectively treated with aerosol solutions, suspensions or dry powders comprising a compound or combination of compounds of the present invention. Administration by inhalation is particularly useful in treating inflammatory conditions of the lung. The aerosol can be administered through the respiratory system or nasal passages. For example, one skilled in the art will recognize that a composition of the present invention can be suspended or dissolved in an appropriate carrier, e.g., a pharmaceutically acceptable propellant, and administered directly into the lungs using a nasal spray or inhalant. For example, an aerosol formulation comprising a MAP kinase and/or HMG CoA reductase inhibitor can be dissolved, suspended or emulsified in a propellant or a mixture of solvent and propellant, e.g., for administration as a nasal spray or inhalant. Aerosol formulations may contain any acceptable propellant under pressure, preferably a cosmetically or dermatologically or pharmaceutically acceptable propellant, as conventionally used in the art.

An aerosol formulation for nasal administration is generally an aqueous solution designed to be administered to the nasal passages in drops or sprays. Nasal solutions can be similar to nasal secretions in that they are generally isotonic and slightly buffered to maintain a pH of about 5.5 to about 6.5, although pH values outside of this range can additionally be used. Antimicrobial agents or preservatives can also be included in the formulation.

An aerosol formulation for inhalations and inhalants can be designed so that the compound or combination of compounds of the present invention is carried into the respiratory tree of the subject when administered by the nasal or oral respiratory route. Inhalation solutions can be administered, for example, by a nebulizer. Inhalations or insufflations, comprising finely powdered or liquid drugs, can be delivered to the respiratory system as a pharmaceutical aerosol of a solution or suspension of the compound or combination of compounds in a propellant, e.g., to aid in disbursement. Propellants can be liquefied gases, including halocarbons, for example, fluorocarbons such as fluorinated chlorinated hydrocarbons, hydrochlorofluorocarbons, and hydrochlorocarbons, as well as hydrocarbons and hydrocarbon ethers.

Halocarbon propellants useful in the present invention include fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Halocarbon propellants are described in Johnson, U.S. Pat. No. 5,376,359, issued Dec. 27, 1994; Byron et al., U.S. Pat. No. 5,190,029, issued Mar. 2, 1993; and Purewal et al., U.S. Pat. No. 5,776,434, issued Jul. 7, 1998. Hydrocarbon propellants useful in the invention include, for example, propane, isobutane, n-butane, pentane, isopentane and neopentane. A blend of hydrocarbons can also be used as a propellant. Ether propellants include, for example, dimethyl ether as well as the ethers. An aerosol formulation of the invention can also comprise more than one propellant. For example, the aerosol formulation can comprise more than one propellant from the same class, such as two or more fluorocarbons; or more than one, more than two, more than three propellants from different classes, such as a fluorohydrocarbon and a hydrocarbon. Pharmaceutical compositions of the present invention can also be dispensed with a compressed gas, e.g., an inert gas such as carbon dioxide, nitrous oxide or nitrogen.

Aerosol formulations can also include other components, for example, ethanol, isopropanol, propylene glycol, as well as surfactants or other components such as oils and detergents. These components can serve to stabilize the formulation and/or lubricate valve components.

The aerosol formulation can be packaged under pressure and can be formulated as an aerosol using solutions, suspensions, emulsions, powders and semisolid preparations. For example, a solution aerosol formulation can comprise a solution of a compound of the invention such as a novel HMG-CoA reductase inhibitor in (substantially) pure propellant or as a mixture of propellant and solvent. The solvent can be used to dissolve the compound and/or retard the evaporation of the propellant. Solvents useful in the invention include, for example, water, ethanol and glycols. Any combination of suitable solvents can be use, optionally combined with preservatives, antioxidants, and/or other aerosol components.

An aerosol formulation can also be a dispersion or suspension. A suspension aerosol formulation may comprise a suspension of a compound or combination of compounds of the instant invention, e.g., an HMG CoA reductase inhibitor, and a dispersing agent. Dispersing agents useful in the invention include, for example, sorbitan trioleate, oleyl alcohol, oleic acid, lecithin and corn oil. A suspension aerosol formulation can also include lubricants, preservatives, antioxidant, and/or other aerosol components.

An aerosol formulation can similarly be formulated as an emulsion. An emulsion aerosol formulation can include, for example, an alcohol such as ethanol, a surfactant, water and a propellant, as well as a compound or combination of compounds of the invention, e.g., an HMG-CoA reductase inhibitor. The surfactant used can be nonionic, anionic or cationic. One example of an emulsion aerosol formulation comprises, for example, ethanol, surfactant, water and propellant. Another example of an emulsion aerosol forumalation comprises, for example, vegetable oil, glyceryl monostearate and propane.

Preferred embodiments of aerosol formulations are described in Example 4. Specifically, Example 4v describes a dry powder aerosol formulation comprising pitavastatin lactone and lactose. Example 4w describes a dry powder aerosol formulation comprising fluvastatin sodium. Example 4x describes a dry powder aerosol formulation comprising atorvastatin lactone. Example 4y describes a metered-dose aerosol formulation comprising atorvastatin lactone.

Pharmaceutical compositions suitable for use in the present invention include compositions wherein the active ingredients are present in an effective amount, i.e., in an amount effective to achieve therapeutic and/or prophylactic benefit in at least one of a MAP kinase-related condition and an HMG-CoA reductase-related condition. The actual amount effective for a particular application will depend on the condition or conditions being treated, the condition of the subject, the formulation, and the route of administration, as well as other factors known to those of skill in the art. Determination of an effective amount of a MAP kinase and/or HMG-CoA reductase inhibitor is well within the capabilities of those skilled in the art, in light of the disclosure herein, and will be determined using routine optimization techniques.

The effective amount for use in humans can be determined from animal models. For example, a dose for humans can be formulated to achieve circulating, liver, topical and/or gastrointestinal concentrations that have been found to be effective in animals. One skilled in the art can determine the effective amount for human use, especially in light of the animal model experimental data described herein. Example 8, provided below, details an experiment where an inflammatory condition was induced in mice, compositions of the present invention were administered, and anti-inflammatory effect observev ed. As described in more detail below, Table II shows the resulting percentage of inhibition and effective amounts of compounds and combinations of compounds of the instant invention. Based on this animal data, and other types of similar data, those skilled in the art can determine the effective amounts of compositions of the present invention appropriate for humans.

The effective amount when referring to a compound or combination of compounds of the invention will generally mean the dose ranges, modes of administration, formulations, etc., that have been recommended or approved by any of the various regulatory or advisory organizations in the medical or pharmaceutical arts (e.g., FDA, AMA) or by the manufacturer or supplier. Effective amounts of HMG-CoA reductase inhibitors can be found, for example, in the Physicians Desk Reference. For example, daily doses for atorvastatin calcium range from about 2 mg to about 50 mg, from about 3 mg to about 30 mg, typically about 10 mg. A daily dose for cerivastatin sodium is about 200 µg, while daily doses for fluvastatin sodium, rosuvastatin sodium, pravastatin sodium and simvastatin are each about 20 mg. Some preferred compounds of this invention, e.g., analogs of HMG-CoA reductase inhibitors, may be useful in about the same dosages, or less than or more than dosages typical of known HMG-CoA reductase inhibitors.

Effective amounts of MAP kinase inhibitors can be found, for example, in published reports of the results of human clinical trials. Generally, the recommended dosage for a MAP kinase inhibitor of the present invention, e.g., a p38α MAP kinase inhibitor, is a dose of about 0.01 mg/kg to about 1,000 mg/kg, more preferably from about 0.1 mg/kg to about 20 mg/kg on a daily basis, provided orally. The inhibitor is typically administered in a dose of about 100 mg, which is in the range of doses that will be useful in the present invention. Using other routes of administration, it is believed that a dose of about 0.01 mg/kg/day to about 1,000 mg/kg/day of a MAP kinase inhibitor will be used; preferably a dose between about 0.1 mg/kg/day and about 20 mg/kg/day will be used.

Generally, the recommended dosage for an HMG-CoA reductase inhibitor of the present invention is a dose of about 0.01 mg/kg to about 1,000 mg/kg, more preferably from about 0.1 mg/kg to about 20 mg/kg on a daily basis, provided orally. The inhibitor is typically administered in a dose of about 10 mg, which is in the range of doses that will be useful in the present invention. Using other routes of administration, it is believed that a dose of about 0.01 mg/kg/day to about 1,000 mg/kg/day of an HMG-CoA reductase inhibitor will be used; preferably a dose between about 0.1 mg/kg/day and about 1 mg/kg/day will be used.

Further, appropriate doses for a statin lactone, hydroxy acid form of a statin or non-statin anti-inflammatory agent can be determined based on in vitro experimental results provided herein. For example, the in vitro potency of a compound in inhibiting HMG-CoA reductase and/or inhibiting inflammation mediators provides information useful in the development of effective in vivo dosages to achieve similar biological effects.

Effective amounts of compounds and/or combinations of compounds of the instant invention for use in increasing HDL levels can similarly be determined based on in vitro experimental data, including animal model data. For example, an animal model can be used to determine a percentage increase in HDL levels that would be desirable in humans, and corresponding effective doses of the compound(s) or combinations of compounds to achive such levels.

In some embodiments, administration of compounds of the present invention may be intermittent, for example administration once every two days, every three days, every five days, once a week, once or twice a month, and the like. In some embodiments, the amount, forms, and/or amounts of the different forms may be varied at different times of administration. For example, at one point in time, the acid form of a compound of the present invention may be administered, while at another time the corresponding lactone form may be used.

A person of skill in the art would be able to monitor in a patient the effect of administration of a particular compound. For example, cholesterol levels can be determined by measuring LDL, HDL, and/or total serum cholesterol levels. The release of pro-inflammatory cytokines can be determined by measuring TNF-α and/or IL-1β. Other techniques would be apparent to one of skill in the art.

IV. Rational Design of Kinase and/or HMG-CoA Reductase Inhibitors

Still another aspect of the present invention relates to methods of obtaining and/or making a composition for inhibiting a MAP kinase and/or HMG CoA reductase by designing a compound of formula I/II/III/IV; testing whether the compound inhibits a MAP kinase and/or HMG CoA reductase; and using the compound in making a composition for inhibiting a MAP kinase and/or HMG-CoA reductase. More preferably, the invention relates to methods for designing and testing compounds of formula I/II that are capable of inhibiting both MAP kinase and HMG-CoA reductase.

By "formula I/II" it is meant that either the δ-lactone or the hydroxy carboxylic acid forms, or both forms, may be responsible for inhibition of a MAP kinase, HMG-CoA reductase or both. FIG. 11 illustrates a design approach for developing compounds that inhibit a MAP kinase and/or HMG-CoA reductase.

Figure 11A:
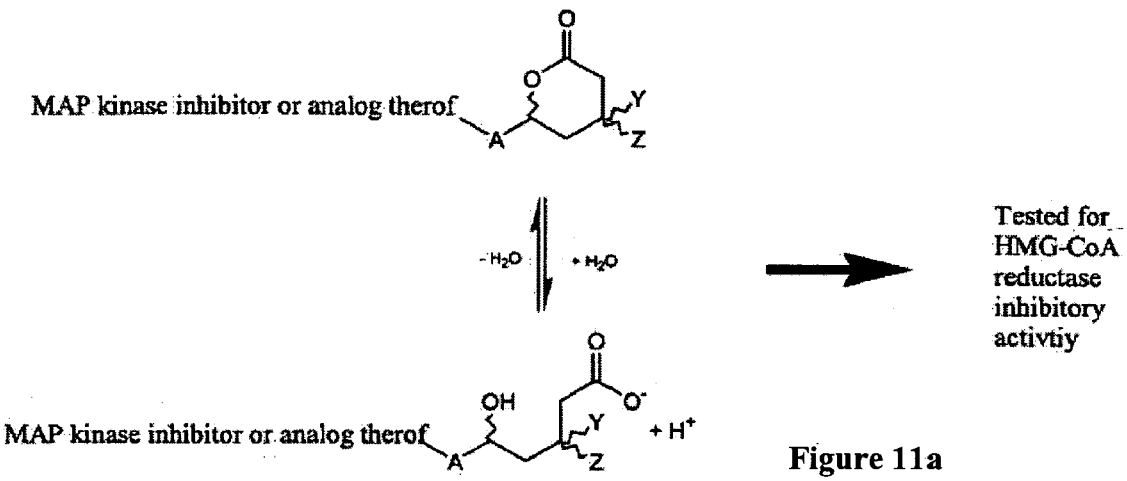
FIG. 11a illustrates an approach in which known inhibitors of MAP kinases are systematically varied and tested for HMG-CoA reductase inhibitory activity.

FIG. 11a illustrates an approach in which known inhibitors of MAP kinases are systematically varied and tested for HMG-CoA reductase inhibitory activity. In this approach, known inhibitors of MAP kinases and analogs thereof are appended or substituted with an A-δ-lactone or an A-hydroxy carboxylic acid group of formulas I or II, respectively. Thus, in some embodiments, the lipophilic moiety (X) is a known MAP kinase inhibitor or a lipophilic moiety thereof. For example, FIG. 4 illustrates known p38α MAP kinase inhibitors that may be used in designing some preferred embodiments. In other embodiments, the lipophilic moiety is an analog of a MAP kinase inhibitor, for example, selected on the basis of structural diversity or similarity to an HMG-CoA reductase inhibitor, preferably to a lipophilic moiety of an HMG-CoA reductase inhibitor, or on the basis of structural compatibility with binding to HMG-CoA reductase, for example, using pharmacophore modeling to indicate binding compatibility. For example, FIG. 5 illustrates MAP kinase analogs preferred in some embodiments.

Figure 11B:
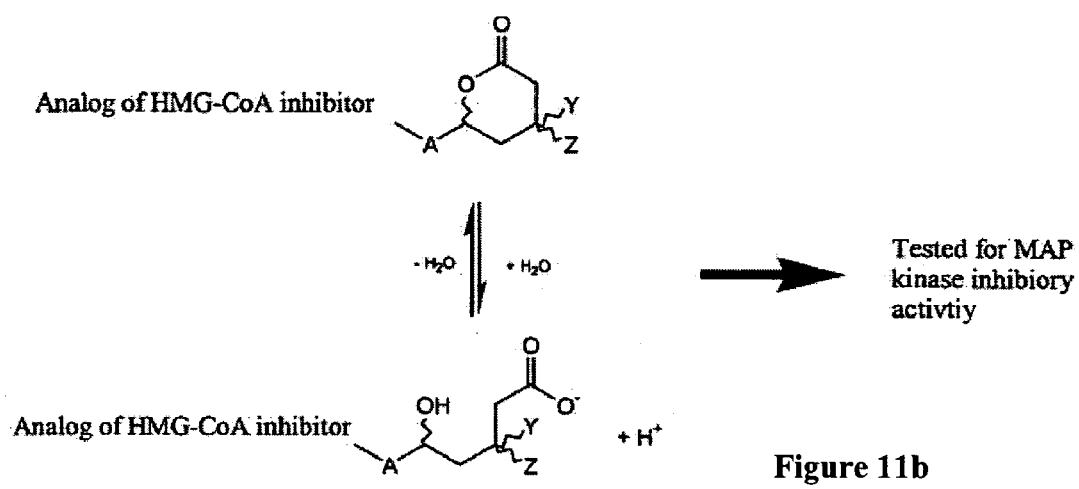
FIG. 11b illustrates an approach in which known inhibitors of HMG-CoA reductase are systematically varied and tested for MAP kinase inhibitory activity.

FIG. 11b illustrates an approach in which known inhibitors of HMG-CoA reductase are systematically varied and tested for MAP kinase inhibitory activity. In this approach, lipophilic moieties (X) of known inhibitors of HMG-CoA reductase are systematically varied, resulting in analogs. FIG. 6, for example, illustrates known statins that can be used in designing some preferred embodiments. In some embodiments, the lipophilic moiety analog is selected on the basis of structural diversity or similarity to a MAP kinase inhibitor, preferably to a lipophilic moiety of a MAP kinase inhibitor, on the basis of structural compatibility with binding to a MAP kinase, such as p38α MAP kinase, for example, using pharmacophore modeling to indicate binding compatibility. For example, FIG. 7 illustrates preferred lipophilic moiety analogs, and FIG. 8 illustrates specific examples of statin analogs, which are even more preferred in some embodiments.

The rational design methods of the present invention are aided by the current understanding of the crystal structures of HMG-CoA reductase and MAP kinases. The X-ray structure of p38α MAP kinase, for example, has been shown to comprise an N-terminal domain with an ATP binding pocket, and a C-terminal domain with a catalytic site, metal binding site, and phophorylation lip. The two domains are connected by a hinge region, to which the substrate binds. Further, a direct correlation has been shown between the "tightness" of binding of a candidate compound to the enzyme and the in vitro cellular activity of the compound.

Figure 11C:
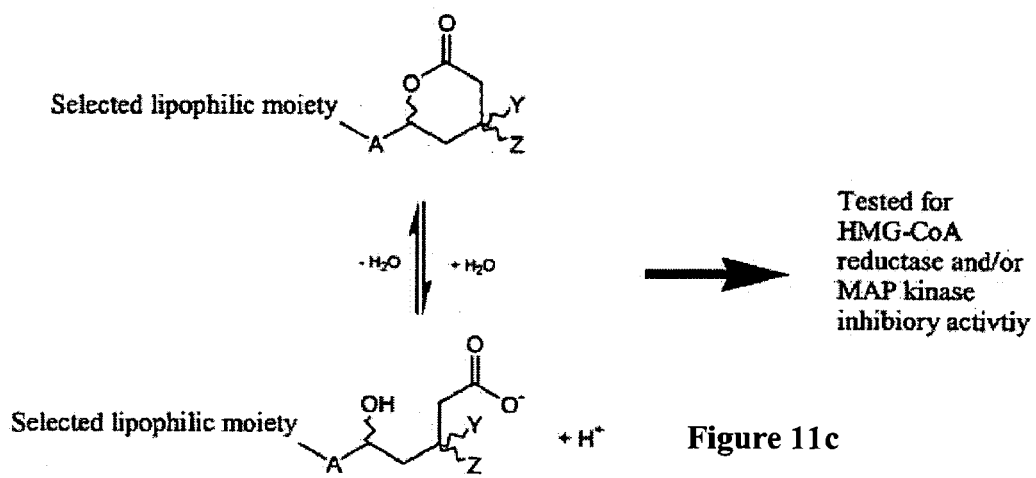
FIG. 11c illustrates an approach in which the lipophilic moiety of compounds of formula I or II is varied and tested for MAP kinase and/or HMG-CoA reductase inhibitory activity.

FIG. 11c illustrates an approach in which the lipophilic moiety of compounds of formula I or II is varied and tested for MAP kinase and/or HMG-CoA reductase inhibitory activity. In some embodiments, the lipophilic moiety is randomly selected. In some embodiments, the lipophilic moiety is selected on the basis of structural diversity or similarity to a MAP kinase inhibitor or on the basis of structural compatibility with binding to a MAP kinase, for example, using pharmacophore modeling to indicate binding compatibility. In some embodiments, the lipophilic moiety is selected on the basis of structural diversity or similarity to an HMG-CoA reductase inhibitor or on the basis of structural compatibility with binding to an HMG-CoA reductase, for example, using pharmacophore modeling to indicate binding compatibility. Selected lipophilic moieties can be appended with an A-δ-lactone or an A-hydroxy carboxylic acid group of formulas I or II, respectively, and then tested for inhibition of a MAP kinase and/or inhibition of an HMG-CoA reductase.

Compounds can be designed and tested entirely using computational methods or a portion of such designing and testing can be done computationally and the remainder done with wet lab techniques.

Testing involves evaluation of the designed compounds for inhibitory activity towards a MAP kinase and/or HMG-CoA reductase. In some embodiments, the collection of designed analogs may be evaluated by computational methods to predict their activity in inhibiting a MAP kinase and/or HMG-CoA reductase, without physically synthesizing the compounds. Such computational methods may also be used to predict other properties of the compounds, such as solubility, membrane penetrability, metabolism and toxicity.

In some embodiments, testing involves synthesizing the designed compounds and evaluating their activity in inhibiting a MAP kinase and/or HMG-CoA reductase in one or more biological assays via wet lab techniques. Known methods for the synthesis of inhibitors of HMG-CoA reductase and MAP kinases can be adapted to prepare the designed analogs in either the δ-lactone or the hydroxy carboxylic acid form, as well as in carboxylate (salt) form.

The activity of the synthesized compound can then be evaluated by a biological assay, which directly or indirectly reflects the inhibition of a MAP kinase, and/or the inhibition of HMG-CoA reductase. Representative biological assays include, but are not limited to, 1) cell-free studies of MAP kinase inhibition; 2) cell-free studies of HMG-CoA reductase inhibition; 3) whole-cell studies of inhibition of inflammatory responses (such as cytokine production and/or release upon challenge by agents, including lipopolysaccharide (LPS)); 4) whole cell studies of terpene and sterol biosynthesis; 5) in vivo models of efficacy against MAP kinase-related conditions, such as inflammatory and/or autoimmune conditions, including arthritis, rheumatoid arthritis, osteoarthritis, vascular inflammatory conditions, inflammatory bowel disease, psoriasis, topical dermatitis, eczema, endotoxemia, sepsis, and toxic shock syndrome, as well as transplant rejection; 6) in vivo models of efficacy in treating HMG-CoA reductase-related conditions, such as hypercholesterolemia, lipid disorders such as hyperlipidemia, and atherogenesis and its sequelae, including atherosclerosis, other vascular inflammatory conditions, myocardial infarction, ischemic stroke, occlusive stroke, peripheral occlusive disease, and other peripheral vascular diseases.

With respect to in vitro assays, the ability of a candidate compound to inhibit MAP kinase and/or HMG-CoA reductase activity can be evaluated by contacting the compound with an assay mixture for measuring activity of a MAP kinase and/or HMG-CoA reductase, and determining the activity of the enzyme in the presence and absence of the compound. A decrease in activity of a MAP kinase in the presence as opposed to the absence of the compound indicates a MAP kinase inhibitor. A decrease in the activity of HMG-CoA reductase in the presence as opposed to the absence of the compound indicates an HMG-CoA reductase inhibitor. Both MAP kinase and HMG-CoA reductase are known and commercially available, facilitating simple in vitro assays for inhibitory activity.

An example of a cell-free MAP kinase assay involves that described in Clerk and Sugden, FEBS Letters, 426:93–96 (1998), incorporated herein by reference. Briefly, serum can be withdrawn from neonatal rats and myocytes exposed to sorbitol (about 30 min) in the absence or presence of about 10 μM or less of a candidate compound. SAPKs/JNKs can be separated by FPLC on a Mono Q HR5/5 column where the MAP kinases are eluted using about a 30 ml linear NaCl gradient (about 0 to about 0.5 M NaCl). They can be assayed by the direct method with myelin basic protein (MBP) or about 0.5 mg/ml glutathione S-transferase-GST-c-Jun (1–135) as substrate, where the assay mix contains about 0.1% (v/v) dimethyl sulphoxide or about 10 μM of a candidate compound (final concentrations). Samples of fractions can be taken for in-gel kinase assays. Fractions may be pooled and concentrated by ultra-filtration and prepared for immunoblot analysis. For MAP-KAPK2, proteins can be applied to a Mono S HR5/5 column and MAP-KAPK2 purified and assayed. GST-c-Jun(1–135) can be used to "pull down" total SAPKs/JNKs from myocyte extracts. Pellets can be washed in kinase assay buffer (for example, about 20 mM HEPES pH about 7.7, about 2.5 mM $MgCl_2$, about 0.1 mM EDTA, about 20 mM β-glycerophosphate) containing the final concentrations of a candidate compound. The pellets can be re-suspended in about 15 μl kinase assay buffer containing twice the final concentrations of a candidate compound and phosphorylation can be initiated with about 15 μl of kinase assay buffer containing about 10 μM ATP and about 1 μCi [γ-$^{32}$P]ATP. JNK1 isoforms can be immunoprecipitated from myocyte extracts using antibodies. The pellets can be washed in kinase assay buffer containing the final concentrations of a candidate compound. GST-c-Jun(1–135) in about 15 μl kinase assay buffer containing twice the final concentrations of a candidate compound can be added and phosphorylation initiated with about 15 μl of kinase assay buffer containing about 20 μM ATP and about 2 μCi [γ-$^{32}$P]ATP. Example 5, below, provides further details of a human p38α MAP kinase inhibition assay, as results using a number of candidate compounds.

An example of a cell-free HMG-CoA reductase assay involves radiometric procedures described in Shum et al., *Ther. Drug Monit.* 20:41–49 (1998), incorporated herein by reference. Briefly, about 150 μg/mL of HMG-CoA reductase can be incubated with a candidate compound, together with about 12 μM [$^{14}$C]HMG-CoA and about 200 μM NADPH in about 200 μL 0.2M phosphate buffer (pH about 7.2) for about 0.5 h at about 37° C. The [$^{14}$C]mevalonate that forms can be converted under acidic conditions to [$^{14}$C]mevalonolactone and separated from un-reacted substrate, for example, by ion-exchange chromatography, and then quantified, for example, by liquid scintillation counting.

An example of a whole cell assay of inhibition of inflammatory responses involves evaluating murine thymic T cell proliferation and IL-2 production or gene expression in the presence and absence of a candidate compound. Methods for measuring T cell proliferation and IL-2 production are standard, well known techniques in the art. Other examples of whole cell assays for inflammation are also known in the art, for example, as described in Welker et al., *Int. Arch. Allergy & Immunology*, 109:110–115 (1996); Suhindler et al., *Blood*, 75:40 (1990); and Gulenboik et al., JBL, 266:19490 (1991), incorporated herein by reference. Example 6, provided below, further details a whole-cell anti-inflammation assay useful in certain rational design embodiments of the present invention. Example 7, provided below, further details a whole-cell LPS-stimulated TNF-α release assay also useful in certain rational design embodiments of the present invention.

Animal models used to reflect inflammatory or immune responses can be utilized to evaluate MAP kinase inhibitory activity in vivo. Exemplary animal models include, but are not limited to, release of inflammatory mediators in response to LPS administration to mice or rats; the mouse acute irritant model; inbred NC/Nga mice, which develop chronic relapsing skin inflammation when reared under non-pathogen-free conditions; Balb/c mice, which develop dermatitis when injected with *Shistosoma japonica* glutathione-S-transferase; mice sensitized by repetitive epicutaneous exposure to ovalbumin antigen that model atopic dermatitis; and dextran sulfate sodium, trinitrobenzene sulfonic acid, and oxazolone-induced colitis, which model inflammatory bowel disease. See also, Nagai et al., *J. Pharmacol. Exp. Therapeutics* 288:43–50 (1999); Boismenu et al., *J. Leukoc. Biol.*, 67:267–278 (2000); and Blumberg et al., *Curr. Opin. Immunol.* 11:648–656 (1999). Further, Example 8 below provides more details of a topical inflammation animal model useful in certain rational design embodiments of the present invention.

In some preferred embodiments, the activity or potency of a compound of formula I/II is similar towards a MAP kinase and HMG-CoA reductase, preferably as measured by whole cell and/or in vivo assays of IC50 or ED50 values, as described in more detail above. In preferred embodiments, potencies with respect to a MAP kinase and HMG-CoA reductase differ by no more than a factor of about 1000. More preferably, potencies differ by no more than a factor of about 100. Most preferably, potencies differ by no more than a factor of about 10. In a highly preferred embodiment, the lactone form of a compound (formula I) is the more potent form against a MAP kinase, the hydroxy carboxylic acid form or carboxylate (salt) form (formula II) is the more potent form against HMG-CoA reductase, and the potencies of these forms against their respective targets differs by no more than a factor of about 10.

In other preferred embodiments, the potency of a compound of formula I/II against a MAP kinase is greater than its potency against HMG-CoA reductase. In such embodiments, potencies with respect to a MAP kinase and HMG-CoA reductase differ by at least a factor of about 10. More preferably, potencies differ by more than a factor of about 100. Most preferably, potencies differ by more than a factor of about 1000.

In yet other preferred embodiments, the potency of a compound of formula I/II against HMG-CoA reductase is greater than its potency against a MAP kinase. In such embodiments, potencies with respect to HMG-CoA reductase and a MAP kinase differ by at least a factor of about 10. More preferably, potencies differ by more than a factor of about 100. Most preferably, potencies differ by more than a factor of about 1000.

All publications, patents, and patent applications mentioned in this specification are herein incorporated by reference to the same extent as if each individual publication, patent, or patent application was specifically and individually indicated to be incorporated by reference.

EXAMPLES

The following examples are intended to illustrate details of the invention, without thereby limiting it in any manner.

Example 1

Synthesis of Atorvastatin Lactone. 5.0 g (8.6 mmole) of atorvastatin calcium was dissolved in 300 mL ethyl acetate and washed with 300 mL 10% (w/v) aqueous sodium hydrogen sulfate solution (pH 3). The organic phase was dried over anhydrous magnesium sulfate, filtered and the solvent removed under reduced pressure to afford 2.85 g (5.11 mmole) of atorvastatin acid. This material was dissolved in 300 mL anhydrous toluene and heated at 60° C. for 40 hours, at which time analytical thin-layer chromatography using 4:1 methylene chloride:acetone eluent indicated near-complete conversion of the starting acid to a less polar product. The toluene was removed under reduced pressure and the reaction mixture was fractionated on 300 cc of silica gel using 4:1 methylene chloride: acetone eluent to afford, after combining, concentrating and drying of the appropriate fractions, 2.14 g (3.96 mmol, 46% overall) of atorvastatin lactone as a white foam. The 400 MHz $^1$H nuclear magnetic resonance (NMR) spectrum and the electrospray mass spectrum (ES-MS) were consistent with the lactone product. $^1$H NMR (Me$_2$SO-d$_6$) δ 9.80 (s, 1H), 7.49 (d, 2H), 7.25–7.15 (m, 6H), 7.05 (s, 4H), 6.99 (t, 2H), 5.15 (d, 1H), 4.46 (br s, 1H), 4.02 (s, 1H), 3.97 (m, 1H), 3.89 (m, 1H), 3.21 (q, 1H), 2.55 (dd, 1H), 2.32 (dd, 1H), 1.74 (br s, 2H), 1.6 (m, 2H), 1.36 (d, 6H). ES-MS: obsvd. m/z 541 ([MH]$^+$).

Example 2

Synthesis of Fluvastatin Lactone. 7.0 g (16 mmole) of fluvastatin sodium was dissolved in 300 mL ethyl acetate and washed with 300 mL 10% (w/v) aqueous sodium hydrogen sulfate solution (pH 3). The organic phase was dried over anhydrous magnesium sulfate, filtered and the solvent removed under reduced pressure to afford 5.76 g (14.0 mmole) of fluvastatin acid. This material was dissolved in 300 mL anhydrous toluene and stirred at room temperature for 7 days, at which time analytical thin-layer chromatography using 5:1 methylene chloride:acetone eluent indicated approximately 30% conversion of the starting acid to a less polar product. The toluene was removed under reduced pressure and the reaction mixture was fractionated on 400 cc of silica gel using 5:1 methylene chloride: acetone eluent to afford, after combining, concentrating and drying of the appropriate fractions, 2.02 g (5.14 mmol, 32% overall) of fluvastatin lactone as a white foam. The 400 MHz $^1$H nuclear magnetic resonance (NMR) spectrum and the electrospray mass spectrum (ES-MS) were consistent with the lactone product. $^1$H NMR (Me$_2$SO-d$_6$) δ 7.7 (d, 1H), 7.4 (br s, 3H), 7.3 (m, 2H), 7.2 (t, 1H), 7.1 (t, 1H), 6.8 (t, 1H), 5.7 (dd, 1H), 5.3 (s, 1H), 5.2 (m, 1H), 4.9 (m, 1H), 4.1 (br s, 1H), 2.7 (dd, 1H), 2.4 (d, 1H), 1.8 (d, 1H), 1.7 (t, 1H), 1.57 (d, 6H). ES-MS: obsvd. m/z 394 ([MH]$^+$).

Also obtained was a slightly more polar product which $^1$H NMR indicated to be the threo-epimer of fluvastatin lactone formed by inversion at the C5 lactone ester center, in accord with the findings of Stokker and Pitzenberger (*Heterocycles* 1987, 26, 157). This isomer was obtained in an amount of 0.173 g (0.440 mmole, 2.8% overall). $^1$H NMR (Me$_2$SO-d$_6$) δ 7.7 (d, 1H), 7.42 (m, 3H), 7.3 (t, 2H), 7.2 (t, 1H), 7.05 (t, 1H), 6.8 (t, 1H), 5.7 (dd, 1H), 5.2 (s, 1H), 4.9 (m, 1H), 4.9 (m, 2H), 4.1 (m, 1H), 2.8 (dd, 1H), 2.7 (dd, 1H), 2.3 (dd, 1H), 2.2 (m, 1H), 1.6 (d, 6H).

Using the procedures outlined in Examples 1 and 2, other compounds of Formula IIa/IIb are converted to compounds of Formula I.

Example 3

Synthesis of Simvastatin Sodium. 1.43 g (3.42 mmole) of simvastatin lactone was dissolved in 10 mL acetonitrile and treated with water (5 mL) and sodium hydroxide (151 mg, 3.78 mmole). The reaction was stirred at room temperature for 3 days, at which time analytical thin-layer chromatography using 4:1 methylene chloride:acetone eluent indicated essentially complete conversion of the starting lactone to a more polar product. The reaction mixture was then diluted to 50 mL with 1:1 acetonitrile:water, frozen and lyophilized to afford 1.22 g (2.66 mmole, 77.8%) of simvastatin sodium as a fluffy white solid. The 400 MHz $^1$H nuclear magnetic resonance (NMR) spectrum was consistent with the sodium carboxylate product. $^1$H NMR (Me$_2$SO-d$_6$) δ 7.6 (br s, 1H), 5.95 (d, 1H), 5.8 (in, 1H), 5.5 (s, 1H), 5.1 (s, 1H), 4.6 (s, 1H), 3.7 (br s, 1H), 3.5 (br s, 1H), 2.3 (m, 2H), 2.2 (d, 1H), 2.0 (m, 2H), 1.8 (m, 2H), 1.6–1.3 (5H), 1.2 (br s, 3H), 1.0 (9H), 0.80 (m, 3H), 0.75 (m, 3H).

Using the procedure outlined in Example 3, other compounds of Formula I are converted to compounds of Formula IIb.

Example 4

Pharmaceutical Compositions Comprising a Compound(s) of Formula I/IIa/IIb or III or IV, Optionally with a Known Anti-Inflammatory Agent(s), for Local/Regional Applications.

Example 4a

Gel Formulation

| | |
|---|---|
| Atorvastatin lactone | 0.1 g |
| Atorvastatin calcium | 0.1 g |
| Polyglyceryl acrylate (Norgel) | 3 g |
| Polyacrylamide/C13–14 isoparaffin/Laureth-7 (Sepigel 305) | 0.2 g |
| Sodium EDTA | 0.01 g |
| Chlorobutanol | 0.4 g |
| Water | 6 g |

Example 4b

Coated Tablets

| | |
|---|---|
| Tablet Cores: | |
| Atorvastatin lactone | 100 g |
| Atorvastatin calcium | 100 g |
| Dibasic calcium phosphate dihydrate | 140 g |
| Microcrystalline cellulose | 24 g |
| Sodium starch glycolate | 10 g |
| Magnesium stearate | 1 g |
| Water | 6 g |
| Coating: | |
| Azopolymer solution | 10% w/v in water |

Example 4c

Coated Tablets of Enteric-Coated Granules

| | |
|---|---|
| Tablet Cores: | |
| Atorvastatin lactone | 100 g |
| Pitavastatin calcium | 100 g |

| Cellulose acetate phthalate solution | 10% w/v in acetone |
|---|---|
| Acacia solution | 10% w/v in water |
| Coating: | |
| Galactomannan solution | 10% w/v in water |

Example 4d

Hydrophilic Ointment USP

| Atorvastatin lactone | 1.0 g |
|---|---|
| Naproxen sodium | 1.0 g |
| Methylparaben | 0.025 g |
| Propylparaben | 0.015 g |
| Sodium lauryl sulfate | 1.0 g |
| Propylene glycol | 12 g |
| Stearyl alcohol | 25 g |
| White petrolatum | 25 g |
| Purified water | 35 g |

Example 4e

Polyethylene Glycol Ointment NF

| Atorvastatin lactone | 1.0 g |
|---|---|
| Diclofenac | 1.0 g |
| Polyethylene glycol 3350 | 40 g |
| Polyethylene glycol 400 | 58 g |

Example 4f

Rectal Suppository

| Atorvastatin lactone | 0.10 g |
|---|---|
| Aminosalicylic acid | 0.90 g |
| Theobroma oil | 1.0 cc |

Example 4g

Ointment in Hydrophilic Petrolatum USP

| Atorvastatin lactone | 1.5 g |
|---|---|
| Indomethacin | 1.5 g |
| Cholesterol | 3.0 g |
| Stearyl alcohol | 3.0 g |
| White wax | 8.0 g |
| White petrolatum | 86 g |

Example 4h

Gel Formulation

| Atorvastatin lactone | 0.1 g |
|---|---|
| Indomethacin | 0.1 g |
| Polyglyceryl acrylate (Norgel) | 3 g |
| Polyacrylamide/C13–14 isoparaffin/Laureth-7 (Sepigel 305) | 0.2 g |
| Sodium EDTA | 0.01 g |
| Chlorobutanol | 0.4 g |
| Water | 6 g |

Example 4i

Cream Formulation

| Phase A: | |
|---|---|
| Atorvastatin lactone | 1 g |
| Indomethacin | 1 g |
| 5-n-Octanoyl salicylic acid | 0.5 g |
| Sweet almond oil | 14.5 g |
| Karate butter | 7 g |
| PPG-3 myristyl ether | 5 g |
| Propyl paraben | 0.1 g |
| Polysorbate 60 | 2.5 g |
| Sorbitan stearate | 2.5 g |
| Phase B: | |
| Cyclomethicone | 4 g |
| Xanthan gum | 0.2 g |
| Carboxyvinyl polymer | 0.5 g |
| Phase C: | |
| Triethanolamine | 0.5 g |
| Water | 2 g |
| Phase D: | |
| Methyl paraben | 0.2 g |
| Glycerol | 5 g |
| Water | 54.5 g |

Example 4j

Atorvastatin Lactone Skin Ointment in Petrolatum USP Ointment

| Atorvastatin lactone | 2.0 g |
|---|---|
| Petrolatum USP | 98 g |

Example 4k

Fluvastatin Lactone Skin Ointment in Hydrophilic Petrolatum USP

| Fluvastatin lactone | 3.0 g |
|---|---|
| Cholesterol | 3.0 g |

Example 4l

Cerivastatin Lactone Skin Ointment in Hydrophilic Ointment USP

| | |
|---|---|
| Stearyl alcohol | 3.0 g |
| White wax | 8.0 g |
| White petrolatum | 86 g |

| | |
|---|---|
| Cerivastatin lactone | 0.5 g |
| Methylparaben | 0.025 g |
| Propylparaben | 0.015 g |
| Sodium lauryl sulfate | 1.0 g |
| Propylene glycol | 12 g |
| Stearyl alcohol | 25 g |
| White petrolatum | 25 g |
| Purified water | 37 g |

Example 4m

Pitavastatin Lactone Skin Ointment in Polyethylene Glycol Ointment NF

| | |
|---|---|
| Pitavastatin lactone | 2.0 g |
| Polyethylene glycol 3350 | 40 g |
| Polyethylene glycol 400 | 60 g |

Example 4n

Isotonic Rosuvastatin Calcium Solution for Ocular Use

| | |
|---|---|
| Rosuvastatin calcium | 1.0 g |
| Sodium chloride USP | 0.9 g |
| Benzalkonium chloride | 0.01 g |
| Sterile distilled water | to 100 mL |

Example 4o

Cerivastatin Lactone Ointment for Ocular Use

| | |
|---|---|
| Cerivastatin lactone | 2.0 g |
| White petrolatum | 97.5 g |
| Chlorobutanol | 0.50 g |

Example 4p

Ointment for Ocular Use

| | |
|---|---|
| Atorvastatin lactone | 1.0 g |
| Cromolyn sodium | 1.0 g |
| White petrolatum | 97.5 g |
| Chlorobutanol | 0.50 g |

Example 4q

Fluvastatin Sodium Solution for Otic Use

| | |
|---|---|
| Fluvastatin sodium | 1.0 g |
| Sodium dihydrogen phosphate | 0.56 g |
| Disodium hydrogen phosphate | 0.28 g |
| Sodium chloride | 0.5 g |
| Disodium edetate | 0.1 g |
| Phenyl mercuric nitrate | 0.005 g |
| Glycerin | 30 mL |
| Sterile distilled water | to 100 mL |

Example 4r

Cerivastatin Sodium Retention Enema

| | |
|---|---|
| Cerivastatin sodium | 0.40 g |
| Sodium dihydrogen phosphate | 1.6 g |
| Disodium hydrogen phosphate | 17.9 g |
| Sodium chloride | 36 g |
| Sodium ascorbate | 2.0 g |
| Tragacanth | 16 g |
| Methylparaben | 8 g |
| Propyl paraben | 2 g |
| Propylene glycol | 100 mL |
| Distilled water | to 4000 mL |

Example 4s

Pitavastatin Lactone Retention Enema

| | |
|---|---|
| Pitavastatin lactone | 0.010 g |
| Sodium carboxymethyl cellulose USP | 1.0 g |
| Distilled water | 100 mL |

Example 4t

Fluvastatin Lactone Rectal Suppository

| | |
|---|---|
| Fluvastatin lactone | 0.10 g |
| Theobroma oil | 2.0 cc |

Example 4u

Atorvastatin Lactone Rectal Suppository

| | |
|---|---|
| Atorvastatin lactone | 0.10 g |
| Polyethylene glycol 1000 | 1.5 g |
| Polyethylene glycol 4000 | 0.5 g |

Example 4v

Pitavastatin Lactone Dry Powder Aerosol Formulation

| | |
|---|---|
| Pitavastatin lactone | 0.004 g |
| Lactose | 0.0085 g |
| (The mixture is micronized to mass median particle size between 3–6 μm) | |

Example 4w

Fluvastatin Sodium Metered-Dose Aerosol Formulation

| | |
|---|---|
| Fluvastatin sodium | 0.080 g |
| (Micronized to mass median particle size between 3–6 μm) | |
| Ethanol USP | 0.20 g |
| Dichlorodifluoromethane | 19.72 g |
| (Propellant) | |

Example 4x

Dry Powder Aerosol Formulation

| | |
|---|---|
| Atorvastatin lactone | 0.004 g |
| Cromolyn sodium | 0.004 g |
| Lactose | 0.0085 g |
| (The mixture is micronized to mass median particle size between 3–6 μm) | |

Example 4y

Metered-Dose Aerosol Formulation

| | |
|---|---|
| Atorvastatin lactone | 0.040 g |
| Cromolyn sodium | 0.04 g |
| (Micronized to mass median particle size between 3–6 μm) | |
| Ethanol USP | 0.20 g |
| Dichlorodifluoromethane | 19.72 g |
| (Propellant) | |

Example 5

Human p38α MAP Kinase Inhibition Assay

In vitro cell-free p38α MAP kinase inhibition assays were conducted by the method as described in Clerk et al., *FEBS Lett.*, 426:93–96 (1998) for a number of lactones in formulas I/IIa/IIb. Briefly, human recombinant p38α protein kinase expressed in *E. coli* (UBI #14–251) was used. Myelin basic protein (MBP, UBI #13–110) was employed as substrate, and microtiter plate wells were coated with MBP (0.01 mg/ml) overnight at 4° C. Candidate compound and/or vehicle was preincubated with 0.075 μg/mL enzyme in modified HEPES buffer pH 7.4 at 25° C. for 15 minutes. The reaction was initiated by addition of 100 μM ATP and allowed to proceed for another 60 minutes. The reaction was terminated by aspirating the solution. Phosphorylated MBP was detected by incubation with a mouse monoclonal IgG2a anti-phosphoMBP antibody. Bound anti-phosphoMBP antibody was quantitated by incubation with a HRP conjugated goat anti-mouse IgG. The protein kinase activity was proportional to the readings of optical density at 405 nm resulting from reaction with an ABTS Microwell Peroxidase Substrate System.

Using this method, $IC_{50}$ data was obtained, with results illustrated in Table I, as discussed above.

Example 6

Whole Cell Anti-Inflammation Assay

The procedure as described in Welker et al., *Int. Arch. Allergy & Immunology* 109:110–115 (1996) can be followed. That is, peripheral blood mononuclear cells (PBMCs) can be prepared from four different donors by differential centrifugation on Ficoll-Hypaque (Seromed, Berlin, Germany). Two donors (1 and 2) may have seasonal rhinoconjunctivitis, e.g., with positive prick tests to inhalant allergens and elevated serum IgE levels. PBMCs may contain approximately 10% CD 14-positive monocytic cells, approximately 90% lymphocytes and approximately <1% granulocytes and platelets.

THP-1 cells are obtained from the ATCC (Rockville, Md., USA; TIB 202) and can be routinely kept in RPMI medium (Gibco, Eggenstein, Germany) with 10% FCS (Seromed) and 50 μM mercaptoethanol (Gibco) added. HL-60 cells (ATCC; No. CCL 240) can be kept in RPMI medium, with 20% FCS, and U-937 cells (ATCC; No. CCL 1593) can be kept in RPMI medium with 10% FCS.

The following glucocorticoids are dissolved in DMSO: Methylprednisolone aceponate (MPA), methylprednisolone-17-propionate (MPP), prednicarbate (PC) and betamethasone valerate (BMV) (Schering, Berlin, Germany). The stock solutions are diluted with medium to <0.1% DMSO before use to avoid toxic effects on the cells.

All cells ($10^6$/ml) can be kept in 24-well polystyrene culture plates and stimulated with lipopolysacharide (LPS; 50 ng/ml; Sigma, St. Louis, Mo., USA) for 24 h at 37° C. in RPMI medium (Gibco) without serum, alone or with $10^{-5}-^{-8}$ M GC added.

THP-1, HL-60 and U-937 cells can also be stimulated with a combination of phorbol myristate acetate (PMA; 25 ng/ml) and the calcium ionophore A23187 (Ion; $2\times^{-7}$ M; both from Sigma). In pre-incubation experiments, cells are cultured for 1 h with the different GCs ($10^{-6}$ M) before addition of the stimulus. As controls, cells are cultured with medium only, without stimulus or GCs and with 0.1%

DMSO. After incubation, cells are centrifuged, and the culture supernatants frozen at −20° C. until analysis.

Cytokines (IL-1β, 1L-8 and TNF-α) in cell supernatants can be quantified by ELISA (Quantikine, Biermann, Bad Nauheim, Germany), and data can be expressed as means of two values calculated for $10^6$ viable cells. Data of duplicate measurements may fluctuate within a very narrow margin (<5%). All experiments can be repeated three (cell lines) or four (PBMC) times. $5 \times 10^7$ THP-1 cells stimulated for 24 h with or without PMA/A23187 and with or without $10^{-6}$ M MPA can be lysed with 3 M lithium chloride and 6 M urea, centrifuged at 20,000 rpm for 60 min, and RNA extracted in phenol-chloroform.

8 μg total RNA per lane can be electrophorased and transferred to nitrocellulose membranes (NEN Research, Boston, Mass., USA) by standard techniques. For Northern blot hybridization, HinIII/Bam-HI DNA fragments of TNF-α (680 bp) can be used. The fragments can be nick translated using $^{32}$P-labeled dCTP (NEN Research) and a random primer labeling kit (Boehringer, Mannheim, Germany). Hybridization can be carried out in SSC (NaCl/sodium citrate) (Sigma) buffer containing 50% formamide (Sigma) and 10% dextran sulfate (Sigma) over-night at 42° C., according to standard procedures. On the following day, nitrocellulose membranes can be washed twice in 2×SSC buffer containing 0.1% sodium dodecyl sulfate (SDS; Sigma) for 15 min at 42° C. and twice in 0.2×SSC containing 0.1 SDS at 50° C. After drying, the blot can be exposed to an X-ray film (Kodak, Rochester, Mass., USA) for up to 7 days.

Statistical significance may be calculated with the two-tailed t-test. The $IC_{50}$ data (inhibitory constants) may be calculated as the GC concentration that cause 50% inhibition of cytokine release, using a computer-assisted program (SPSS, Microsoft).

Example 7

Whole Cell LPS-Stimulated TNF-α Release Assay

The procedure as described in Welker et al., *Int. Arch. Allergy and Immunol.* 109:110–115 (1996) can be followed. Briefly, a candidate compound and/or vehicle can be preincubated with human peripheral blood mononuclear leukocytes (PBML, $5 \times 10^5$/ml) cells in AIM-V medium pH 7.4 for 2 hours. Lipopolysaccharide (LPS, 25 ng/ml) can be added to stimulate the cells, which can be incubated overnight at 37° C. TNF-α cytokine levels in the conditioned medium can then be quantitated using a sandwich ELISA kit.

Example 8

Model for Inhibition of Topical Inflammation Groups of 5 BALB/c male mice weighing 22±2 g were sensitized by application of oxazolone (100 μL, 1.5% v/v in acetone) to the shaved abdominal surface. Seven days after sensitization, a candidate compound (0.1–5 mg in 20 μL acetone, methanol or ethanol vehicle) or vehicle alone (20 μL) was applied topically to the anterior and posterior surfaces of the right ear 30 minutes before and 15 minutes after oxazolone (1% v/v, 25 μL/ear) challenge was applied in the same manner to the right ear. Left ears were untreated. The thickness of both ears of each animal was measured with a Dyer model micrometer gauge 24 hours after oxazolone challenge, and the net increase in thickness of right ears versus left ears was calculated for each animal. Percent inhibition was calculated according to the formula: [(Iv−It)/Iv]×100, where Iv and It respectively refer to the average net increase in right ear thickness (mm) for vehicle and candidate compound treated mice.

Table II summarizes the results obtained using statin lactones, salt forms of hydroxy acid statins, indomethacin, and combinations thereof using this method.

TABLE II

Results of inhibition of oxazolone-induced mouse ear swelling by statin lactones, indomethacin, salt forms of hydroxy acid statins, and combinations thereof.

| Compound | Dose | % Inh. | Compound | Dose | % Inh. |
|---|---|---|---|---|---|
| Atorvastatin lactone | 2 × 2 mg | 50 | Atorvastatin sodium | 2 × 2 mg | 63 |
| Atorvastatin lactone | 2 × 1 mg | 58 | Atorvastatin sodium | 2 × 1 mg | 31 |
| Atorvastatin lactone | 2 × 0.3 mg | 40 | Atorvastatin sodium | 2 × 0.3 mg | 9 |
| Simvastatin lactone | 2 × 0.3 mg | 7 | Simvastatin sodium | 2 × 0.3 mg | 31 |
| Rosuvastatin lactone | 2 × 0.3 mg | 4 | Rosuvastatin sodium | 2 × 0.3 mg | 20 |
| Pitavastatin lactone | 2 × 2 mg | 4 | Pitavastatin calcium | 2 × 2 mg | 60 |
| Pitavastatin lactone | 2 × 0.3 mg | 24 | Pitavastatin calcium | 2 × 0.3 mg | 9 |
| Fluvastatin lactone | 2 × 0.3 mg | 15 | Fluvastatin sodium | 2 × 0.3 mg | 28 |
|  |  |  | Pravastatin sodium | 2 × 0.3 mg | 24 |
| Indomethacin | 2 × 0.3 mg | 44 |  |  |  |
| Atorvastatin lactone + Indomethacin | 2 × 0.3 mg | 64 |  |  |  |

Table II shows a 50%, 58% or 40% inhibition of inflammatory ear swelling upon admininstration of atorvastatin lactone at a dose of 2×0.3 mg, while the administration of the non-statin anti-inflammatory agent indomethacin showed a 44% inhibition. Table II also shows 64% inhibition of inflammation where the treatment comprised administration of atorvastatin lactone and indomethacin. The 64% inhibition is an example of a synergistic effect by the combination of the statin lactone and the non-statin anti-inflammatory agent.

Several observations may be made from this data. First, atorvastatin lactone exhibits the most potent anti-inflammatory activity in this assay, with 40% inhibition of ear swelling at a dose of 2×0.3 mg. Second, atorvastatin lactone displays similar potency to the non-steroidal anti-inflammatory drug indomethacin. Third, a combination of atorvastatin lactone and indomethacin is more effective at reducing ear swelling than either agent alone. Fourth, atorvastatin sodium and pitavastatin calcium effectively inhibit ear swelling by 63% and 60%, respectively, at a dose of 2×2 mg.

Example 9

Scheme for Side Chain Synthesis

An overall scheme for synthesizing the lactone/hydroxy acid hydroxy side chains of compounds of formula I/II is provided below. Two approaches for carrying out the overall scheme are detailed in Examples 9a and 9b.

Example 9a

Approach 1 for Carrying Out Side Chain Synthesis Scheme

In one approach, the structure indicated below is used in attaching the side chain and is prepared in eight steps (steps 1–8)

Step 1: ethyl 5-hydroxy-3-oxo-7-(trimethylsilyl)hept-6-ynoate, 1, is prepared as follows:

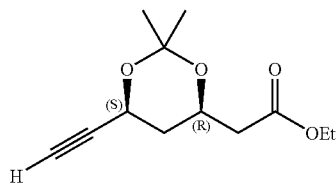

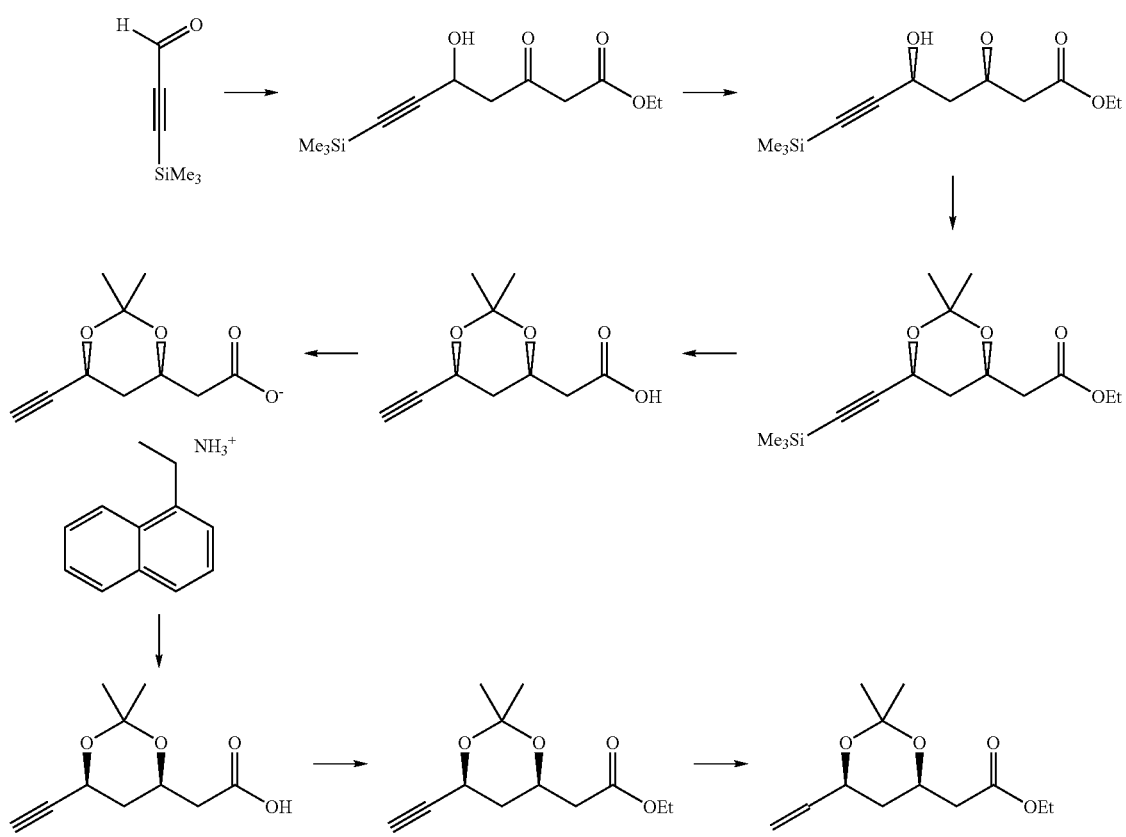

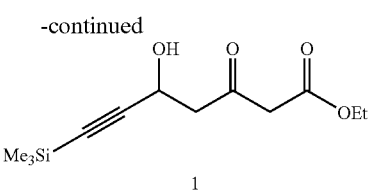

1

All glassware is pre-dried in a high temperature oven and the reaction mixture is maintained under constant nitrogen flow. To a solution of diisopropylamine (174.3 mL) in tetrahydrofuran (1500 mL) at −78° C. is added n-butyllithium (2.5M in hexanes, 666.6 mL) via cannula. The mixture is warmed to −40° C. for 0.5 h (h), then cooled back to −78° C. and ethyl acetoacetate (104.3 g) is added neat, dropwise. The cooling bath is removed and the mixture left to warm for 1 h, then re-cooled to −78° C. and the aldehyde (103.0 g) is added neat, dropwise. After allowing the reaction to warm to ambient temperature over 16 h, the mixture is partitioned between ethyl acetate and water, acidifying the aqueous layer to pH 2. The aqueous layer is extracted with further portions of ethyl acetate and the combined organics washed with brine twice, dried over magnesium sulfate, filtered, and concentrated to a brown oil (266 g) which is used crude in the next step.

The compound obtained in this step shows the following NMR data: $^1$H-NMR (270 MHz, CDCl$_3$, δ) 0.17 (s, 9H), 1.26 (t, 3H), 2.97–3.00 (m, 2H), 3.50 (s, 2H), 4.18–4.23 (q, 2H), 4.82 (dd, 1H).

Step 2: ethyl 3,5-dihydroxy-7-(trimethylsilyl)hept-6-ynoate, 2, is prepared as follows:

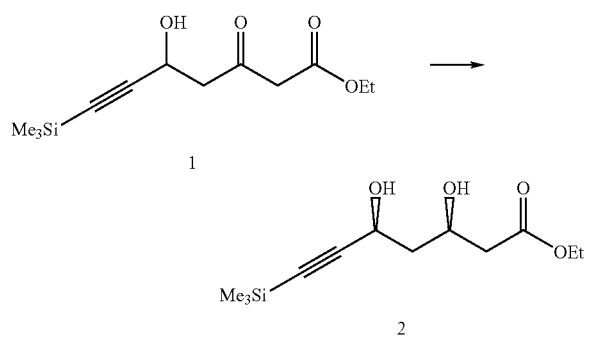

All glassware is pre-dried in a high temperature oven and the reaction mixture is maintained under constant nitrogen flow. A solution of crude ethyl 5-hydroxy-3-oxo-7-(trimethylsilyl)hept-6-ynoate, 1 in a mixture of anhydrous tetrahydrofuran (2000 mL) and anhydrous methanol (220 mL) is cooled to −78° C. and diethylmethoxyborane (107.3 mL) is added neat, dropwise. The mixture is left to stir for 1 h then sodium borohydride (30.9 g) is added portionwise. The mixture is left to warm to ambient temperature over 16 h, then cooled in an ice-bath and acetic acid (170 g) added. After stirring for 0.5 h, the reaction mixture is partitioned between ethyl acetate and aqueous sodium hydrogen carbonate and the organic layer washed until pH 8, washed with brine, dried over magnesium sulfate, filtered and concentrated to a brown oil. This oil is dissolved in methanol, and concentrated in vacuo at 60° C. After 3 further repetitions of this, the crude title compound (152 g) is taken on to the next step.

The compound obtained in this step shows the following NMR data: $^1$H-NMR (270 MHz, CDCl$_3$, δ) 0.17 (s, 9H), 1.26 (t, 3H), 1.82–1.96 (m, 2H), 3.06 (brs, 1H), 3.58 (brs, 1H), 4.17 (q, 2H), 4.21–4.29 (m, 1H), 4.60–4.67 (dd, 1H).

Step 3: ethyl 2-(2,2-dimethyl-6-((trimethylsilyl)ethynyl)-1,3-dioxan-4-yl)acetate, 3, is prepared as follows:

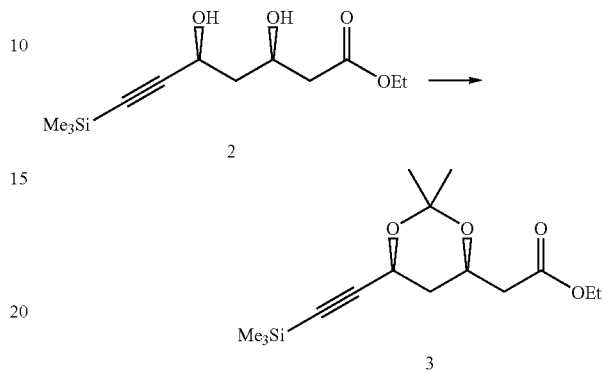

All glassware is pre-dried in a high temperature oven and the reaction mixture is maintained under constant nitrogen flow. A solution containing crude ethyl 3,5-dihydroxy-7-(trimethylsilyl)hept-6-ynoate, 2 (152.0 g), 2,2-dimethoxypropane (362.0 mL), p-toluenesulphonic acid monohydrate (56.0 g) and 3 Å molecular sieves (200 g) in anhydrous ethyleneglycol dimethylether (1100 mL) is shaken at ambient temperature for 16 h. The reaction mixture is diluted with dichloromethane and partitioned versus aqueous sodium hydrogen carbonate. The organic layer is washed with brine, dried over magnesium sulfate, filtered and concentrated. Purification by flash chromatography affords the title compound (89.6 g) as an oil.

The compound obtained in this step shows the following NMR data: $^1$H-NMR (270 MHz, CDCl$_3$, δ) 0.17 (s, 9H), 1.26 (t, 3H), 1.43 (s, 3H), 1.48 (s, 3H), 1.52° 1.89 (m, 2H), 2.35–2.62 (m, 2H), 4.16 (q, 2H), 4.22–4.37 (m, 1H), 4.70 (dd, 1H).

Step 4: 2-(6-ethynyl-2,2-dimethyl-1,3-dioxan-4-yl)acetic acid, 4, is prepared as follows:

To a solution of ethyl 2-(2,2-dimethyl-6-((trimethylsilyl)ethynyl)-1,3-dioxan-4-yl)acetate, 3 (30.0 g) in ethanol (155 mL) at 0° C. is added a solution of sodium hydroxide (2 M, 105.7 mL) dropwise. After 3 h of stirring at ambient temperature, the mixture is partitioned between ethyl acetate and water. The aqueous layer is washed with 3 portions of ethyl acetate and the organics discarded. The aqueous layer is acidified to pH 4 and extracted with 4 portions of ethyl acetate. The combined organics are dried over magnesium sulfate, filtered and concentrated to afford the title compound (16.6 g).

The compound obtained in this step shows the following NMR data: $^1$H-NMR (270 MHz, CDCl$_3$, δ) 1.43 (s, 3H), 1.47 (s, 3H), 1.61–1.95 (m, 2H), 2.45–2.65 (m, 3H), 4.23–4.40 (m, 1H), 4.68–4.72 (m, 1H).

Step 5: (R)-1-(naphthalen-1-yl)ethanaminium, (4R,6S)- and (4S,6R)-2-(6-ethynyl-2,2-dimethyl-1,3-dioxan-4-yl)acetate salt, 5, is prepared as follows:

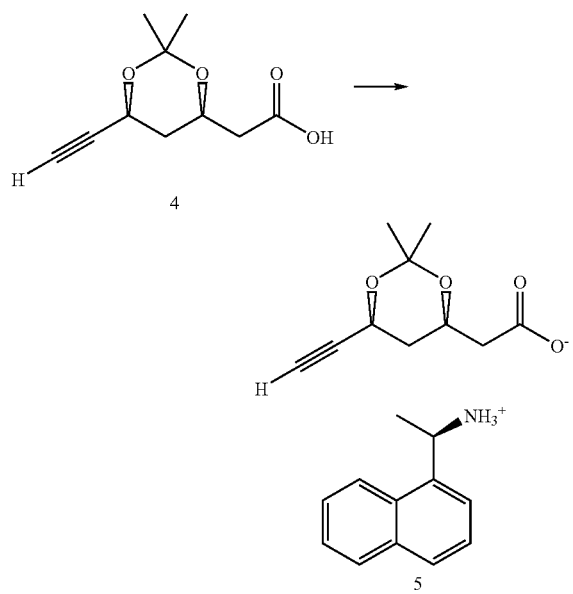

To a cooled solution of 2-(6-ethynyl-2,2-dimethyl-1,3-dioxan-4-yl)acetic acid, 4 (63.4 g) in diethyl ether (200 mL) at 0° C. is added a solution of (R)-1-(naphthalen-1-yl)ethanamine (54.9 g) in diethyl ether (200 mL). The mixture is stirred for 0.5 h and the solvent is removed in vacuo to give a mixture of the diastereomeric salts, 5 (117.0 g).

Step 6: (R)-1-(naphthalen-1-yl)ethanaminium, 2-((4R,6S)-6-ethynyl-2,2-dimethyl-1,3-dioxan-4-yl)acetate salt, 6, is prepared as follows:

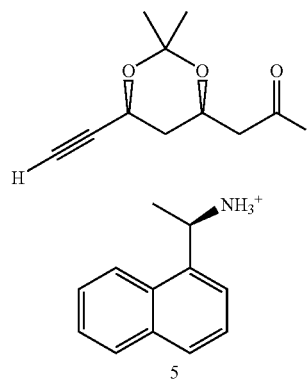

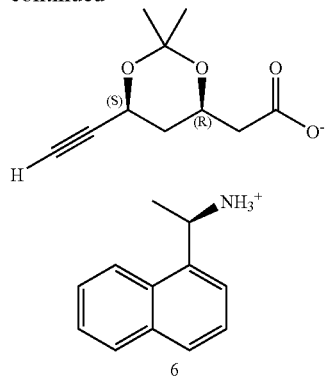

The crude salt, 5 (117 g) is recrystallized from hot methyl isobutyl ketone at a concentration of 45 mg/mL. The resulting crystals are filtered, washing with ice-cold methyl isobutyl ketone then hexanes and dried in vacuo. This process is repeated twice more, at which point the material is diastereomerically pure as assessed by chiral HPLC (Chiralpak AD column, eluting with 1–8% ethanol in hexane) and by $^1$H NMR (29.8 g).

The compound obtained in this step shows the following NMR data: $^1$H-NMR (270 MHz, CDCl$_3$, δ) 1.30 (s, 3H), 1.32 (s, 3H), 1.63 (d, 3H), 1.24–1.71 (m, 2H), 2.07 (ddd, 2H), 2.45 (s, 1H), 3.95–4.05 (m, 1H), 4.48 (m, 1H), 5.03–5.13 (q, 1H), 6.20–6.65 (brs, 3H), 7.48–7.62 (m, 3H), 7.66 (d, 1H), 7.79 (d, 1H), 7.88 (d, 1H), 8.03 (d, 1H).

Step 7: 2-((4R,6S)-6-ethynyl-2,2-dimethyl-1,3-dioxan-4-yl)acetic acid, 7, is prepared as follows:

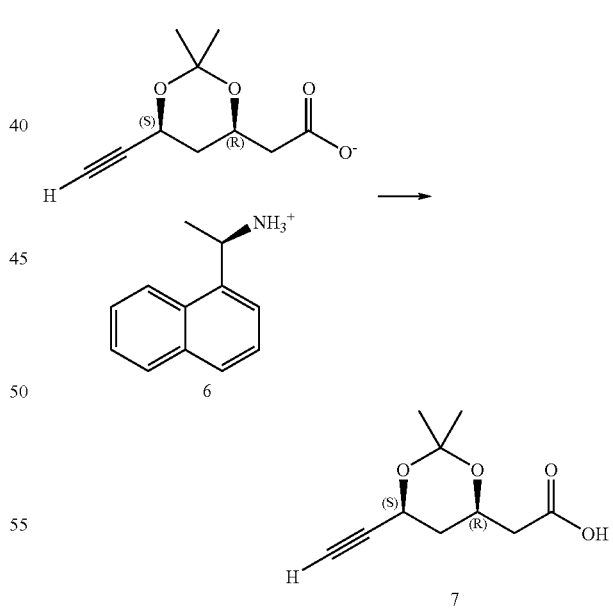

(R)-1-(naphthalen-1-yl)ethanaminium, 2-((4R,6S)-6-ethynyl-2,2-dimethyl-1,3-dioxan-4-yl)acetate salt, 6 (6.58 g) is partitioned between ethyl acetate and dilute hydrochloric acid (0.2 M, 89.2 mL). The organic layer is dried over magnesium sulfate, filtered and concentrated to give 2-((4R,6S)-6-ethynyl-2,2-dimethyl-1,3-dioxan-4-yl)acetic acid, 7 as a yellow oil (3.60 g) which is used without further purification.

The compound obtained in this step shows the following NMR data: $^{1}$H-NMR (270 MHz, CDCl$_3$, δ) 1.43 (s, 3H), 1.47 (s, 3H), 1.61–1.95 (m, 2H), 2.45–2.65 (m, 3H), 4.23–4.40 (m, 1H), 4.68–4.72 (m, 1H).

Step 8: ethyl 2-((4R,6S)-6-ethynyl-2,2-dimethyl-1,3-dioxan-4-yl)acetate, 8, is prepared as follows:

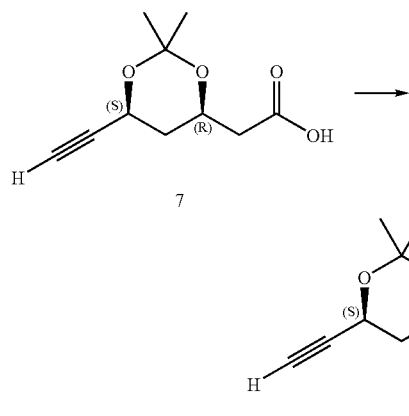

To a solution of 2-((4R,6S)-6-ethynyl-2,2-dimethyl-1,3-dioxan-4-yl)acetic acid, 7 (3.60 g) in anhydrous acetonitrile (40 mL) is added a solution of iodoethane (4.25 g) in anhydrous acetonitrile (10 mL) followed by a solution of 1,8-diazabicyclo[5.4.0]undec-7-ene (4.15 g) in anhydrous acetonitrile (10 mL). The mixture is warmed to 55° C. for 1.5 h, then cooled and the solvent is removed in vacuo. The residue is partitioned between ethyl acetate and aqueous sodium hydrogen carbonate. The organic layer is washed with 0.05 M hydrochloric acid solution, then brine and dried over magnesium sulfate, filtered and concentrated to an oil (3.01 g).

The compound obtained in this step shows the following NMR data: $^{1}$H-NMR (270 MHz, CDCl$_3$, δ) 1.26 (t, 3H), 1.43 (s, 3H), 1.47 (s, 3H), 1.50–1.95 (m, 2H), 2.34–2.64 (m, 3H), 4.16 (q, 2H), 4.20–4.40 (m, 1H), 4.66–4.72 (m, 1H).

Example 9b

Approach 2 for Carrying Out Side Chain Synthesis Scheme

In a second approach, the structure indicated below is used in attaching the side chain. This structure can be prepared in one step (Step 1) from the product obtained in Example 9a, as detailed below.

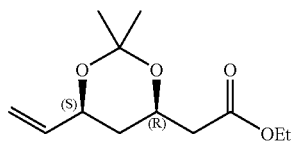

Step 1: ethyl 2-((4S,6R)-2,2-dimethyl-6-vinyl-1,3-dioxan-4-yl)acetate, 9, is prepared as follows:

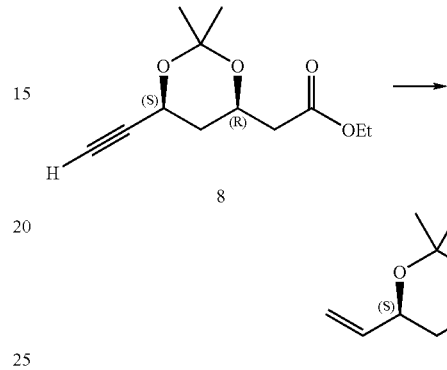

To a solution of ethyl 2-((4R,6S)-6-ethynyl-2,2-dimethyl-1,3-dioxan-4-yl)acetate, 8 (0.70 g) in ethanol (15 mL) is added ammonium formate (1.95 g), quinoline (13 μL) and palladium on calcium carbonate (0.07 g). The reaction mixture is heated to reflux with periodical additions of ammonium formate and palladium on calcium carbonate until the reaction is complete. The reaction is then filtered through Celite and partitioned between ethyl acetate and water. The organic phase is separated, dried over magnesium sulfate, filtered again and evaporated to afford the title compound (0.62 g).

The compound obtained in this step shows the following NMR data: $^{1}$H-NMR (270 MHz, CDCl$_3$, δ) 1.26 (t, 3H), 1.43 (s, 3H), 1.48 (s, 3H), 1.30–1.70 (m, 2H), 2.46 (ddd, 2H), 4.12–4.19 (m, 2H), 4.33–4.41 (m, 2H), 5.12 (d, 1H), 5.28 (d, 1H), 5.77–5.86 (m, 1H).

Example 10

Scheme for Synthesis of N-Pyridyl Pyrazole Compounds

An overall scheme for synthesizing N-pyridyl substituted pyrazole compounds of formula VI of the instant invention is provided below. Examples 10a, 10b, 10c and 10d below detail four specific examples following the overall scheme.

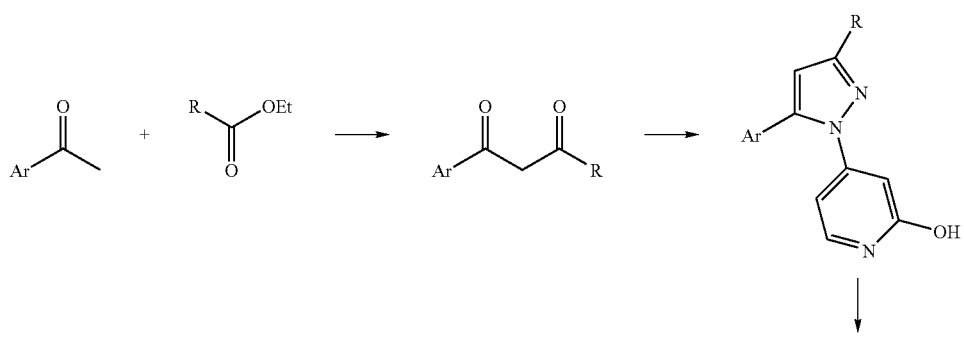

115 116
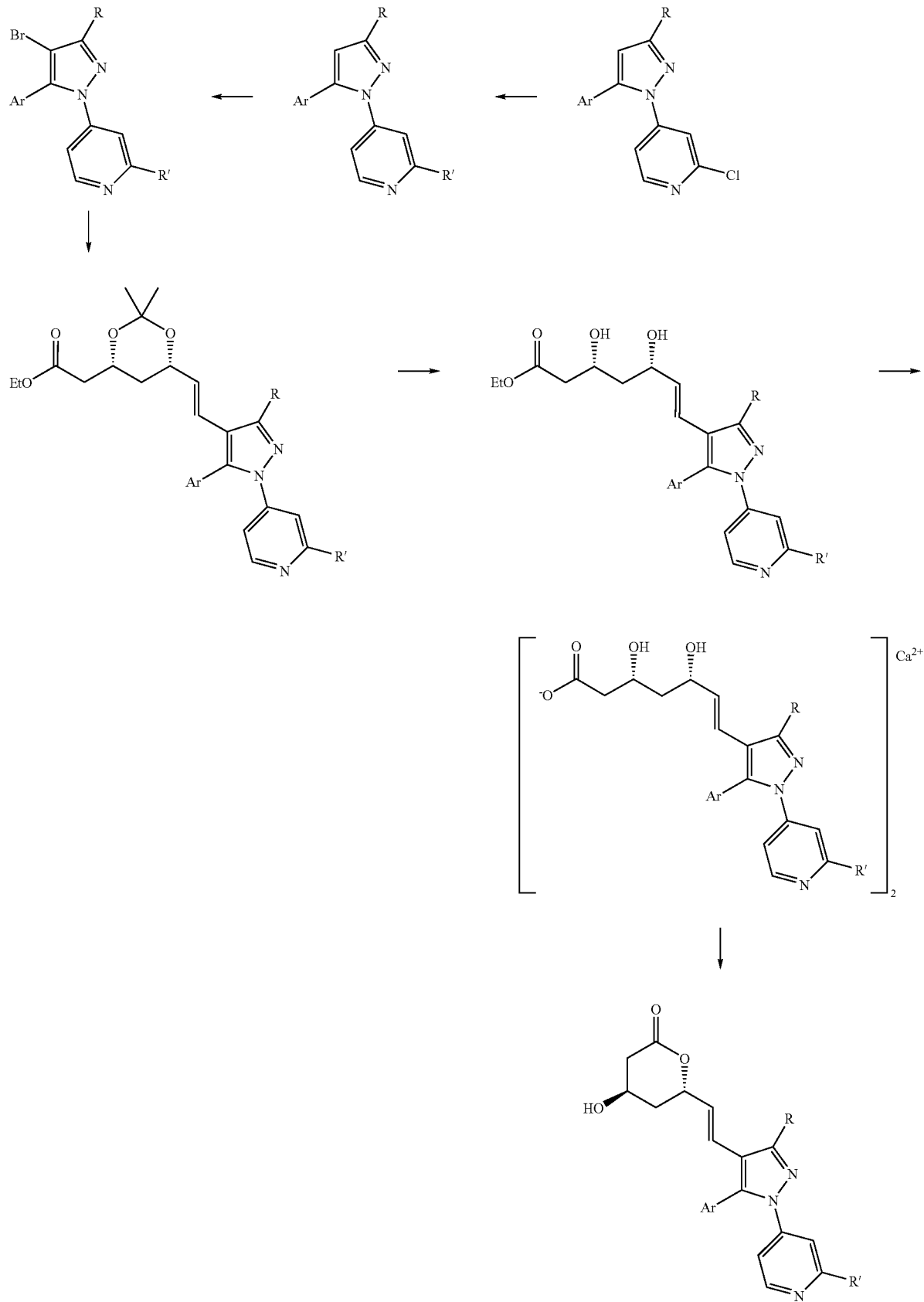

Example 10a

Synthesis of an N-Pyridyl Pyrazole

In one specific example, a compound having the structure indicated below is prepared in nine steps (Steps 1–9).

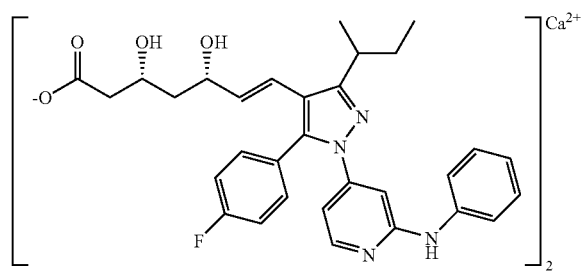

Step 1: 1-(4-fluorophenyl)-4-methylhexane-1,3-dione, 10, is prepared as follows:

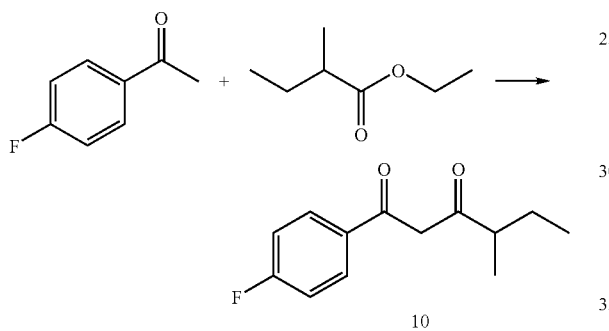

To a 0° C. suspension of sodium hydride (15 g) in anhydrous 1,4-dioxane (150 mL) under nitrogen is added dropwise a solution of 1-(4-fluorophenyl)ethanone in 1,4-dioxane (50 mL), followed by dropwise addition of a solution of ethyl-2-methylbutanoate in 1,4-dioxane (50 mL). The resulting solution is heated to 80° C. for 4 h during which time vigorous gas evolution occurs. The reaction mixture is poured into iced 1N hydrochloric acid, then extracted twice with ethyl acetate. The combined organic layers are washed with brine, then dried over magnesium sulfate, filtered and concentrated. Distillation under reduced pressure affords 12.4 g of the title compound as an oil.

The compound obtained in this step shows the following boiling point and mass spectral data:

b.p. 101–104° C. at 1 mm Hg LC/MS: $C_{13}H_{15}FO_2$ requires 222.1; observed M/Z 221.3 [M–H]$^-$. RT (RT) 5.62 min (min).

Step 2: 4-hydrazinylpyridin-2(1H)-one, 11, is prepared as follows:

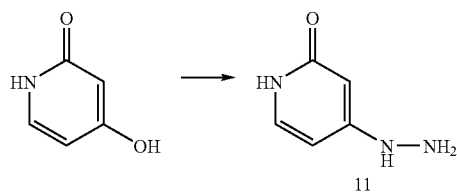

To a suspension of 4-hydroxypyridin-2(1H)-one (5 g) in 2-ethoxyethanol (20 mL) is added hydrazine (10 mL). The mixture is flushed with nitrogen, then heated to reflux for 4 days. Upon cooling to 0° C., the title compounds forms a precipitate which is filtered, then taken up in boiling ethanol and re-filtered, washing with further hot ethanol. Removal of the solvent in vacuo yields 2.2 g of the title compound.

The compound obtained in this step shows the following mass spectral data: LC/MS: $C_5H_7N_3O$ requires 125.1; observed M/Z 126.1 [M+H]$^+$. RT 0.50 min.

Step 3: 4-(3-sec-butyl-5-(4-fluorophenyl)-1H-pyrazol-1-yl)pyridine-2(1H)-one, 12a and 4-(5-sec-butyl-3-(4-fluorophenyl)-1H-pyrazol-1-yl)pyridine-2(1H)-one, 12b are prepared as follows:

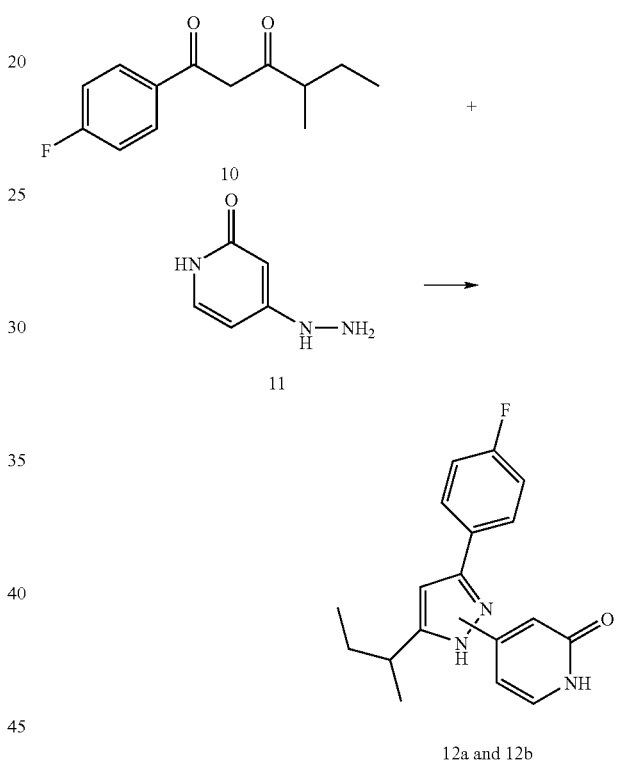

12a and 12b

A solution of 1-(4-fluorophenyl)-4-methylhexane-1,3-dione, 10 (0.200 g) and 4-hydrazinylpyridin-2(1H)-one, 11 (0.113 g) is dissolved in acetic acid (3 mL) and the mixture heated to 90° C. for 2 h. On cooling, the solution is quenched with sodium hydrogen carbonate and extracted with ethyl acetate. The aqueous layer is extracted with a further portion of ethyl acetate and the combined organic layer is dried over magnesium sulfate, filtered and concentrated to an oil that crystallizes on standing. The residue is triturated with 9:1 iso-hexanes/ethyl acetate to give 0.145 g of 12a and 12b as a mixture.

The compound obtained in this step shows the following mass spectral data: LC/MS: $C_{18}H_{18}FN_3O$ requires 311.1; observed M/Z 312.2 [M+H]$^+$, 310.3 [M–H]$^-$. RT 5.25 mm.

Step 4: 4-(5-sec-butyl-3-(4-fluorophenyl)-1H-pyrazol-1-yl)-2-chloropyridine, 13a and 4-(3-sec-butyl-5-(4-fluorophenyl)-1H-pyrazol-1-yl)-2-chloropyridine, 13b are prepared as follows:

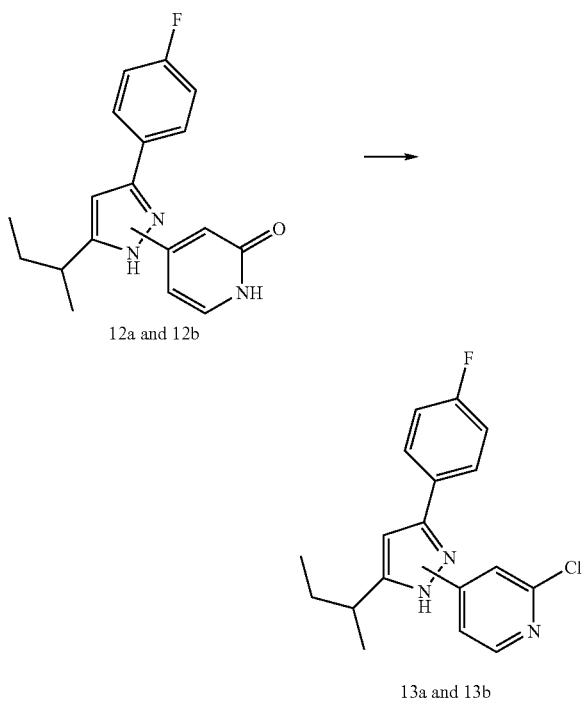

12a and 12b

The mixture of regioisomers, 12a and 12b (5.3 g) are dissolved in phosphorous oxychloride (30 mL) and heated to 95° C. for 16 h. On cooling the reaction mixture is poured into ice-water, then extracted with ethyl acetate. The organic layer is washed with aqueous sodium hydrogen carbonate and brine then dried over magnesium sulfate, filtered and concentrated. Flash chromatography affords 2.77 g of 4-(5-sec-butyl-3-(4-fluorophenyl)-1H-pyrazol-1-yl)-2-chloropyridine, 13a and 0.54 g of 4-(3-sec-butyl-5-(4-fluorophenyl)-1H-pyrazol-1-yl)-2-chloropyridine, 13b as well as 0.57 g of mixed fractions.

4-(5-sec-butyl-3-(4-fluorophenyl)-1H-pyrazol-1-yl)-2-chloropyridine, 13a shows the following mass spectral and NMR data:

LC/MS: $C_{18}H_{17}ClFN_3$ requires 329.1; observed M/Z 330.1/332.0 (Cl) [M+H]$^+$. RT 7.40 min $^1$H-NMR (270 MHz, CDCl$_3$, δ) 0.96 (t, 3H), 1.30 (d, 3H), 1.52–1.80 (m, 2H), 2.77–2.89 (m, 1H), 6.31 (s, 1H), 7.03 (d, 1H), 7.09–7.15 (m, 2H), 7.21–7.28 (m, 2H), 7.41 (s, 1H), 8.22 (d, 1H).

4-(3-sec-butyl-5-(4-fluorophenyl)-1H-pyrazol-1-yl)-2-chloropyridine, 13b shows the following mass spectral data:

LC/MS: $C_{18}H_{17}ClFN_3$ requires 329.1; observed M/Z 330.1/332.0 (Cl) [M+H]$^+$. RT 7.40 min Step 5: 4-(4-bromo-5-sec-butyl-3-(4-fluorophenyl)-1H-pyrazol-1-yl)-2-chloropyridine, 14 is prepared as follows:

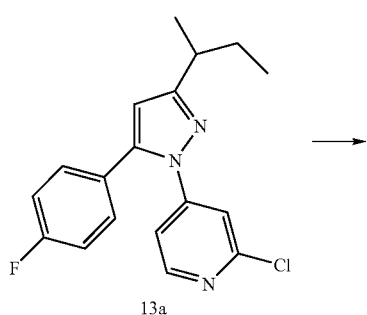

13a

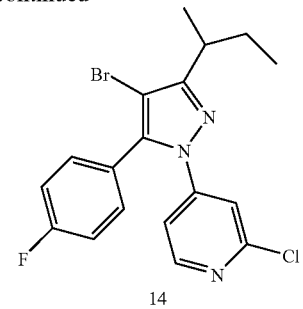

14

A solution of 4-(5-sec-butyl-3-(4-fluorophenyl)-1H-pyrazol-1-yl)-2-chloropyridine, 13a (2.49 g) and N-bromosuccinimide (2.69 g) are dissolved in N,N-dimethylformamide (40 mL) and stirred for 3 h at room temperature. The crude mixture is partitioned between water and dichloromethane and the aqueous phase is extracted with further portions of dichloromethane. The combined organic layers are washed with brine, dried over magnesium sulfate, filtered and concentrated. Flash chromatography affords 2.54 g of the title compound.

The compound obtained in this step shows the following mass spectral data: LC/MS: $C_{18}H_{16}BrClFN_3$ requires 407.0; observed M/Z 407.8/409.9/411.9 (Br/Cl) [M+H]$^+$. RT 8.21 min Step 6: 4-(4-bromo-5-sec-butyl-3-(4-fluorophenyl)-1H-pyrazol-1-yl)-N-phenylpyridin-2-amine, 15 is prepared as follows:

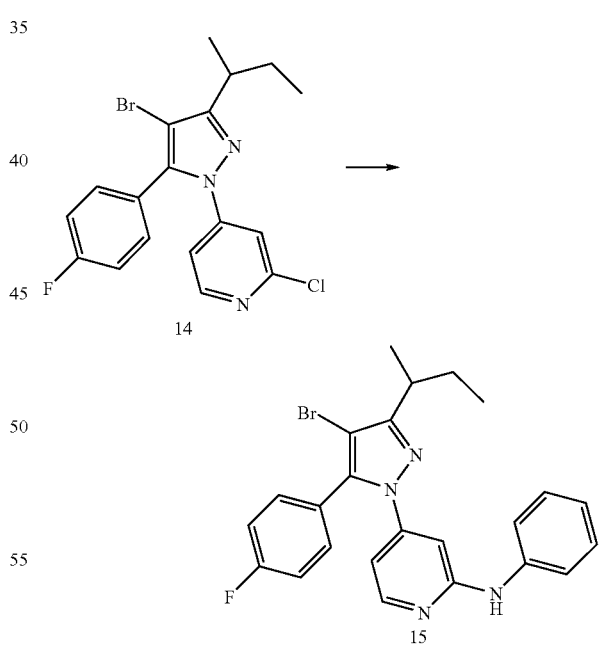

To a solution of 4-(4-bromo-5-sec-butyl-3-(4-fluorophenyl)-1H-pyrazol-1-yl)-2-chloropyridine, 14 (2.53 g) and aniline (1.13 g) in 2,2,2-trifluoroethanol (20 mL) is added trifluoroacetic acid (2.21 mL) dropwise and the mixture heated to 80° C. for 36 h. On cooling the reaction mixture is partitioned between sodium hydrogen carbonate and ethyl acetate. The organic layer is washed with brine, dried over magnesium sulfate, filtered and concentrated. Purification by flash chromatography provides 1.10 g of the title compound.

The compound obtained in this step shows the following mass spectral data: LC/MS: $C_{24}H_{22}BrFN_4$ requires 464.1; observed M/Z 464.9/466.9 (Br) [M+H]$^+$, 463.0/465.0 (Br) [M–H]$^-$. RT 7.72 min Step 7: Ethyl 2-((4R,6S)-6-((E)-2-(5-sec-butyl-3-(4-fluorophenyl)-1-(2-(phenylamino)pyridine-4-yl)-1H-pyrazol-4-yl)vinyl)-2,2-dimethyl-1,3-dioxan-4-yl)acetate, 16 is prepared as follows:

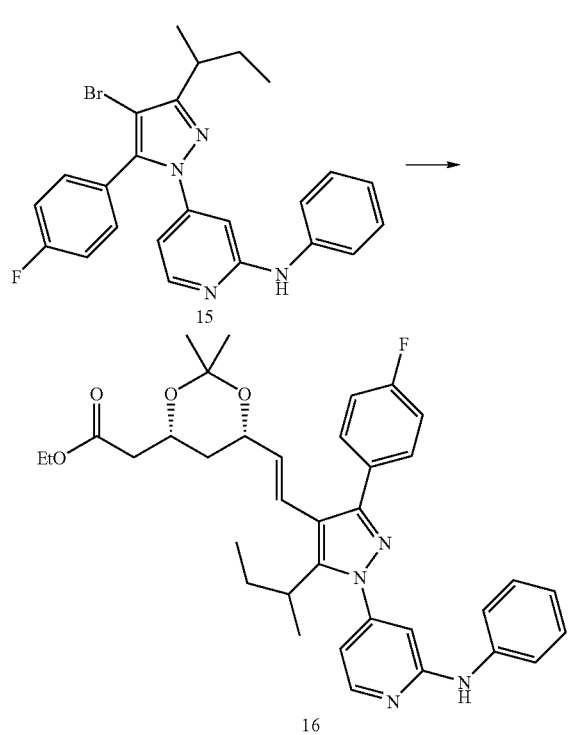

To a 0° C. solution of ethyl 2-((4R,6S)-ethynyl-2,2-dimethyl-1,3-dioxan-4-yl)acetate, 9 (1.34 g) and dichlorobis(triphenylphosphine)palladium(II) (0.040 g) under nitrogen in anhydrous tetrahydrofuran (3 mL) is added neat tributyltin hydride (1.79 g) dropwise. The resulting mixture is stirred for 30 min, then added to a solution containing 4-(4-bromo-5-sec-butyl-3-(4-fluorophenyl)-1H-pyrazol-1-yl)-N-phenylpyridin-2-amine, 15 (1.10 g) and dichlorobis(triphenylphosphine)palladium(II) (80 mg) in N,N-dimethylformamide (4 mL). The reaction mixture is flushed with nitrogen and heated to 80° C. for 16 h. On cooling, the mixture is partitioned between ethyl acetate and brine and the organic layer washed with further brine, dried over magnesium sulfate, filtered and concentrated. Purification by flash chromatography affords 0.57 g of the title compound.

The compound obtained in this step shows the following mass spectral data: LC/MS: $C_{36}H_{41}FN_4O_4$ requires 612.3; observed M/Z 613.1 [M+H]$^+$, 611.3 [M–H]$^-$. RT 7.60 min.

Step 8: (3R,5S,E)-ethyl 7-(3-sec-butyl-5-(4-fluorophenyl)-1-(2-phenylamino)pyridin-4-yl)-1H-pyrazol-4-yl)-3,5-dihydroxyhept-6-enoate, 17 is prepared as follows:

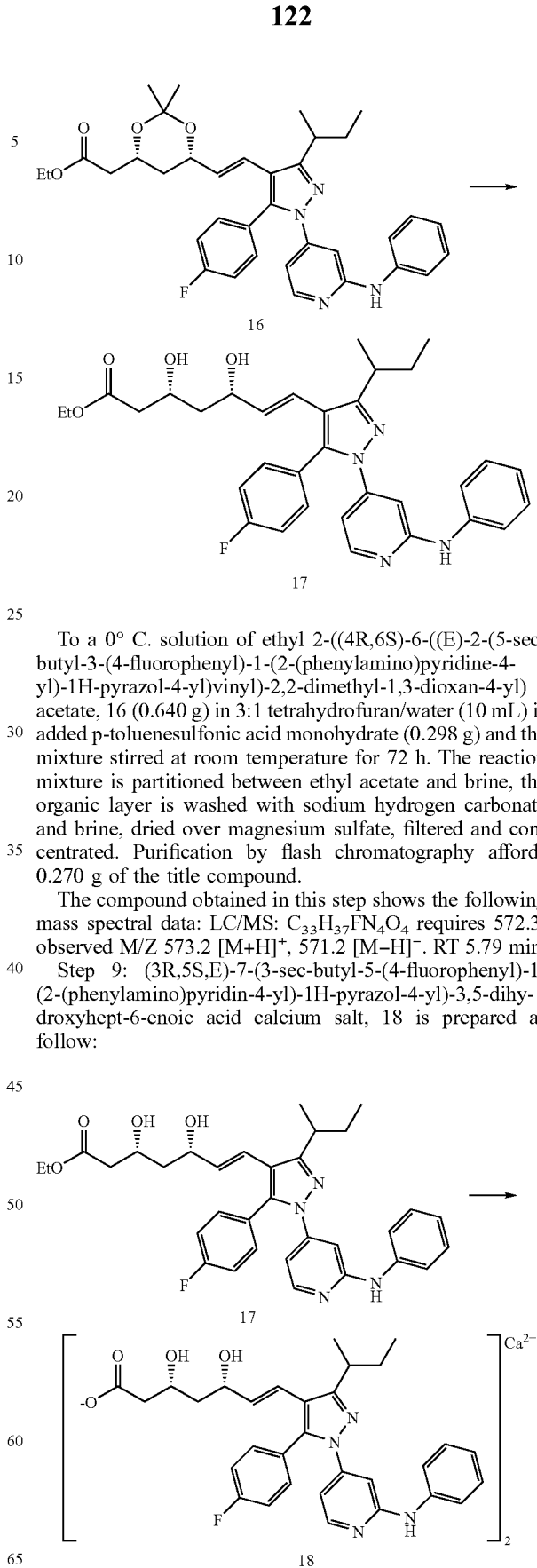

To a 0° C. solution of ethyl 2-((4R,6S)-6-((E)-2-(5-sec-butyl-3-(4-fluorophenyl)-1-(2-(phenylamino)pyridine-4-yl)-1H-pyrazol-4-yl)vinyl)-2,2-dimethyl-1,3-dioxan-4-yl) acetate, 16 (0.640 g) in 3:1 tetrahydrofuran/water (10 mL) is added p-toluenesulfonic acid monohydrate (0.298 g) and the mixture stirred at room temperature for 72 h. The reaction mixture is partitioned between ethyl acetate and brine, the organic layer is washed with sodium hydrogen carbonate and brine, dried over magnesium sulfate, filtered and concentrated. Purification by flash chromatography affords 0.270 g of the title compound.

The compound obtained in this step shows the following mass spectral data: LC/MS: $C_{33}H_{37}FN_4O_4$ requires 572.3; observed M/Z 573.2 [M+H]$^+$, 571.2 [M–H]$^-$. RT 5.79 min.

Step 9: (3R,5S,E)-7-(3-sec-butyl-5-(4-fluorophenyl)-1-(2-(phenylamino)pyridin-4-yl)-1H-pyrazol-4-yl)-3,5-dihydroxyhept-6-enoic acid calcium salt, 18 is prepared as follow:

To a 0° C. solution of (3R,5S,E)-ethyl 7-(3-sec-butyl-5-(4-fluorophenyl)-1-(2-phenylamino)pyridin-4-yl)-1H-pyrazol-4-yl)-3,5-dihydroxyhept-6-enoate, 17 (0.135 g) in ethanol (0.6 mL) is added a 1M solution of sodium hydroxide (0.236 mL) dropwise and the mixture stirred at room temperature for 2 h. Ethanol is removed in vacuo until the compound starts to precipitate, then an aqueous solution of calcium chloride (0.118M, 2.0 mL) is added dropwise. The resulting precipitate is filtered, washed with water, acetonitrile, water, acetonitrile and dried in vacuo to afford the title compound (0.077 g).

The compound obtained in this step shows the following mass spectral and NMR data:

LC/MS as free acid: $C_{31}H_{33}FN_4O_4$ requires 544.2; observed M/Z 545.1 [M+H]$^+$, 545.0 [M–H]$^-$. RT 2.99 min. $^1$H-NMR (270 MHz, DMSO-d$_6$, δ) 0.91 (t, 3H), 1.28 (d, 3H), 1.20–1.32 (m, 2H) 1.48–1.59 (m, 2H), 1.80–2.12 (m, 2H), 2.93–3.01 (m, 1H), 3.69–3.76 (m, 1H), 4.09–4.15 (m, 1H), 4.92 (brs, 1H), 5.64 (dd, 1H), 6.19 (d, 1H), 6.30 (d, 1H), 6.80 (s, 1H), 6.89 (t, 1H), 7.21 (t, 2H), 7.29–7.36 (m, 4H), 7.48 (2H), 8.02 (d, 1H), 9.15 (s, 1H).

Example 10b

Synthesis of an N-pyridyl Pyrazole

In a second specific example, a compound having the structure indicated below is prepared in one step (Steps 1) from the product obtained in Example 10a, detailed above.

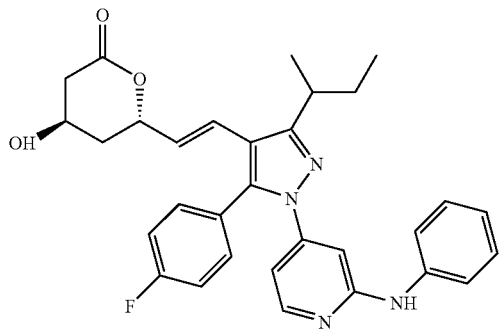

Step 1: (4R,6S,E)-6-(2-(3-sec-butyl-5-(4-fluorophenyl)-1-(2-(phenylamino)pyridine-4-yl)-1H-pyrazol-4-yl)vinyl)-4-hydroxy-tetrahydropyran-2-one, 19 is prepared as follows:

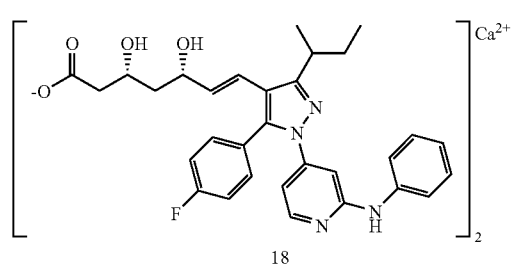

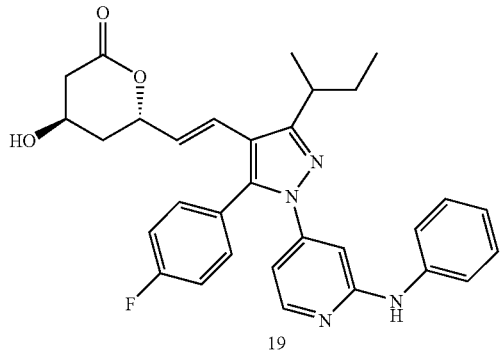

(3R,5S,E)-7-(3-sec-butyl-5-(4-fluorophenyl)-1-(2-(phenylamino)pyridin-4-yl)-1H-pyrazol-4-yl)-3,5-dihydroxyhept-6-enoic acid calcium salt, 18 (0.050 g) is dissolved in toluene (2.5 mL) and heated to 90° C. for 10 h. The solution is concentrated in vacuo and purified by flash chromatography to give 0.026 g of the title compound as a powder.

The compound obtained in this step shows the following mass spectral and NMR data:

LC/MS: $C_{31}H_{31}FN_4O_3$ requires 526.2; observed M/Z 527.1 [M+H]$^+$, 525.2 [M–H]$^-$. RT 5.59 min. $^1$H-NMR (270 MHz, CDCl$_3$, δ) 0.97 (t, 3H), 1.33 (d, 3H), 1.48–2.05 (m, 4H), 2.41–2.80 (m, 2H), 2.87–2.96 (m, 1H), 4.34–4.37 (m, 1H), 5.11–5.14 (m, 1H), 5.62 (dd, 1H), 6.31 (d, 1H), 6.48–6.54 (m, 2H), 6.77 (d, 1H), 6.88 (d, 2H), 7.05 (t, 1H), 7.09–7.32 (m, 5H), 8.08 (d, 1H).

Examples 10c and 10d

Syntheses of N-Pyridyl Pyrazoles

In two additional specific examples, compounds having the structures indicated below are prepared in two steps (Steps 1–2) from intermediate 17 obtained in Example 10a above.

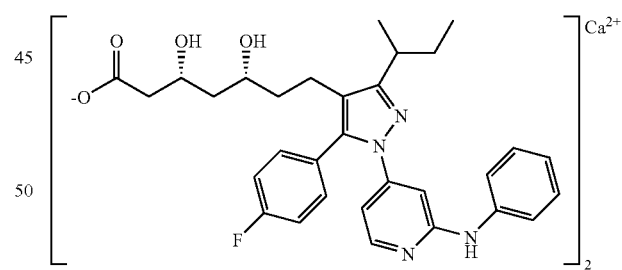

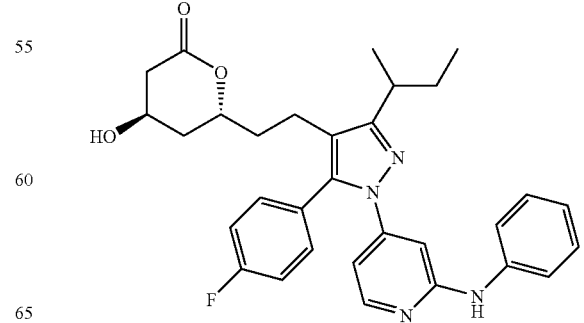

Step 1: (3R,5R)-ethyl 7-(3-sec-butyl-5-(4-fluorophenyl)-1-(2-(phenylamino)pyridin-4-yl)-1H-pyrazol-4-yl)-3,5-dihydroxyheptanoate, 20 and (4R,6R)-6-(2-(3-sec-butyl-5-(4-fluorophenyl)-1-(2-(phenylamino)pyridin-4-yl)-1H-pyrazol-4-yl)ethyl)-4-hydroxy-tetrahydropyran-2-one, 21 is prepared as follows:

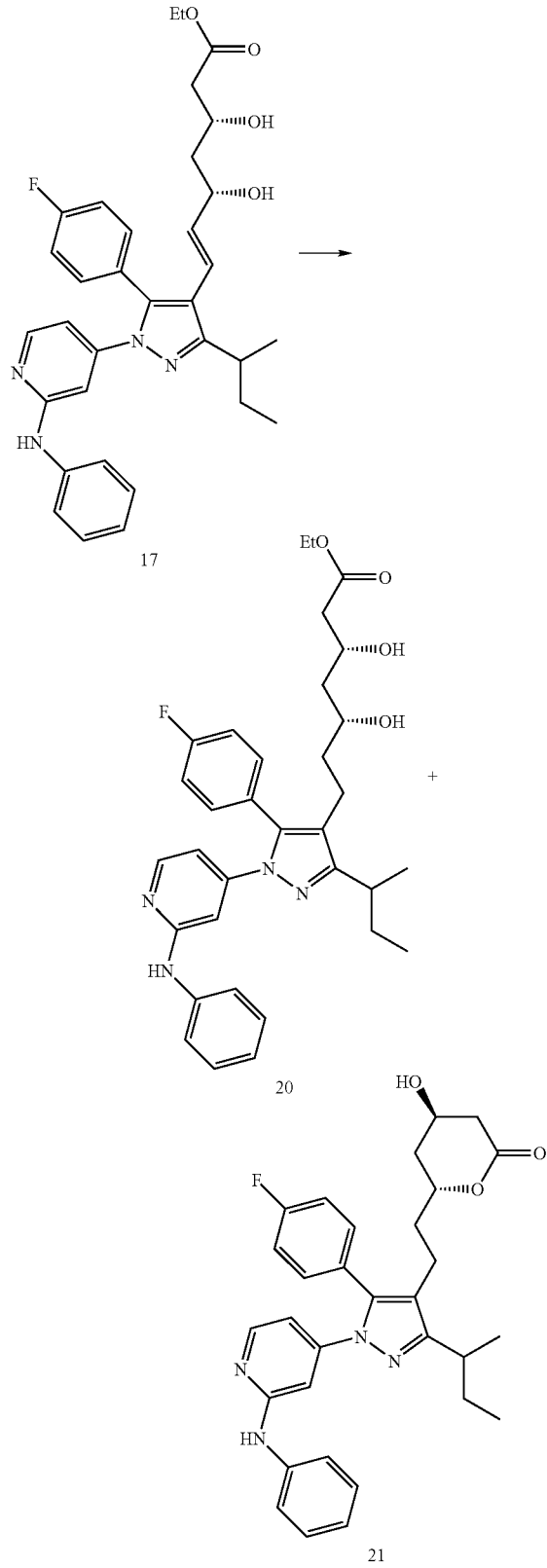

A flask containing (3R,5S,E)-ethyl 7-(3-sec-butyl-5-(4-fluorophenyl)-1-(2-phenylamino)pyridin-4-yl)-1H-pyrazol-4-yl)-3,5-dihydroxyhept-6-enoate, 17 (0.100 g), ammonium formate (0.220 g) and palladium on carbon (0.020 g) in ethanol (5 mL) is heated to 80° C. for 3 h, adding further portions of ammonium formate and catalyst every 1 h. The resulting mixture is filtered through celite and concentrated in vacuo, then purified by flash chromatography to furnish 0.043 g of (3R,5R)-ethyl 7-(3-sec-butyl-5-(4-fluorophenyl)-1-(2-(phenylamino)pyridin-4-yl)-1H-pyrazol-4-yl)-3,5-dihydroxyheptanoate, 20 and (4R,6R)-6-(2-(3-sec-butyl-5-(4-fluorophenyl)-1-(2-(phenylamino)pyridin-4-yl)-1H-pyrazol-4-yl)ethyl)-4-hydroxy-tetrahydropyran-2-one, 21 (0.002 g).

(3R,5R)-ethyl 7-(3-sec-butyl-5-(4-fluorophenyl)-1-(2-(phenylamino)pyridin-4-yl)-1H-pyrazol-4-yl)-3,5-dihydroxyheptanoate, 20 shows the following mass spectral data: C/MS: $C_{33}H_{39}FN_4O_4$ requires 574.3; observed M/Z 575.1 [M+H]$^+$. RT 5.85 min.

(4R,6R)-6-(2-(3-sec-butyl-5-(4-fluorophenyl)-1-(2-(phenylamino)pyridin-4-yl)-1H-pyrazol-4-yl)ethyl)-4-hydroxy-tetrahydropyran-2-one, 21 shows the following mass spectral data: LC/MS: $C_{31}H_{33}FN_4O_3$ requires 528.3; observed M/Z 529.1 [M+H]$^+$. RT 5.50 min.

Step 2: (3R,5R)-7-(3-sec-butyl-5-(4-fluorophenyl)-1-(2-(phenylamino)pyridin-4-yl)-1H-pyrazol-4-yl)-3,5-dihydroxyheptanoic acid calcium salt, 22 is prepared as follows:

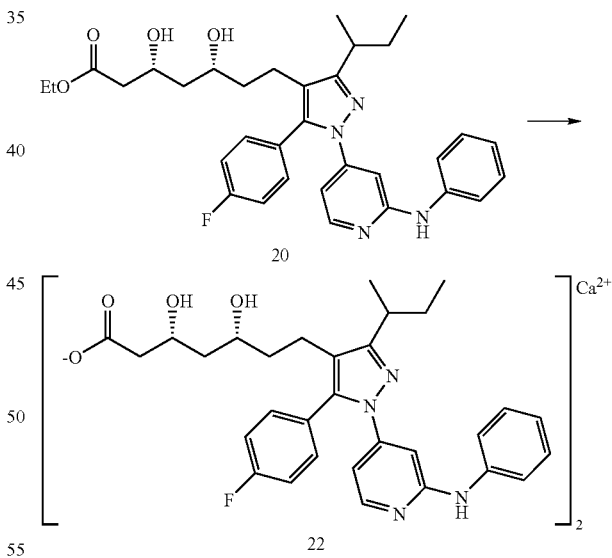

(3R,5R)-7-(3-sec-butyl-5-(4-fluorophenyl)-1-(2-(phenylamino)pyridin-4-yl)-1H-pyrazol-4-yl)-3,5-dihydroxyheptanoic acid calcium salt, 22 (0.026 g) is obtained as a powder in the same manner as Example 10a, Step 9 from (3R,5R)-ethyl 7-(3-sec-butyl-5-(4-fluorophenyl)-1-(2-(phenylamino)pyridin-4-yl)-1H-pyrazol-4-yl)-3,5dihydroxyheptanoate, 20 (0.043 g).

The compound obtained in this step shows the following mass spectral and NMR data:

LC/MS: $C_{31}H_{35}FN_4O_4$ requires 546.3; observed M/Z 547.2 [M+H]$^+$. RT 3.07 min. $^1$H-NMR (270 MHz, DMSO-d$_6$, δ) 0.90 (t, 3H), 1.25 (d, 3H), 1.23–1.51 (m, 4H), 1.52–1.64 (m, 1H), 1.70–1.82 (m, 1H), 1.82–2.12 (m, 2H), 2.34 (m, 1H), 2.72–2.85 (m, 1H), 3.45–3.55 (m, 1H), 3.70–3.85 (m, 1H), 4.55–6.69 (m, 1H), 6.26 (d, 1H), 6.83 (s, 1H), 6.88 (t, 1H), 7.15 (t, 2H), 7.25–7.36 (m, 4H), 7.53 (d, 2H), 7.95 (d, 1H), 9.11 (s, 1H).

Example 11

Scheme for Synthesis of N-Pyrimidinyl Pyrazole Compounds

An overall scheme for synthesizing N-pyrimidinyl substituted pyrazole compounds of formula VI of the invention is provided below. Examples 11a–g and 11i below detail eight specific examples following the overall scheme.

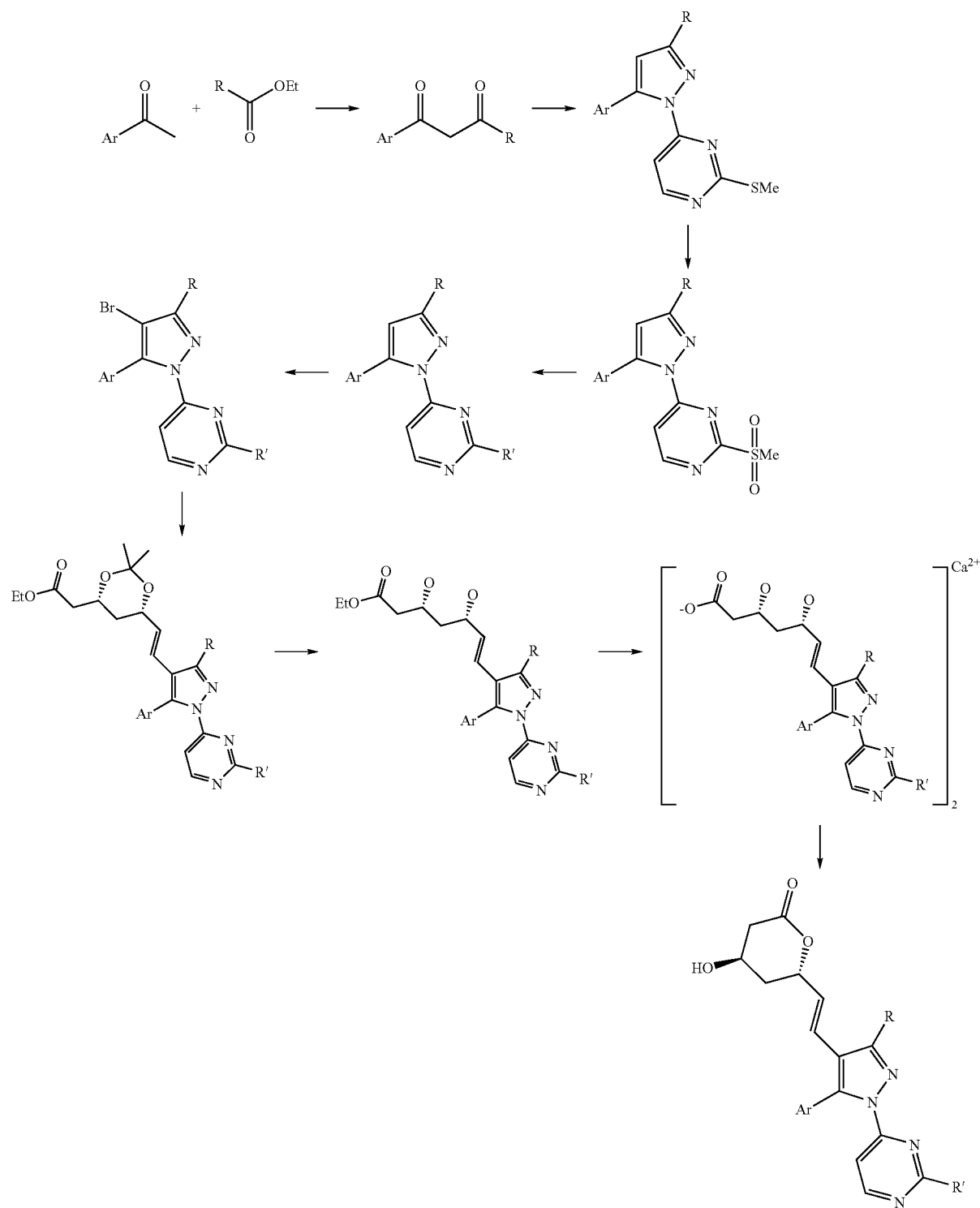

Example 11a

Synthesis of an N-Pyrimidinyl Pyrazole

In one specific example, a compound having the structure indicated below is prepared in 8 steps (Steps 1–8).

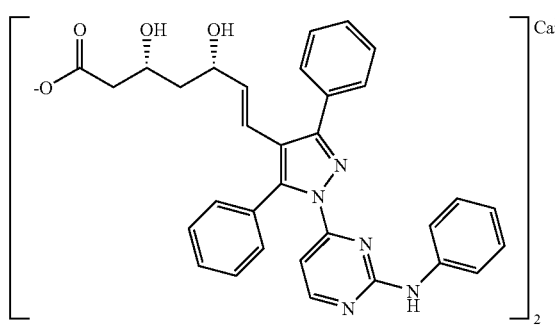

Step 1: 3,5-diphenyl-1H-pyrazole, 22 is prepared as follows:

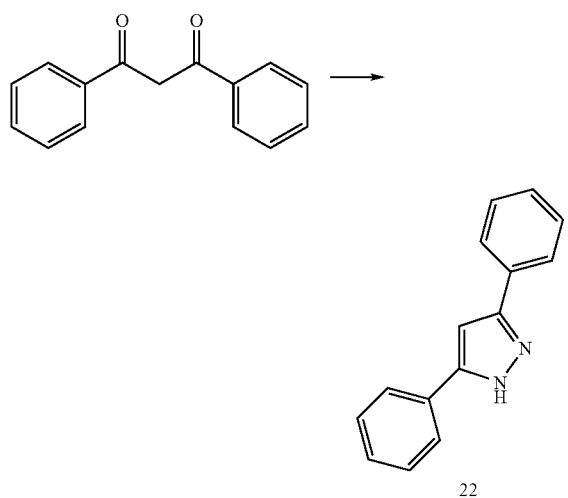

Hydrazine monohydrate (2.16 mL) is added to a solution of 1,3-diphenylpropane-1,3-dione (10.0 g) in ethanol (100 mL) and the mixture is heated to 60° C. for 2.5 h forming a white precipitate over this time. Ethanol is removed in vacuo and the residue is taken up in ethyl acetate. The resulting suspension is filtered to give 3,5-diphenyl-1H-pyrazole, 22 (3.44 g) as a white powder. The filtrate is washed with water (2×100 mL), dried over magnesium sulfate and concentrated to give further 3,5-diphenyl-1H-pyrazole, 22 (5.90 g) as a solid.

The compound obtained in this step shows the following mass spectral data: LC/MS: $C_{15}H_{12}N_2$ requires 220.1; observed M/Z 221.3 [M−H]$^-$, 219.4 [M−H]$^-$. RT 4.84 min.

Step 2: 4-(3,5-diphenyl-1H-pyrazol-1-yl)-2-(methylthio) pyrimidine, 23 is prepared as follows:

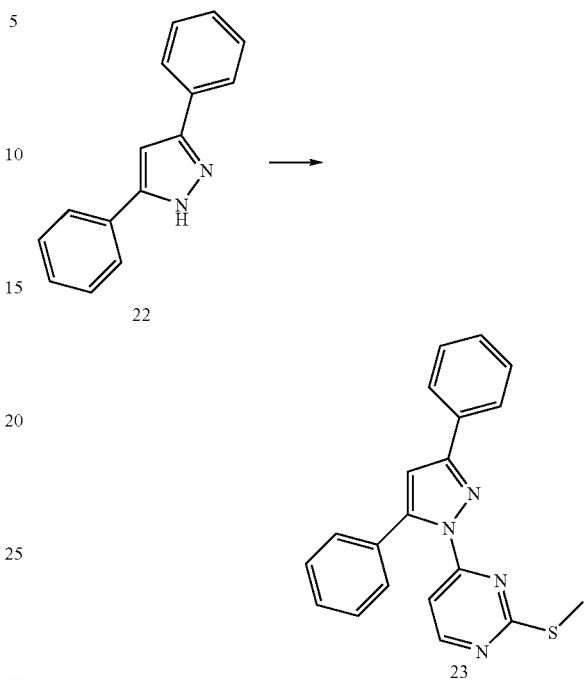

A solution of 3,5-diphenyl-1H-pyrazole, 22 (9.34 g) in anhydrous N,N-dimethylformamide (71 mL) is added dropwise to a suspension of sodium hydride (1.87 g of a 60% dispersion in mineral oil) in N,N-dimethylformamide (36 mL) under nitrogen. After addition is complete, a solution of 4-chloro-2-(methylthio)pyrimidine (6.82 g) in anhydrous N,N-dimethylformamide (24 mL) is added dropwise and the reaction mixture stirred at ambient temperature for 1 h. Water is then added cautiously and the product extracted with ethyl acetate. The organic layer is washed with water, brine and dried over magnesium sulfate, filtered and concentrated. Purification by flash chromatography yields 8.06 g of the title compound.

The compound obtained in this step shows the following mass spectral data: LC/MS: $C_{20}H_{16}N_4S$ requires 344.1; observed M/Z 345.1 [M+H]$^+$. RT 6.60 min.

Step 3: 4-(3,5-diphenyl-1H-pyrazol-1-yl)-2-(methylsulfonyl)pyrimidine, 24 is prepared as follows:

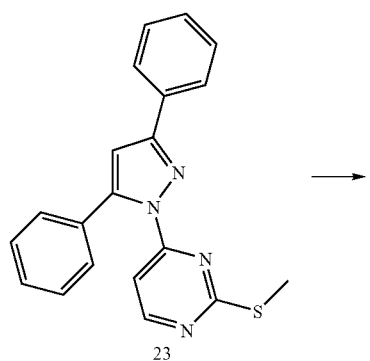

-continued

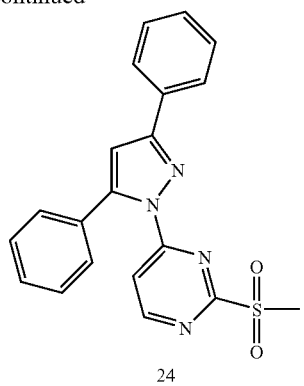
24

To a solution of 4-(3,5-diphenyl-1H-pyrazol-1-yl)-2-(methylthio)pyrimidine, 23 (8.06 g), in a mixture of tetrahydrofuran (145 mL) and methanol (320 mL) is added a slurry of Oxone (57.60 g) and sodium acetate trihydrate (44.64 g) in water (80 mL). The flask is flushed with nitrogen then left to stir at ambient temperature for 20 h, after which time the mixture is partitioned between water and dichloromethane. The organic layer is washed with brine, dried over magnesium sulfate and concentrated to afford a solid. Purification by trituration with diethyl ether furnishes the title compound (7.70 g).

The compound obtained in this step shows the following mass spectral data: LC/MS: $C_{20}H_{16}N_4O_2S$ requires 376.1; observed M/Z 377.1 [M+H]$^+$. RT 6.10 min.

Step 4: 4-(4-bromo-3,5-diphenyl-1H-pyrazol-1-yl)-2-(methylsulfonyl)pyrimidine, 25 is prepared as follows:

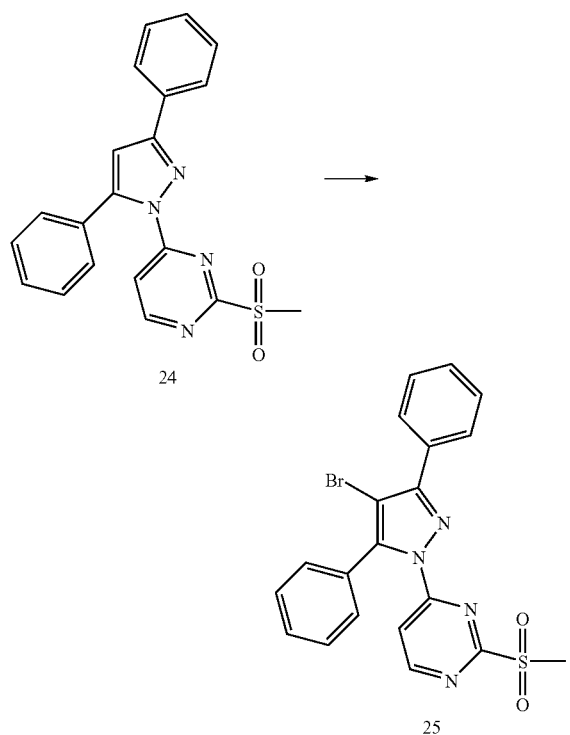

To a solution of 4-(3,5-diphenyl-1H-pyrazol-1-yl)-2-(methylsulfonyl)pyrimidine, 24 (3.50 g) in N,N-dimethylformamide (35 mL) is added solid N-bromosuccinimide (2.49 g) and the mixture left to stir for 16 h at ambient temperature. The reaction mixture is partitioned between water and ethyl acetate, washing the organic layer with brine. The combined organic layers are dried over magnesium sulfate, filtration and concentration in vacuo, the resulting solid is triturated with diethyl ether to furnish the title compound (4.06 g).

The compound to be prepared at this step shows the following mass spectral data: LC/MS: $C_{20}H_{15}BrN_4O_2S$ requires 454.0; observed M/Z 454.9/456.9 (Br) [M+H]$^+$. RT 6.04 mm.

Step 5: 4-(4-bromo-3,5-diphenyl-1H-pyrazol-1-yl)-N-phenylpyrimidin-2-amine, 26 is prepared as follows:

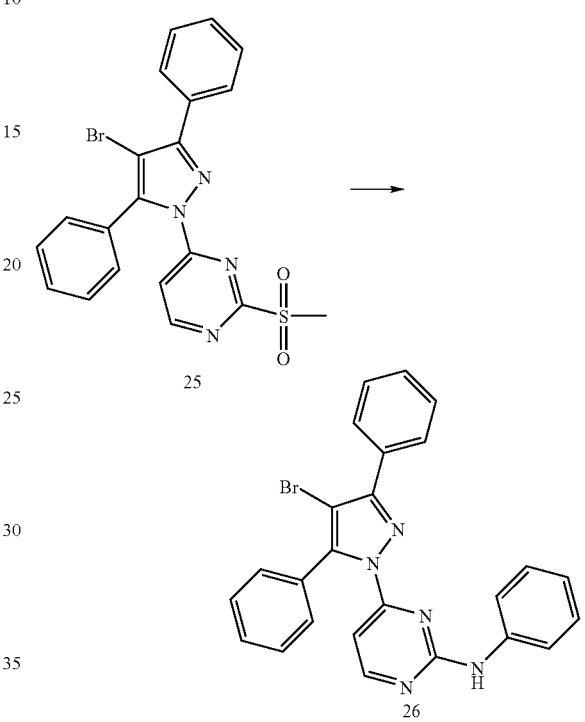

A solution of 4-(4-bromo-3,5-diphenyl-1H-pyrazol-1-yl)-2-(methylsulfonyl)pyrimidine, 25 (4.00 g) and aniline (1.60 mL) in dimethyl sulfoxide (40 mL) are heated to 110° C. for 60 h. The reaction mixture is then partitioned between ethyl acetate and brine, extracting the aqueous layer with further ethyl acetate. The combined organic layers are dried over magnesium sulfate, filtered and concentrated. Purification by flash chromatography affords the title compound (1.13 g).

The compound obtained in this step shows the following mass spectral data: LC/MS: $C_{25}H_{18}BrN_5$ requires 467.1; observed M/Z 467.9/469.9 [M+H]$^+$. RT 6.92 min.

Step 6: ethyl 2-((4R,6S)-6-((E)-2-(3,5-diphenyl-1-(2-(phenylamino)pyrimidin-4-yl)-1H-pyrazol-4-yl)vinyl)-2,2-dimethyl-1,3-dioxan-4-yl)acetate, 27 is prepared as follows:

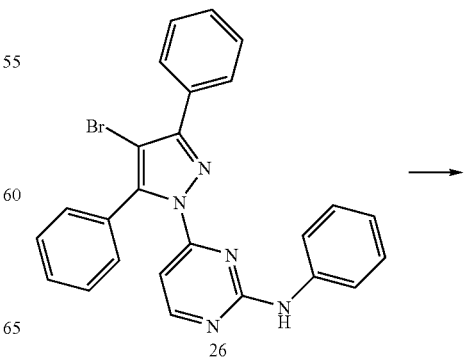

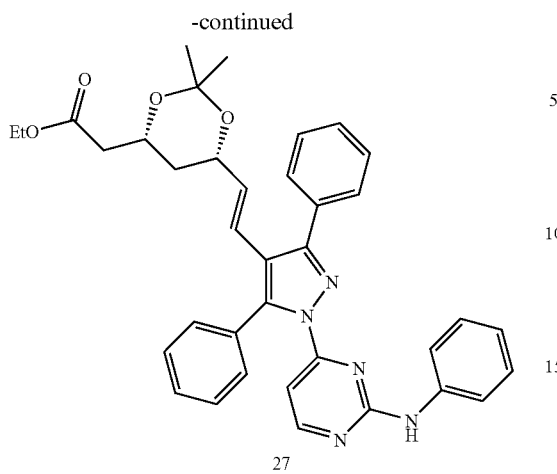

27

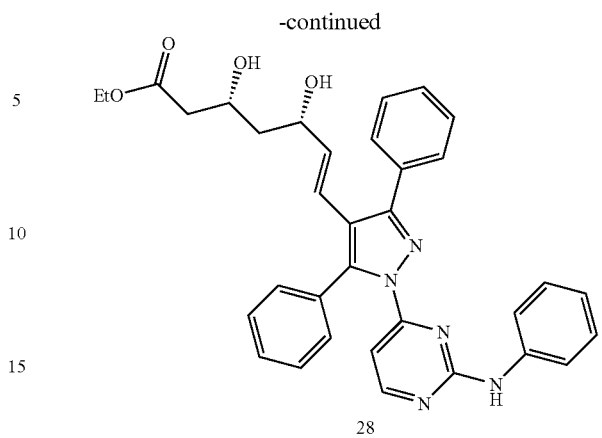

28

4-(4-bromo-3,5-diphenyl-1H-pyrazol-1-yl)-N-phenylpyrimidin-2-amine, 26 (0.300 g), ethyl 2-((4S,6R)-2,2-dimethyl-6-vinyl-1,3-dioxan-4-yl)acetate, 9 (0.249 g) and dichlorobis-(triphenylphosphine)palladium(II) (0.012 g) are dissolved in a mixture of N,N-dimethyl-formamide (1 mL) and triethylamine (1 mL) under nitrogen and the mixture heated to 110° C. for 36 h adding 2 further portions of catalyst during this time. The reaction is cooled, filtered through celite and solvent removed in vacuo. The resulting residue is partitioned between dichloromethane and water, washing the organic layer with brine. The organic layer is dried over magnesium sulfate, and after filtering and concentrating, the crude residue is purified by flash chromatography to afford the title compound (0.195 g).

Alternatively, product 27 (0.585 g) is obtained as an off-white powder in the same manner as Example 10a, Step 7 from 4-(4-bromo-3,5-diphenyl-1H-pyrazol-1-yl)-N-phenylpyrimidin-2-amine, 26 (0.886 g)

The compond to be obtained at this step shows the following mass spectral data: LC/MS: $C_{37}H_{37}N_5O_4$ requires 615.3; observed M/Z 616.2 $[M+H]^+$, 614.4 $[M-H]^-$. RT 7.34 min.

Step 7: (3R,5S,E)-ethyl 7-(3,5-diphenyl-1-(2-(phenylamino)pyrimidin-4-yl)-1H-pyrazol-4-yl)-3,5-dihydroxyhept-6-enoate, 28 is prepared as follows:

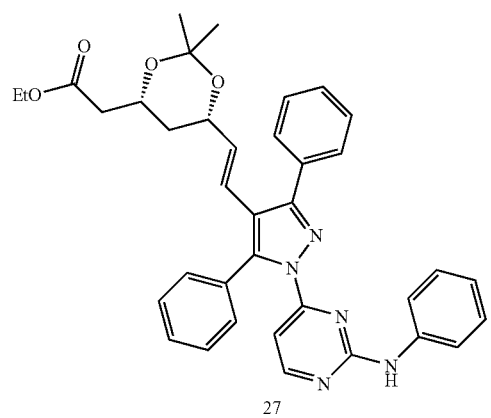

27

The product (0.347 g) is obtained in the same manner as Example 10a, Step 8 from ethyl 2-((4R,6S)-6-((E)-2-(3,5-diphenyl-1-(2-(phenylamino)pyrimidin-4-yl)-1H-pyrazol-4-yl)vinyl)-2,2-dimethyl-1,3-dioxan-4-yl)acetate, 27 (0.574 g)

The compound obtained in this step shows the following mass spectral data: LC/MS: $C_{34}H_{33}N_5O_4$ requires 575.3; observed M/Z 576.2 $[M+H]^+$. RT 5.62 min.

Step 8: (3R,5S,E)-7-(3,5-diphenyl-1-(2-(phenylamino)pyrimidin-4-yl)-1H-pyrazol-4-yl)-3,5-dihydroxyhept-6-enoic acid calcium salt, 29 is prepared as follows:

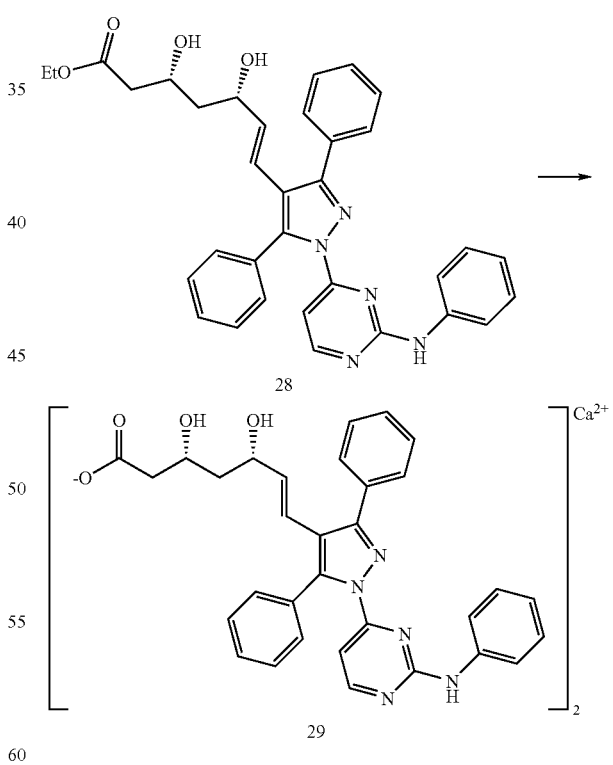

The product (0.072 g) is obtained in the same manner as Example 10a, Step 9 from (3R,5S,E)-ethyl 7-(3,5-diphenyl-1-(2-(phenylamino)pyrimidin-4-yl)-1H-pyrazol-4-yl)-3,5-dihydroxyhept-6-enoate, 28 (0.160 g)

The compound obtained in this step shows the following mass spectral and NMR data:

LC/MS as free acid: $C_{32}H_{29}N_5O_4$ requires 547.2; observed 548.1 [M+H]$^+$, 546.2 [M−H]$^−$. RT 2.84 min. $^1$H-NMR (270 MHz, DMSO-d$_6$, δ) 1.11–1.25 (m, 2H), 1.86–2.12 (m, 2H), 3.63–3.68 (m, 1H), 4.04–4.10 (m, 1H), 4.84 (brs, 1H), 5.46 (dd, 1H), 6.33 (d, 1H), 6.84 (t, 1H), 6.89–6.94 (m, 2H), 7.05 (t, 2H), 7.12 (d, 1H), 7.30–7.40 (m, 3H), 7.42–7.54 (m, 5H), 7.69 (d, 2H), 8.56 (d, 1H), 9.66 (s, 1H).

Example 11b

Synthesis of an N-Pyrimidinyl Pyrazole

In a second specific example, a compound having the structure indicated below is prepared in one step (Step 1) from the product obtained in Example 11a, detailed above.

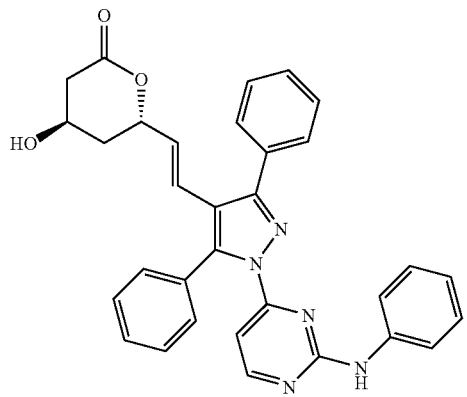

Step 1: (4R,6S,E)-6-(2-(3,5-diphenyl-1-(2-(phenylamino)pyrimidin-4-yl)-1H-pyrazol-4-yl)vinyl)-4-hydroxy-tetrahydropyran-2-one, 30 is prepared as follows:

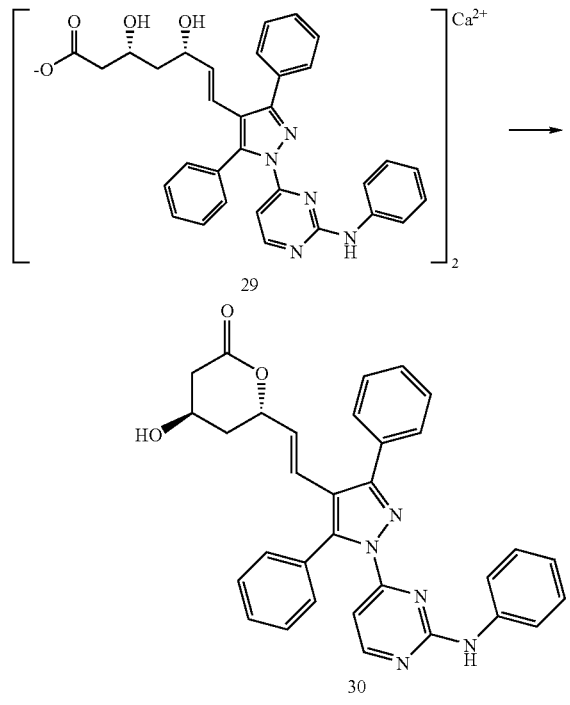

The product (0.018 g) is obtained in the same manner as Example 10b, Step 1 from (3R,5S,E)-7-(3,5-diphenyl-1-(2-(phenylamino)pyrimidin-4-yl)-1H-pyrazol-4-yl)-3,5-dihydroxyhept-6-enoic acid calcium salt, 29 (0.050 g).

The compound obtained in this step shows the following mass spectral and NMR data:

LC/MS: $C_{32}H_{27}N_5O_3$ requires 529.2; observed 530.1 [M+H]$^+$, 528.2 [M−H]$^−$. RT 5.20 $^1$H-NMR (270 MHz, CDCl$_3$, δ) 1.73–1.80 (m, 2H), 2.47–2.64 (m, 2H), 4.18–4.22 (m, 1H), 5.00–5.04 (m, 1H), 5.45 (dd, 1H), 6.39 (d, 1H), 6.70 (brs, 1H), 6.90 (t, 1H), 6.95–7.03 (m, 2H), 7.09–7.12 (m, 3H), 7.30–7.41 (m, 8H), 7.61 (d, 2H), 8.34 (d, 1H).

Examples 11c and 11d

Syntheses of N-Pyrimidinyl Pyrazoles

In two additional specific examples, compounds having the structures indicated below are prepared in two steps (Steps 1–2) from intermediate 28 obtained in Example 11a above.

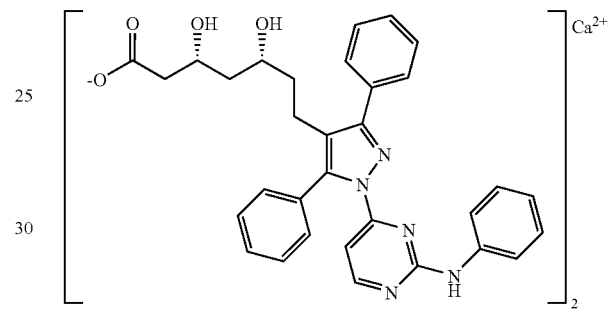

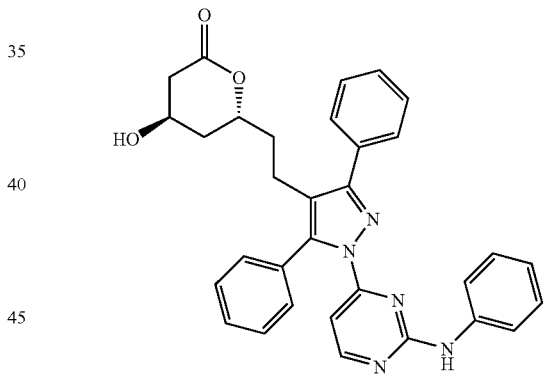

Step 1: (3R,5R)-ethyl 7-(3,5-diphenyl-1-(2-(phenylamino)pyrimidin-4-yl)-1H-pyrazol-4-yl)-3,5-dihydroxyheptanoate, 31 and (4R,6R)-6-(2-(3,5-diphenyl-1-(2-(phenylamino)pyrimidin-4-yl)-1H-pyrazol-4-yl)ethyl)-4-hydroxy-tetrahydropyran-2-one, 32 is prepared as follows:

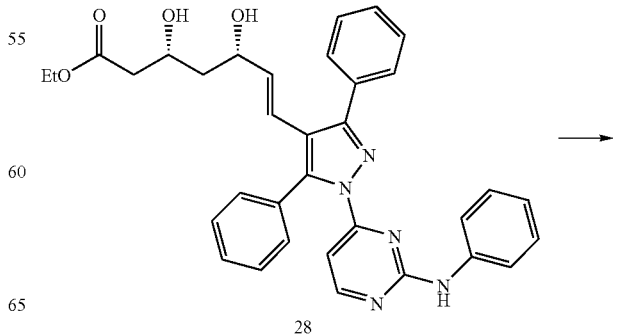

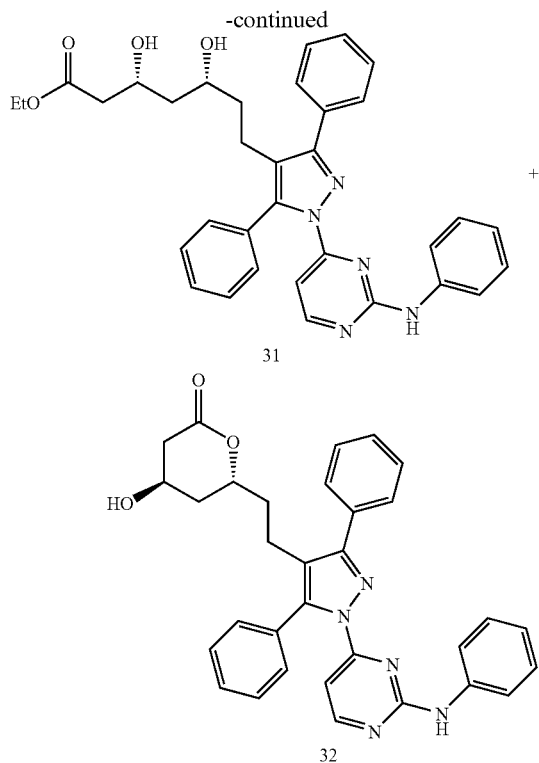

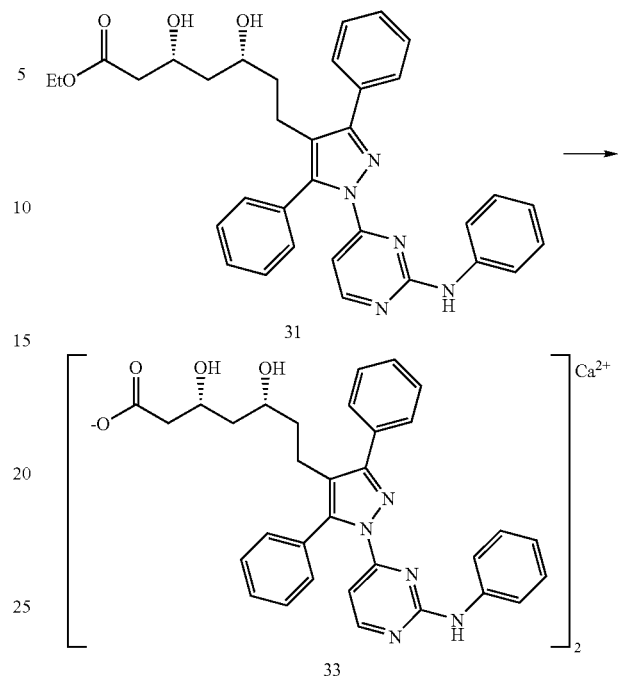

A flask containing (3R,5S,E)-ethyl 7-(3,5-diphenyl-1-(2-(phenylamino)pyrimidin-4-yl)-1H-pyrazol-4-yl)-3,5-dihydroxyhept-6-enoate, 28 (0.227 g), ammonium formate (0.500 g) and palladium on carbon (0.050 g) in ethanol (10 mL) is heated to 86° C. for 2 h adding extra portions of catalyst and ammonium formate every 45 min. The reaction mixture is left at ambient temperature for 16 h, then filtered through celite and concentrated. The resulting residue is partitioned between ethyl acetate and water and the organic layer dried over magnesium sulfate, filtered and concentrated. Purification by flash chromatography affords (3R, 5R)-ethyl 7-(3,5-diphenyl-1-(2-(phenylamino)pyrimidin-4-yl)-1H-pyrazol-4-yl)-3,5-dihydroxyheptanoate, 31 (0.162 g) and (4R,6R)-6-(2-(3,5-diphenyl-1-(2-(phenylamino)pyrimidin-4-yl)-1H-pyrazol-4-yl)ethyl)-4-hydroxy-tetrahydropyran-2-one, 32 (0.023 g).

(3R,5R)-ethyl 7-(3,5-diphenyl-1-(2-(phenylamino)pyrimidin-4-yl)-1H-pyrazol-4-yl)-3,5-dihydroxyheptanoate, 31 shows the following mass spectral data:

LC/MS: $C_{34}H_{35}N_5O_4$ requires 577.3; observed M/Z 578.1 [M+H]$^+$, 576.2 [M−H]$^−$. RT of 5.72 min.

(4R,6R)-6-(2-(3,5-diphenyl-1-(2-(phenylamino)pyrimidin-4-yl)-1H-pyrazol-4-yl)ethyl)-4-hydroxy-tetrahydropyran-2-one, 32 shows the following mass spectral and NMR data:

LC/MS: $C_{32}H_{29}N_5O_3$ requires 531.2; observed M/Z 532.1 [M+H]$^+$, 530.2 [M−H]$^−$. RT 5.34 min. $^1$H-NMR (270 MHz, CDCl$_3$, δ) 1.22–1.83 (m, 4H), 2.41–2.72 (m, 2H), 2.72–2.91 (m, 2H), 4.18–4.21 (m, 1H), 4.37–4.49 (m, 1H), 6.75 (s, 1H), 6.93 (t, 1H), 7.03 (d, 2H), 7.10–7.23 (m, 3H), 7.33–7.52 (m, 8H), 7.73 (d, 2H), 8.37 (d, 1H).

Step 2: (3R,5R)-7-(3,5-diphenyl-1-(2-(phenylamino)pyrimidin-4-yl)-1H-pyrazol-4-yl)-3,5-dihydroxyheptanoic acid, 33 is prepared as follows:

The product (0.090 g) is obtained in the same manner as Example 10a, Step 9 from (3R,5R)-ethyl-7-(3,5-diphenyl-1-(2-(phenylamino)pyrimidin-4-yl)-1H-pyrazol-4-yl)-3,5-dihydroxyheptanoic acid, 31 (0.162 g).

The compound obtained in this step shows the following mass spectral and NMR data:

LC/MS as free acid: $C_{32}H_{31}N_5O_4$ requires 549.2; observed M/Z 550.1 [M+H]$^+$, 548.2 [M−H]$^−$. RT 3.04 min. $^1$H-NMR (270 MHz, DMSO-d$_6$, δ) 1.12–1.42 (m, 4H), 1.79–2.07 (m, 2H), 2.43–2.61 (m, 1H), 2.64–2.80 (m, 1H), 3.42–3.53 (m, 1H), 3.62–3.75 (m, 1H), 4.56–4.67 (brs, 1H), 6.82 (t, 1H), 6.83–6.94 (d, 2H), 6.99–7.10 (t, 2H), 7.15 (d, 1H), 7.30–7.55 (m, 8H), 7.78 (d, 2H), 8.55 (d, 1H), 9.59 (s, 1H).

Example 11e

Synthesis of an N-Pyrimidinyl Pyrazole

In a fifth specific example, a compound having the structure indicated below is prepared in nine steps (Steps 1–9).

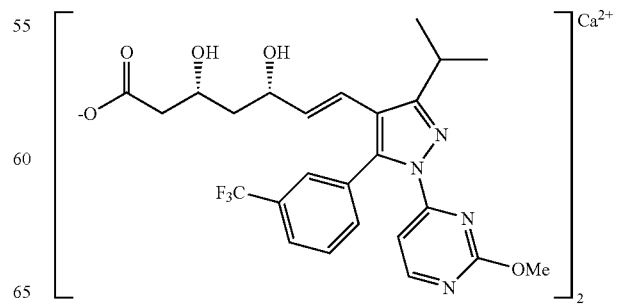

Step 1: 4-methyl-1-(3-(trifluoromethyl)phenyl)pentane-1,3-dione, 34 is prepared as follows:

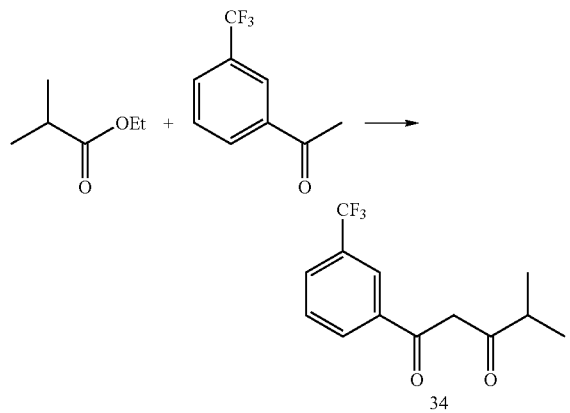

The product (4.91 g) is obtained as a clear oil in the same manner as Example 10a, Step 1 from 1-(3-(trifluoromethyl)phenyl)ethanone (10.00) g and ethyl isobutyrate (6.00 g).

The compound obtained in this step shows the following boiling point and mass spectral data:

b.p 67–80° C. at 1 mm Hg LC/MS: $C_{13}H_{13}F_3O_2$ requires 258.1; observed M/Z 257.3 [M−H]⁻. RT 5.09 min.

Step 2: 4-hydrazinyl-2-(methylthio)pyrimidine, 35 is prepared as follows:

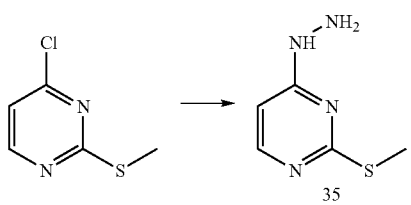

To a solution of 4-chloro-2-(methylthio)pyrimidine (50.0 g) in ethanol (200 mL) is added hydrazine (15.58 g) in one portion and the mixture left to stir for 16 h at ambient temperature, during which time a precipitate forms. This precipitate is filtered and washed with copious ice-cold ethanol to furnish the title compound (25.0 g) as a white powder.

The compound obtained in this step shows the following mass spectral data: LC/MS: $C_5H_8N_4S$ requires 156.0, observed M/Z 157.2 [M+H]⁺, 155.3 [M−H]⁻. RT 1.79 min.

Step 3: 4-(3-isopropyl-5-(3-(trifluoromethyl)phenyl)-1H-pyrazol-1-yl)-2-(methylthio)pyrimidine, 36 is prepared as follows:

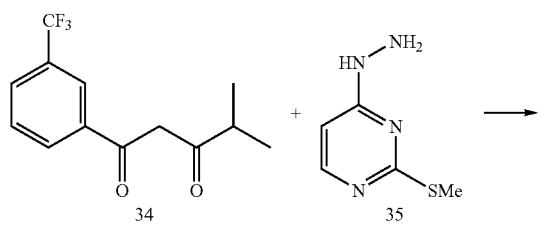

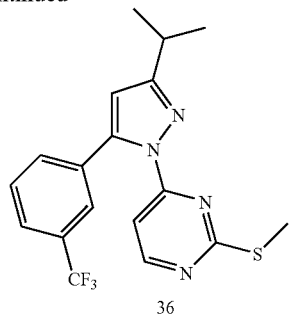

4-methyl-1-(3-(trifluoromethyl)phenyl)pentane-1,3-dione, 34 (1.65 g) and 4-hydrazinyl-2-(methylthio)pyrimidine, 35 (1.00 g) are dissolved in acetic acid (15 mL) and the mixture heated to 90° C. for 2 h. On cooling, the mixture is partitioned between dichloromethane and aqueous sodium hydrogen carbonate and the aqueous layer washed with two further portions of dichloromethane. The combined organics are washed with brine, dried over magnesium sulfate, filtered and concentrated. Purification by flash chromatography affords the title compound (1.29 g).

The compound obtained in this step shows the following mass spectral data: LC/MS: $C_{18}H_{17}F_3N_4S$ requires 378.1; observed M/Z 379.0 [M+H]⁺. RT 7.43 min.

Step 4: 4-(3-isopropyl-5-(3-(trifluoromethyl)phenyl)-1H-pyrazol-1-yl)-2-(methylsulfonyl)pyrimidine, 37 is prepared as follows:

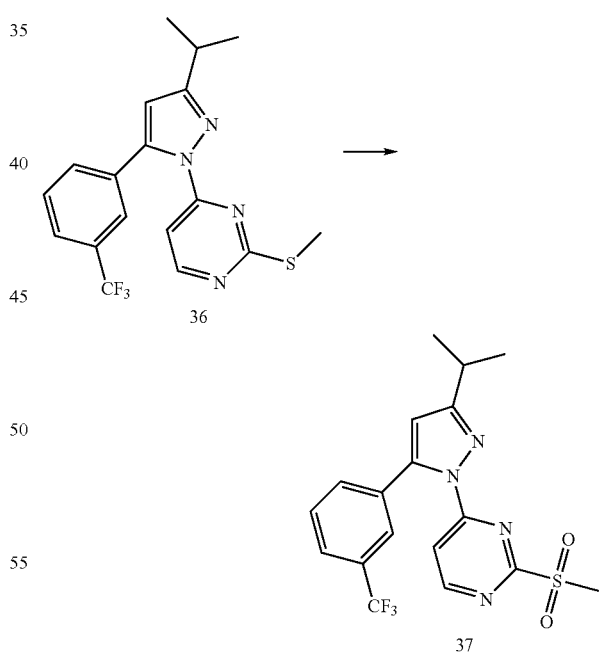

The product (0.485 g) is obtained in the same manner as Example 11a, Step 3 from 4-(3-isopropyl-5-(3-(trifluoromethyl)phenyl)-1H-pyrazol-1-yl)-2-(methylthio)pyrimidine, 36 (0.500 g).

The compound obtained in this step shows the following mass spectral data: LC/MS: $C_{18}H_{17}F_3N_4O_2S$ requires 410.1; observed M/Z 411.0 [M+H]⁺. RT 5.68 min.

Step 5: 4-(4-bromo-3-isopropyl-5-(3-(trifluoromethyl)phenyl)-1H-pyrazol-1-yl)-2-(methylsulfonyl)pyrimidine, 38 is prepared as follows:

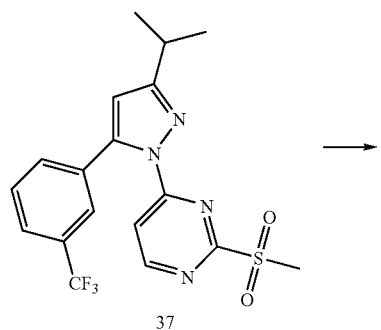

37

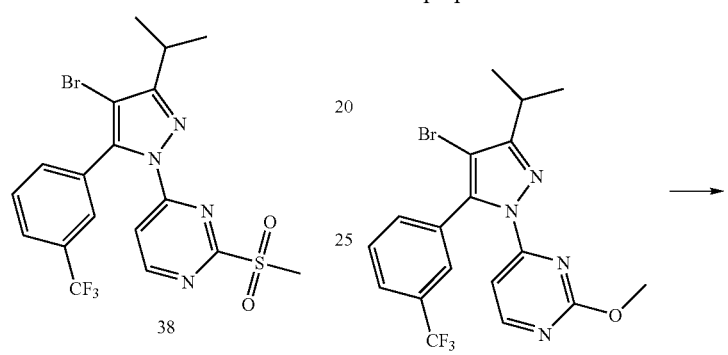

38

The product (0.524 g) is obtained in the same manner as Example 11a, Step 4 from 4-(3-isopropyl-5-(3-(trifluoromethyl)phenyl)-1H-pyrazol-1-yl)-2-(methylsulfonyl)pyrimidine, 37 (0.496 g), after flash chromatography.

The compound obtained in this step shows the following NMR data: $^1$H-NMR (400 MHz, CDCl$_3$, δ) 1.40 (d, 6H), 2.51 (s, 3H), 3.13–3.22 (m, 1H), 7.58 (d, 1H), 7.61–7.69 (m, 2H), 7.76 (d, 1H), 8.17 (d, 1H), 8.88 (d, 1H).

Step 6: 4-(4-bromo-3-isopropyl-5-(3-(trifluoromethyl)phenyl)-1H-pyrazol-1-yl)-2-methoxypyrimidine, 39 is prepared as follows:

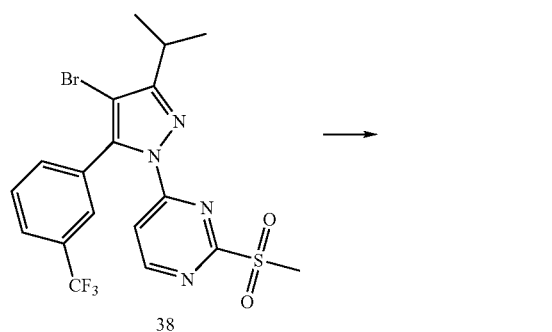

38

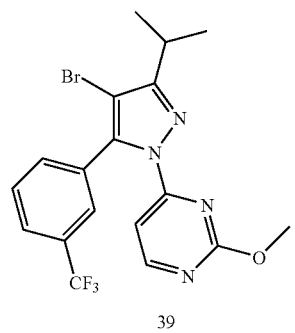

39

A mixture of 4-(4-bromo-3-isopropyl-5-(3-(trifluoromethyl)phenyl)-1H-pyrazol-1-yl)-2-(methylsulfonyl)pyrimidine, 38 (0.745 g) and sodium methoxide (0.087 g) in methanol (3 mL) are heated to 60° C. for 2 h. On cooling, the solvent is removed by evaporation and the residue purified by flash chromatography to furnish the title compound (0.582 g).

The compound obtained in this step shows the following mass spectral data: LC/MS: C$_{18}$H$_{16}$BrF$_3$N$_4$O requires 440.0; observed M/Z 440.9/442.9 (Br) [M+H]$^+$. RT 6.92 min.

Step 7: ethyl 2-((4R,6S)-6-((E)-2-(3-isopropyl-1-(2-methoxypyrimidin-4-yl)-5-(3-(trifluoromethyl)phenyl)-1H-pyrazol-4-yl)vinyl)-2,2-dimethyl-1,3-dioxan-4-yl)acetate, 40 is prepared as follows:

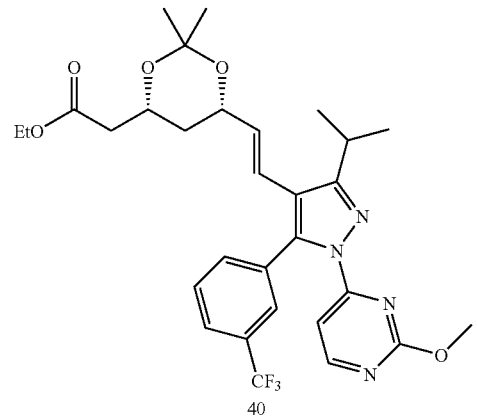

40

4-(4-bromo-3-isopropyl-5-(3-(trifluoromethyl)phenyl)-1H-pyrazol-1-yl)-2-methoxy-pyrimidine, 39 (0.500 g), ethyl 2-((4S,6R)-2,2-dimethyl-6-vinyl-1,3-dioxan-4-yl)acetate, 9 (0.440 g) and dichlorobis(triphenylphosphine)palladium(II) (0.024 g) are dissolved in a mixture of N,N-dimethylformamide (2 mL) and triethylamine (2 mL) under nitrogen and the mixture heated to 110° C. for 36 h adding two further portions of catalyst during this time. The reaction is cooled, filtered through celite and solvent removed in vacuo. The resulting residue is partitioned between dichloromethane and water, washing the organic layer with brine. After drying the organic layer over magnesium sulfate, filtering and concentrating, the crude residue is purified by flash chromatography to afford the title compound (0.118 g).

The compound obtained in this step has the following mass spectral data: LC/MS: C$_{30}$H$_{35}$F$_3$N$_4$O$_5$ requires 588.3; observed M/Z 589.1 [M+H]$^+$. RT 8.07 min.

Step 8: (3R,5S,E)-ethyl 3,5-dihydroxy-7-(3-isopropyl-1-(2-methoxypyrimidin-4-yl)-5-(3-(trifluoromethyl)phenyl)-1H-pyrazol-4-yl)hept-6-enoate, 41 is prepared as follows:

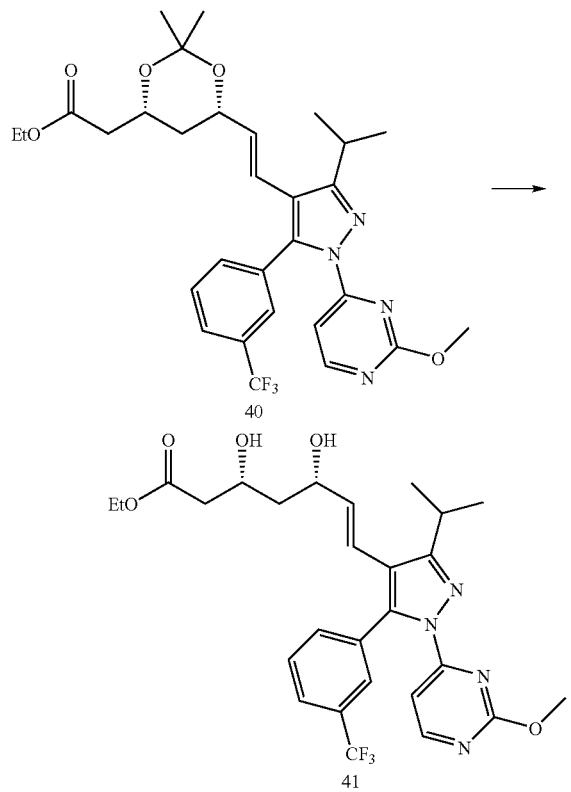

The product (0.045 g) is obtained in the same manner as Example 10a, Step 8 from ethyl 2-((4R,6S)-6-((E)-2-(3-isopropyl-1-(2-methoxypyrimidin-4-yl)-5-(3-(trifluoromethyl)-1H-pyrazol-4-yl)vinyl)-2,2-dimethyl-1,3-dioxan-4-yl)acetate, 40 (0.118 g).

The compound obtained in this step has the following mass spectral data: LC/MS: $C_{27}H_{31}F_3N_4O_5$ requires 548.2; observed M/Z 549.1 $[M+H]^+$. RT 5.50 min.

Step 9: (3R,5S,E)-3,5-dihydroxy-7-(3-isopropyl-1-(2-methoxypyrimidin-4-yl)-5-(3-(trifluoromethyl)phenyl)-1H-pyrazol-4-yl)hept-6-enoic acid calcium salt, 42 is prepared as follows:

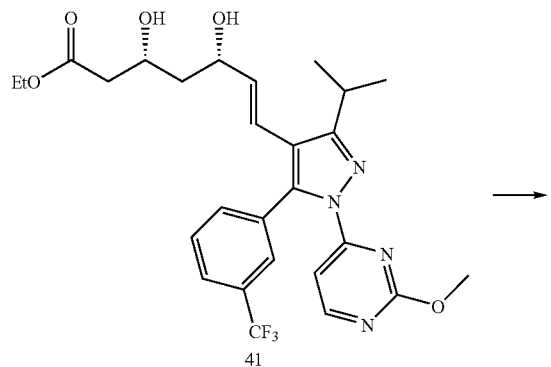

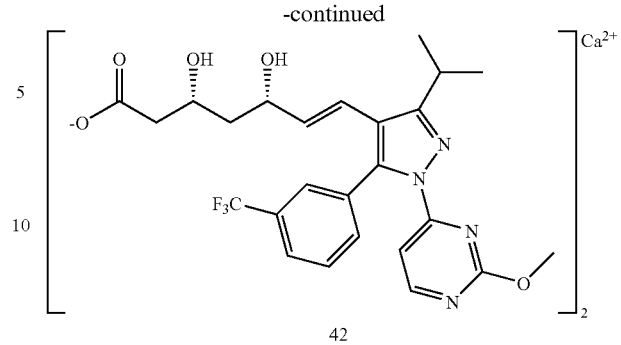

The product (0.015 g) is obtained in the same manner as Example 10a, Step 9 from (3R,5S,E)-ethyl 3,5-dihydroxy-7-(3-isopropyl-1-(2-methoxypyrimidin-4-yl)-5-(3-(trifluoromethyl)phenyl)-1H-pyrazol-4-yl)hept-6-enoate, 41 (0.045 g).

The compound obtained in this step has the following mass spectral and NMR data:

LC/MS as free acid: $C_{25}H_{27}F_3N_4O_5$ requires 520.2; observed M/Z 521.0 $[M+H]^+$, 519.2 $[M-H]^-$. RT 2.67 min. $^1$H-NMR (270 MHz, $CD_3OD$, δ) 1.37 (d, 6H), 1.38–1.71 (m, 2H), 2.18–2.36 (m, 2H), 3.05–3.09 (m, 1H), 3.07 (s, 3H), 3.88–3.98 (m, 1H), 4.18–4.28 (m, 1H), 5.65 (dd, 1H), 6.24 (d, 1H), 7.53–7.76 (m, 5H), 8.46 (d, 1H).

Example 11f

Synthesis of an N-Pyrimidinyl Pyrazole

In a sixth specific example, a compound having the structure indicated below is prepared in two steps (Steps 1–2) from intermediate 41 obtained in Example 11e above.

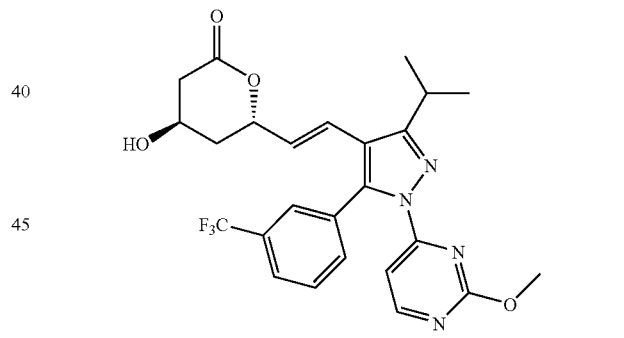

Step 1: (3R,5S,E)-3,5-dihydroxy-7-(3-isopropyl-1-(2-methoxypyrimidin-4-yl)-5-(3-(trifluoromethyl)phenyl)-1H-pyrazol-4-yl)hept-6-enoic acid, 43 is prepared as follows:

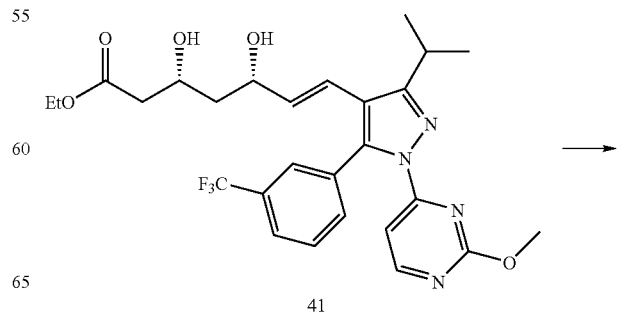

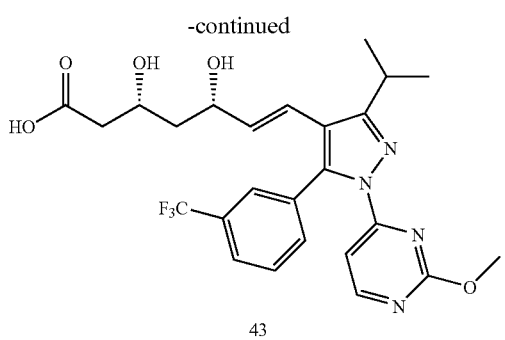

43

To a solution of (3R,5S,E)-ethyl 3,5-dihydroxy-7-(3-isopropyl-1-(2-methoxypyrimidin-4-yl)-5-(3-(trifluoromethyl)phenyl)-1H-pyrazol-4-yl)hept-6-enoate, 41 (0.031 g) in ethanol (0.5 mL) is added aqueous sodium hydroxide (57 μL of a 1M solution). After stirring at room temperature for 0.25 h, organic solvent is removed in vacuo and aqueous hydrochloric acid (57 μL of a 1M solution) is added, along with water (2 mL). The solution is extracted with ethyl acetate, then washed with brine, dried over magnesium sulfate and concentrated to afford the title compound (0.024 g).

The compound obtained in this step shows the following mass spectral data: LC/MS: $C_{25}H_{27}F_3N_4O_5$ requires 520.2; observed M/Z 521.0 [M+H]$^+$, 519.2 [M−H]$^−$, RT 2.67 min.

Step 2: (4R,6S,E)-4-hydroxy-6-(2-(3-isopropyl-1-(2-methoxypyrimidin-4-yl)-5-(3-(trifluoromethyl)phenyl)-1H-pyrazol-4-yl)vinyl)-tetrahydropyran-2-one, 44 is prepared as follows:

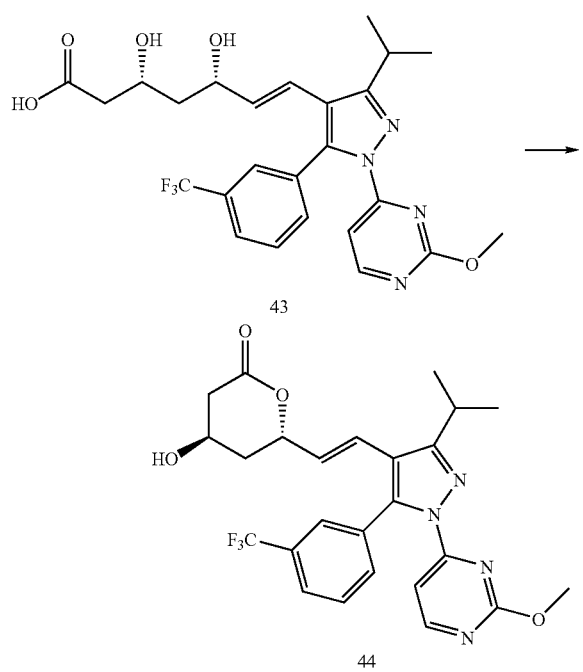

44

(3R,5S,E)-3,5-dihydroxy-7-(3-isopropyl-1-(2-methoxypyrimidin-4-yl)-5-(3-(trifluoromethyl)phenyl)-1H-pyrazol-4-yl)hept-6-enoic acid, 43 (0.024 g) is dissolved in toluene (3 mL) and heated to 90° C. for 16 h. On cooling, the residue is concentrated in vacuo, then purified by flash chromatography to give the title compound (0.010 g).

The compound obtained in this step shows the following mass spectral and NMR data:

LC/MS: $C_{25}H_{25}F_3N_4O_4$ requires 502.2; observed M/Z 503.0 [M+H]$^+$, 501.2 [M+H]$^−$. RT 5.84 min. $^1$H-NMR (270 MHz, CDCl$_3$, δ) 1.37 (d, 6H), 1.53–1.95 (m, 2H), 2.52–2.77 (m, 2H), 3.08 (s, 3H), 3.07–3.22 (m, 1H), 4.30–4.33 (m, 1H), 5.08–5.12 (m, 1H), 5.58 (dd, 1H), 6.27 (d, 1H), 7.41–7.70 (m, 5H), 8.45 (d, 1H).

Example 11g

Synthesis of an N-Pyrimidinyl Pyrazole

In a seventh specific example, a compound having the structure indicated below is prepared in eight steps (Steps 1–8).

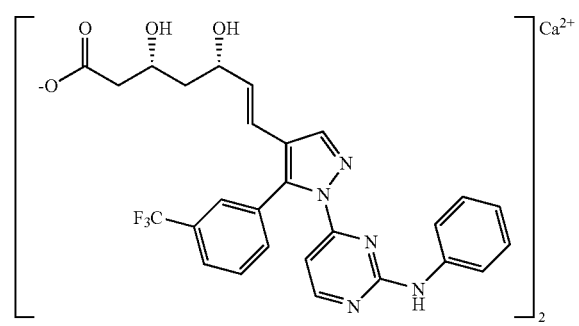

Step 1: 3-oxo-3-(3-(trifluoromethyl)phenyl)propanal, 45 is prepared as follows:

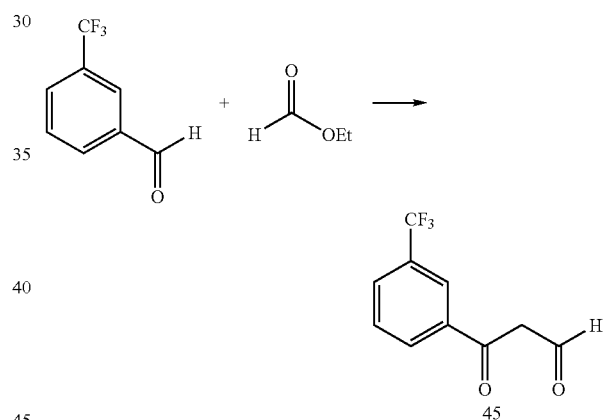

The product (4.81 g) is obtained as an oil in the same manner as Example 10a, Step 1 from 3-(trifluoromethyl)benzaldehyde (10.00 g) and ethyl formate (3.94 g)

The compound obtained in this step shows the following boiling point and mass spectral data:

b.p 67–75° C. at 1 mmHg. LC/MS: $C_{10}H_7F_3O_2$ requires 216.0; observed M/Z 215.2 [M−H]$^−$. RT 7.49 min.

Step 2: 2-(methylthio)-4-(5-(3-(trifluoromethyl)phenyl)-1H-pyrazol-1-yl)pyrimidine, 46 is prepared as follows;

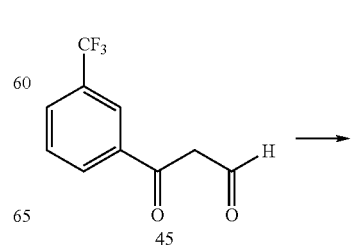

45

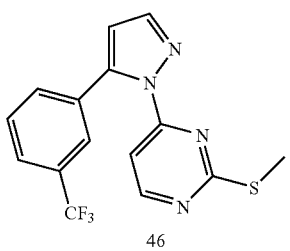
46

The product (2.33 g) is obtained in the same manner as Example 11e, Step 2 from 3-oxo-3-(3-(trifluoromethyl)phenyl)propanal, 45 (2.59 g).

The compound obtained in this step shows the following NMR data: $^1$H-NMR (270 MHz, CDCl$_3$, δ) 1.73 (s, 3H), 6.52 (d, 1H), 7.52–7.55 (m, 1H), 7.60 (d, 1H), 7.61–7.72 (m, 3H), 7.80 (s, 1H), 8.55 (d, 1H).

Step 3: 2-(methylsulfonyl)-4-(5-(3-(trifluoromethyl)phenyl)-1H-pyrazol-1-yl)pyrimidine, 47 is prepared as follows:

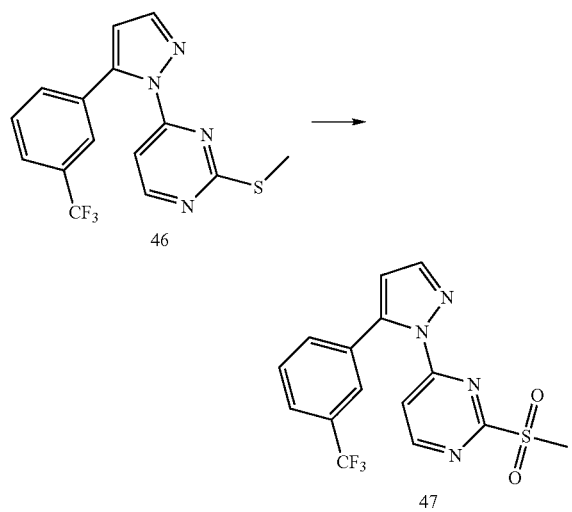

The product (2.04 g) is obtained in the same manner as Example 11a, Step 3 from 2-(methylthio)-4-(5-(3-(trifluoromethyl)phenyl)-1H-pyrazol-1-yl)pyrimidine, 46 (2.33 g). The material is used crude after work-up in the next step.

Step 4: 4-(4-bromo-5-(3-(trifluoromethyl)phenyl)-1H-pyrazol-1-yl)-2-(methylsulfonyl)pyrimidine, 48 is prepared as follows:

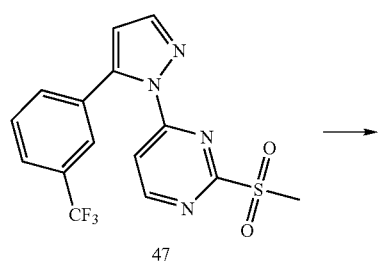
47

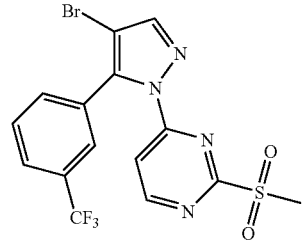
48

The product (1.50 g) is obtained in the same manner as Example 10a, Step 5 from 2-(methylsulfonyl)-4-(5-(3-(trifluoromethyl)phenyl)-1H-pyrazol-1-yl)pyrimidine, 47 (1.84 g).

The compound obtained in this step shows the following mass spectral data: LC/MS: $C_{15}H_{10}BrF_3N_4O_2S$ requires 446.0; observed M/Z 446.8/448.8 (Br) [M+H]$^+$. RT 5.12 min.

Step 5: 4-(4-bromo-5-(3-(trifluoromethyl)phenyl)-1H-pyrazol-1-yl)-N-phenylpyrimidin-2-amine, 49 is prepared as follows:

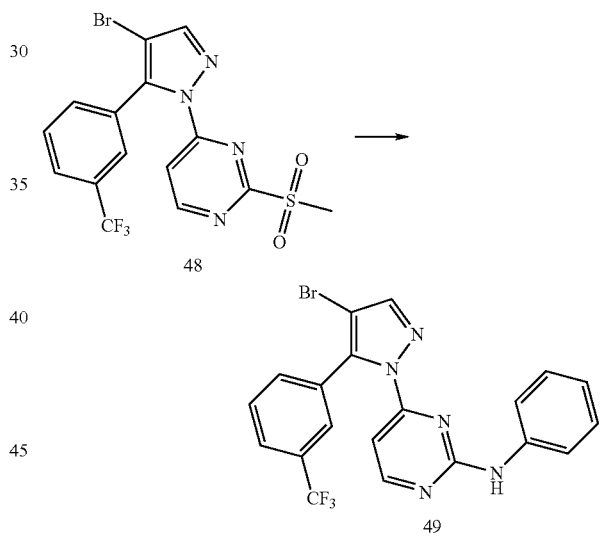

A solution of 4-(4-bromo-5-(3-(trifluoromethyl)phenyl)-1H-pyrazol-1-yl)-2-(methylsulfonyl)pyrimidine, 48 (0.100 g) and aniline (42 μL) in dimethyl sulfoxide (1 mL) and trifluoroacetic acid (40 μl) are heated to 90° C. for 16 h. The reaction mixture is then partitioned between ethyl acetate and brine, extracting the aqueous layer with further ethyl acetate. The combined organic layers are dried over magnesium sulfate, filtered and concentrated. Purification by flash chromatography affords the title compound (0.06 g).

The compound obtained in this step shows the following mass spectral data: LC/MS: $C_{20}H_{13}BrF_3N_5$, requires 459.0; observed M/Z 459.9/461.9 (Br) [M+H]$^+$, 458.0/460.0 (Br) [M−H]$^−$. RT 6.30 min.

Step 6: ethyl 2-((4R,6S)-2,2-dimethyl-6-((E)-2-(1-(2-(phenylamino)pyrimidin-4-yl)-5-(3-(trifluoromethyl)phenyl)-1H-pyrazol-4-yl)vinyl)-1,3-dioxan-4-yl)acetate, 50 is prepared as follows:

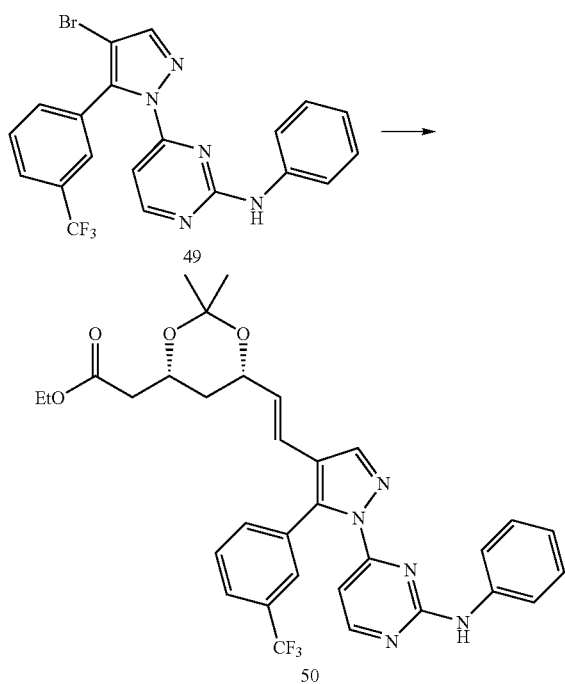

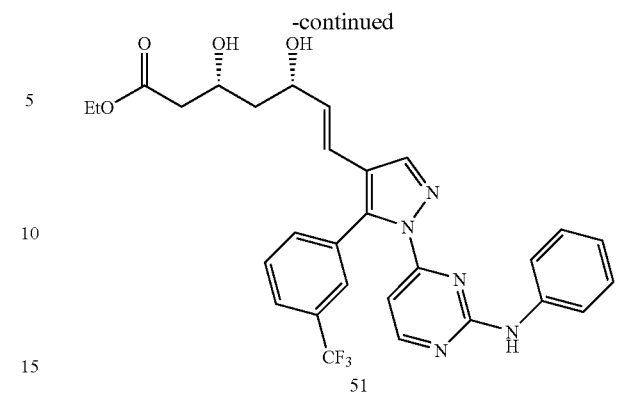

Bistriphenylphosphine palladium (II) chloride (0.16 g) is added to a degassed solution of 4-(4-bromo-5-(3-(trifluoromethyl)phenyl)-1H-pyrazol-1-yl)-N-phenylpyrimidin-2-amine, 49 (0.86 g), ethyl 2-((4S,6R)-2,2-dimethyl-6-vinyl-1,3-dioxan-4-yl)acetate, 9 (0.72 g) and triethylamine (3 mL) in DMF (3 mL) and the mixture is heated to 100° C. After 18 h a further portion of bistriphenylphosphine palladium (II) chloride (0.16 g) is added and heating continued. After a further 24 h the reaction mixture is filtered through celite and evaporated to dryness. The residue is partitioned between ethyl acetate and aqueous sodium hydrogen carbonate and the organic layer is washed with water and brine, evaporated to dryness and purified flash chromatography to afford title compound (0.103 g).

The compound obtained in this step shows the following mass spectral data: LC/MS: $C_{32}H_{32}F_3N_5O_4$ requires 607.2; observed M/Z 608.1 [M+H]$^+$. RT 7.74 min.

Step 7: (3R,5S,E)-ethyl 3,5-dihydroxy-7-(1-(2-(phenylamino)pyrimidin-4-yl)-5-(3-(trifluoromethyl)phenyl)-1H-pyrazol-4-yl)hept-6-enoate, 51 is prepared as follows:

ethyl 2-((4R,6S)-2,2-dimethyl-6-((E)-2-(1-(2-(phenylamino)pyrimidin-4-yl)-5-(3-(trifluoromethyl)phenyl)-1H-pyrazol-4-yl)vinyl)-1,3-dioxan-4-yl)acetate, 50 (0.100 g) and p-toluene sulfonic acid monohydrate (0.033 g) are dissolved in a mixture of tetrahydrofuran (1.5 mL) containing water (0.5 mL). After 18 h a further portion of p-toluenesulfonic acid (0.033 g) is added and stirring continued. After 4 days the reaction mixture is partitioned between ethyl acetate and aqueous sodium hydrogen carbonate. The organic layer is dried over potassium carbonate and evaporated in vacuo to furnish a brown oil. Purification by flash column chromatography affords the title compound (0.031 g).

The compound obtained in this step shows the following NMR data: LC/MS: $C_{29}H_{28}F_3N_5O_4$ requires 567.2; observed M/Z 568.0 [M+H]$^+$, 566.2 [M−H]$^-$. RT 5.05 min.

Step 8: (3R,5S,E)-3,5-dihydroxy-7-(1-(2-(phenylamino)pyrimidin-4-yl)-5-(3-(trifluoromethyl)phenyl)-1H-pyrazol-4-yl)hept-6-enoic acid calcium salt, 52 is prepared as follows:

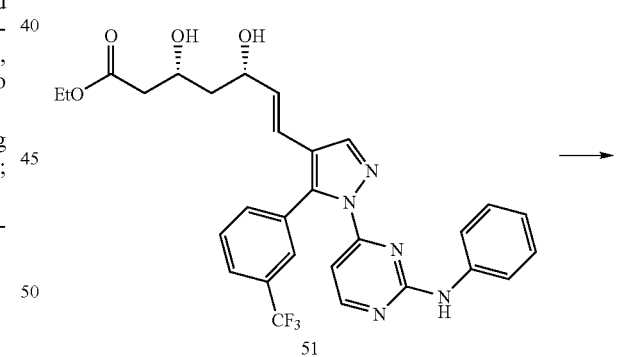

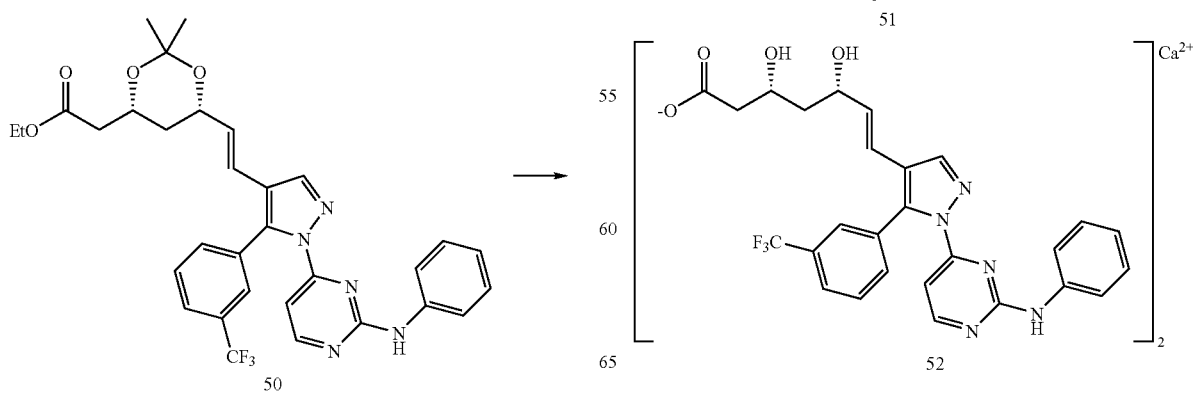

Aqueous sodium hydroxide solution (0.054 mL of a 1 M solution) is added to a solution of (3R,5S,E)-ethyl 3,5-dihydroxy-7-(1-(2-(phenylamino)pyrimidin-4-yl)-5-(3-(trifluoromethyl)phenyl)-1H-pyrazol-4-yl)hept-6-enoate, 51 (0.031 g) in ethanol (0.4 mL) and the mixture is stirred at room temperature. After 0.5 h the ethanol is removed in vacuo and the remaining aqueous solution is cooled to 0° C. Aqueous calcium chloride solution (0.23 mL of a 0.118 M solution) is added and the target molecule is collected by filtration as a solid.

The compound obtained in this step shows the following mass spectral and NMR data:

LC/MS as free acid: $C_{27}H_{24}F_3N_5O_4$ requires 539.2; observed M/Z 540.0 $[M+H]^+$, 538.2 $[M-H]^-$. RT 2.79 min. $^1$H-NMR (DMSO-$d_6$, δ) 1.44 (m, 1H), 1.58 (m, 1H), 1.99 (m, 1H), 2.14 (dd, 1H), 3.82 (bm, 1H), 4.22 (q, 1H), 6.21 (dd, 1H), 6.30 (dd, 1H), 6.79 (t, 1H), 6.86 (bs, 1H), 6.88 (bs, 1H), 6.94–6.98 (m, 2H), 7.23 (d, 1H), 7.60–7.76 (m, 4H), 8.27 (s, 1H), 8.56 (d, 1H), 9.56 (bs, 1H).

Example 11h

Synthesis of an N-Pyrimidinyl Pyrazole Using an Alternative Route to Intermediate 46 of Example 11g Above Intermediate 46 above can also be obtained in two steps (Steps 1–2) detailed below:

Step 1: (E)-3-(dimethylamino)-1-(3-(trifluoromethyl)phenyl)prop-2-en-1-one, 53 is prepared as follows:

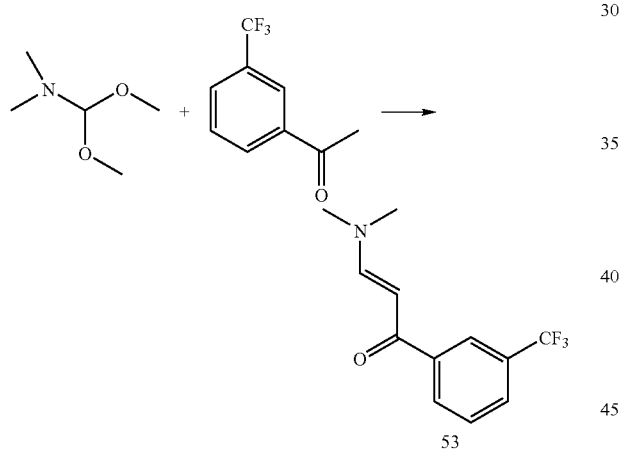

A mixture of N,N-dimethylformamide dimethylacetal (2.5 g) and 3'-(trifluoromethyl)acetophenone (4.0 g) is heated to 100° C. for 7 h. The crude reaction product (5.22 g) is used without further purification.

The compound obtained in this step shows the following mass spectral data: LC/MS: $C_{12}H_{12}F_3NO$ requires 243.1; observed M/Z 244.3 $[M+H]^+$. RT 4.17 min.

Step 2: 2-(methylthio)-4-(5-(3-(trifluoromethyl)phenyl)-1H-pyrazol-1-yl)pyrimidine, 46 is prepared as follows:

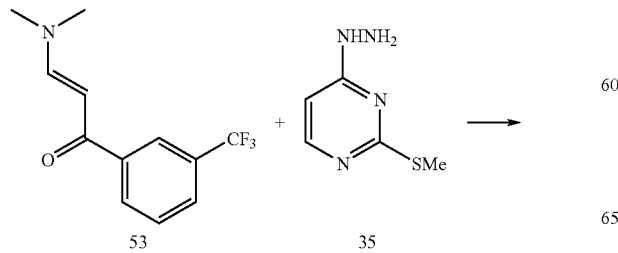

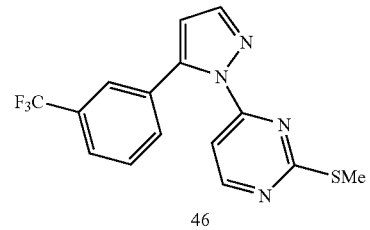

A solution of (E)-3-(dimethylamino)-1-(3-(trifluoromethyl)phenyl)prop-2-en-1-one, 53 (0.50 g) and 4-hydrazinyl-2-(methylthio)pyrimidine, 35 (0.32 g) in acetic acid (5.0 mL) is heated to 80° C. for 12 h. The reaction mixture is diluted with dichloromethane and washed with saturated aqueous sodium hydrogen carbonate until the aqueous washings are basic. The organic layer is dried over magnesium sulfate, filtered and concentrated in vacuo to afford an oil. $^1$H NMR analysis indicates a 4:1 ratio of isomers in favour of 2-(methylthio)-4-(5-(3-(trifluoromethyl)phenyl)-1H-pyrazol-1-yl)pyrimidine, 46.

Example 11i

Synthesis of an N-Pyrimidinyl Pyrazole

In an eighth specific example, a compound having the structure indicated below is prepared in two steps (Steps 1–2).

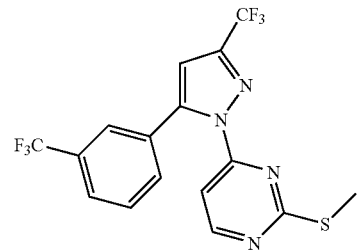

Step 1: 4,4,4-trifluoro-1-(3-(trifluoromethyl)methyl)butane-1,3-dione, 55 is prepared as follows:

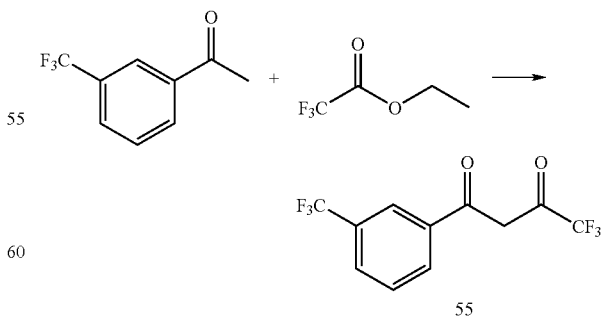

To a flask at 0° C. containing sodium hydride (8.5 g) under nitrogen is added dropwise a solution of 3'-(trifluoromethyl)acetophenone (20 g) in anhydrous 1,4-dioxane (200 mL). After stirring for 15 min a solution of ethyl trifluoroacetate (15.1 g) in anhydrous 1,4-dioxane (200 mL) is added dropwise, during which time vigorous gas evolution occurs. The reaction is left to stir overnight at ambient temperature. The reaction is poured into iced hydrochloric acid solution, then extracted twice with ethyl acetate. The combined organic layers are washed with brine, dried over magnesium sulfate, filtered and concentrated to a brown oil. The oil is purified by flash chromatography to afford 18 g of the title compound as an oil.

The compound obtained in this step shows the following mass spectral data: LC/MS: $C_{11}H_6F_6O_2$ requires 284.0; observed M/Z 283.2 [M−H]⁻, RT 2.85 min.

Step 2: 2-(methylthio)-4-(3-(trifluoromethyl)-5-(3-(trifluoromethyl)phenyl)-1H-pyrazol-1-yl)pyrimidine, 56 is prepared as follows:

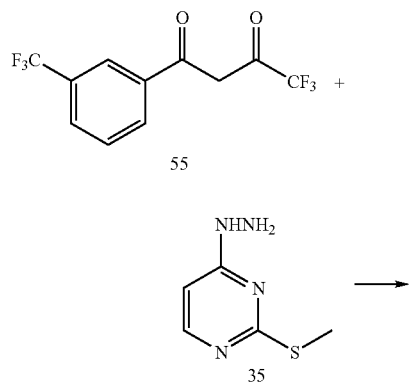

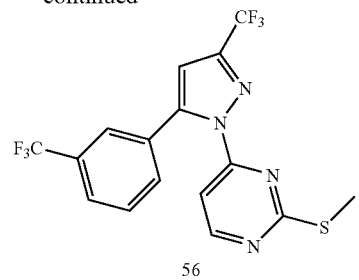

56

To a solution of 4,4,4-trifluoro-1-(3-(trifluoromethyl)methyl)butane-1,3-dione, 55 (1.00 g) in acetic acid (10 mL) is added 4-hydrazinyl-2-(methylthio)pyrimidine, 35 (0.55 g) and the reaction is left to heat to reflux for 48 h. On cooling, the solution is quenched with sodium hydrogen carbonate and extracted with ethyl acetate. The aqueous layer is extracted with a further portion of ethyl acetate and the combined organic layers dried over magnesium sulfate, filtered and concentrated to an oil. Flash chromatography affords the title compound (0.11 g) an oil.

The compound obtained in this step shows the following mass spectral and NMR data:

LC/MS: $C_{16}H_{10}F_6N_4S$ requires 404.1; observed M/Z 404.9 [M+H]⁺, RT 6.43 min. ¹H NMR (270 MHz, CDCl₃, δ) 1.72 (s, 3H), 6.77 (s, 1H), 7.54 (m, 2H), 7.63 (d, 1H), 7.69 (m, 2H), 8.60 (d, 1H).

Example 12

Scheme for Synthesis of Pyrrole Compounds

An scheme for synthesizing a substituted pyrrole compounds of formula VII of the instant invention is provided below. A compound of structure 65 can be prepared in nine steps (Steps 1–9) as detailed below.

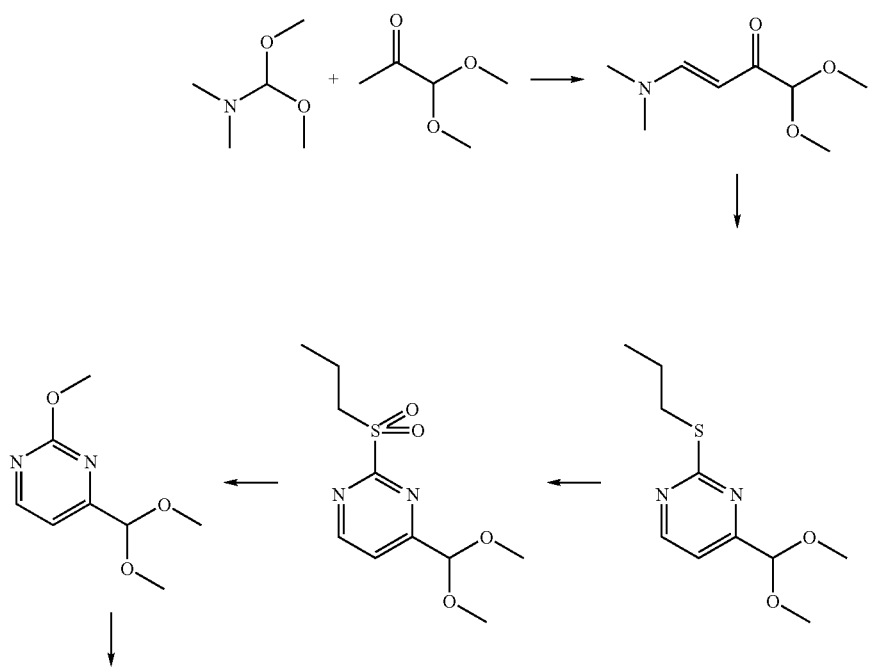

-continued

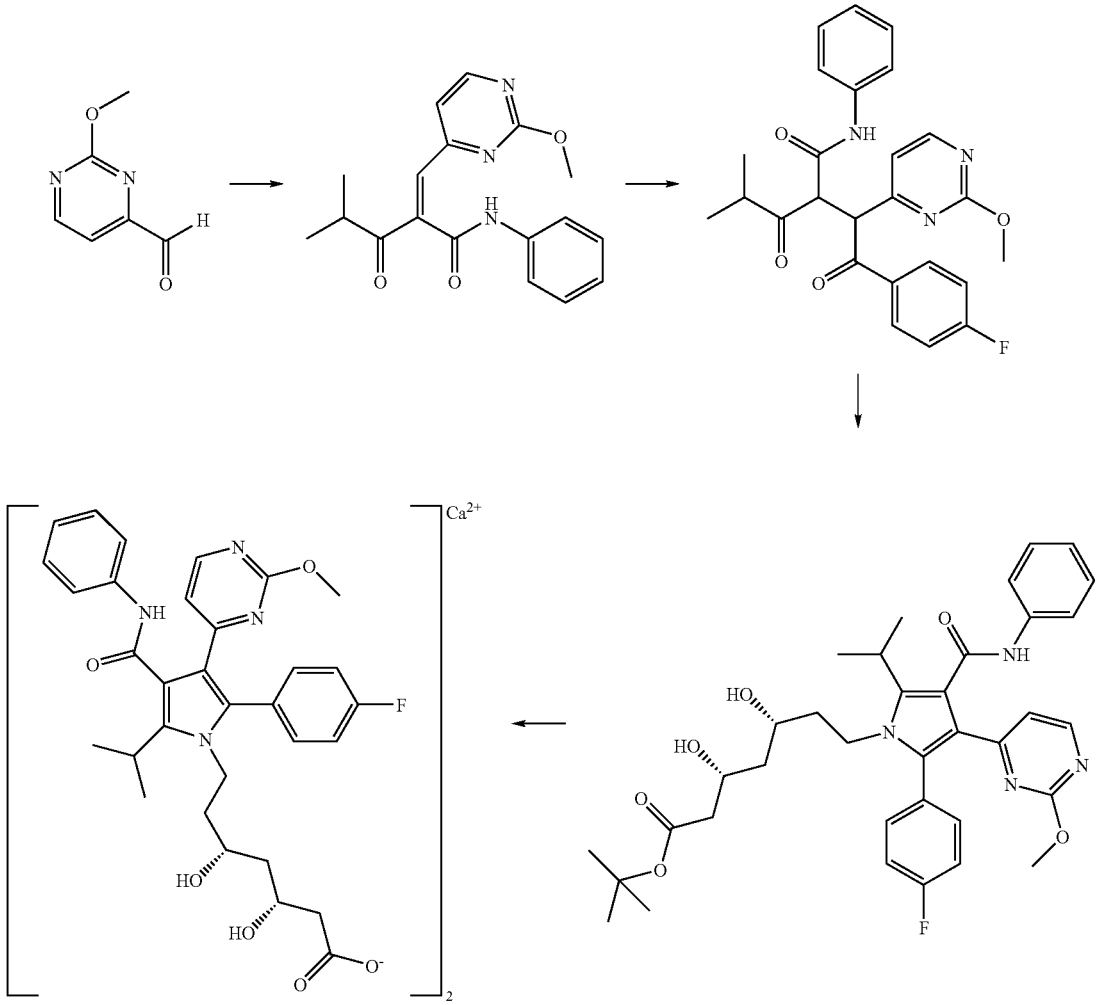

Step 1: (E)-4-(dimethylamino)-1,1-dimethoxybut-3-en-2-one, 57 is prepared as follows:

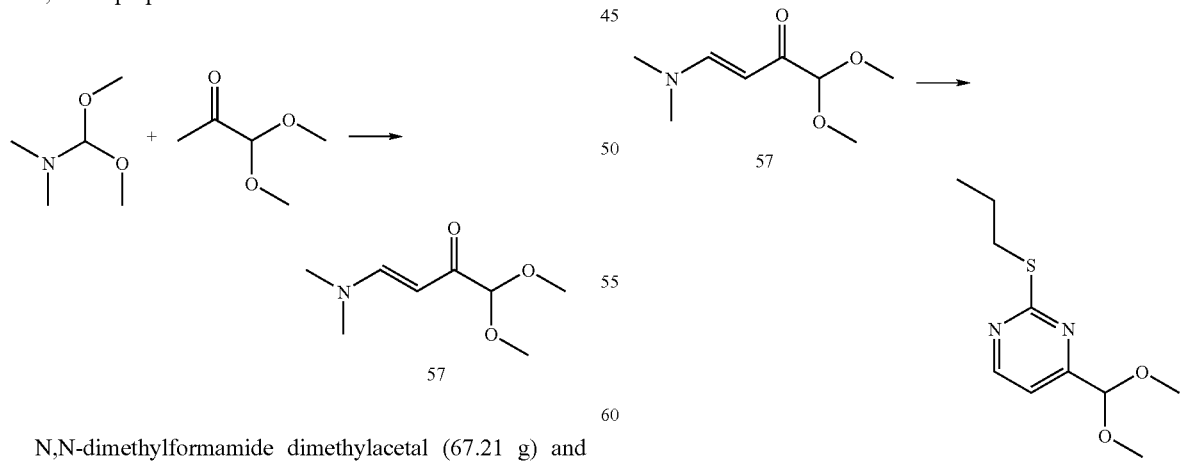

N,N-dimethylformamide dimethylacetal (67.21 g) and 1,1-dimethoxypropan-2-one (66.62 g), are heated together at 100° C. for 16 h. Residual methanol is removed in vacuo and the product used crude in the next step.

Step 2: 4-(dimethoxymethyl)-2-(propylthio)pyrimidine, 58 is prepared as follows:

(E)-4-(dimethylamino)-1,1-dimethoxybut-3-en-2-one, 57 (10.0 g), and thiourea (4.40 g) are dissolved in methanol (50 mL) at 0° C. and sodium methoxide (3.12 g) is added portionwise. The mixture is heated to 80° C. for 22 h, then left at ambient temperature for 24 h. 1-Bromopropane (5.25 mL) is added and the mixture warmed to 50° C. for 5 h. The mixture is concentrated in vacuo and partitioned between ethyl acetate and water. The aqueous layer is washed with further ethyl acetate and the combined organics dried (magnesium sulphate), filtered and concentrated. Purification by flash chromatography affords the title compound as an oil (8.53 g).

The compound obtained in this step shows the following mass spectral data: LC/MS: $C_{10}H_{16}N_2O_2S$ requires 228.1; observed M/Z 229.2 [M+H]$^+$. RT 4.75 min.

Step 3: 4-(dimethoxymethyl)-2-(propylsulfonyl)pyrimidine, 59 is prepared as follows:

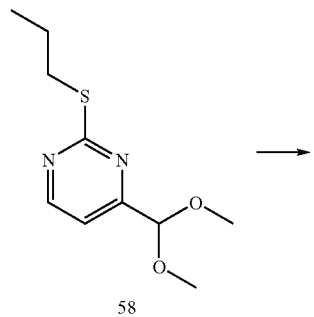

58

To a solution of 4-(dimethoxymethyl)-2-(propylthio)pyrimidine, 58 (8.35 g) in a mixture of tetrahydrofuran (144 mL) and methanol (320 mL) is added a suspension of Oxone (90.05 g) and sodium acetate trihydrate (50.00 g) in water (80 mL). The resulting suspension is stirred for 16 h at ambient temperature after which time the organic solvent is removed in vacuo. The residue is partitioned between ethyl acetate and water. The organic layer is washed with aqueous sodium hydrogen carbonate, brine, dried (magnesium sulfate), filtered and concentrated to afford the title compound (8.66 g) as an oil.

The compound obtained in this step shows the following mass spectral data: LC/MS: $C_{10}H_{16}N_2O_4S$ requires 260.1; observedd M/Z 261.1 [M+H]$^+$. RT 3.13 min.

Step 4: 4-(dimethoxymethyl)-2-methoxypyrimidine, 60 is prepared as follows:

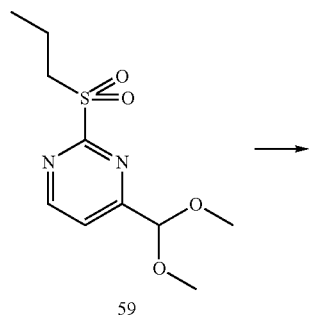

59

-continued

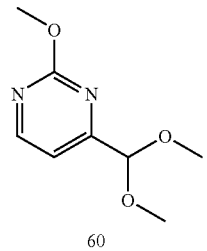

60

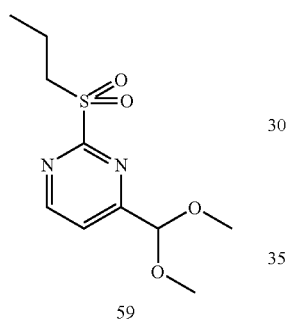

59

4-(dimethoxymethyl)-2-(propylthio)pyrimidine, 59, is dissolved in methanol (40 mL) and sodium methoxide (1.57 g) is added. The mixture is heated to 60° C. for 1 h, then the solvent removed in vacuo. The residue is partitioned between ethyl acetate and water, extracting the aqueous layer with further ethyl acetate. The combined organics are dried (magnesium sulfate), filtered and concentrated to give the title compound (4.53 g) as an oil.

The compound obtained in this step shows the following mass spectral data: LC/MS: $C_8H_{12}N_2O_3$ requires 184.1; observed M/Z 185.2 [M+H]$^+$. RT 2.57 min.

Step 5: 2-methoxypyrimidine-4-carbaldehyde, 61 is prepared as follows:

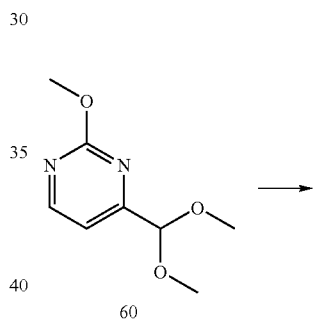

60

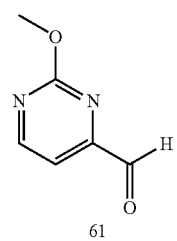

61

4-(dimethoxymethyl)-2-methoxypyrimidine, 60 (1.50 g) is dissolved in dilute hydrochloric acid (1M, 12.3 mL) and the mixture heated to 55° C. for 3 h. The reaction mixture is partitioned between water and dichloromethane and the aqueous layer extracted with further portions of dichloromethane. The combined organics are dried (magnesium sulfate), filtered and concentrated to a yellow gum (1.10 g). The aldehyde is used immediately in the next step without further purification.

The compound obtained in this step shows the following mass spectral data: LC/MS: $C_6H_6N_2O_2$ requires 138.0; observed M/Z 139.1 [M+H]$^+$. RT 0.85 min.

Step 6: (Z)-2-((2-methoxypyrimidin-4-yl)methylene)-4-methyl-3-oxo-N-phenylpentanamide, 62 is prepared as follows:

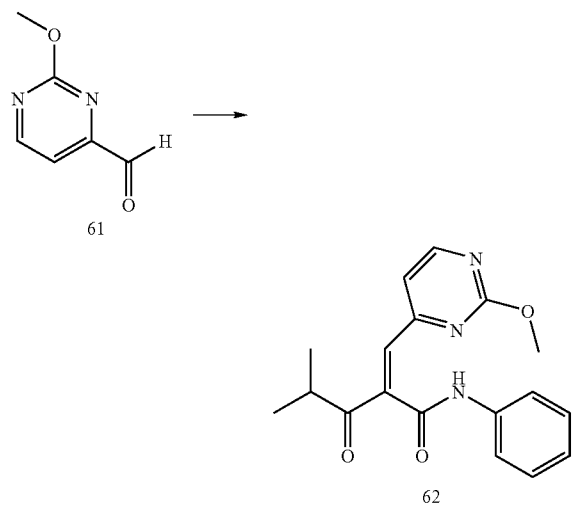

To a mixture of 2-methoxypyrimidine-4-carbaldehyde, 61 (0.833 g) and 4-methyl-3-oxo-N-phenylpentanamide (1.23 g) are added piperidine (4 drops) and acetic acid (4 drops). The mixture is heated to 65° C. for 3 h after which time it is partitioned between water and dichloromethane. The aqueous layer is extracted with further dichloromethane and the combined organics dried (magnesium sulfate), filtered and concentrated. Purification by flash chromatography followed by trituration with toluene affords the title compound (0.221 g) as a powder.

The compound obtained in this step shows the following mass spectral data: LC/MS: $C_{18}H_{19}N_3O_3$ requires 325.1; observed M/Z 326.1 [M+H]$^+$, 324.2 [M−H]$^−$. RT 4.02 min.

Step 7: 2-(2-(4-fluorophenyl)-1-(2-methoxypyrimidin-4-yl)-2-oxoethyl)-4-methyl-3-oxo-N-phenylpentanamide, 63 is prepared as follows:

To a solution of 3-benzyl-5-(2-hydroxyethyl)-4-methylthiazolium chloride (0.166 g) in anhydrous tetrahydrofuran (2 mL) are added (Z)-2-((2-methoxypyrimidin-4-yl)methylene)-4-methyl-3-oxo-N-phenylpentanamide, 62 (0.200 g), triethylamine (63 μL) and 4-fluorobenzaldehyde (66 μL). The mixture is heated to 60° C. for 3 h, then partitioned between water and dichloromethane. The organic layer is dried (magnesium sulfate), filtered and concentrated. The residue is purified by flash chromatography to give the title compound (0.046 g).

The compound obtained in this step shows the following mass spectral data: LC/MS: $C_{25}H_{24}FN_3O_4$ requires 449.2; observed M/Z 450.0 [M+H]$^+$, 448.2 [M−H]$^−$. RT 5.05 min.

Step 8: (3R,5R)-tert-butyl 7-(2-(4-fluorophenyl)-5-isopropyl-3-(2-methoxypyrimidin-4-yl)-4-(phenylcarbamoyl)-1H-pyrrol-1-yl)-3,5-dihydroxyheptanoate, 64 is prepared as follows:

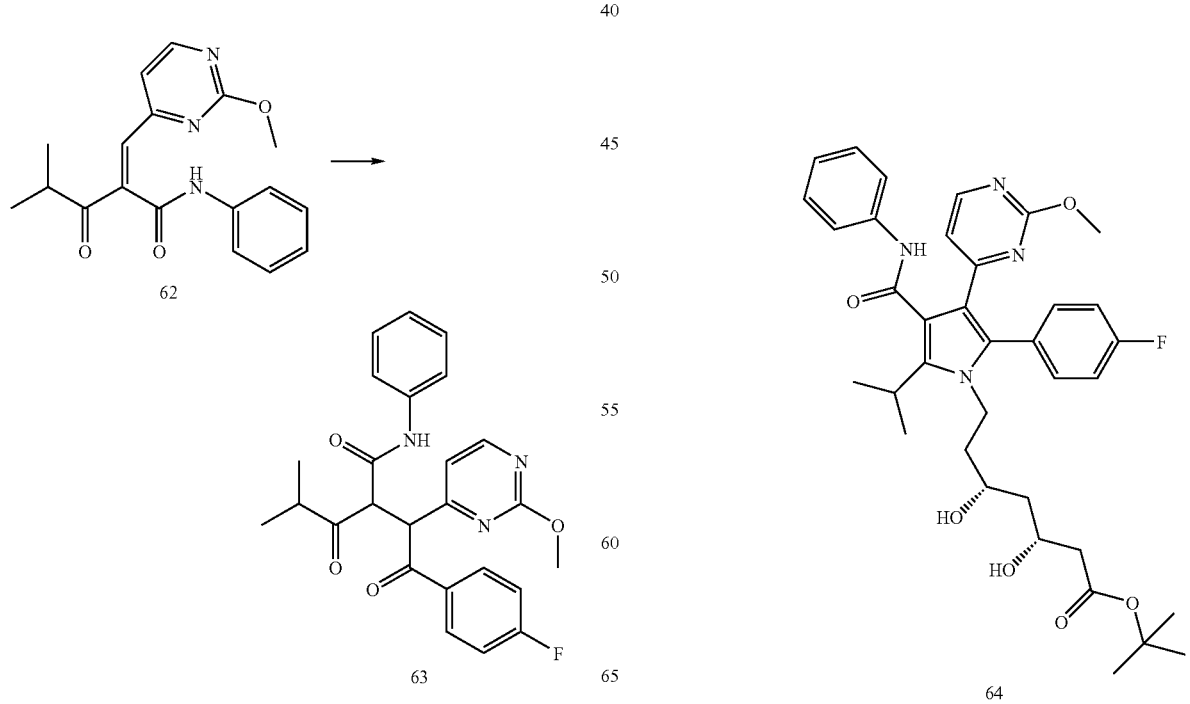

A mixture of 2-(2-(4-fluorophenyl)-1-(2-methoxypyrimidin-4-yl)-2-oxoethyl)-4-methyl-3-oxo-N-phenylpentanamide, 63 (0.046 g), tert-butyl 2-((4R,6R)-6-(2-aminoethyl)-2-phenyl-1,3,2-dioxaborinan-4-yl)acetate (0.032 g) and pivalic acid (0.010 g) are heated to 80° C. for 16 h. The solvent is then removed in vacuo and the residue purified by flash chromatography, during which the boronate moiety is hydrolysed, to give the title compound (0.024 g).

The compound obtained in this step shows the following mass spectral data: LC/MS: $C_{36}H_{43}FN_4O_6$ requires 646.3; observed M/Z 647.2 [M+H]$^+$, 645.3 [M–H]$^-$. RT 5.24 min.

Step 9: (3R,5R)-7-(2-(4-fluorophenyl)-5-isopropyl-3-(2-methoxypyrimidin-4-yl)-4-(phenylcarbamoyl)-1H-pyrrol-1-yl)-3,5-dihydroxyheptanoic acid calcium salt, 65 is prepared as follows:

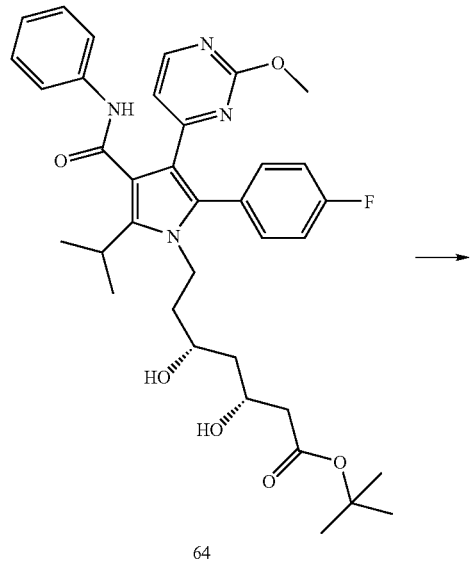

64

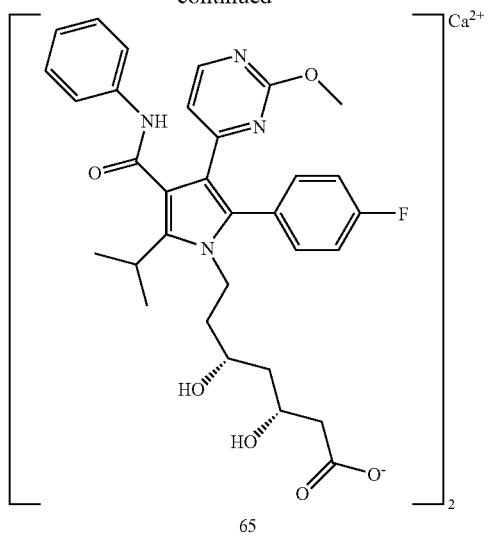

65

To a solution of (3R,5R)-tert-butyl 7-(2-(4-fluorophenyl)-5-isopropyl-3-(2-methoxypyrimidin-4-yl)-4-(phenylcarbamoyl)-1H-pyrrol-1-yl)-3,5-dihydroxyheptanoate, 64 (0.019 g) in tetrahydrofuran (0.4 mL) is added aqueous sodium hydroxide solution (33 μL of a 1 M solution) and the mixture is stirred for 5 h at ambient temperature. The organic solvent is removed in vacuo and the residue dissolved in water (0.5 mL). Aqueous calcium chloride (265 μL of a 0.118 M solution) is added and the resulting precipitate is collected by filtration and washed with water and acetonitrile to afford the title compound (0.003 g).

The compound obtained in this step shows the following mass spectral and NMR data: LC/MS as free acid: $C_{32}H_{35}FN_4O_6$ requires 590.3; observed M/Z 591.1 [M+H]$^+$, 589.3 [M–H]$^-$. RT 2.62 min.

$^1$H-NMR (270 MHz, DMSO-d$_6$, δ) 1.35(d, 6H), 1.53–1.64(m, 2H), 1.81–1.93(m, 2H), 1.99–2.11(m, 2H), 3.16(m, 1H), 3.24–3.36(m, 1H), 3.42(s, 3H), 3.47–3.57(m, 1H), 3.82–3.93(m, 2H), 4.77(brs, 1H), 6.35(d, 1H), 7.00(t, 1H), 7.10–7.15(m, 1H), 7.22–7.43(m, 5H), 7.64(d, 2H), 8.14(d, 1H), 10.18(s, 1H).

Example 13

Scheme for Synthesis of Imidazole Cmpounds Via Condensation with Sidechain

An overall scheme for synthesizing substituted imidazole compounds of Formula V of the instant invention is provided below. Examples 13a and 13b below detail two specific examples following the overall scheme.

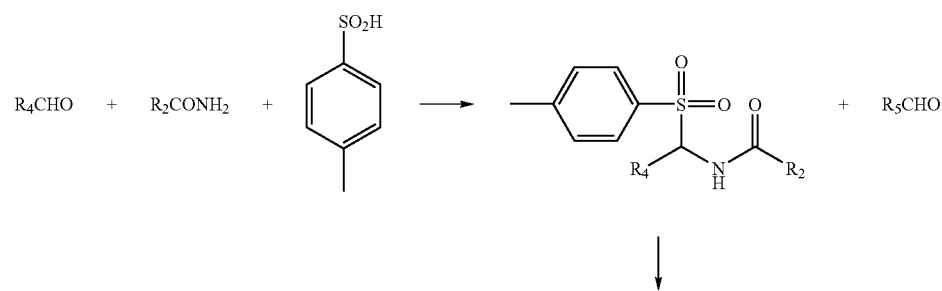

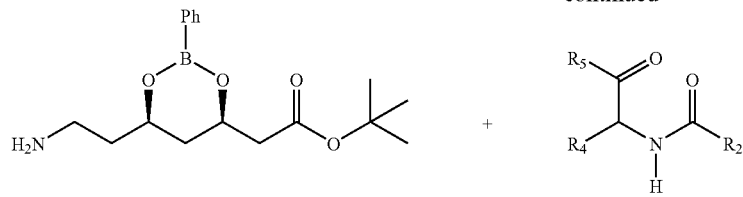

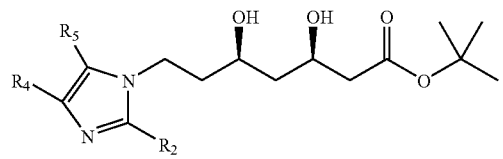

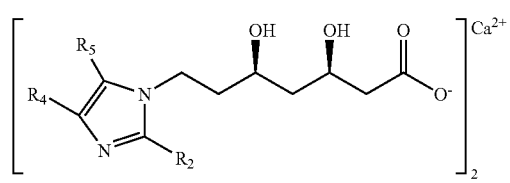

Example 13a

Synthesis of Imidazole Cmpound (3R,5R)-7-(2,5-diphenyl-4-(pyridin-4-yl)-1H-imidazol-1-yl)-3,5-dihydroxyheptanoic acid, calcium salt via Condensation with Sidechain In one specific example, (3R,5R)-7-(2,5-diphenyl-4-(pyridin-4-yl)-1H-imidazol-1-yl)-3,5-dihydroxyheptanoic acid, calcium salt, having the structure below, is prepared in four steps (Steps 1–4) below.

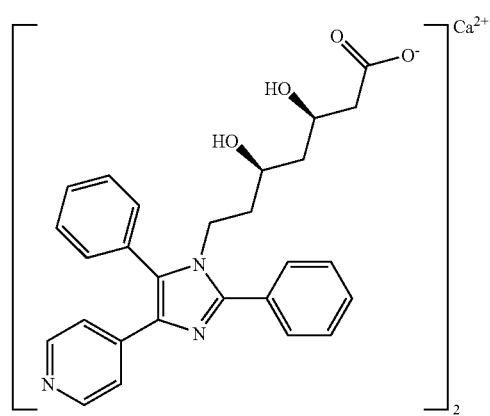

Step 1: N-(pyridin-4-yl(tosyl)methyl)benzamide 66 is prepared as follows;

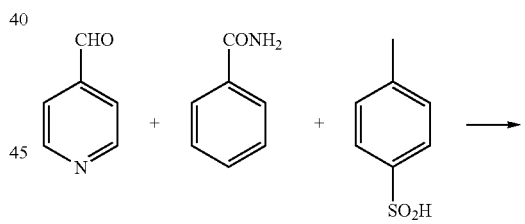

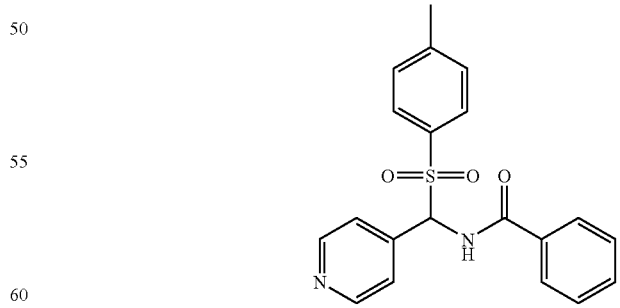

66

To a mixture of pyridine-4-carboxyaldehyde (6.2 g) and benzamide (5.4 g) in 2,2,2-trifluoroethanol (50 mL) is added chlorotrimethylsilane (32.5 mL). Upon heating under reflux for 3 h the solvent is evaporated and the following added; acetonitrile (20 mL), toluene (20 mL), 4-toluenesulfinic acid (14.0 g) and chlorotrimethylsilane (8.5 mL) in that order. The suspension is subsequently heated at 55° C. for 4 h, cooled to room temperature and poured slowly. Into a stirred mixture of saturated aqueous sodium hydrogen carbonate (300 mL) and tert-butylmethylether (100 mL). After brief agitation, the precipitate is collected and washed with tert-butylmethylether to give the title compound, 66 (10.0 g).

The compound obtained in this step shows the following mass spectral data: LC/MS: $C_{20}H_{18}N_2O_3S$ requires 367.1; observed M/Z 228.3 [{M-($C_7H_7O_2S$)}+$NH_3$]$^+$. RT 2.45 min.

Step 2: N-(2-oxo-2-phenyl-1-(pyridin-4-yl)ethyl)benzamide 67 is prepared as follows:

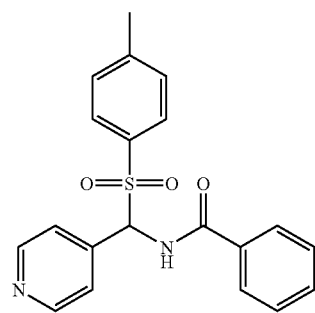

66

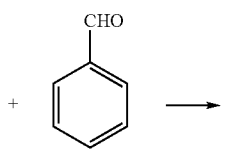

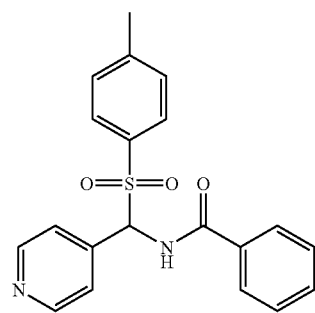

67

A flask containing a mixture of N-(pyridin-4-yl(tosyl)methyl)benzamide, 66 (10.0 g), and 3,4-dimethyl-5-(2-hydroxyethyl)-thiazolium iodide (1.1 g) is flushed with nitrogen for 15 min. Dichloromethane (150 mL) and benzaldehyde are added and the solution heated to 45° C., then triethylamine (42 mL) is added. After heating for 16 h, the solution is cooled to room temperature and saturated aqueous sodium hydrogen carbonate is added. The layers are separated, the aqueous phase extracted with additional dichloromethane, and the combined organic layers are washed with brine. Drying (magnesium sulfate), filtration, concentration and chromatography furnished the title compound, 67 (1.6 g).

The compound obtained in this step shows the following mass spectral data: LC/MS: $C_{20}H_{16}N_2O_2$ requires 316.1; observed M/Z 317.1 [M+H]$^+$. RT 4.05 min.

Step 3: (3R,5R)-tert-butyl 7-(2,5-diphenyl-4-(pyridin-4-yl)-1H-imidazol-1-yl)-3,5-dihydroxyheptanoate 68 is prepared as follows:

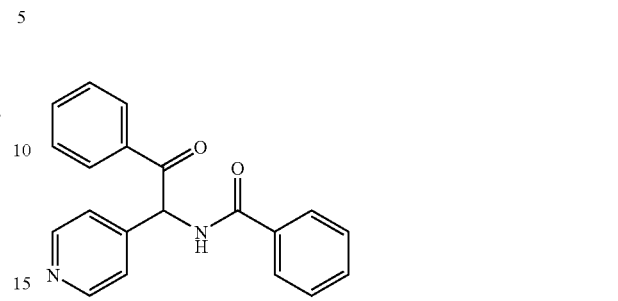

67

+

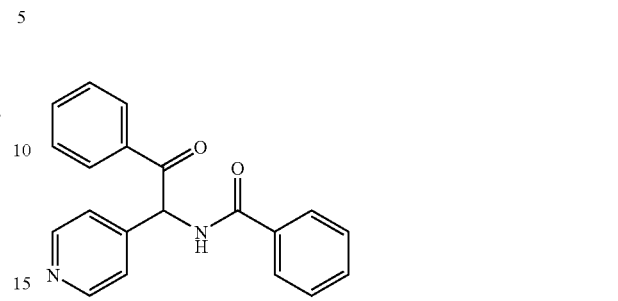

68

To a solution of N-(2-oxo-2-phenyl-1-(pyridin-4-yl)ethyl)benzamide, 67 (1.6 g) and acetic acid (1.5 mL) in ethanol (50 mL) is added tert-butyl 2-((4R,6R)-6-(2-aminoethyl)-2-phenyl-1,3,2-dioxaborinan-4-yl)acetate (7.9 g). Upon heating under reflux for 16 h, the solution is cooled to room temperature and the solvent is evaporated. The residue is partitioned between saturated aqueous sodium hydrogen carbonate and dichloromethane, the layers separated and the organic phase washed with brine, dried (magnesium sulfate), filtered and concentrated. Purification of the residue via chromatography affords the title compound, 68 (0.35 g).

The compound obtained at this step shows the following mass spectral data: LC/MS: $C_{31}H_{35}N_3O_4$ requires 513.3; observed M/Z 514.1 [M+H]$^+$. RT 4.64 min.

Step 4: (3R,5R)-7-(2,5-diphenyl-4-(pyridin-4-yl)-1H-imidazol-1-yl)-3,5-dihydroxyheptanoic acid, calcium salt 69 is prepared as follows:

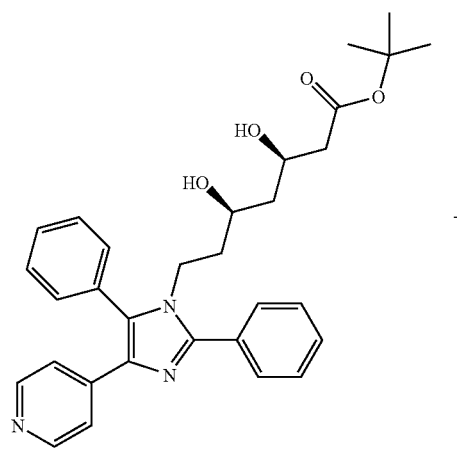
68

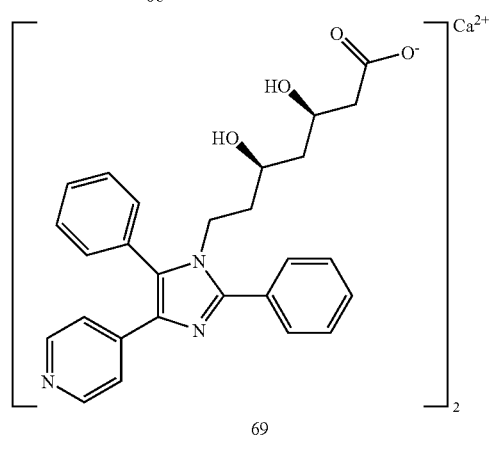
69

To a 0° C. solution of (3R,5R)-tert-butyl 7-(2,5-diphenyl-4-(pyridin-4-yl)-1H-imidazol-1-yl)-3,5-dihydroxyheptanoate, 68 (100 mg) in tetrahydrofuran (2 mL) is added a 1M solution of sodium hydroxide (0.19 mL) dropwise and the mixture is stirred at room temperature for 16 h. Tetrahydrofuran is removed in vacuo until the solution becomes turbid, then an aqueous solution of calcium chloride (0.118M, 0.17 mL) added dropwise. The resulting precipitate is filtered, washed with water, acetonitrile, water, acetonitrile and dried in vacuo, affording the title compound, 69 (22 mg).

The compound obtained at this step shows the following mass spectral data: LC/MS: (as free acid) $C_{27}H_{27}N_3O_4$ requires 457.2; observed M/Z 458.1 $[M+H]^+$. RT 2.11 min.

Example 13b

Synthesis of Imidazole Cmpound (3R,5R)-7-(5-(4-fluorophenyl)-2-phenyl-4-(pyridin-4-yl)-1H-imidazol-1-yl)-3,5-dihydroxyheptanoic acid, calcium salt via Condensation with Sidechain In another specific example, (3R,5R)-7-(5-(4-fluorophenyl)-2-phenyl-4-(pyridin-4-yl)-1H-imidazol-1-yl)-3,5-dihydroxyheptanoic acid, calcium salt, having the structure below, is prepared in three steps (Steps 1–3) below, using an intermediate obtained in Example 13a.

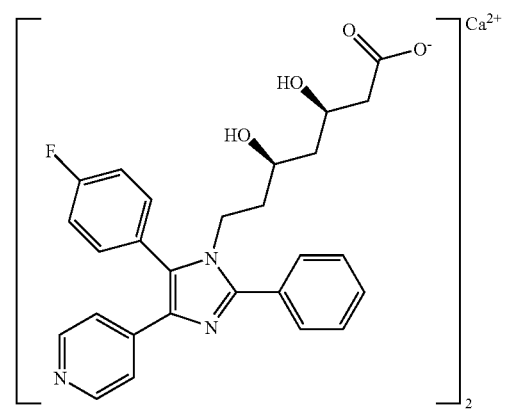

Step 1: N-(2-(4-fluorophenyl)-2-oxo-1-(pyridin-4-yl)ethyl)benzamide 70 prepared as follows:

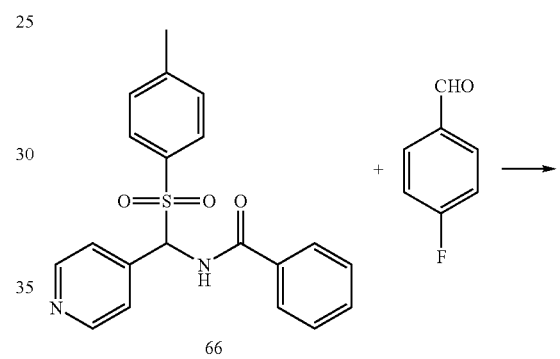
66

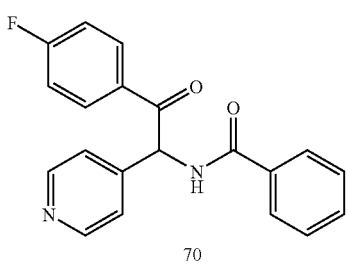
70

The product, N-(2-(4-fluorophenyl)-2-oxo-1-(pyridin-4-yl)ethyl)benzamide, 70 (23 mg, is prepared from 66 and obtained in the same manner as Example 13a, Step 2 from 4-fluorobenzaldehyde (37 mg).

The compound obtained in this step shows the following mass spectral data: LC/MS: $C_{20}H_{15}FN_2O_2$ requires 334.1; observed M/Z 335.1 $[M+H]^+$. RT 4.18 min.

Step 2: (3R,5R)-tert-butyl 7-(5-(4-fluorophenyl)-2-phenyl-4-(pyridin-4-yl)-1H-imidazol-1-yl)-3,5-dihydroxyheptanoate 71 is prepared as follows:

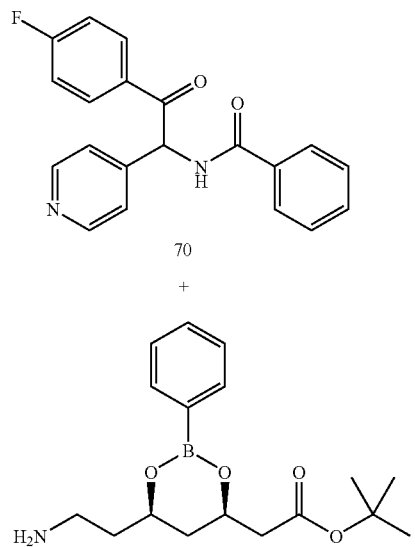

70

+

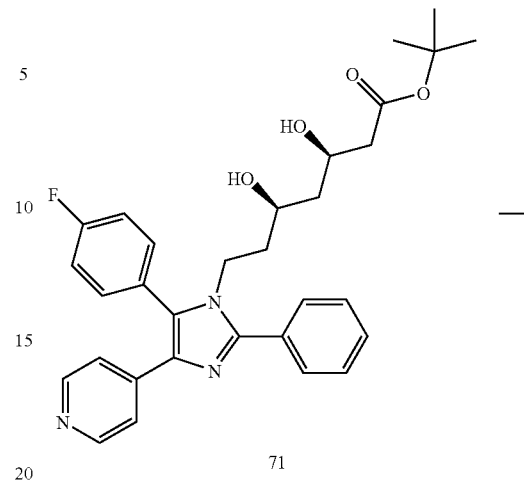

71

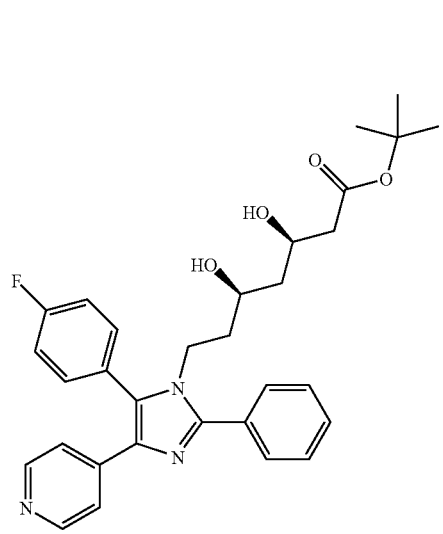

71

The product, (3R,5R)-tert-butyl 7-(5-(4-fluorophenyl)-2-phenyl-4-(pyridin-4-yl)-1H-imidazol-1-yl)-3,5-dihydroxyheptanoate, 71 (5 mg), is obtained in the same manner as Example 13a, Step 3 from N-(2-(4-fluorophenyl)-2-oxo-1-(pyridin-4-yl)ethyl)benzamide, 70 (23 mg).

The compound obtained in this step shows the following mass spectral data: LC/MS: $C_{31}H_{34}FN_3O_4$ requires 531.3; observed M/Z 532.2 [M+H]$^+$. RT 4.70 min.

Step 3: (3R,5R)-7-(5-(4-fluorophenyl)-2-phenyl-4-(pyridin-4-yl)-1H-imidazol-1-yl)-3,5-dihydroxyheptanoic acid, calcium salt 72 is prepared as follows:

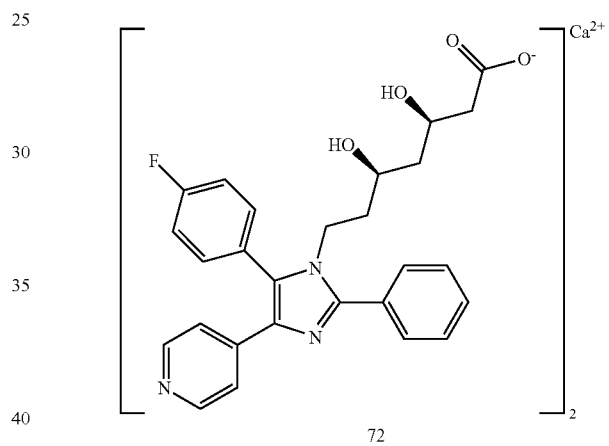

72

The product, ((3R,5R)-7-(5-(4-fluorophenyl)-2-phenyl-4-(pyridin-4-yl)-1H-imidazol-1-yl)-3,5-dihydroxyheptanoic acid, calcium salt, 72 (1 mg), is obtained in the same manner as Example 13a, Step 4 from (3R,5R)-tert-butyl 7-(5-(4-fluorophenyl)-2-phenyl-4-(pyridin-4-yl)-1H-imidazol-1-yl)-3,5-dihydroxyheptanoate, 71 (5 mg).

The compound obtained in this step shows the following mass spectral data: LC/MS: (as free acid) $C_{27}H_{26}FN_3O_4$ requires 475.2; observed M/Z 476.0 [M+H]$^+$. RT 2.34 mm.

Example 14

Scheme for Synthesis of Imidazole Cmpounds Via N-Alkylation

An overall scheme for synthesizing substituted imidazole compouds of Formula V of the instant invention via N-alkylation is provided below. Example 14a provides a scheme for synthesizing the sidechain for use in the N-alkylatoin scheme. Example 14b details a specific example following the overall N-alkylation scheme.

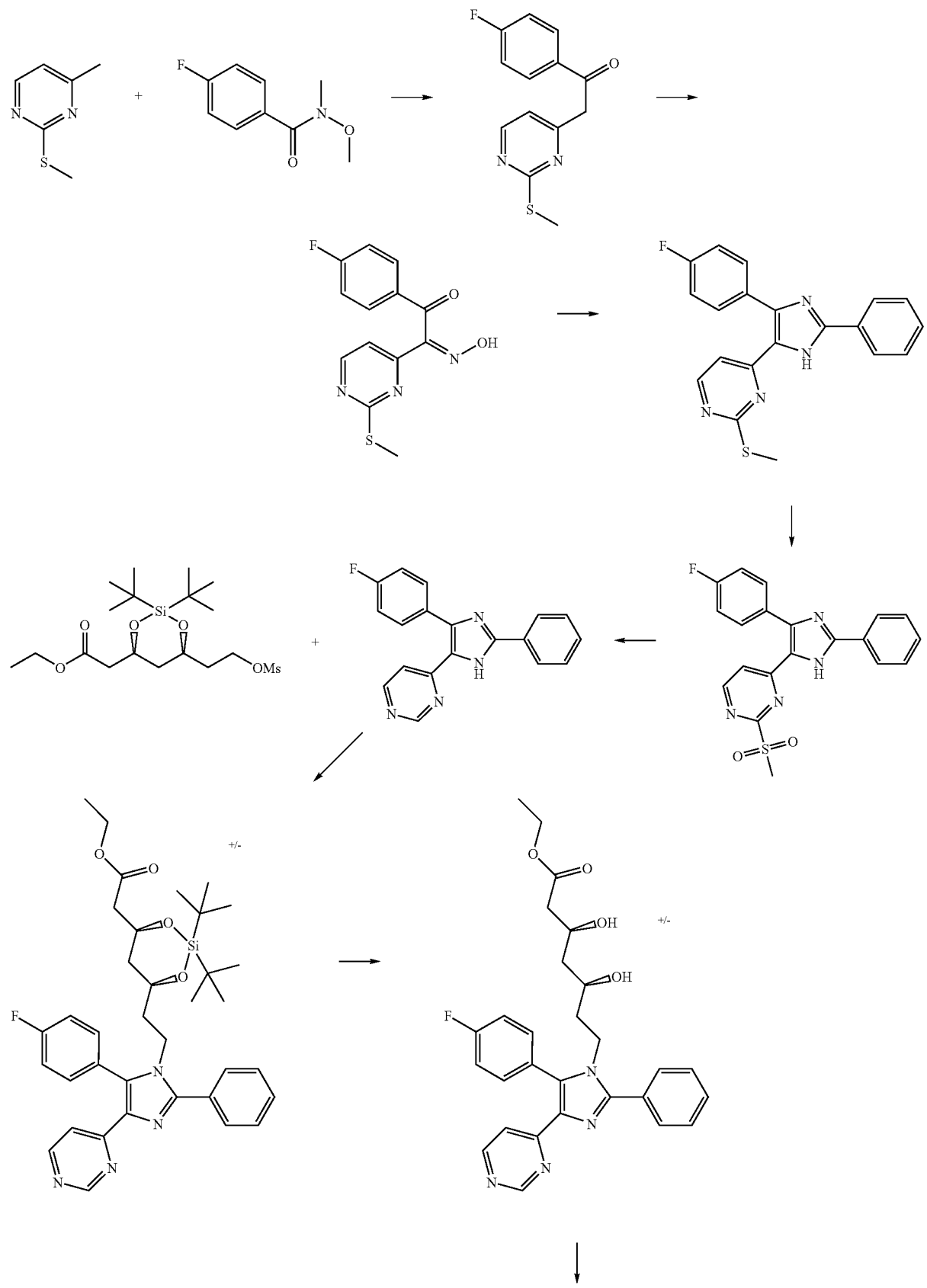

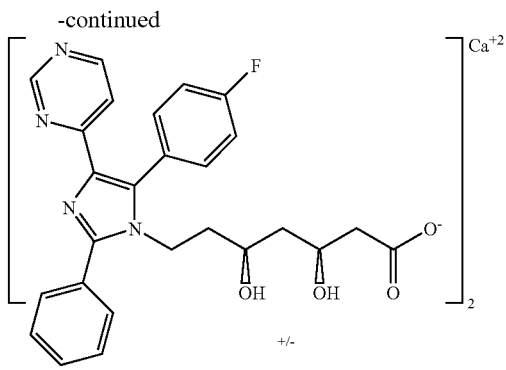

Example 14a

Scheme for Synthesis of Sidechain Used for Synthesis of Imidazole Compound Via N-Alkylation A sidechain for use in synthesizing imidazole compounds via N-alkylation can be prepared as follows:

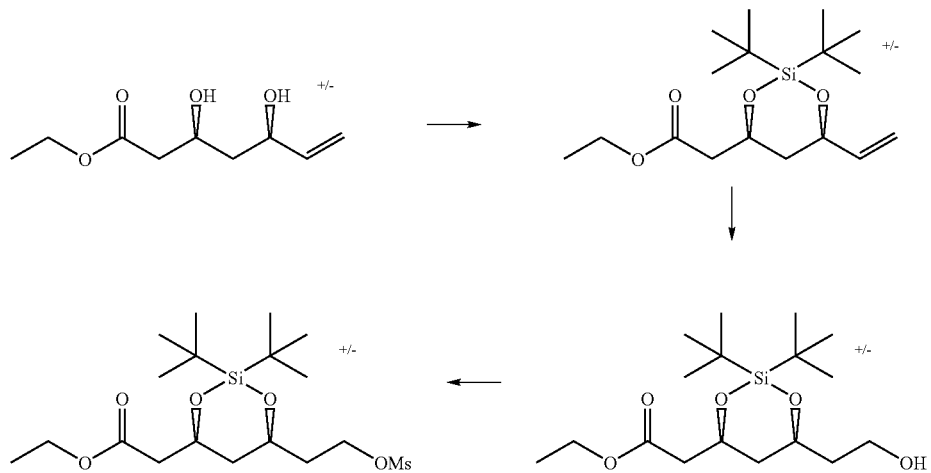

Example 14b

Synthesis of Imidazole Cmpound (3S,5S), (3R,5R)-6-(5-(4-fluorophenyl)-2-phenyl-4-(pyrimidin-4-yl)-1H-imidazol-1-yl)-3,5-dihydroxyhexanoic acid, calcium salt via N-alkylation

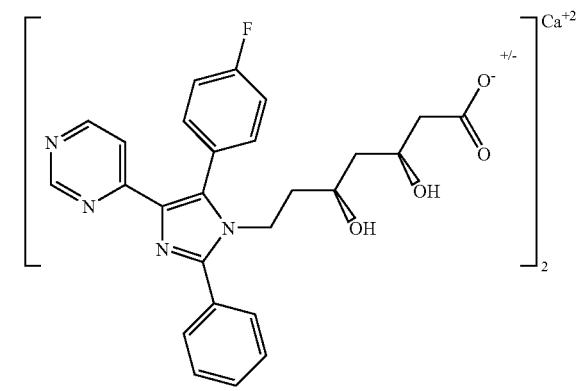

In one specific example, (3S,5S), (3R,5R)-6-(5-(4-fluorophenyl)-2-phenyl-4-(pyrimidin-4-yl)-1H-imidazol-1-yl)-3,5-dihydroxyhexanoic acid, calcium salt, having the structure below, is prepared in ten steps (Steps 1–10) below.

Step 1: 1-(4-fluorophenyl)-2-(2-(methylthio)pyrimidin-4-yl)ethanone 73 is prepared as follows:

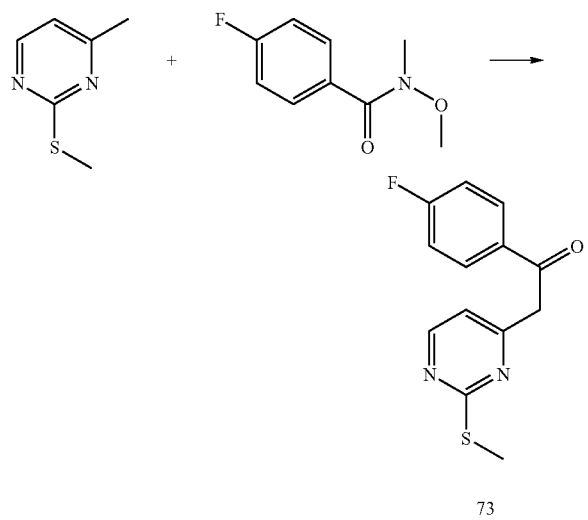

73

Under an atmosphere of nitrogen at −78° C., n-BuLi (1.6 M in hexanes, 8.4 mL) is added dropwise to a solution of diisopropylamine (2.9 mL) in anhydrous tetrahyrofuran (40 mL). After stirring for 5 min, a solution of 4-methyl-2-(methylthio)pyrimidine (2.0 g) in anhydrous tetrahydrofuran (20 mL) is added and stirring continued for a further 30 min at −78° C., whereupon a solution 4-fluoro-N-methoxy-N-methylbenzamide (2.8 g) in anhydrous tetrahyrofuran (20 mL) is added. The solution is allowed to warm to room temperature and then poured into a mixture of ethyl acetate and water.

The layers are separated, the aqueous extracted with ethyl acetate and the combined organic phases dried over sodium sulfate. Filtration and evaporation of the solvent followed by tituration of the residue with a mixture of diethyl ether and hexanes (1:10) furnishes the title compound, 73 (3.1 g).

The compound obtained in this step shows the following mass spectral data: LC/MS: $C_{13}H_{11}FN_2OS$ requires 262.1; observed M/Z 263.2 [M+H]$^+$. RT 4.81 min.

Step 2: (Z)-1-(4-fluorophenyl)-2-(hydroxyimino)-2-(2-(methylthio)pyrimidin-4-yl)ethanone 74 is prepared as follows:

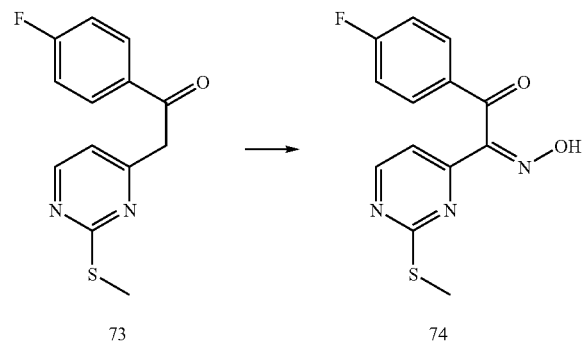

73 74

To a suspension of 1-(4-fluorophenyl)-2-(2-(methylthio)pyrimidin-4-yl)ethanone, 73 (1.0 g) in ethanol (20 mL) at −10° C., under an atmosphere of nitrogen, is added dropwise t-butyl nitrite (0.5 mL) followed by hydrogen chloride in n-propanol (2.5 to 3 N, 0.6 mL) while maintaining the temperature below −5° C. Once the addition is complete, the solution is allowed to warm to room temperature with stirring and after 2 h the solvent is evaporated and the residue partitioned between saturated aqueous sodium hydrogen carbonate and ethyl acetate. The layers are separated; the aqueous phase is extracted with ethyl acetate and the combined organic phases dried over sodium sulfate. Filtration and evaporation of the solvent affords the title compound, 74 (1.0 g).

The compound obtained in this step shows the following mass spectral data: LC/MS: $C_{13}H_{10}FN_3O_2S$ requires 291.1; observed M/Z 292.0 [M+H]$^+$. RT 3.74 min.

Step 3: 4-(4-(4-fluorophenyl)-2-phenyl-1H-imidazol-5-yl)-2-(methylthio)pyrimidine 75 is prepared as follows:

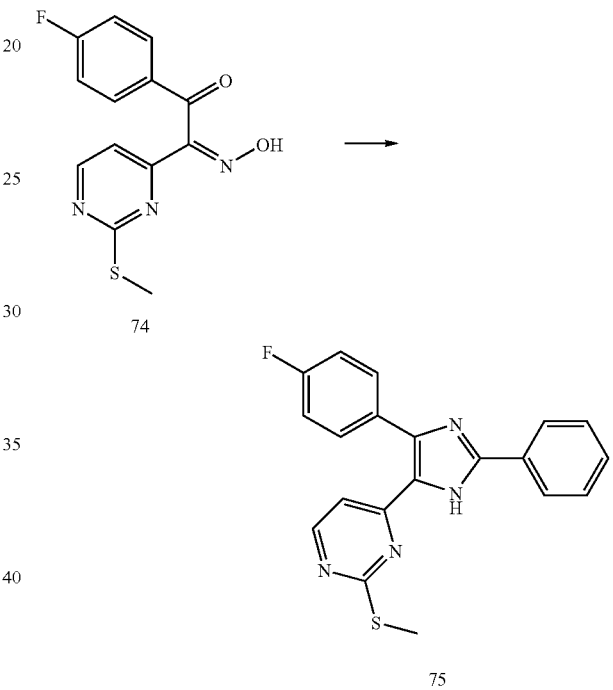

A mixture of (Z)-1-(4-fluorophenyl)-2-(hydroxyimino)-2-(2-(methylthio)pyrimidin-4-yl)ethanone (0.5 g), ammonium acetate (2.7 g) and benzaldehyde (0.2 g) in acetic acid (11 mL) are heated under reflux for 4 h, cooled to room temperature and the majority of the solvent evaporated. The residue is partitioned between ice-cold saturated aqueous sodium hydrogen carbonate and ethyl acetate. The layers are separated and the aqueous phase is extracted with ethyl acetate. The combined organic phases are dried over sodium sulfate, filtered and the solvent evaporated. The residue is dissolved in methanol (8 mL). This solution is treated with a solution of titanium (III) chloride in hydrochloric acid (0.44 mL, 15 wt %, 20–30% hydrochloric acid), followed by stirring at room temperature for 3 h and solvent evaporation. The residue is partitioned between ice-cold saturated aqueous sodium hydrogen carbonate and ethyl acetate, then the layers are separated and the aqueous phase is extracted with ethyl acetate. The combined organic phases are dried over sodium sulfate, filtered, the solvent evaporated and the residue purified by chromatography to give the title compound, 75 (0.15 g).

The compound obtained in this step shows the following mass spectral data: LC/MS: $C_{20}H_{15}FN_4S$ requires 262.1; observed M/Z 263.1 [M+H]$^+$. RT 4.39 min.

Step 4: 4-(4-(4-fluorophenyl)-2-phenyl-1H-imidazol-5-yl)-2-(methylsulfonyl)pyrimidine 76 is prepared as follows;

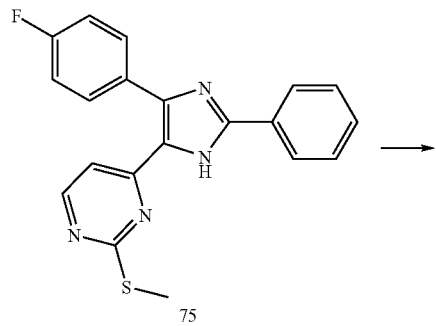
75

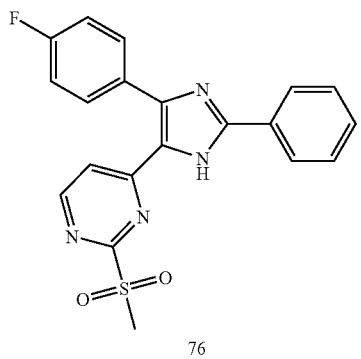
76

An aqueous solution (40 mL) of Oxone (10.4 g) is added dropwise to a stirred ice-cold solution of 4-(4-(4-fluorophenyl)-2-phenyl-1H-imidazol-5-yl)-2-(methylthio)pyrimidine, 75 (2.1 g) in methanol (40 mL). After stirring for 4 h at room temperature, the methanol is evaporated, the solution diluted with saturated aqueous sodium hydrogen carbonate and extracted with ethyl acetate. The combined organic phases are dried over sodium sulphate. Evaporation of the solvent furnishes the title compound, 76 (2.1 g).

The compound obtained in this step shows the following mass spectral data: LC/MS: $C_{20}H_{15}FN_4O_2S$ requires 394.1; observed M/Z 395.0 [M+H]$^+$. RT 4.13 min.

Step 5: 4-(4-(4-fluorophenyl)-2-phenyl-1H-imidazol-5-yl)pyrimidine 77 is prepared as follows:

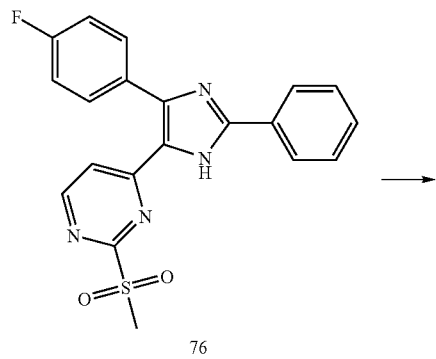
76

-continued

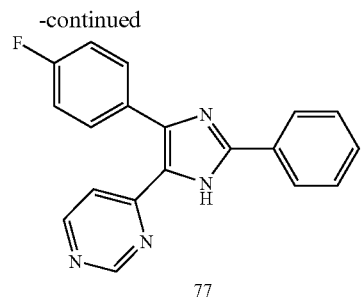
77

To a suspension of 4-(4-(4-fluorophenyl)-2-phenyl-1H-imidazol-5-yl)-2-(methylsulfonyl)pyrimidine, 76 (0.50 g) in ethanol (20 mL) was added in portions, sodium borohydride (0.28 g). After stirring overnight, hydrochloric acid (20 mL, 0.5 M) is added and the solution is allowed to stir for 30 min, whereupon, the solution is neutralized with saturated aqueous sodium hydrogen carbonate and extracted with dichloromethane. The combined organic phases are washed with water and brine, dried over sodium sulfate, filtered and evaporated. The residue is then subjected to chromatography, furnishing the title compound, 77 (0.29 g).

The compound obtained in this step shows the following mass spectral data: LC/MS: $C_{19}H_{13}FN_4$ requires 316.1; observed M/Z 317.1 [M+H]$^+$. RT 5.32 min.

Step 6: Ethyl 2-((4S,6R), (4R,6S)-2,2-di-tert-butyl-6-vinyl-1,3,2-dioxasilinan-4-yl)acetate 78 is prepared as follows:

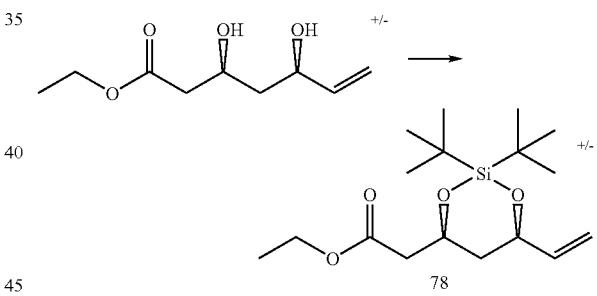
78

All glassware is pre-dried in a high temperature oven and the reaction mixture is maintained under an atmosphere of nitrogen. Dichlorodi-tert-butylsilane (0.37 g) is added to a solution of silver nitrate (0.59 g) and (3S,5R),(3R,5S)-ethyl 3,5-dihydroxyhept-6-enoate (prepared according to *Syn Comm;* 24(13), 1833, (1994)) (0.25 g) in dimethylformamide (5 mL) at 0° C. After 5 min the solution is allowed to warm to room temperature and stirring is continued for 30 min. Triethylamine (0.41 g) is added and after 10 min the mixture is partitioned between ethyl acetate and saturated aqueous sodium hydrogen carbonate solution. The aqueous layer is extracted with further portions of ethyl acetate and the combined organic extracts are dried over magnesium sulfate, filtered, and concentrated to give the title compound, 78 (0.48 g).

The compound obtained in this step shows the following NMR data: $^1$H-NMR (270 MHz, CDCl$_3$, δ) 0.99 (s, 9H), 1.03 (s, 9H), 1.27 (t, 3H) 1.52 (m, 1H), 1.78 (dt 1H), 2.40 (dd, 1H), 2.52 (dd, 1H), 4.10–4.25 (overlapping m, 3H), 4.57 (m, 1H), 5.07 (d, 1H), 5.32 (d, 1H), 5.83 (ddd, 1H)

Step 7: Ethyl 2-((4S,6S), (4R,5R)-2,2-di-tert-butyl-6-(2-hydroxyethyl)-1,3,2-dioxasilinan-4-yl)acetate 79 is prepared as follows:

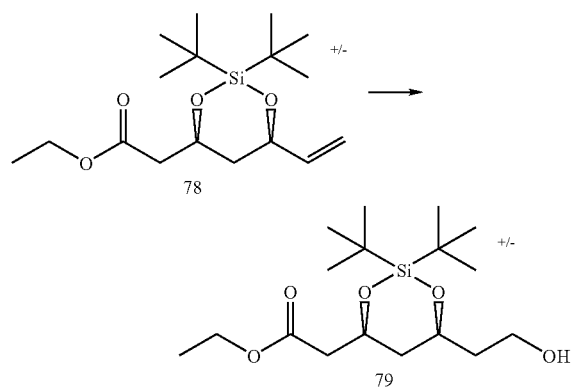

All glassware is pre-dried in a high temperature oven and the reaction mixture is maintained under an atmosphere of nitrogen. A solution of 9-borabicyclononane in tetrahydrofuran (18.3 mL of a 0.5 M solution) is added over 0.5 h to a solution of ethyl 2-((4S,6R), (4R,6S)-2,2-di-tert-butyl-6-vinyl-1,3,2-dioxasilinan-4-yl)acetate, 78 (1.0 g) in tetrahydrofuran (10 mL) at 0° C. The reaction mixture is set aside at 4° C. for 64 h then cooled to 0° C. Sodium hydroxide (2.9 mL of a 3 M solution) and hydrogen peroxide (7.1 mL of a 35% solution in water) are added simultaneously over 1 h, while the temperature is maintained below 5° C. The reaction mixture is allowed to warm to room temperature over 3 h then partitioned between ethyl acetate and brine. The aqueous layer is extracted with further portions of ethyl acetate and the combined organic extracts are dried over magnesium sulfate, filtered, and concentrated to an oil which is purified by flash column chromatography to afford the title molecule, 79 (0.41 g).

The compound obtained in this step shows the following NMR data: $^1$H-NMR (270 MHz, CDCl$_3$, δ) 0.98 (s, 9H), 1.03 (s, 9H), 1.26 (t, 3H) 1.65 (m, 4H), 2.40 (dd, 1H), 2.52 (dd, 1H), 3.84 (m, 2H), 4.13 (q, 2H), 4.35 (m, 1H), 4.52 (m, 1H).

Step 8: Ethyl 2-((4S,6S), (4R,6R)-2,2-di-tert-butyl-6-(2-(methylsulfonyloxy)ethyl)-1,3,2-dioxasilinan-4-yl)acetate 80 is prepared as follows:

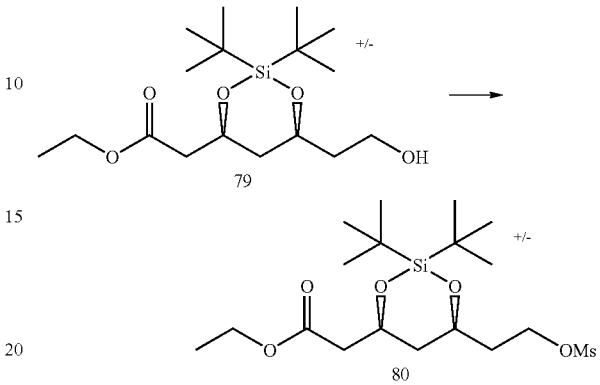

All glassware is pre-dried in a high temperature oven and the reaction mixture is maintained under an atmosphere of nitrogen. Diisopropylethylamine (0.23 g) is added to a solution of ethyl 2-((4S,6S), (4R,5R)-2,2-di-tert-butyl-6-(2-hydroxyethyl)-1,3,2-dioxasilinan-4-yl)acetate, 79 (0.30 g) in dichloromethane (5 mL) at −40° C. After 3 min methanesulfonyl chloride (0.15 g) is added and the mixture is allowed to warm to room temperature. After 16 h the reaction mixture is washed with saturated aqueous sodium hydrogen carbonate solution and brine, dried over magnesium sulfate and concentrated in vacuo to afford the title compound, 80 (0.16 g) which is used without further purification.

Step 9: Ethyl 2-((4S,6S), (4R,6R)-2,2-di-tert-butyl-6-(2-(5-(4-fluorophenyl)-2-phenyl-4-(pyrimidin-4-yl)-1H-imidazol-1-yl)ethyl)-1,3,2-dioxasilinan-4-yl)acetate 81 is prepared as follows:

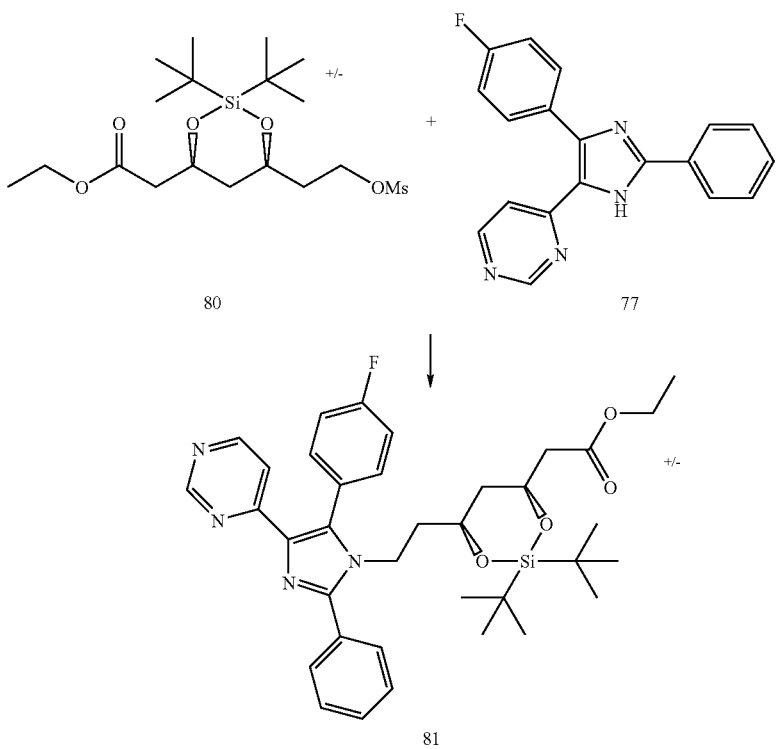

All glassware is pre-dried in a high temperature oven and the reaction mixture is maintained under an atmosphere of nitrogen. To a solution of 4-(4-(4-fluorophenyl)-2-phenyl-1H-imidazol-5-yl)pyrimidine, 77 (162 mg) in anhydrous dimethylformamide (1.6 mL) at −40° C. is added dropwise a solution of potassium hexamethyldisilylamide in toluene (1.03 mL, 0.5 M). The solution is allowed to warm to room temperature and subsequently cooled again to −40° C., whereupon a solution of ethyl 2-((4S,6S), (4R,6R)-2,2-di-tert-butyl-6-(2-(methylsulfonyloxy)ethyl)-1,3,2-dioxasilinan-4-yl)acetate, 80 (327 mg) in anhydrous dimethylformamide (1 mL) is added. The solution is then allowed to warm to room temperature, heated at 85° C. for 20 h and cooled to room temperature. The solution is poured into a mixture of saturated aqueous sodium hydrogen carbonate and ethyl acetate, the layers separated, and the organic layer is washed with three portions of saturated aqueous sodium hydrogen carbonate and brine. Drying (magnesium sulfate), filtration, evaporation of the solvent and chromatography of the residue furnishes the title compound as a mixture of enantiomers, 81 (37 mg).

The compound obtained in this step shows the following mass spectral data: LC/MS: $C_{36}H_{45}FN_4O_4Si$ requires 664.3; observed M/Z 645.3 $[M+H]^+$. RT 8.10 min.

Step 10: (3S,5S),(3R,5R)-7-(5-(4-fluorophenyl)-2-phenyl-4-(pyrimidin-4-yl)-1H-imidazol-1-yl)-3,5-dihydroxyheptanoic acid 82 is prepared as follows:

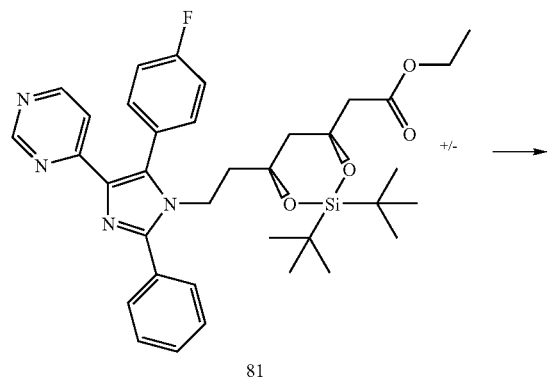

81

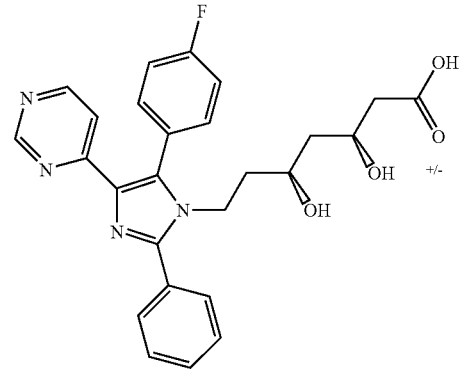

82

To a solution of ethyl 2-((4S,6S), (4R,6R)-2,2-di-tert-butyl-6-(2-(5-(4-fluorophenyl)-2-phenyl-4-(pyrimidin-4-yl)-1H-imidazol-1-yl)ethyl)-1,3,2-dioxasilinan-4-yl)acetate, 81 (0.037 g) in anhydrous tetrahydrofuran (0.45 mL) is added tetrabutylammonium fluoride (1 M solution in tetrahydrofuran, 0.115 mL) and the resulting solution stirred at 50° C. for 1 h, affording the title compound.

The compound obtained in this step shows the following mass spectral data: LC/MS: $C_{26}H_{25}FN_4O_4$ requires 476.2; observed M/Z 477.0 $[M+H]^+$, 475.2 $[M-H]^-$. RT 2.09 min.

Reported HPLC retention times (RT) provided in the Examples above were determined under the following conditions:
Column Waters Xterra MS C18 5 micron, 4.6 mm×50 mm
Particle Size 5 micron
Dimensions 4.6 mm×50 mm
Solvent A water containing 0.1% v/v aqueous ammonia
Solvent B acetonitrile containing 0.1% v/v aqueous ammonia
Flow rate 1.5 mL/min
Initial Conditions 95% A: 5% B
Time=7.0 mins 5% A: 95% B
Time=7.9 mins 5% A: 95% B
Time=8.0 mins 95% A: 5% B
Time=10.0 mins 95% A: 5% B
Detection UV at 215 and 254 nm.

Example 15

In Vitro Assays for HMG-CoA Reductase and/or MAP Kinase Inhibitory Activity Using Specific Pyrazole Compounds Described Herein Table III below summarizes the results of in vitro assays described above for HMG-CoA and/or MAP kinase inhibitory activity of specific pyrazole compounds. Pyrazole compounds obtained according to Examples 11a, 11b, 11c, 11d, 11e, 11f, 11g, 10a and 10b were tested as indicated, as the results obtained are provided below.

| Compound made in Example # | IC50 HMG-CoA R[a] | IC50 p38α MAPK[b] | IC50 Whole cell[c] |
|---|---|---|---|
| 11a | 33 nM | 11 μM | 31 μM |
| 11b |  | 6 μM | 21 μM |
| 11e | 2 nM | 36 μM | 30 μM |
| 11f |  | >100 μM | 16 μM |
| 11g | >100 nM | 14 μM | 52 μM |
| 10a | 3 nM | 11 μM | 21 μM |
| 10b |  | 6 μM | 14 μM |
| 11c | >100 nM | 32 μM | 18 μM |
| 11d |  | 8 μM | 11 μM |

[a]Concentration of compound required to inhibit rat liver HMG-CoA reductase by 50%.
[b]Concentration of compound required to inhibit phosphorylation of myelin basic protein by recombinant human p38α MAP kinase by 50%.
[c]Concentration of compound required to inhibit LPS-induced TNF-α release from human peripheral blood mononuclear cells by 50%.

The above examples are in no way intended to limit the scope of the instant invention. Further, it can be appreciated to one of ordinary skill in the art that many changes and modifications can be made thereto without departing from the spirit or scope of the appended claims, and such changes and modifications are contemplated within the scope of the instant invention.

What is claimed is:
1. A compound comprising formula VII:

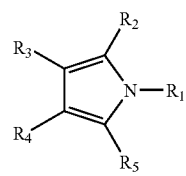

Formula VII wherein R₁ is

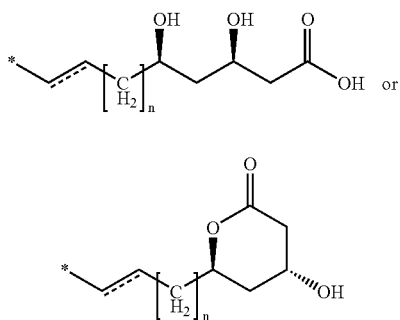 or

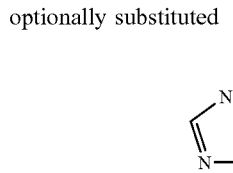

n being 0 or any integer;
R₂ is optionally substituted alkyl, aryl, or heteroaryl;
R₃ is any substituent;
R₄ is optionally substituted

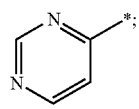

optionally substituted

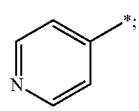

or substituted

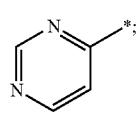

and R₅ is optionally substituted aryl or heteroaryl, or a salt thereof.

2. The compound as recited in claim 1 wherein R₂ is a C₃₋₄ branched alkyl group.

3. The compound as recited in claim 1 wherein R₂ is isopropyl.

4. The compound as recited in claim 1 wherein R₄ is

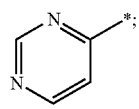

5. The compound as recited in claim 1 wherein R₅ is an optionally substituted phenyl group.

6. The compound as recited in claim 1 wherein R₅ is 4-fluorophenyl.

7. The compound as recited in claim 1 wherein R₃ is —CONH-aryl.

8. The compound as recited in claim 1 wherein R₃ is —CONH-phenyl.

9. A compound comprising at least one structure selected from:

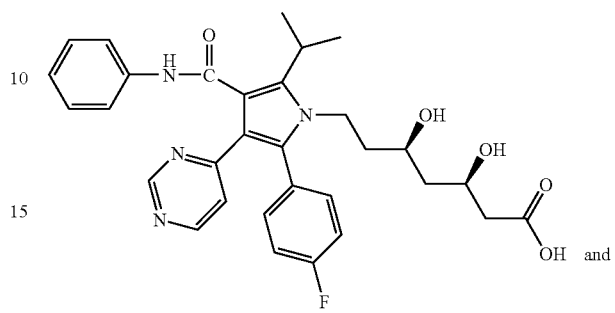 and

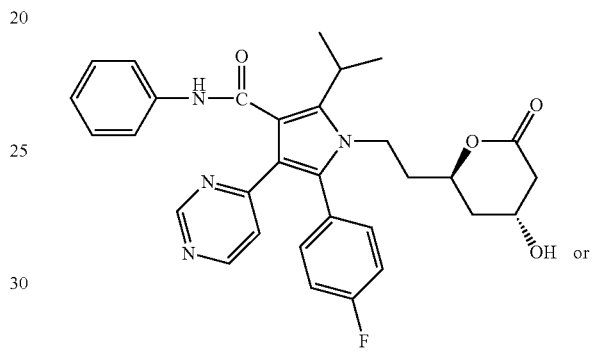 or a salt and/or a solvate thereof.

10. A compound comprising at least one structure selected from:

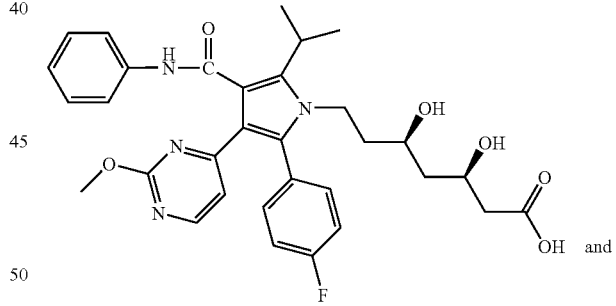 and

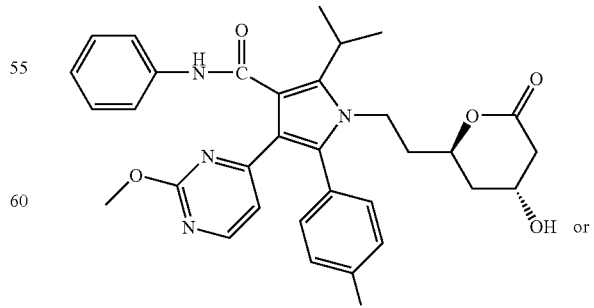 or a salt and/or a solvate thereof.

11. A compound comprising at least one structure selected from:

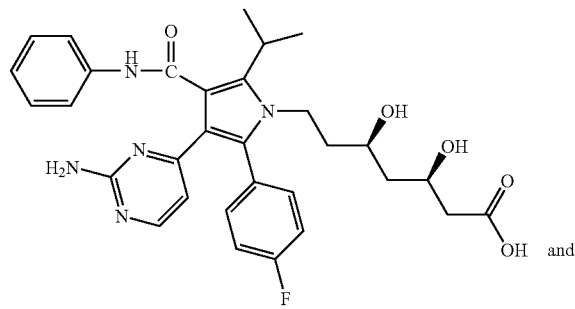

and

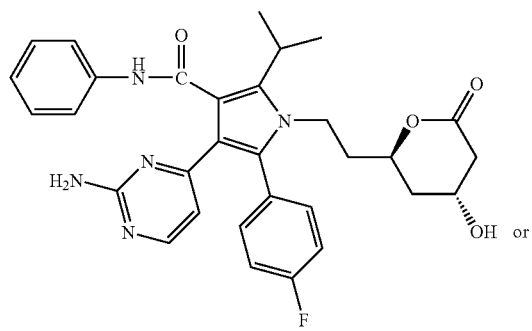

or a salt and/or a solvate thereof.

12. A compound comprising at least one structure selected from:

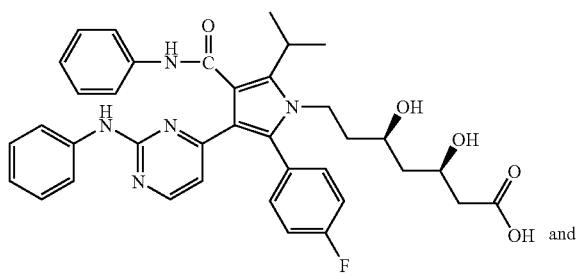

and

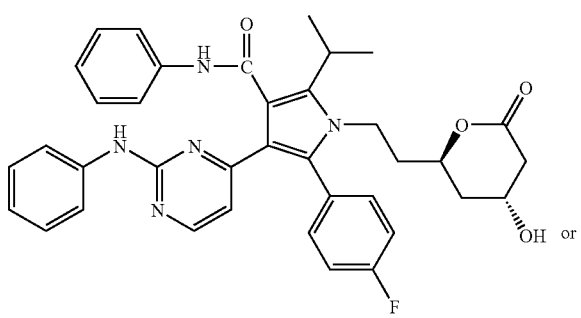

or a salt and/or a solvate thereof.

13. A compound comprising formula VII:

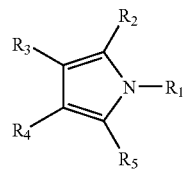

Formula VII wherein $R_1$ is

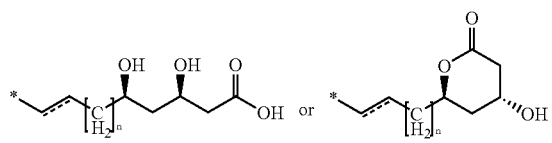

n being 0 or any integer;
$R_2$ is optionally substituted alkyl, aryl, or heteroaryl;
$R_3$ is any substituent;
$R_4$ is substituted

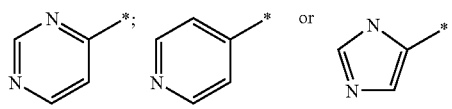

wherein said $R_4$ is substituted with one or more optionally substituted amino groups or optionally substituted alkoxy groups;
and $R_5$ is optionally substituted aryl or heteroaryl, or a salt thereof.

14. A compound comprising formula VIIa:

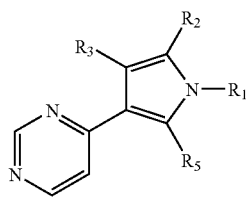

Formula VIIa wherein $R_1$ is

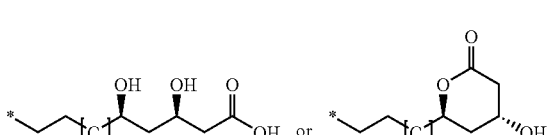

n being 0 or any integer;
$R_2$ is optionally substituted alkyl, aryl, or heteroaryl;
the pyridinyl ring is substituted;
and $R_5$ is optionally substituted aryl or heteroaryl, or a salt thereof.

15. A compound comprising formula VIIb:
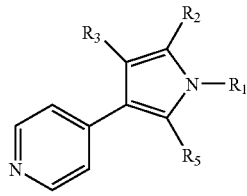
Formula VIIb
wherein $R_1$ is
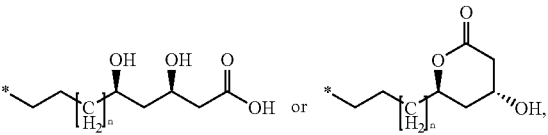
n being 0 or any integer;
$R_2$ is optionally substituted alkyl, aryl, or heteroaryl;
the pyrimidinyl ring is optionally substituted;
and $R_5$ is optionally substituted aryl or heteroaryl, or a salt thereof.
* * * * *

UNITED STATES PATENT AND TRADEMARK OFFICE
CERTIFICATE OF CORRECTION

| | | |
|---|---|---|
| PATENT NO. | : 7,183,285 B2 | Page 1 of 1 |
| APPLICATION NO. | : 11/118066 | |
| DATED | : February 27, 2007 | |
| INVENTOR(S) | : Griffin et al. | |

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by (10) days Delete the phrase "by 10 days" and insert -- by 32 days--

Signed and Sealed this

Second Day of October, 2007

JON W. DUDAS
*Director of the United States Patent and Trademark Office*